US012701914B2

(12) United States Patent
Groarke et al.

(10) Patent No.: US 12,701,914 B2
(45) Date of Patent: Aug. 4, 2026

(54) ORGANIC ELECTROLUMINESCENCE DEVICE COMPRISING AN AZINE COMPOUND AND A RARE EARTH METAL, RARE EARTH METAL COMPOUND, AND/OR RARE EARTH METAL COMPLEX AND AN ELECTRONIC EQUIPMENT COMPRISING SAID ORGANIC ELECTROLUMINESCENCE DEVICE

(71) Applicant: Idemitsu Kosan Co., Ltd., Tokyo (JP)

(72) Inventors: Michelle Groarke, Binningen (CH); Heinz Wolleb, Fehren (CH); Natalia Chebotareva, Hagenthal le Bas (FR); Hiroaki Toyoshima, Sodegaura (JP); Masatoshi Saito, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 899 days.

(21) Appl. No.: 17/655,278

(22) Filed: Mar. 17, 2022

(65) Prior Publication Data

US 2022/0310933 A1 Sep. 29, 2022

(30) Foreign Application Priority Data

Mar. 19, 2021 (EP) .................................... 21163692

(51) Int. Cl.
*H10K 85/60* (2023.01)
*C07D 401/10* (2006.01)
(Continued)

(52) U.S. Cl.
CPC ......... *H10K 85/654* (2023.02); *C07D 401/10* (2013.01); *C07D 471/04* (2013.01);
(Continued)

(58) Field of Classification Search
CPC ............................ H10K 85/654; H10K 50/16
See application file for complete search history.

(56) References Cited

U.S. PATENT DOCUMENTS 10,505,122 B2 * 12/2019 Lee ...................... H10K 85/654
11,495,748 B2 * 11/2022 Ma ..................... H10K 85/6574
(Continued)

FOREIGN PATENT DOCUMENTS

CN 111039881 A * 4/2020 ........... C07D 213/22
EP 3598515 A1 * 1/2020 ........... C07D 221/18
(Continued)

OTHER PUBLICATIONS

Wolfe et al., "Highly Active Palladium Catalysts for Suzuki Coupling Reactions", Journal of American Chemistry Society, vol. 121, No. 41, 1999, 12 Pages.

(Continued)

*Primary Examiner* — Vu A Nguyen
(74) *Attorney, Agent, or Firm* — Oblon, McClelland, Maier & Neustadt, L.L.P.

(57) ABSTRACT

An organic electroluminescence device comprising an electron-transporting zone comprising i) at least one compound represented by formula (I), and
ii) at least one rare earth metal, rare earth metal compound, and/or rare earth metal complex, wherein the electron-transporting zone does not comprise an alkali metal, an alkali metal compound, an alkali metal complex, an alkaline earth metal, an alkaline earth metal compound, and an alkaline earth metal complex; a material for an organic electroluminescence device comprising a combination of at least one compound of formula (I) and at least one rare earth metal, rare earth metal compound, and/or rare earth metal complex; an organic electroluminescence device comprising said organic electroluminescence device and the use of a compound of formula (I) in combination with at least one rare earth metal, rare earth metal compound, and/or rare earth metal complex, in an electron- (Continued)

transporting zone of an organic electroluminescence device, wherein the electron-transporting zone does not comprise an alkali metal, an alkali metal compound, an alkali metal complex, an alkaline earth metal, an alkaline earth metal compound, and an alkaline earth metal complex.

(I)

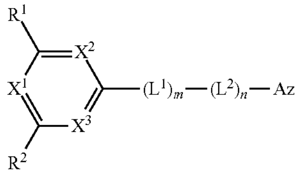

16 Claims, 1 Drawing Sheet

(51) Int. Cl.

| | |
|---|---|
| ***C07D 471/04*** | (2006.01) |
| ***C09K 11/06*** | (2006.01) |
| ***H10K 50/16*** | (2023.01) |
| ***H10K 50/17*** | (2023.01) |

(52) U.S. Cl.

CPC ............ *C09K 11/06* (2013.01); *H10K 85/615* (2023.02); *H10K 85/6572* (2023.02); *C09K 2211/1018* (2013.01); *H10K 50/16* (2023.02); *H10K 50/171* (2023.02)

(56) References Cited

U.S. PATENT DOCUMENTS

| | | | | |
|---|---|---|---|---|
| 2017/0179402 | A1* | 6/2017 | Kim ................... | H10K 85/6572 |
| 2019/0027699 | A1 | 1/2019 | Ko et al. | |
| 2020/0058881 | A1 | 2/2020 | Groarke et al. | |

FOREIGN PATENT DOCUMENTS

| | | | | |
|---|---|---|---|---|
| KR | 10-2018-0072245 | 6/2018 | | |
| WO | WO 2010/134350 A1 | 11/2010 | | |
| WO | WO 2017/102822 A1 | 6/2017 | | |
| WO | WO-2017156698 A1 * | 9/2017 | ........... | C07D 417/10 |
| WO | WO 2019/086568 A1 | 5/2019 | | |
| WO | WO 2020/120794 A2 | 6/2020 | | |

OTHER PUBLICATIONS

Miyaura et al., “Palladium-Catalyzed Cross-Coupling Reactions of Organoboron Compounds”, Chemical Reviews, vol. 95, No. 7, 1995, 27 Pages.

Ackermann et al., “Air-Stable Secondary Phosphine Oxide or Chloride (Pre) Ligands for Cross-Couplings of Unactivated Alkyl Chlorides”, Organic Letters, vol. 12, No. 10, 2010, 4 Pages.

Frisch et al., “Palladium-katalysierte Kupplung von Alkylchloriden mit Grignard-Reagentien”, Zuschriften, Angew. Chem.,114, Nr. 21, 2002, 4 Pages.

* cited by examiner

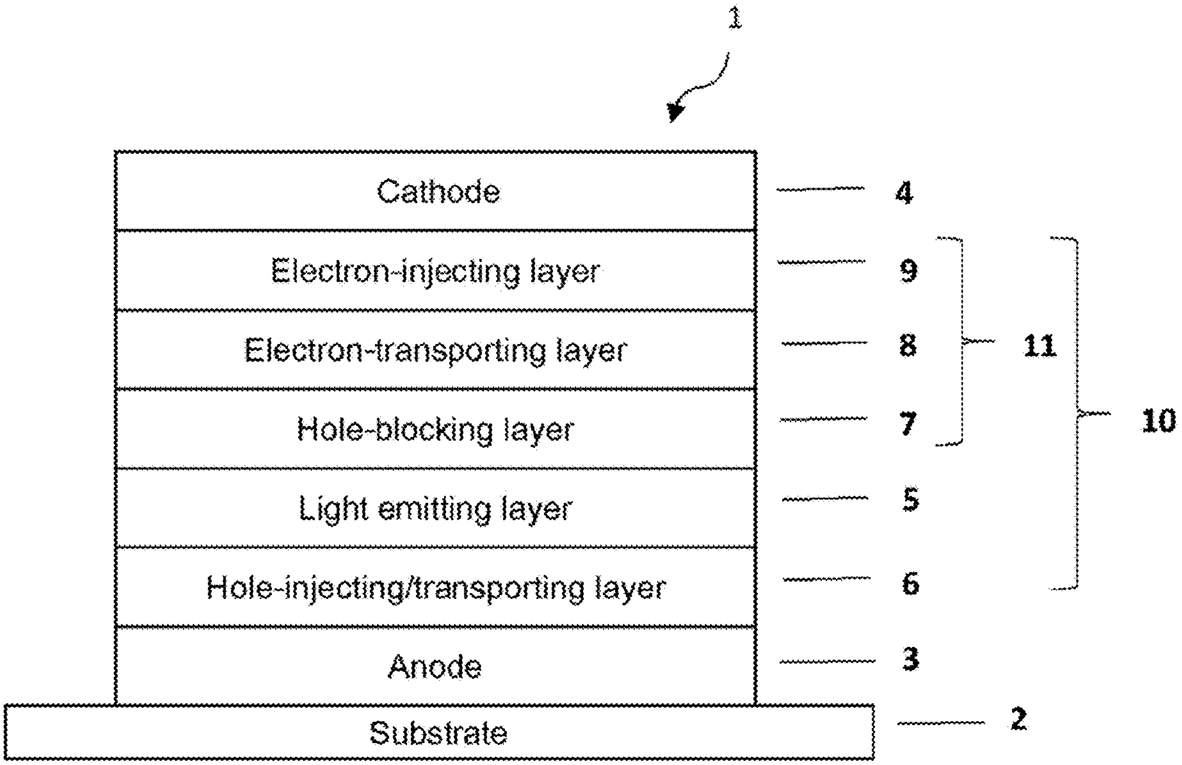
1
Cathode
Electron-injecting layer
Electron-transporting layer
Hole-blocking layer
Light emitting layer
Hole-injecting/transporting layer
Anode
Substrate
4
9
8
7
5
6
3
2
11
10

ORGANIC ELECTROLUMINESCENCE DEVICE COMPRISING AN AZINE COMPOUND AND A RARE EARTH METAL, RARE EARTH METAL COMPOUND, AND/OR RARE EARTH METAL COMPLEX AND AN ELECTRONIC EQUIPMENT COMPRISING SAID ORGANIC ELECTROLUMINESCENCE DEVICE

The present invention relates to an organic electroluminescence device comprising a specific azine compound and a rare earth metal, rare earth metal compound, and/or rare earth metal complex, an electronic equipment comprising said organic electroluminescence device and the use of said compounds in combination with at least one rare earth metal, rare earth metal compound, and/or rare earth metal complex, in an electron-transporting zone of an organic electroluminescence device.

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

An organic EL device essentially comprises an emitting layer between the anode and the cathode. Further, there may be a case where it has a stacked layer structure comprising one or more additional organic layers. One example is an organic electroluminescence device comprising a cathode, an anode and one or more organic thin film layers comprising an emitting layer disposed between the cathode and the anode, and an electron-transporting zone provided between the emitting layer and the cathode.

WO2017/102822 A1 relates to an organic light emitting diode comprising at least one emission layer, an electron injection layer and at least one cathode electrode, wherein the electron injection layer comprises an organic phosphine compound, wherein the electron injection layer is free of a metal, metal salt, metal complex and metal organic compound; the cathode electrode comprises at least a first cathode electrode layer, wherein the first cathode electrode layer comprises a first zero-valent metal selected from the group comprising alkali metal, alkaline earth metal, rare earth metal and/or a group 3 transition metal; and the electron injection layer is arranged in direct contact to the first cathode electrode layer.

WO2019/086568 A1 relates to a compound of the general formula (I) and an organic electroluminescence device comprising the same.

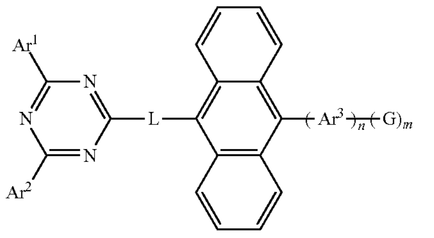

In the examples in WO2019/086568 A1 organic electroluminescence devices comprising an electron transport layer comprising a compound of the following formulae in combination with an alkali metal compound (AMC) are disclosed.

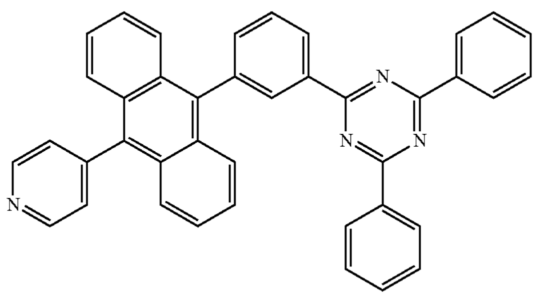

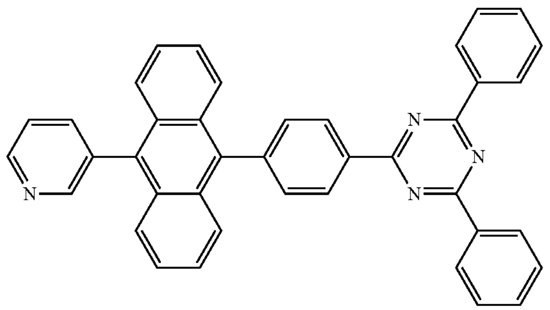

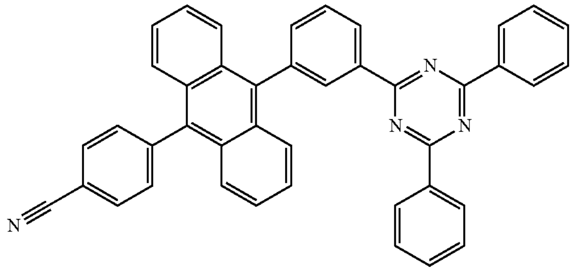

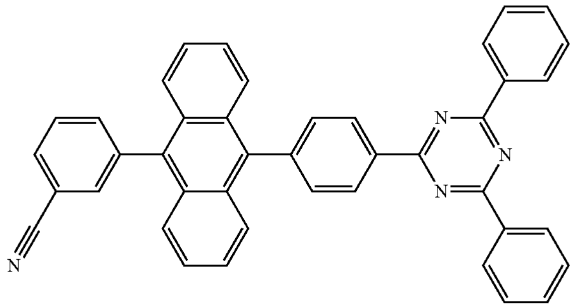

WO2020/120794 A2 relates to an organic light emitting device comprising a cathode, an anode, a light emitting layer, at least one first electron transport layer and at least one second electron transport layer, wherein the light emitting layer, the first electron transport layer and the second electron transport layer are arranged between the cathode and the anode, wherein the first electron transport layer comprises a compound of formula (I) L-M, wherein the following compounds are exemplified

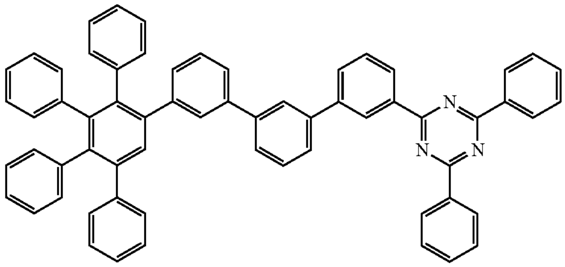
,
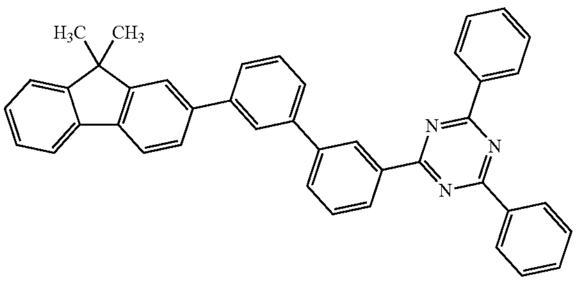
or
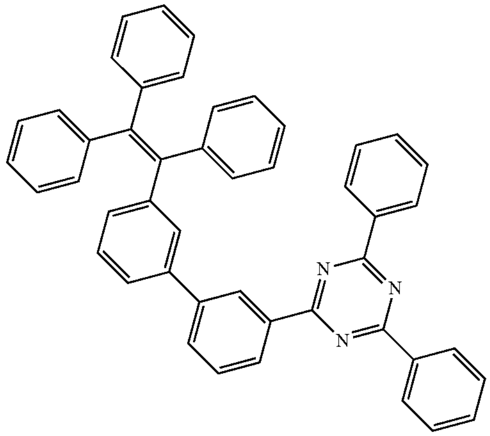
wherein the second electron transport layer comprises a compound of formula (II)
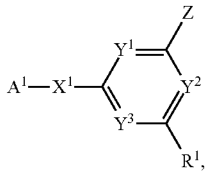
wherein the following compounds are exemplified
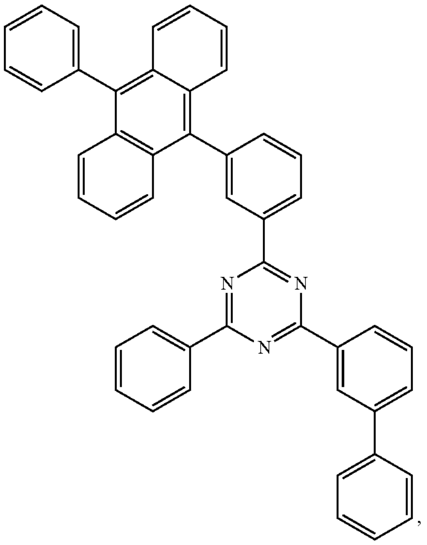
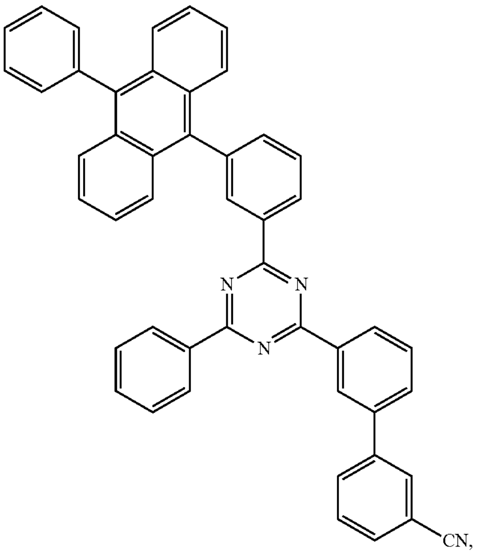
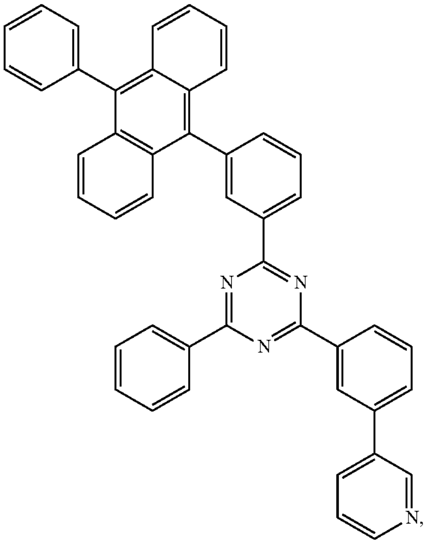

-continued

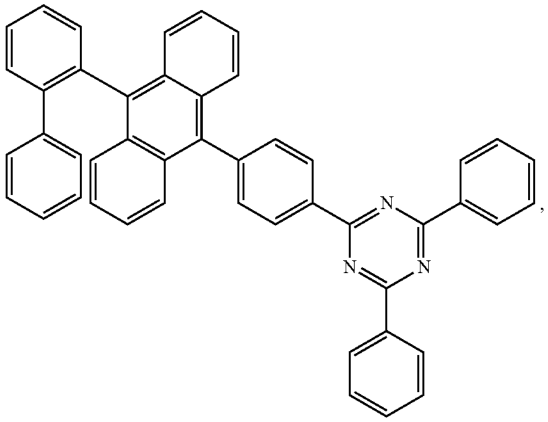

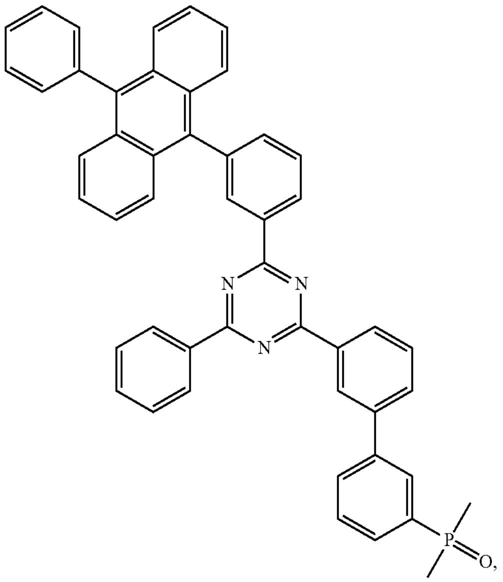

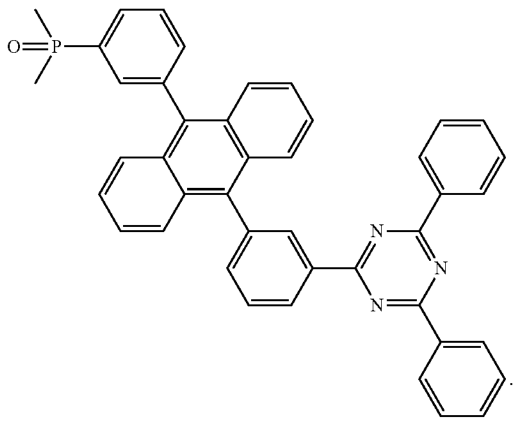

In addition to formula (II) or as an alternative, the second electron transport layer may comprise a compound of formula (III)

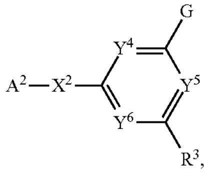

wherein exemplified compounds of formula (III) are for example

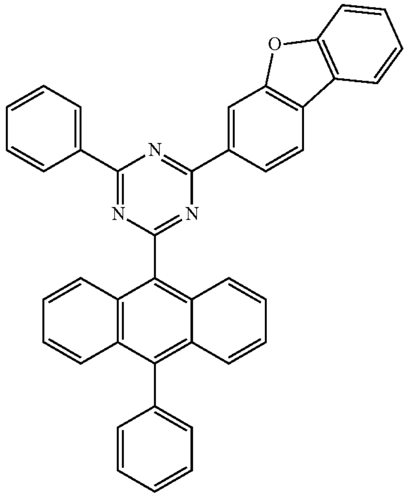

or

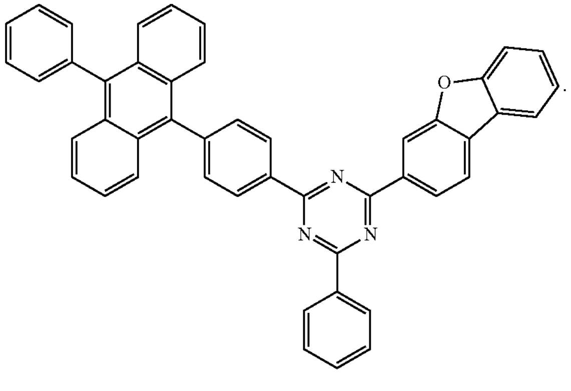

KR20180072245 A relates to an organic electroluminescent device comprising: a positive electrode; a negative electrode; and an organic matter layer composed of one or more layers interposed between the positive electrode and the negative electrode and including a light emitting layer and an electron transporting layer. The organic electroluminescent device further includes an electron transporting auxiliary layer (aETL) between the light emitting layer and the electron transporting layer. The electron transporting auxiliary layer includes an electron transporting compound and an n-type dopant.

The following electron transporting compounds are exemplified among others:

LE-01

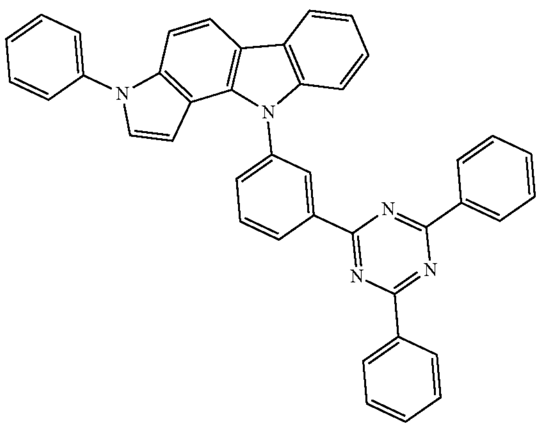

LE-02

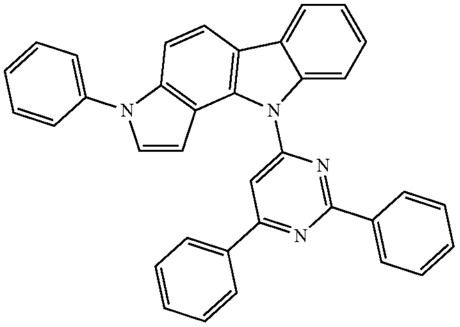

LE-03

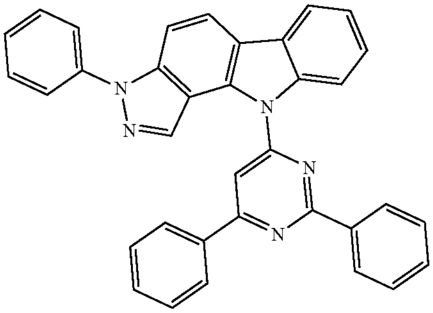

LE-04

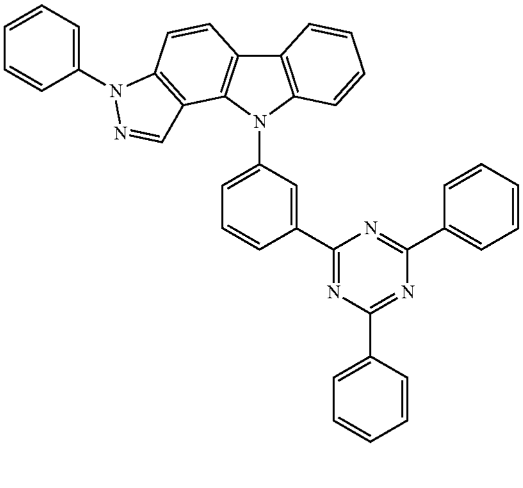

US2020/058881 A1 relates to a compound of formula (I), a material for an organic electroluminescence device comprising at least one compound of formula (I); an organic electroluminescence device which comprises an organic thin film layer between a cathode and an anode, wherein the organic thin film layer comprises one or more layers and comprises a light emitting layer, and at least one layer of the organic thin film layer comprises at least one compound of formula (I); an electronic equipment comprising the organic electroluminescence device; and a process for preparing the compound of formula (I).

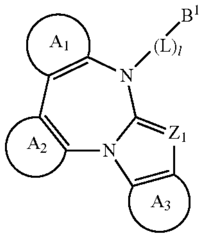

(I)

The following compounds are exemplified among others:

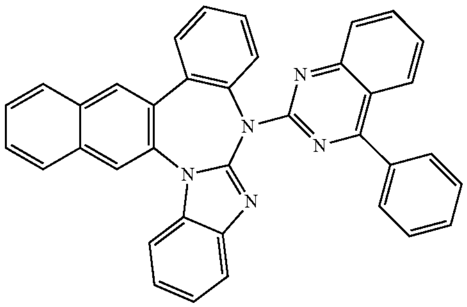

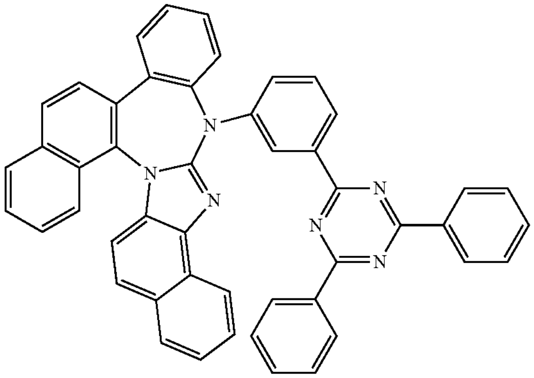

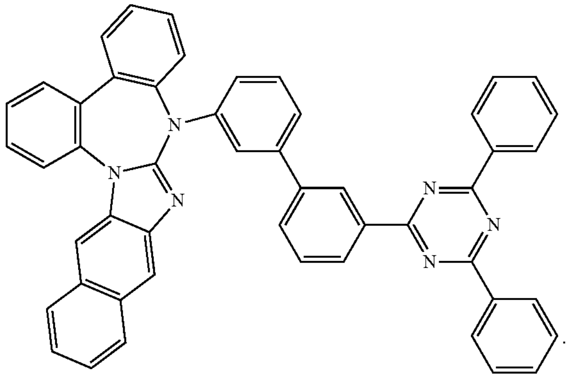

US2019/027699 A1 relates to an organic light-emitting device comprising an organometallic compound. The electron transport region in the organic light-emitting device described in US2019/027699 A1 may comprise one of the following exemplified compounds:

ET22

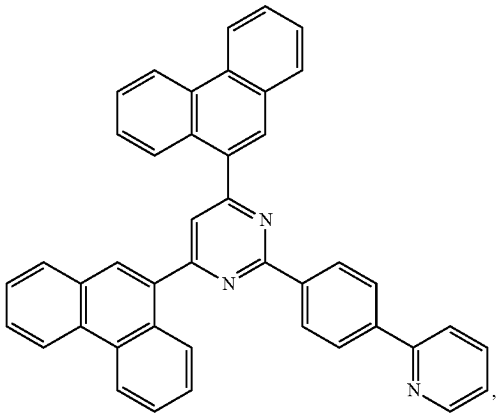

, (ET25)

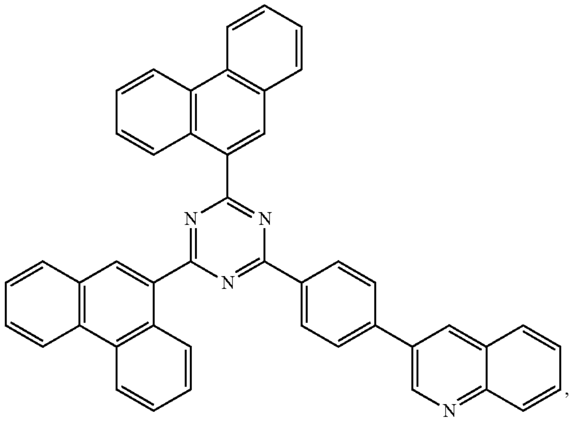

, (ET27)

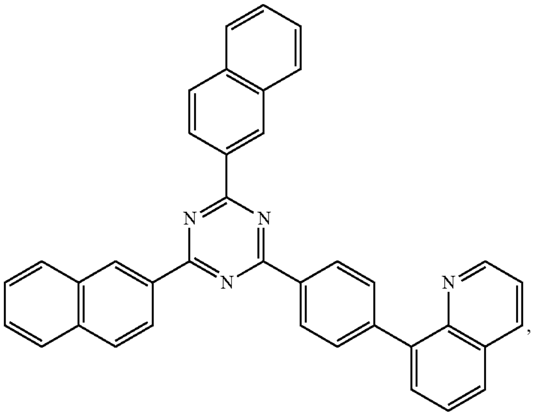

,

-continued (ET35)

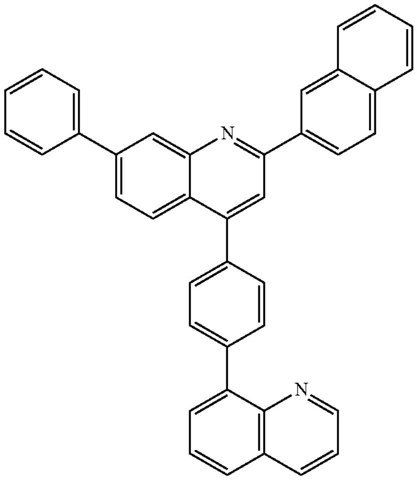

The specific combination of the components in organic electronic devices has a significant impact on the performance of the organic electronic devices.

Accordingly, it is an object of the present invention, with respect to the aforementioned related art, to provide new material combinations suitable in the electron-transporting zone of organic electroluminescence devices, allowing for an improved performance of electroluminescence devices.

Furthermore, the materials should be suitable for providing organic electroluminescence devices which ensure good overall performance of the organic electroluminescence devices, especially a long lifetime, a high EQE (external quantum efficiency) and/or a low driving voltage.

Said object is solved by an organic electroluminescence device comprising a cathode, an anode and one or more organic thin film layers comprising an emitting layer disposed between the cathode and the anode, and an electron-transporting zone provided between the emitting layer and the cathode, wherein the electron-transporting zone comprises i) at least one compound represented by formula (I), and ii) at least one rare earth metal, rare earth metal compound, and/or rare earth metal complex, wherein the electron-transporting zone does not comprise an alkali metal, an alkali metal compound, an alkali metal complex, an alkaline earth metal, an alkaline earth metal compound, and an alkaline earth metal complex;

wherein the compound of formula (I) is represented by the following formula (I)

(I)

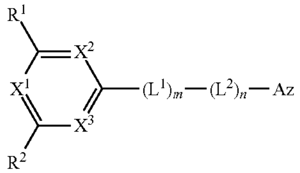

wherein $R^1$ and $R^2$ each independently represents an unsubstituted or substituted aromatic hydrocarbon group containing 6 to 30 ring atoms, or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms, CN or $R^aR^bPO$;

$X^1$, $X^2$ and $X^3$ are each independently N or $CR^3$, wherein at least two of $X^1$, $X^2$ and $X^3$ are N; $R^a$ and $R^b$ each independently represents an unsubstituted or substituted aromatic hydrocarbon group containing 6 to 30 ring atoms, or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms;

$R^3$ represents hydrogen, an unsubstituted or substituted aromatic hydrocarbon group containing 6 to 30 ring atoms, or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms, CN or $R^aR^bPO$;

$L^1$ represents an unsubstituted or substituted aromatic hydrocarbon group containing 6 to 30 ring atoms or an unsubstituted or substituted heteroaromatic group containing 3 to 30 ring atoms; in the case that more than one group $L^1$ is present, the groups $L^1$ can be different or the same;

$L^2$ represents an unsubstituted or substituted aromatic hydrocarbon group containing 6 to 30 ring atoms or an unsubstituted or substituted heteroaromatic group containing 3 to 30 ring atoms containing at least one ring nitrogen atom; in the case that more than one group $L^2$ is present, the groups $L^2$ can be different or the same;

m is 0, 1 or 2;

n is 0, 1 or 2;

wherein the sum of n and m is at least 2;

Az represents an heteroaromatic group containing 3 to 30 ring atoms containing at least one ring nitrogen atom, which is unsubstituted or substituted.

The term organic EL device (organic electroluminescence device) is used interchangeably with the term organic light-emitting diode (OLED) in the present application.

The specific combination of compounds of formula (I) and at least one rare earth metal, rare earth metal compound, and/or rare earth metal complex in the electron transporting zone results in organic electroluminescence devices having a good overall performance, especially a long lifetime, a high EQE and/or a low driving voltage.

According to the present invention, the presence of an alkali metal, an alkali metal compound, an alkali metal complex, an alkaline earth metal, an alkaline earth metal compound, and an alkaline earth metal complex in the electron-transporting zone is not necessary for obtaining an organic electroluminescence devices having a good overall performance. Therefore, the electron-transporting zone does not comprise an alkali metal, an alkali metal compound, an alkali metal complex, an alkaline earth metal, an alkaline earth metal compound, and an alkaline earth metal complex. Most preferably, the electron-transporting zone does not comprise an alkali metal and an alkaline earth metal in any form.

In a further preferred embodiment, the electron-transporting zone additionally does not comprise a metal belonging to Group 13 of the Periodic Table of Elements (IUPAC, 2018), a compound containing a metal belonging to Group 13 of the Periodic Table of Elements (IUPAC, 2018) and a complex containing a metal belonging to Group 13 of the Periodic Table of Elements (IUPAC, 2018). Most preferably, a further preferred embodiment, the electron-transporting zone does not comprise metal belonging to Group 13 of the Periodic Table of Elements (IUPAC, 2018) in any form.

A further subject of the present invention is directed to a material for an organic electroluminescence device comprising a combination of at least one compound of formula (I) according to the present invention and at least one rare earth metal, rare earth metal compound, and/or rare earth metal complex. Preferably, the material does not comprise an alkali metal, an alkali metal compound, an alkali metal complex, an alkaline earth metal, an alkaline earth metal compound, and an alkaline earth metal complex. Most preferably, the material does not comprise an alkali metal and an alkaline earth metal in any form. More preferably, the material additionally does not comprise a metal belonging to Group 13 of the Periodic Table of Elements (IUPAC, 2018), a compound containing a metal belonging to Group 13 of the Periodic Table of Elements (IUPAC, 2018) and a complex containing a metal belonging to Group 13 of the Periodic Table of Elements (IUPAC, 2018). Most preferably, the material additionally does not does not comprise metal belonging to Group 13 of the Periodic Table of Elements (IUPAC, 2018) in any form.

A further subject of the present invention is directed to an electronic equipment comprising the organic electroluminescence device according the present invention.

A further subject of the present invention is directed to the use of a combination of at least one compound of formula (I) according to the present invention and at least one rare earth metal, rare earth metal compound, and/or rare earth metal complex in an electron-transporting zone of the organic electroluminescence device.

In the meaning of the present invention, the electron-transporting zone includes at least an electron-transporting layer and preferably also an electron-injection layer and/or a hole-blocking layer.

The electron-transporting layer and/or—if also an electron-injection layer is present—the electron-injection layer comprises or consists of at least one rare earth metal, rare earth metal compound, and/or rare earth metal complex, or the at least one rare earth metal, rare earth metal compound, and/or rare earth metal complex forms a separate interfacial layer or island between the cathode and the electron-transporting layer or—between the cathode and the electron-injecting layer, if an electron-injecting layer is present.

The presence of at least one rare earth metal, rare earth metal compound, and/or rare earth metal complex in a separate layer or island as well as the presence of the at least one rare earth metal, rare earth metal compound, and/or rare earth metal complex as a dopant in any other layer of the electron transporting zone is discussed below.

The electron-transporting layer and/or—if also an electron-injection layer and/or a hole-blocking layer is/are present—the electron-injection layer and/or the hole-blocking layer comprises or consists of at least one compound represented by formula (I).

The terms unsubstituted or substituted aromatic hydrocarbon group containing 6 to 30 ring atoms, an unsubstituted or substituted heteroaromatic group containing 3 to 30 ring atoms, unsubstituted or substituted heteroaromatic group containing 3 to 30 ring atoms containing at least one ring nitrogen, an unsubstituted or substituted alkyl group having 1 to 25 carbon atoms, an unsubstituted or substituted cycloalkyl group having 3 to 18 ring carbon atoms, are known in the art and generally have the following meaning, if said groups are not further specified in specific embodiments mentioned below:

The unsubstituted or substituted aromatic hydrocarbon group containing 6 to 30 ring atoms, preferably 6 to 24 ring atoms, more preferably 6 to 18 ring atoms may be a non-condensed aryl group or a condensed aryl group. Specific examples thereof include phenyl group, naphthyl group, phenanthryl group, biphenyl group, terphenyl group, quaterphenyl group, fluoranthenyl group, triphenylenyl group, phenanthrenyl group, fluorenyl group, anthracenyl, chrysenyl, spirofluorenyl group, 9,9-diphenylfluorenyl group, 9,9'-spirobi[9H-fluorene]-2-yl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, di benzo[a,c]triphenylenyl group, benzo[a]fluoranthenyl group, benzo[j]fluoranthenyl group, benzo[k]fluoranthenyl group and benzo[b]fluoranthenyl group, with phenyl group, naphthyl group, biphenyl group, terphenyl group, phenanthryl group, triphenylenyl group, fluorenyl group, spirobifluorenyl group anthracenyl, and fluoranthenyl group being preferred, and phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, 9,9-dimethylfluorene-4-yl group, 9,9-diphenylfluorene-2-yl group, 9,9-diphenylfluorene-4-yl group, fluoranthene-3-yl group, fluoranthene-2-yl group, fluoranthene-8-yl, anthracen-3-yl and anthracen-9-yl group being most preferred.

In the case that the linkers $L^1$ and $L^2$ represent an unsubstituted or substituted aromatic hydrocarbon group containing 6 to 30 ring atoms, $L^1$ and $L^2$ are divalent aromatic hydrocarbon group containing 6 to 30 ring atoms, which are unsubstituted or (further) substituted. Further preferred groups $L^1$ and $L^2$ are mentioned below.

The unsubstituted or (further) substituted divalent aromatic hydrocarbon group containing 6 to 30 ring atoms, preferably 6 to 18 ring atoms, more preferably 6 to 14 ring atoms, may be a non-condensed or a condensed divalent aromatic hydrocarbon group. Specific examples thereof include phenylene group, naphthylene group, biphenylene group, terphenylene group, quaterphenylene group, fluoranthene-diyl group, triphenylene-diyl group, phenanthrene-diyl group, fluorene-diyl group, anthracene-diyl, chrysene-diyl, spirofluorene-diyl group, 9,9-diphenylfluorene-diyl group, 9,9'-spirobi[9H-fluorene]-2-diyl group, 9,9-dimethylfluorene-diyl group, benzo[c]phenanthrene-diyl group, benzo[a]triphenylene-diyl group, naphtho[1,2-c]phenanthrene-diyl group, naphtho[1,2-a]triphenylene-diyl group, di benzo[a,c]triphenylene-diyl group, benzo[a]fluoranthene-diyl group, benzo[j]fluoranthene-diyl group, benzo[k]fluoranthene-diyl group and benzo[b]fluoranthene-diyl group, with phenylene group, naphthylene group, biphenylene group, terphenylene group, phenanthrene-diyl group, triphenylene-diyl group, fluorene-diyl group, spirobifluorene-diyl group, anthracene-diyl and fluoranthene-diyl group being preferred.

The unsubstituted or substituted heteroaromatic group containing 3 to 30 ring atoms, preferably 5 to 18 ring atoms, may be a non-condensed heteroaromatic group or a condensed heteroaromatic group. Specific examples thereof include the residues of pyrrole ring, isoindole ring, imidazopyridine ring, imidazopyrimidine ring, imidazopyrazin ring, benzofuran ring, isobenzofuran ring, benzothiophene, dibenzothiophene ring, isoquinoline ring, quinoxaline ring, quinazoline, phenanthridine ring, phenanthroline ring, pyridine ring, pyrazine ring, pyrimidine ring, pyridazine ring, indole ring, quinoline ring, acridine ring, carbazole ring, furan ring, thiophene ring, benzoxazole ring, benzothiazole ring, benzimidazole ring, dibenzofuran ring, triazine ring, oxazole ring, oxadiazole ring, thiazole ring, thiadiazole ring, triazole ring, aza-dibenzofuran, aza-dibenzothiophene, aza-carbazole, and imidazole ring with the residues of dibenzofuran ring, carbazole ring, benzimidazole ring, pyridine ring, and dibenzothiophene ring being preferred.

In the case that the linker $L^1$ represents an unsubstituted or substituted heteroaromatic group containing 3 to 30 ring atoms, $L^1$ is a divalent aromatic heteroaromatic group containing 3 to 30 ring atoms, which is unsubstituted or (further) substituted. Further preferred groups $L^1$ are mentioned below.

The unsubstituted or (further) substituted divalent heteroaromatic group containing 3 to 30 ring atoms, preferably 5 to 18 ring atoms, may be a non-condensed heteroaromatic group or a condensed heteroaromatic group. Specific examples thereof include pyrrole-diyl, isoindole-diyl, benzofuran-diyl, isobenzofuran-diyl, benzothiophene-diyl, dibenzothiophene-diyl, isoquinoline-diyl, quinoxaline-diyl, quinazoline-diyl, phenanthridine-diyl, phenanthroline-diyl, pyridine-diyl, pyrazine-diyl, pyrimidine-diyl, pyridazine-diyl, indole-diyl, quinoline-diyl, acridine-diyl, carbazole-diyl, furan-diyl, thiophene-diyl, benzoxazole-diyl, benzothiazole-diyl, benzimidazole-diyl, dibenzofuran-diyl, triazine-diyl, oxazole-diyl, oxadiazole-diyl, thiazole-diyl, thiadiazole-diyl, triazole-diyl, aza-dibenzothiophene-diyl, azadibenzofuran-diyl, aza-carbazole-diyl, and imidazole-diyl.

In the case of Az, the unsubstituted or substituted heteroaromatic group containing 3 to 30 ring atoms containing at least one ring nitrogen atom, preferably containing 5 to 18 ring atoms containing at least one ring nitrogen, may be a non-condensed heteroaromatic group or a condensed heteroaromatic group, containing at least one ring nitrogen. Specific examples are pyridyl, a quinoline group, a phenanthroline group, a pyridazine group, a pyrimidine group, a pyrazine group, a triazine group, a isoquinoline group, a quinolizine group, a cinnoline group, a quinoxaline group, a quinazoline group, a phthalazine group, a naphthyridine group, an acridine group, a phenanthridine group, a phenazine group, a pteridine group, a thiazole group, an oxazole group, an imidazole group, a benzothiazole group, a benzoxazole group, a benzimidazole group, an imidazopyridine group wherein the aforementioned groups are unsubstituted or substituted, preferably unsubstituted or substituted pyridyl, for example a bipyridyl group, an unsubstituted or substituted quinoline group or an unsubstituted or substituted phenanthroline group. Further preferred groups Az are mentioned below.

In the case that the linker $L^2$ represents an unsubstituted or substituted heteroaromatic group containing 3 to 30 ring atoms containing at least one ring nitrogen atom, $L^2$ is a divalent aromatic heteroaromatic group containing 3 to 30 ring atoms containing at least one ring nitrogen atom, which is unsubstituted or (further) substituted. Further preferred groups $L^2$ are mentioned below.

The unsubstituted or (further) substituted divalent heteroaromatic group containing 3 to 30 ring atoms, preferably 5 to 18 ring atoms, containing at least one ring nitrogen atom, may be a non-condensed heteroaromatic group or a condensed heteroaromatic group. Specific examples thereof include pyrrole-diyl, isoindole-diyl, isoquinoline-diyl, quinoxaline-diyl, quinazoline-diyl, quinoline-diyl, phenanthridine-diyl, phenanthroline-diyl, pyridine-diyl, pyrazine-diyl, pyrimidine-diyl, pyridazine-diyl, indole-diyl, quinoline-diyl, acridine-diyl, carbazole-diyl, benzoxazole-diyl, benzothiazole-diyl, benzimidazole-diyl, triazine-diyl, oxazole-diyl, oxadiazole-diyl, thiazole-diyl, thiadiazole-diyl, triazole-diyl, aza-dibenzothiophene-diyl, azadibenzofuran-diyl, aza-carbazole-diyl also, and imidazole-diyl with the residues of pyridine-diyl, quinoline-diyl, benzimidazole-diyl, phenanthroline-diyl being preferred.

Examples of the unsubstituted or substituted alkyl group having 1 to 25 carbon atoms, preferably 1 to 8 carbon atoms, are methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group and 1-methylpentyl group.

Further preferred are alkyl groups having 1 to 6 carbon atoms. Examples of the alkyl group having 1 to 6 carbon atoms are methyl group, ethyl group, n-propyl group, isopropyl group, n-butyl group, s-butyl group, isobutyl group, t-butyl group, n-pentyl group, n-hexyl group, neopentyl group and 1-methylpentyl group, with methyl group, ethyl group, n-propyl group, isopropyl group, n-butyl group, s-butyl group, isobutyl group and t-butyl group being preferred.

Examples of the unsubstituted or substituted cycloalkyl group having 3 to 18 ring carbon atoms, preferably 3 to 12 ring carbon atoms include cyclopropyl group, cyclobutyl group, cyclopentyl group, cyclohexyl group, cyclooctyl group, and adamantyl group. Most preferred are cycloalkyl groups having 3 to 6 ring carbon atoms, i.e. a cyclopropyl group, a cyclobutyl group, a cyclopentyl group or a cyclohexyl group.

Examples of the optional substituent(s) indicated by "substituted or unsubstituted" and "may be substituted" referred to above or hereinafter include a halogen atom, a cyano group, $R^aR^bPO$, an alkyl group having 1 to 25, preferably 1 to 8 carbon atoms, a cycloalkyl group having 3 to 18, preferably 3 to 12 ring carbon atoms, an alkoxy group having 1 to 25, preferably 1 to 8 carbon atoms, an alkylamino group having 1 to 25 carbon atoms, preferably 1 to 5 carbon atoms, a carboxyalkyl group having 1 to 25 carbon atoms, preferably 1 to 5 carbon atoms, a carboxamidalkyl group having 1 to 25 carbon atoms, preferably 1 to 5 carbon atoms, a silyl group, a $C_6$ to $C_{24}$ aryl group, preferably a $C_6$ to $C_{18}$ aryl group, an aryloxy group having 6 to 24, preferably 6 to 18 ring carbon atoms, an aralkyl group having 7 to 24, preferably 7 to 20 carbon atoms, an alkylthio group having 1 to 25, preferably 1 to 5 carbon atoms, an arylthio group having 6 to 24, preferably 6 to 18 ring carbon atoms, an arylamino group having 6 to 30 carbon atoms, preferably 6 to 18 carbon atoms, a carboxyaryl group having 6 to 24 carbon atoms, preferably 6 to 18 carbon atoms, a carboxamidaryl group having 6 to 24 carbon atoms, preferably 6 to 18 carbon atoms, and a heteroaromatic group having 3 to 30 ring atoms, preferably 5 to 18 ring atoms. The substituents may in turn be unsubstituted or substituted, preferably unsubstituted.

$R^a$ and $R^b$ each independently represents an unsubstituted or substituted aromatic hydrocarbon group containing 6 to 30 ring atoms, or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms.

The alkyl group having 1 to 25, preferably 1 to 8 carbon atoms, the $C_6$ to $C_{24}$ aryl group, preferably $C_6$ to $C_{18}$ aryl group, and cycloalkyl group having 3 to 18 ring carbon atoms, preferably 3 to 12 ring carbon atoms, are defined above.

Examples of the alkenyl group having 2 to 25 carbon atoms include those disclosed as alkyl groups having 2 to 25 carbon atoms but comprising at least one double bond, preferably one, or where possible, two or three double bonds.

Examples of the alkynyl group having 2 to 25 carbon atoms include those disclosed as alkyl groups having 2 to 25 carbon atoms but comprising at least one triple bond, preferably one, or where possible, two or three triple bonds.

The silyl group is an alkyl and/or aryl substituted silyl group. Examples of alkyl and/or aryl substituted silyl groups include alkylsilyl groups having 1 to 10 carbon atoms, preferably 1 to 5 carbon atoms, including trimethylsilyl group, triethylsilyl group, tributylsilyl group, dimethylethylsilyl group, t-butyldimethylsilyl group, propyldimethylsilyl group, dimethylisopropylsilyl group, dimethylpropylsilyl group, dimethylbutylsilyl group, dimethyltertiarybutylsilyl group, diethylisopropylsilyl group, alkylarylsilyl groups having 6 to 30 carbon atoms, preferably 6 to 18 carbon atoms in the aryl part and 1 to 10 carbon atoms, preferably 1 to 5 carbon atoms, in the alkyl part including phenyldimethylsilyl group, diphenylmethylsilyl group, diphenyltertiarybutylsilyl group, and arylsilyl groups having 6 to 30 carbon atoms, preferably 6 to 18 carbon atoms, including a triphenylsilyl group, with trimethylsilyl, triphenylsilyl, diphenyltertiarybutylsilyl group and t-butyldimethylsilyl group being preferred.

Examples of halogen atoms include fluorine, chlorine, bromine, and iodine.

Examples of an alkylamino group (alkyl substituted amino group), preferably an alkylamino group having 1 to 25 ring carbon atoms include those having an alkyl portion selected from the alkyl groups mentioned above.

Examples of an arylamino group (aryl substituted amino group), preferably an arylamino group having 6 to 24 ring carbon atoms include those having an aryl portion selected from the aromatic hydrocarbon groups mentioned above.

Examples of the optional aralkyl group having 6 to 30 ring carbon atoms include benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

Examples of a carboxyalkyl group (alkyl substituted carboxyl group), preferably a carboxyalkyl group having 1 to 25 carbon atoms, preferably 1 to 5 carbon atoms, include those having an alkyl portion selected from the alkyl groups mentioned above.

Examples of a carboxyaryl group (aryl substituted carboxyl group), preferably a carboxyaryl group having 6 to 24 carbon atoms, preferably 6 to 18 carbon atoms, include those having an aryl portion selected from the aromatic hydrocarbon groups mentioned above.

Examples of a carboxamidalkyl group (alkyl substituted amide group), preferably a carboxamidalkyl group having 1 to 25 carbon atoms, preferably 1 to 5 carbon atoms include those having an alkyl portion selected from the alkyl groups mentioned above.

Examples of a carboxamidaryl group (aryl substituted amide group), preferably a carboxamidaryl group having 6 to 24 carbon atoms, preferably 6 to 18 carbon atoms, include those having an aryl portion selected from the aromatic hydrocarbon groups mentioned above.

The optional substituent is preferably a halogen atom, a cyano group, an alkyl group having 1 to 25 carbon atoms, an aryl group having 6 to 24 ring carbon atoms, preferably 6 to 18 ring carbon atoms, and an heterocyclic group having 3 to 30 ring atoms, preferably 5 to 18 ring atoms; more preferably a cyano group, a phenyl group, a naphthyl group, a biphenyl group, a terphenyl group, a phenanthryl group, a triphenylenyl group, a fluorenyl group, a spirobifluorenyl group, a fluoranthenyl group, a residue based on a dibenzofuran ring, a residue based on a carbazole ring, and a residue based on a dibenzothiophene ring, a methyl group, an ethyl group, a n-propyl group, an isopropyl group, a n-butyl group, a s-butyl group, an isobutyl group, a t-butyl group, a cyclopentyl group, and a cyclohexyl group.

The optional substituent mentioned above may be further substituted by one or more of the optional substituents mentioned above.

The number of the optional substituents depends on the group which is substituted by said substituent(s). Preferred are 1, 2, 3 or 4 optional substituents, more preferred are 1, 2 or 3 optional substituents, most preferred are 1 or 2 optional substituents. In a further preferred embodiment, the groups mentioned above are unsubstituted.

The “carbon number of a to b” in the expression of “substituted or unsubstituted X group having a to b carbon atoms” is the carbon number of the unsubstituted X group and does not include the carbon atom(s) of an optional substituent.

The hydrogen atom referred to herein includes isotopes different from neutron numbers, i.e., light hydrogen (protium), heavy hydrogen (deuterium) and tritium.

The term “unsubstituted” referred to by “unsubstituted or substituted” means that a hydrogen atom is not substituted by one of the groups mentioned above.

The Compounds of Formula (I)

In the compounds of formula (I), $L^1$ represents an unsubstituted or substituted aromatic hydrocarbon group containing 6 to 30 ring atoms or an unsubstituted or substituted heteroaromatic group containing 3 to 30 ring atoms; in the case that more than one group $L^1$ is present, the groups $L^1$ can be different or the same.

Preferably, $L^1$ represents an unsubstituted or substituted aromatic hydrocarbon group containing 6 to 24 ring atoms, preferably 6 to 18 ring atoms, or an unsubstituted or substituted heteroaromatic group containing 3 to 24 ring atoms, preferably 6 to 18 ring atoms. More preferably $L^1$ represents an unsubstituted or substituted phenyl group, an unsubstituted or substituted naphthyl group, an unsubstituted or substituted anthryl group, an unsubstituted or substituted phenanthrenyl group, an unsubstituted or substituted triphenylenyl group, an unsubstituted or substituted 9,9-dimethyl fluorene group, an unsubstituted or substituted 9,9-diphenyl fluorene group, an unsubstituted or substituted pyrrole group, an unsubstituted or substituted isoindole group, an unsubstituted or substituted imidazopyridine group, an unsubstituted or substituted imidazopyrimidine group, an unsubstituted or substituted imidazopyrazin group, an unsubstituted or substituted benzofuran group, an unsubstituted or substituted isobenzofuran group, an unsubstituted or substituted benzothiophene group, an unsubstituted or substituted dibenzothiophene group, an unsubstituted or substituted isoquinoline group, an unsubstituted or substituted quinoxaline group, an unsubstituted or substituted quinazoline group, an unsubstituted or substituted phenanthridine group, an unsubstituted or substituted phenanthroline group, an unsubstituted or substituted pyridine group, an unsubstituted or substituted pyrazine group, an unsubstituted or substituted pyrimidine group, an unsubstituted or substituted pyridazine group, an unsubstituted or substituted indole group, an unsubstituted or substituted quinoline group, an unsubstituted or substituted acridine group, an unsubstituted or substituted carbazole group, an unsubstituted or substituted furan group, an unsubstituted or substituted thiophene group, an unsubstituted or substituted benzoxazole group, an unsubstituted or substituted benzothiazole group, an unsubstituted or substituted benzimidazole group, an unsubstituted or substituted dibenzofuran group, an unsubstituted or substituted triazine group, an unsubstituted or substituted oxazole group, an unsubstituted or substituted oxadiazole group, an unsubstituted or substituted thiazole group, an unsubstituted or substituted thiadiazole group, an unsubstituted or substituted triazole group, an unsubstituted or substituted aza-dibenzofuran, an unsubstituted or substituted aza-dibenzothiophene, an unsubstituted or substituted aza-carbazole or an unsubstituted or substituted imidazole group. Most preferably, $L^1$ represents an unsubstituted or substituted phenyl group, an unsubstituted or substituted naphthyl group, an unsubstituted or substituted anthryl group, an unsubstituted or substituted phenanthrenyl group, an unsubstituted or substituted triphenylenyl group, an unsubstituted or substituted 9,9-dimethyl fluorene group, an unsubstituted or substituted 9,9-diphenyl fluorene group, preferably, the aforementioned groups are unsubstituted. Further most preferably, $L^1$ represents an unsubstituted divalent phenyl group, an unsubstituted divalent naphthyl group, an unsubstituted divalent triphenylenyl group, an unsubstituted divalent 9,9-dimethyl fluorene group, an unsubstituted divalent anthryl group, an unsubstituted divalent phenanthrenyl group, or an unsubstituted divalent 9,9-diphenyl fluorene group.

$L^2$ represents an unsubstituted or substituted aromatic hydrocarbon group containing 6 to 30 ring atoms or an unsubstituted or substituted heteroaromatic group containing 3 to 30 ring atoms containing at least one ring nitrogen atom; in the case that more than one group $L^2$ is present, the groups $L^2$ can be different or the same.

Preferably, $L^2$ represents an unsubstituted or substituted aromatic hydrocarbon group containing 6 to 24 ring atoms, preferably 6 to 18 ring atoms, or an unsubstituted or substituted heteroaromatic group containing 3 to 24 ring atoms, preferably 6 to 18 ring atoms, containing at least one N atom, more preferably $L^2$ represents an unsubstituted or substituted phenyl group, an unsubstituted or substituted naphthyl group, an unsubstituted or substituted anthryl group, an unsubstituted or substituted phenanthrenyl group, an unsubstituted or substituted triphenylenyl group, an unsubstituted or substituted 9,9-dimethyl fluorene group, an unsubstituted or substituted 9,9-diphenyl fluorene group, an unsubstituted or substituted pyridyl group, an unsubstituted or substituted quinoline group, an unsubstituted or substituted phenanthroline group, an unsubstituted or substituted pyridazine group, an unsubstituted or substituted pyrimidine group, an unsubstituted or substituted pyrazine group, an unsubstituted or substituted triazine group, an unsubstituted or substituted isoquinoline group, an unsubstituted or substituted quinolizine group, an unsubstituted or substituted cinnoline group, an unsubstituted or substituted quinoxaline group, an unsubstituted or substituted quinazoline group, an unsubstituted or substituted phthalazine group, an unsubstituted or substituted naphthyridine group, an unsubstituted or substituted acridine group, an unsubstituted or substituted phenanthridine group, an unsubstituted or substituted phenazine group, an unsubstituted or substituted pteridine group, an unsubstituted or substituted thiazole group, an unsubstituted or substituted oxazole group, an unsubstituted or substituted imidazole group, an unsubstituted or substituted benzothiazole group, an unsubstituted or substituted benzoxazole group, an unsubstituted or substituted benzimidazole group, an unsubstituted or substituted imidazopyridine group, an unsubstituted or substituted aza-dibenzofuran group, an unsubstituted or substituted aza-dibenzothiophene group or an unsubstituted or substituted aza-carbazole group. Most preferably, $L^2$ represents an unsubstituted or substituted divalent phenyl group, an unsubstituted or substituted naphthyl group, an unsubstituted or substituted anthryl group, an unsubstituted or substituted phenanthrenyl group, an unsubstituted or substituted triphenylenyl group, an unsubstituted or substituted 9,9-dimethyl fluorene group, an unsubstituted or substituted 9,9-diphenyl fluorene group, an unsubstituted or substituted pyridyl group, an unsubstituted or substituted pyrimidyl group, an unsubstituted or substituted quinoline group, or an unsubstituted or substituted isoquinoline group, preferably, the aforementioned groups are unsubstituted. Further most preferably, $L^2$ represents an unsubstituted divalent phenyl group, an unsubstituted divalent naphthyl group, an unsubstituted divalent anthryl group, an unsubstituted divalent triphenylenyl group, an unsubstituted divalent 9,9-dimethyl fluorene group, an unsubstituted divalent 9,9-diphenyl fluorene group, or an unsubstituted divalent pyridyl group.

m is 0, 1 or 2;

n is 0, 1 or 2, preferably 1;

wherein the sum of m and n is at least 2. Preferably, the sum of n and m is 2 or 3.

Preferred groups $-(L^1)_m-(L^2)_n-$ are:

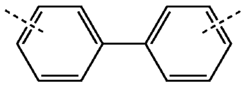
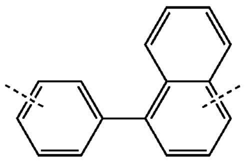
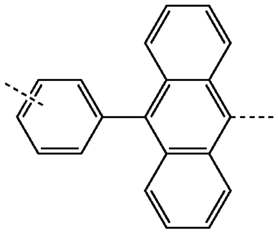
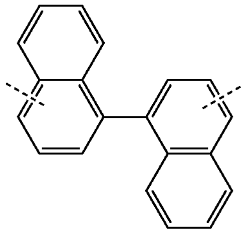

-continued

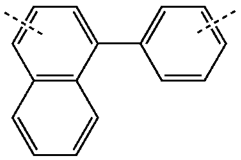
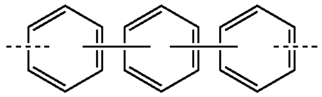
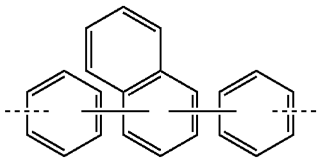
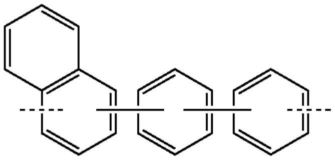
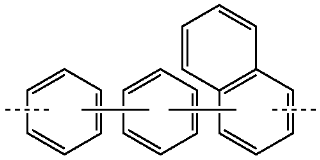
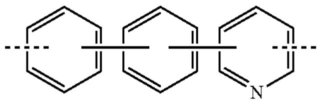
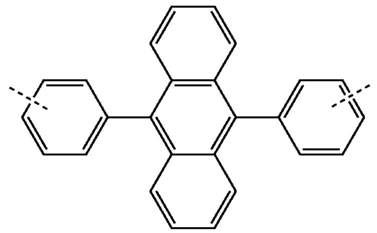
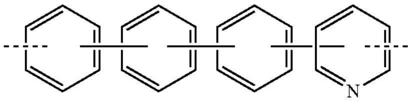
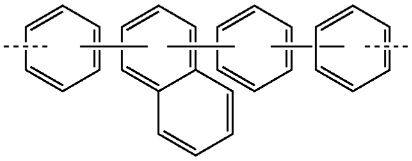
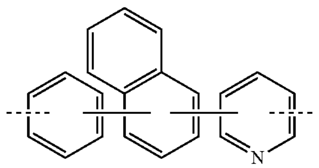
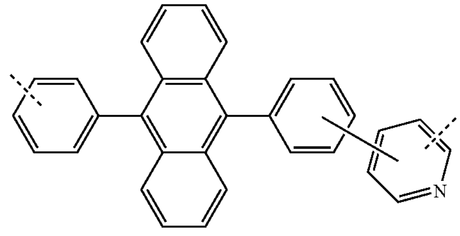

-continued

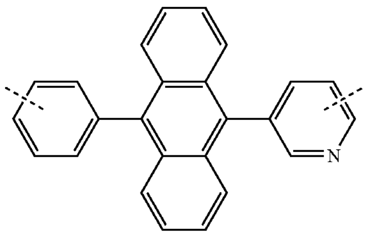
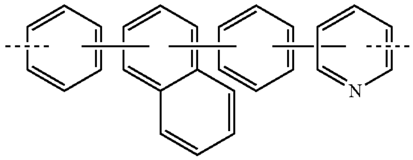
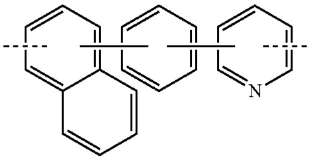
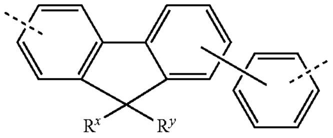
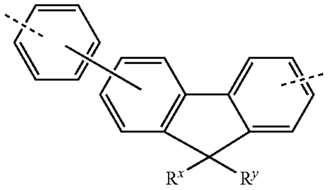
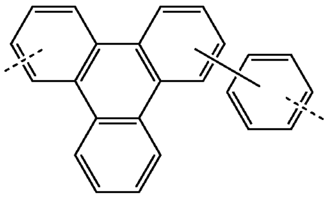
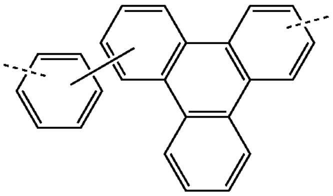
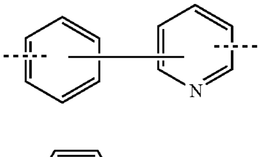
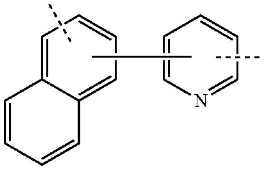
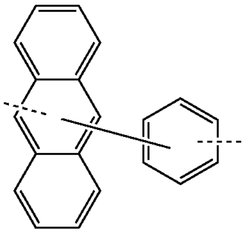
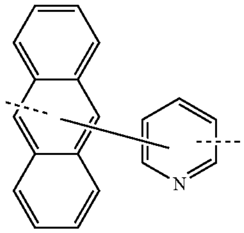

-continued

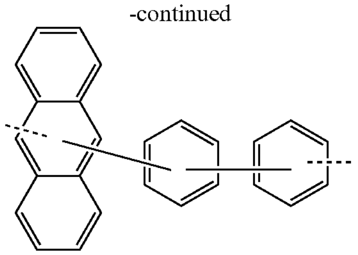
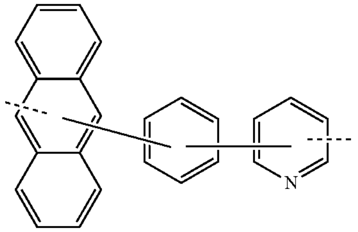
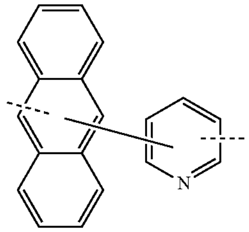
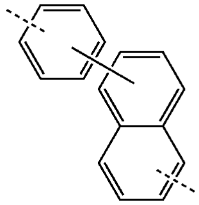
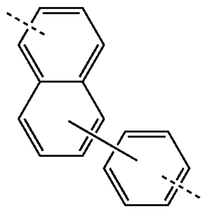
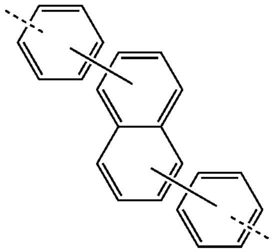
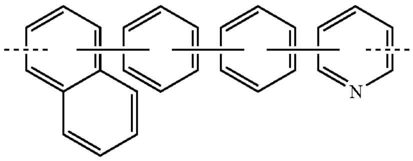

wherein the dotted lines are bonding sites.

Az represents an heteroaromatic group containing 3 to 30 ring atoms containing at least one ring nitrogen atom, which is unsubstituted or substituted, preferably containing 5 to 18 ring atoms. Preferably, Az represents pyridyl, a quinoline group, a phenanthroline group, a pyridazine group, a pyrimidine group, a pyrazine group, a triazine group, a isoquinoline group, a quinolizine group, a cinnoline group, a quinoxaline group, a quinazoline group, a phthalazine group, a naphthyridine group, an acridine group, a phenanthridine group, a phenazine group, a pteridine group, a thiazole group, an oxazole group, an imidazole group, a benzothiazole group, a benzoxazole group, a benzimidazole group, an aza-dibenzofuran group, an aza-dibenzothiophene group, an aza-carbazole group or an imidazopyridine group, wherein the aforementioned groups are unsubstituted or substituted by 1 or 2 substituents selected from the group consisting of an unsubstituted aromatic hydrocarbon group containing 6 to 18 ring atoms, or an unsubstituted heteroaromatic group containing 3 to 18 ring atoms, an unsubstituted alkyl group having 1 to 8 carbon atoms and an unsubstituted cycloalkyl group having 3 to 10 ring carbon atoms, or 2 adjacent substitutents can form together a fused ring.

More preferably, Az represents pyridine, quinoline or phenanthroline, wherein each of the aforementioned groups is unsubstituted or substituted by 1 or 2 substituents selected from the group consisting of an unsubstituted aromatic hydrocarbon group containing 6 to 18 ring atoms, or an unsubstituted heteroaromatic group containing 3 to 18 ring atoms, an unsubstituted alkyl group having 1 to 8 carbon atoms and an unsubstituted cycloalkyl group having 3 to 10 ring carbon atoms;

Most preferably 2-, 3-, or 4-pyridine, 2-, 3-, 4-, 5-, 6-, 7-, or 8-quinoline, or 2-, 3-, 4-, or 5-phenanthroline, wherein each of the aforementioned groups is unsubstituted or substituted by 1 or 2 substituents selected from the group consisting of an unsubstituted aromatic hydrocarbon group containing 6 to 18 ring atoms, or an unsubstituted heteroaromatic group containing 3 to 18 ring atoms, an unsubstituted alkyl group having 1 to 8 carbon atoms and an unsubstituted cycloalkyl group having 3 to 10 ring carbon atoms.

$R^1$ and $R^2$ each independently represents an unsubstituted or substituted aromatic hydrocarbon group containing 6 to 30 ring atoms, or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms, CN or $R^aR^bPO$. Preferably, $R^1$ and $R^2$ each independently represents an unsubstituted or substituted aromatic hydrocarbon group containing 6 to 18 ring atoms, more preferably unsubstituted or substituted phenyl, unsubstituted or substituted biphenyl, unsubstituted or substituted naphthyl, or unsubstituted or substituted fluorenyl, wherein the aforementioned groups are most preferably unsubstituted, especially unsubstituted phenyl, biphenyl, naphthyl, fluorenyl as shown below or an unsubstituted or substituted heteroaromatic group containing 5 to 18 ring atoms, more preferably unsubstituted or substituted dibenzofuran, unsubstituted or substituted dibenzothiophen, unsubstituted or substituted spiro-fluorene, wherein the aforementioned groups are most preferably unsubstituted, especially unsubstituted dibenzofuran, dibenzothiophen or spiro-fluorene as shown below

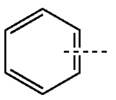
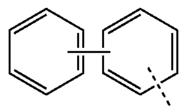
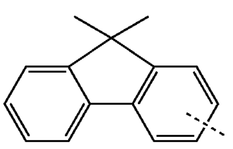
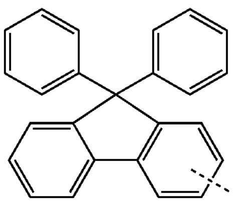
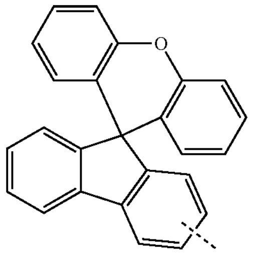
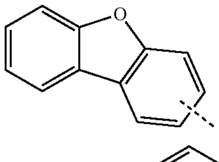
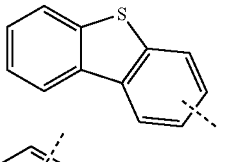
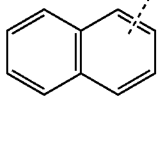

wherein the dotted lines are bonding sites.

$R^a$ and $R^b$ each independently represents an unsubstituted or substituted aromatic hydrocarbon group containing 6 to 30 ring atoms, or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms; preferably, $R^a$ and $R^b$ each independently represents an unsubstituted or substituted aromatic hydrocarbon group containing 6 to 30 ring atoms, preferably 6 to 24 ring atoms, more preferably 6 to 18 ring atoms; an unsubstituted or substituted alkyl group having 1 to 25 carbon atoms, preferably 1 to 8 carbon atoms; or an unsubstituted or substituted cycloalkyl group having 3 to 18 ring carbon atoms, preferably 3 to 12 ring carbon atoms, more preferably 5 or 6 ring carbon atoms.

$X^1$, $X^2$ and $X^3$ are each independently N or $CR^3$, wherein at least two of $X^1$, $X^2$ and $X^3$ are N.

$R^3$ represents hydrogen, an unsubstituted or substituted aromatic hydrocarbon group containing 6 to 30 ring atoms, or an unsubstituted or substituted heteroaromatic group containing 3 to 30 ring atoms, an unsubstituted or substituted alkyl group having 1 to 25 carbon atoms, an unsubstituted or substituted cycloalkyl group having 3 to 18 ring carbon atoms, CN or $R^aR^bPO$.

Preferably, $R^3$ represents hydrogen, an unsubstituted or substituted aromatic hydrocarbon group containing 6 to 18 ring atoms, more preferably hydrogen, unsubstituted or substituted phenyl, unsubstituted or substituted biphenyl, unsubstituted or substituted naphthyl, or unsubstituted or substituted fluorenyl, most preferably hydrogen or unsubstituted or substituted phenyl, wherein the aforementioned groups are most preferably unsubstituted.

Preferred compounds of formula (I) are defined as follows (formula (IA)):

(IA)

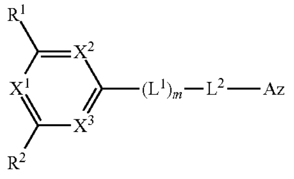

wherein

- $L^1$ represents an unsubstituted phenyl group, an unsubstituted naphthyl group, an unsubstituted triphenylenyl group, an unsubstituted phenanthrenyl group, an unsubstituted anthryl group, an unsubstituted 9,9-dimethyl fluorene group, or an unsubstituted 9,9-diphenyl fluorene group; m is 1 or 2;
- $L^2$ represents an unsubstituted phenyl group, an unsubstituted naphthyl group, an unsubstituted anthryl group, an unsubstituted triphenylenyl group, an unsubstituted phenanthrenyl group, an unsubstituted 9,9-dimethyl fluorene group, an unsubstituted 9,9-diphenyl fluorene group, or an unsubstituted pyridyl group;
- $R^1$ and $R^2$ each independently represents unsubstituted or substituted phenyl, unsubstituted or substituted biphenyl, unsubstituted or substituted naphthyl, or unsubstituted or substituted fluorenyl;
- $X^1$, $X^2$ and $X^3$ are each independently N or $CR^3$, wherein at least two of $X^1$, $X^2$ and $X^3$ are N;

$R^3$ represents hydrogen; and

Az represents unsubstituted or substituted pyridine, unsubstituted or substituted quinoline or unsubstituted or substituted phenanthroline, preferably 2-, 3-, or 4-pyridine, 2-, 3-, 4-, 5-, 6-, 7-, or 8-quinoline, or 2-, 3-, 4-, or 5-phenanthroline.

Suitable substituents of $L^1$, $L^2$, $R^1$ and $R^2$ are the substituents mentioned above.

Below, examples for compounds of formula (I) are given:

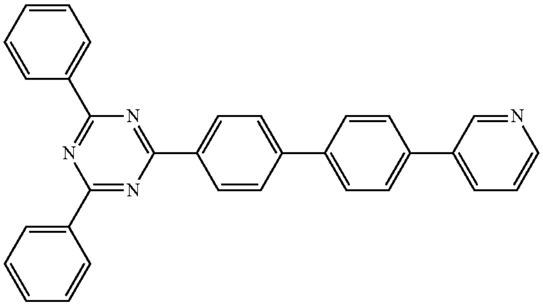

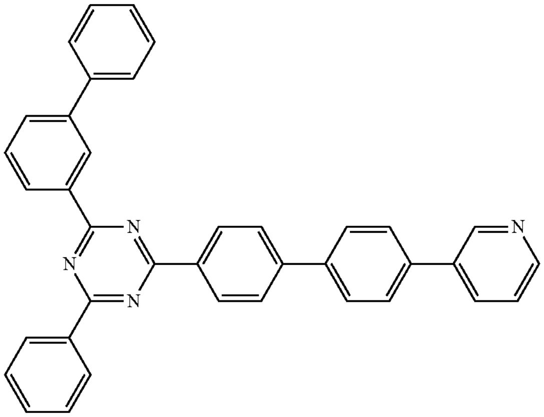

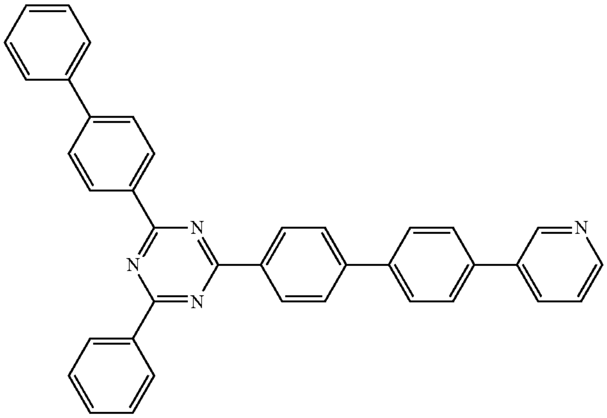

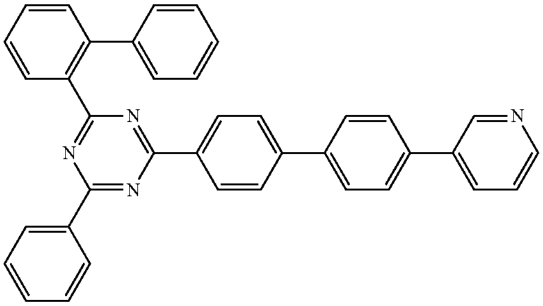

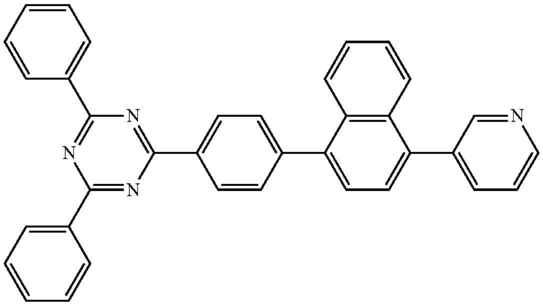

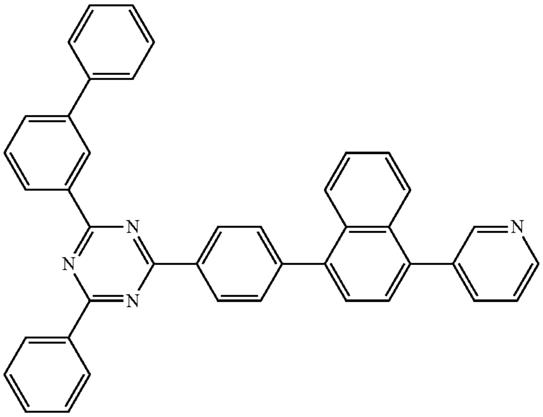

-continued
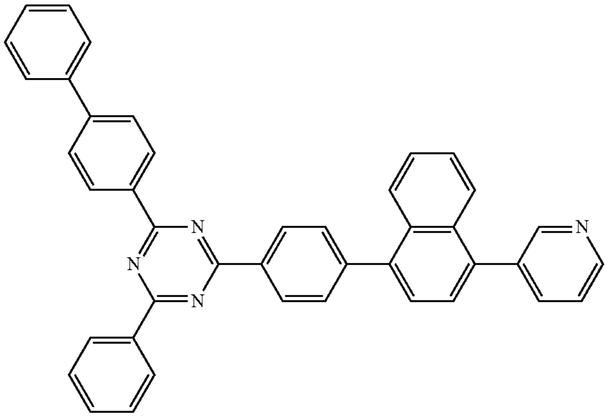
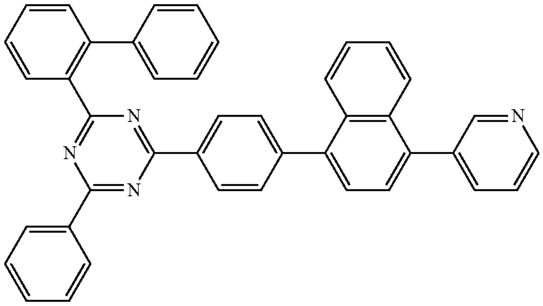
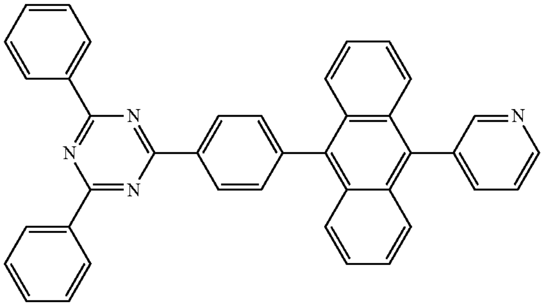
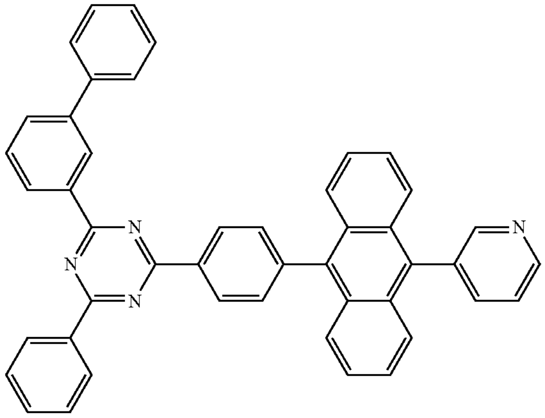
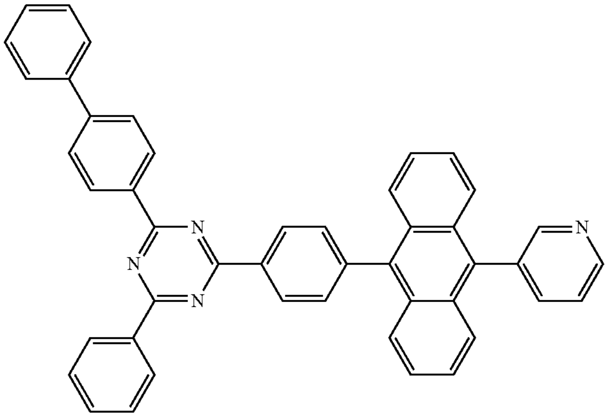
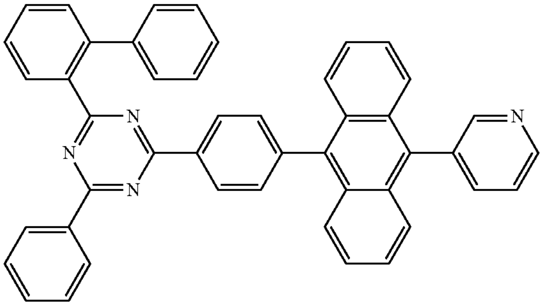
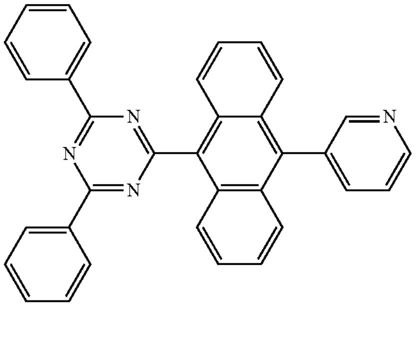
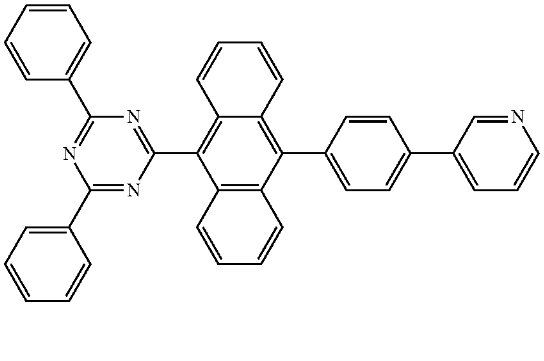

-continued
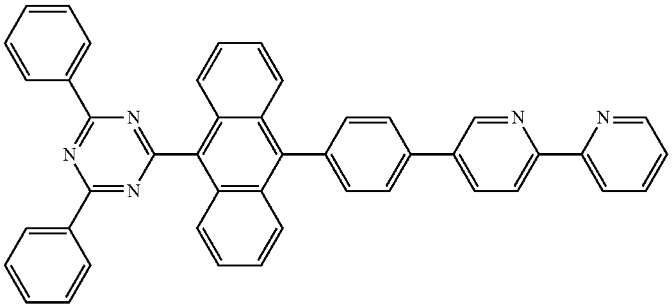
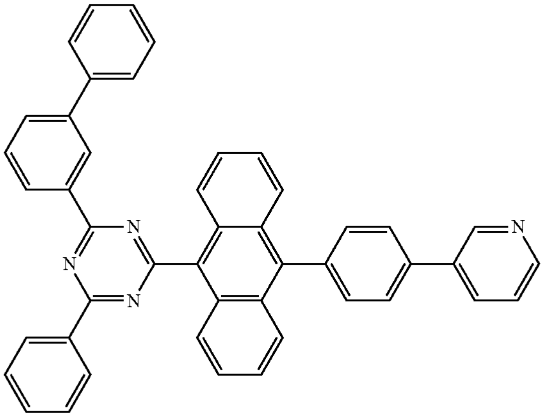
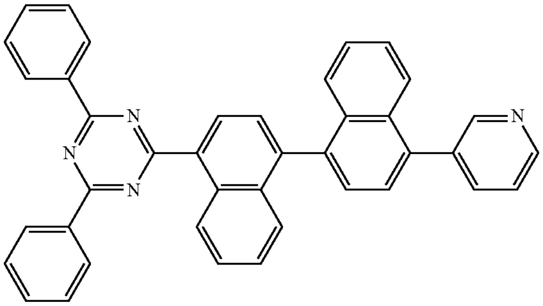
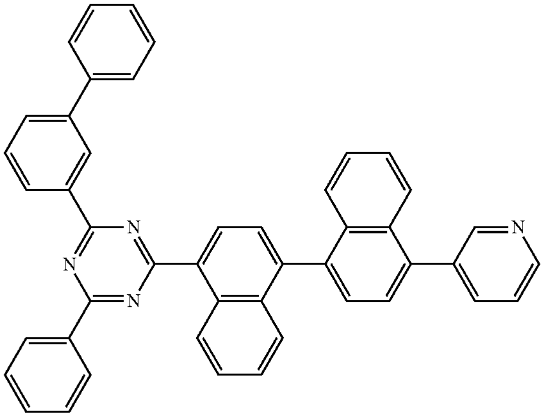
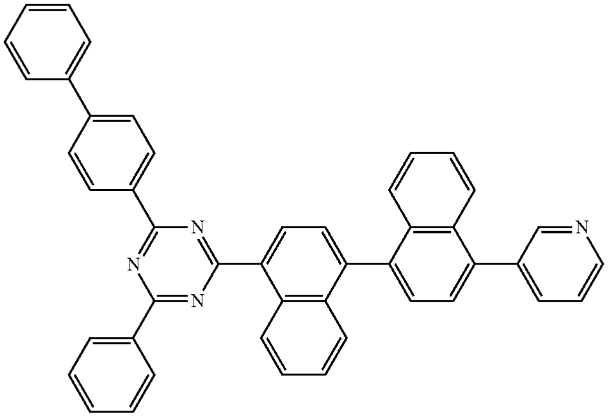
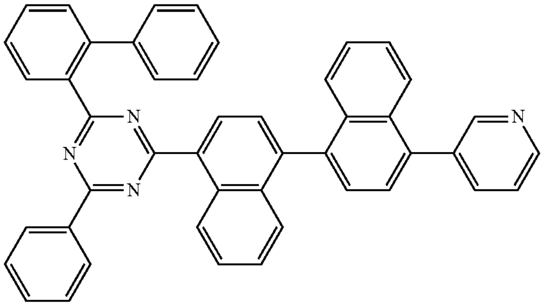
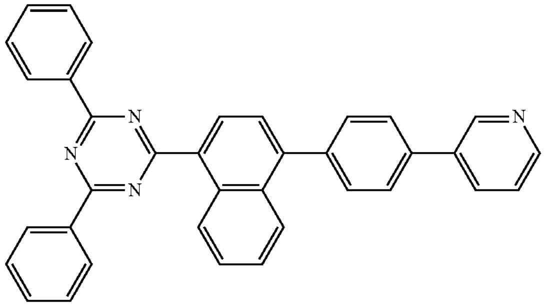

-continued
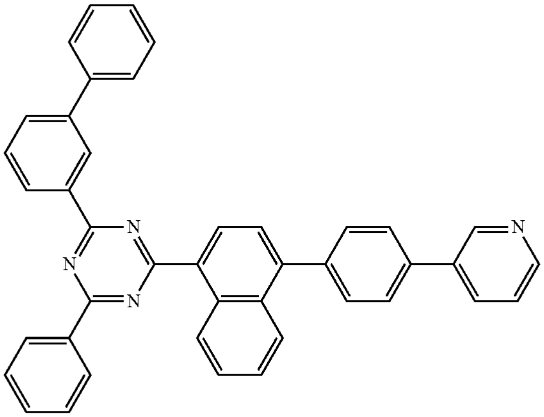
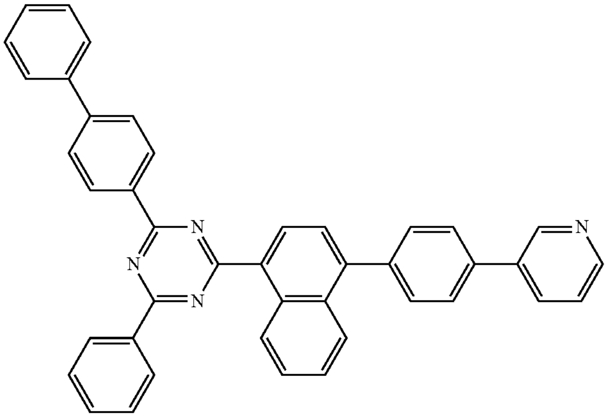
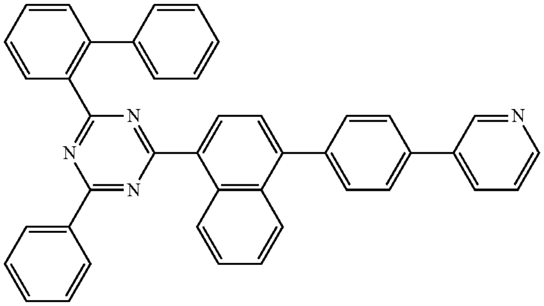
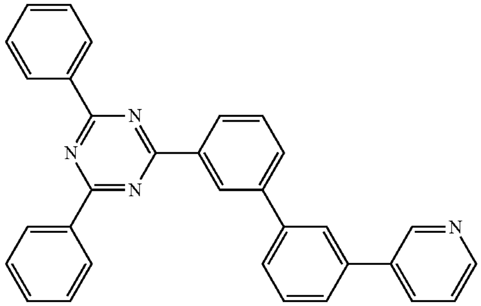
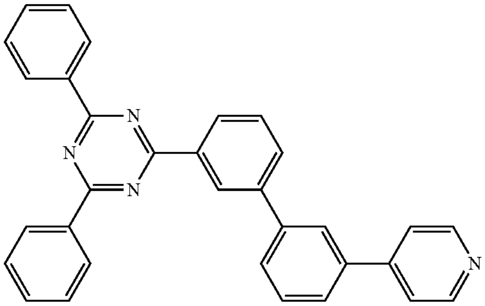
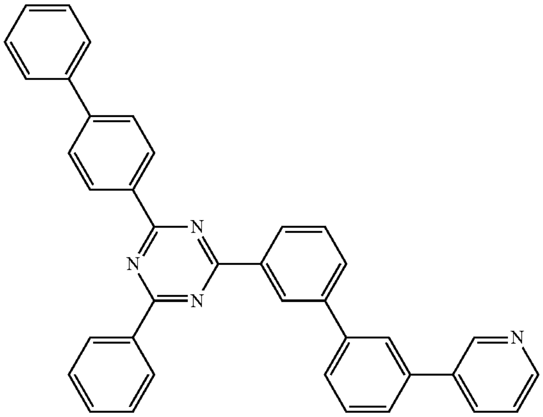
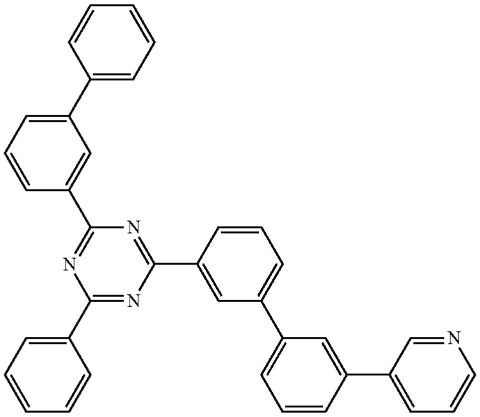
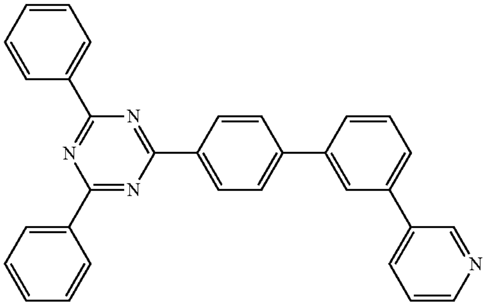

-continued
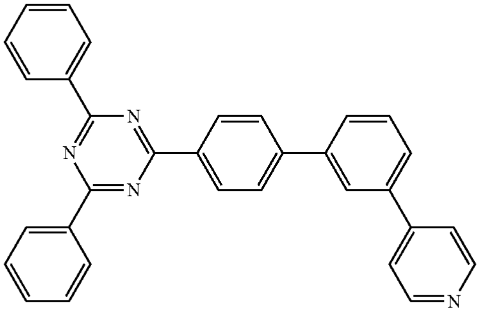
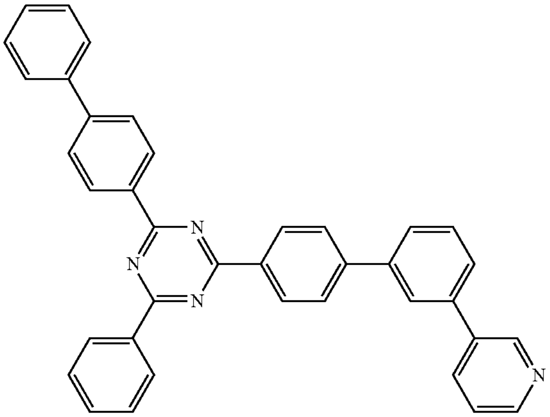
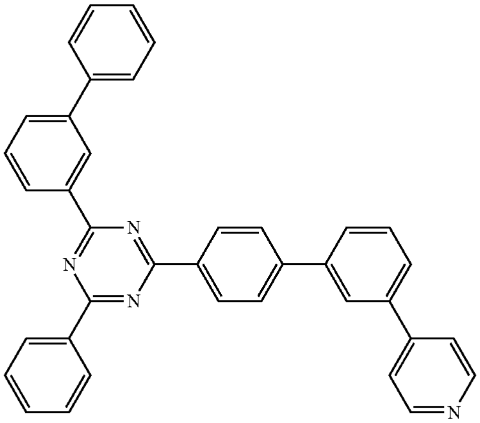
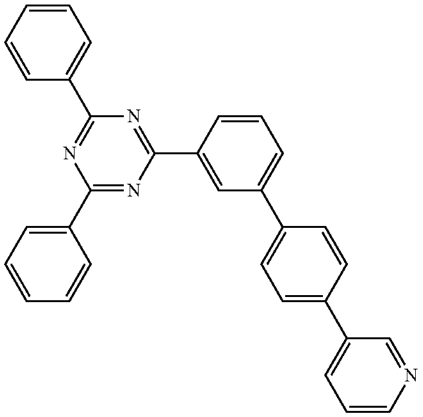
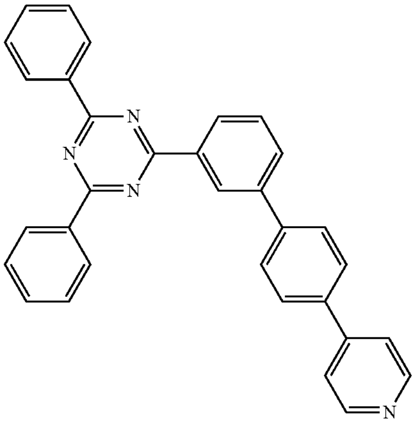
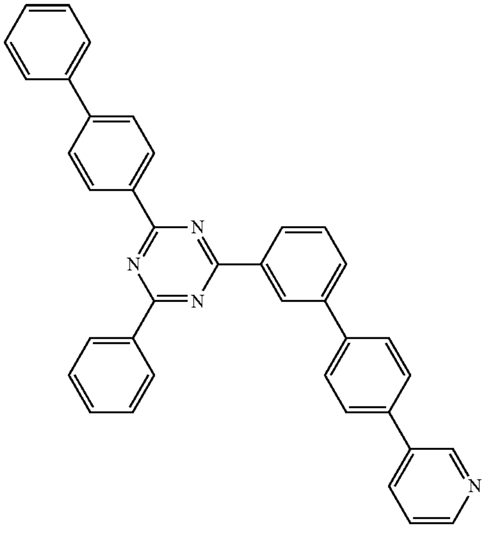

-continued
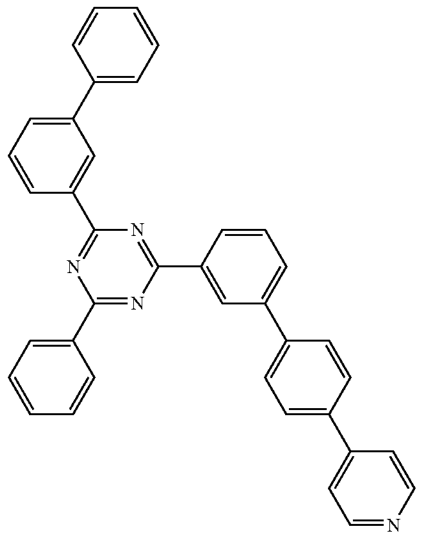
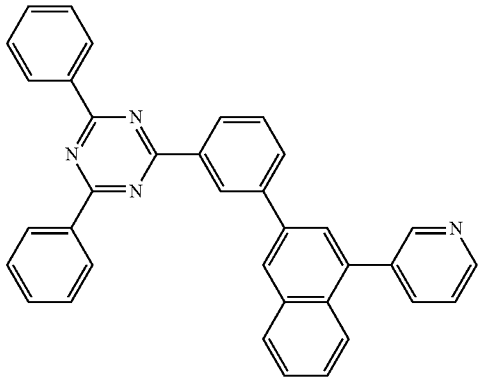
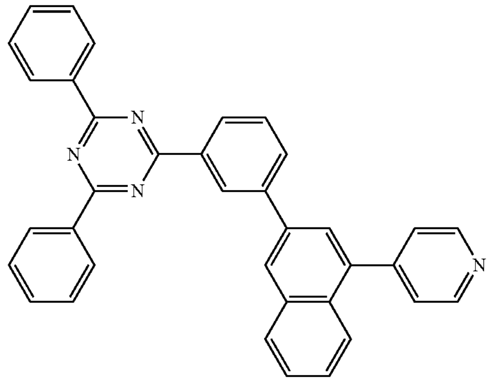
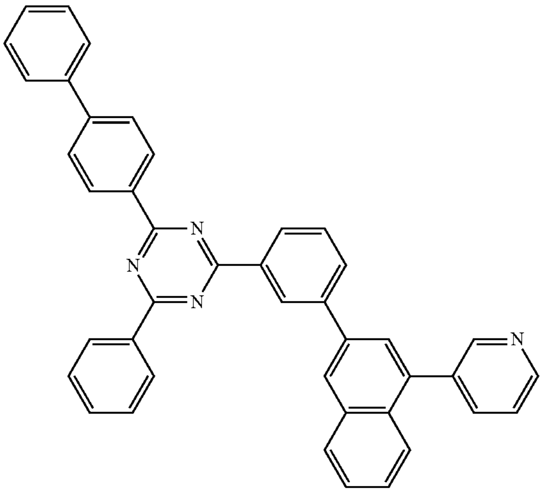
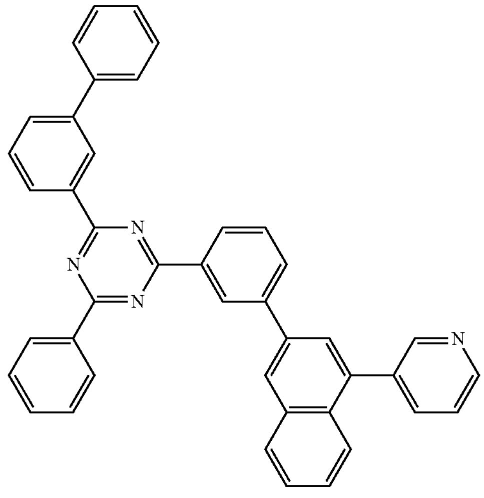
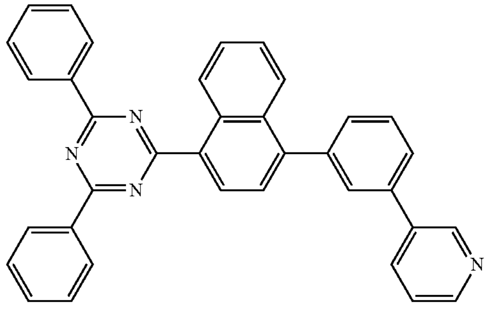

-continued
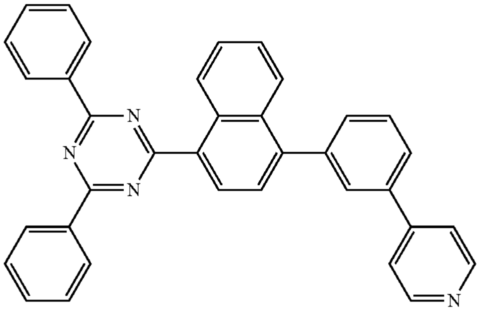
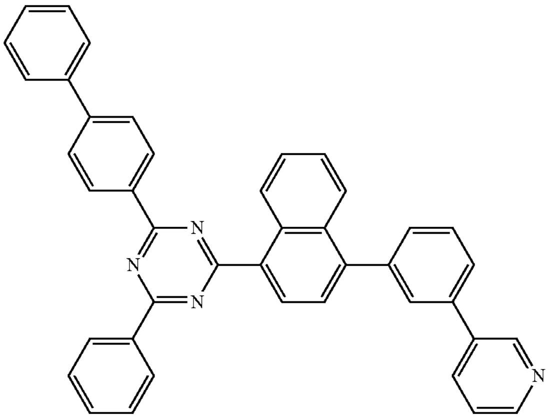
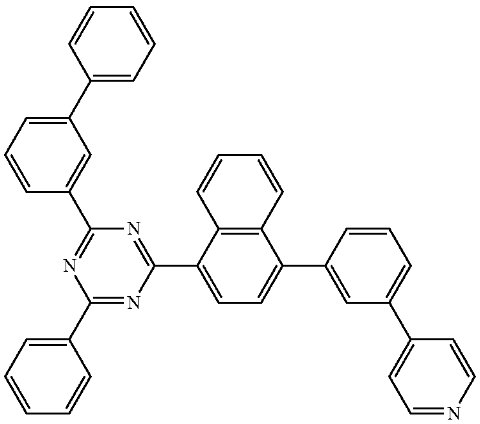
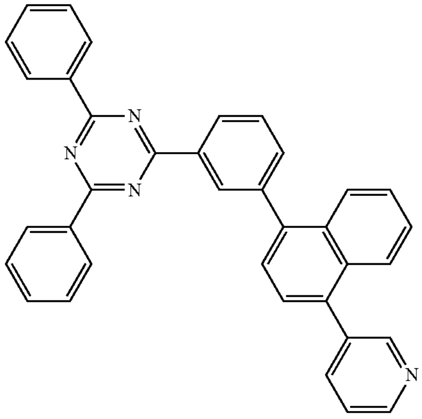
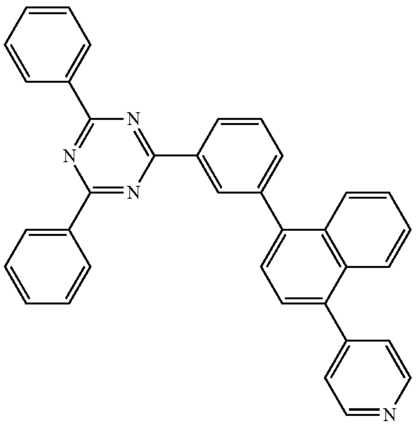
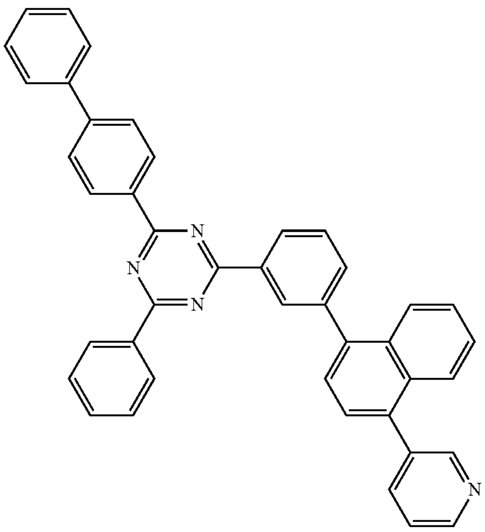

-continued
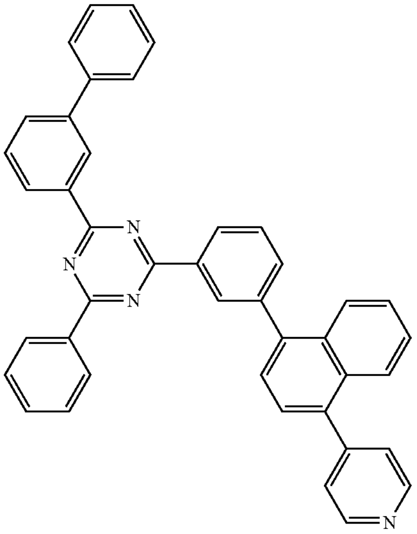
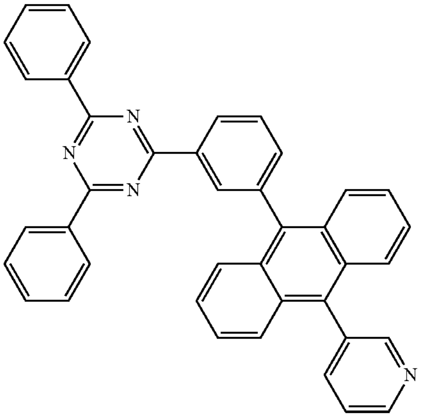
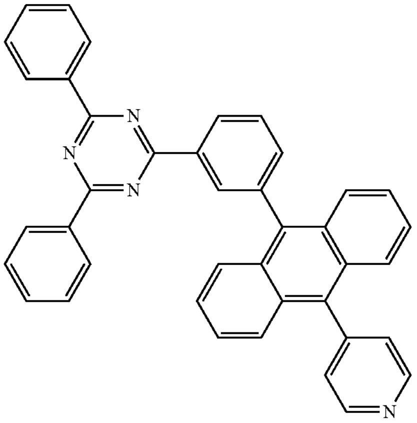
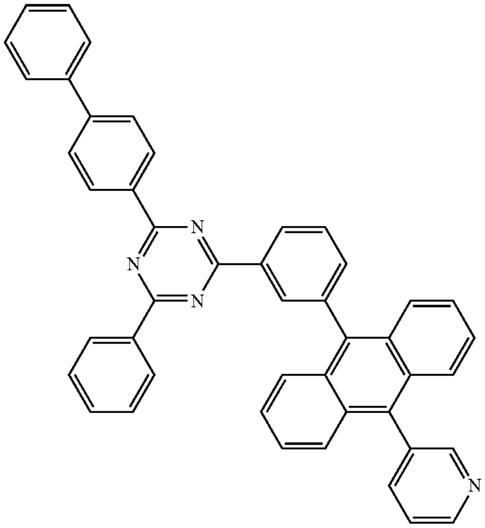
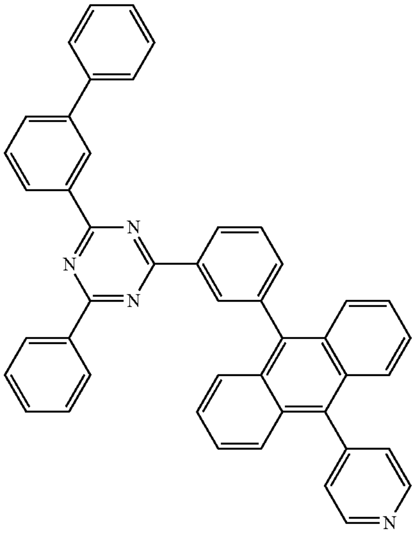
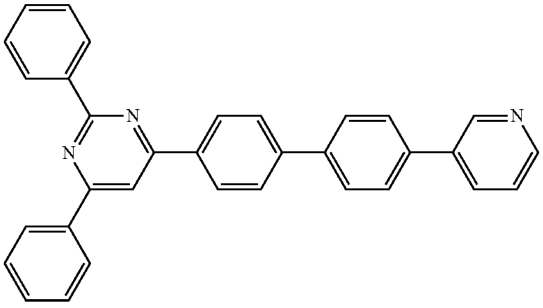

-continued
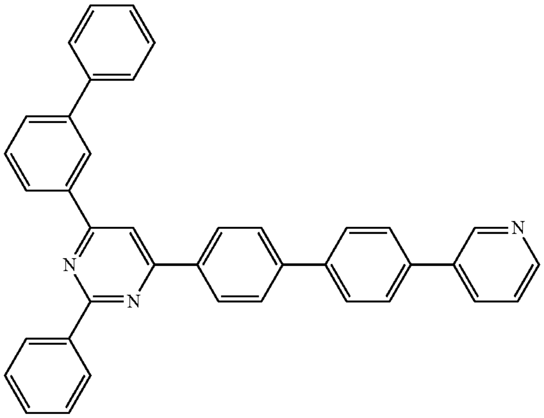
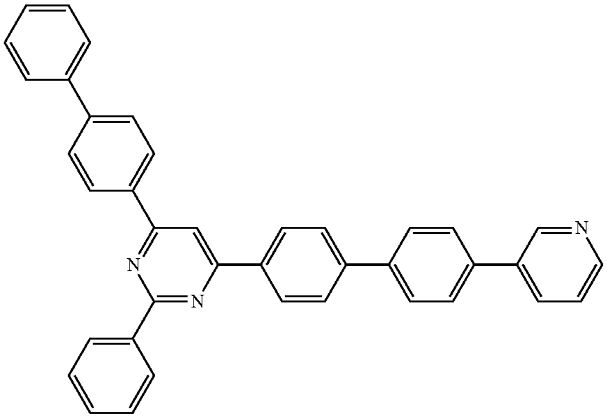
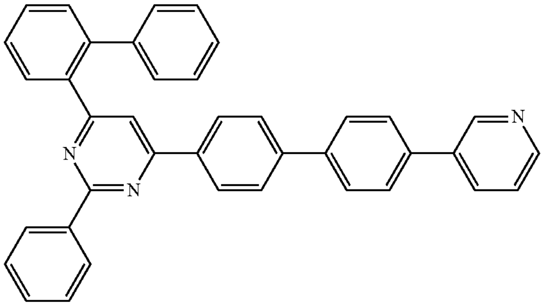
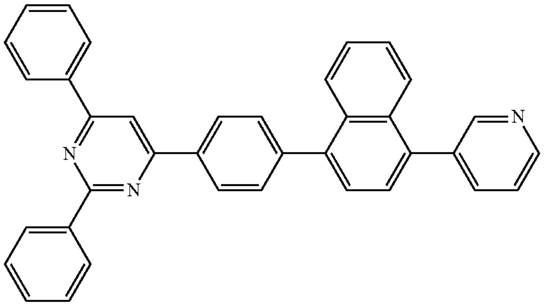
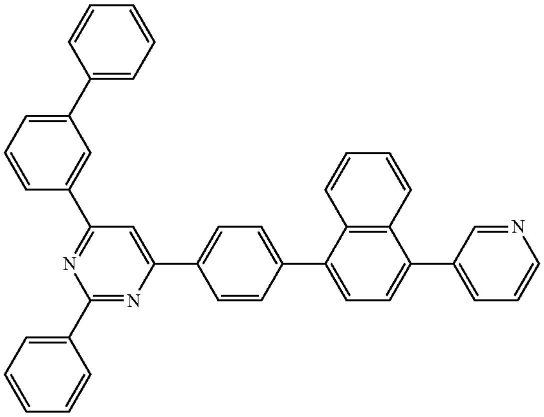
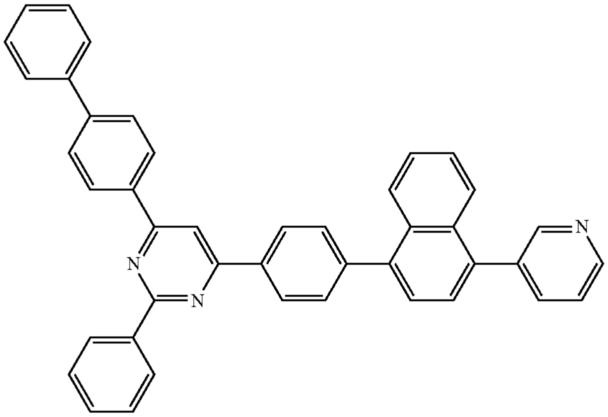
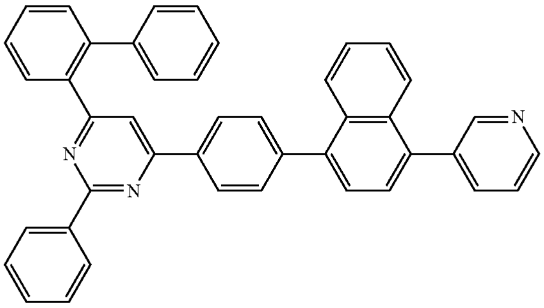
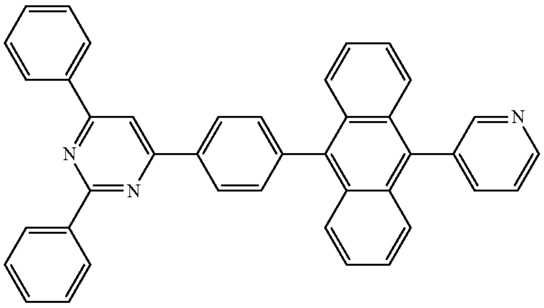

-continued
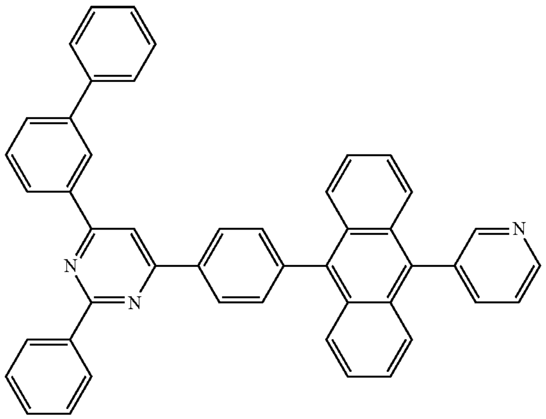
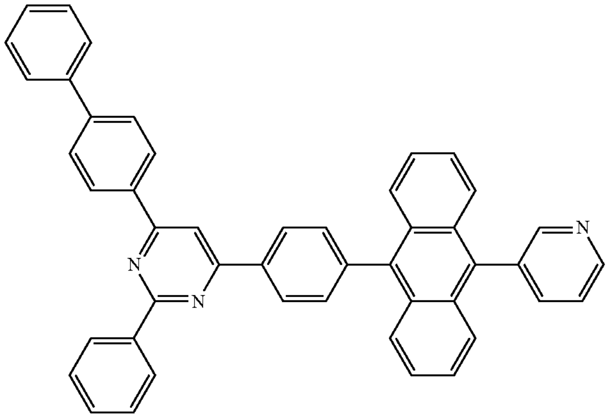
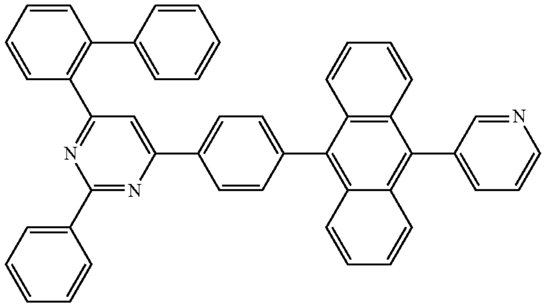
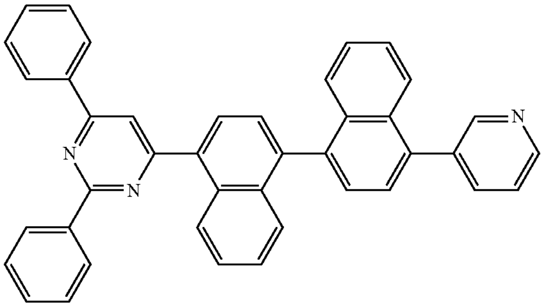
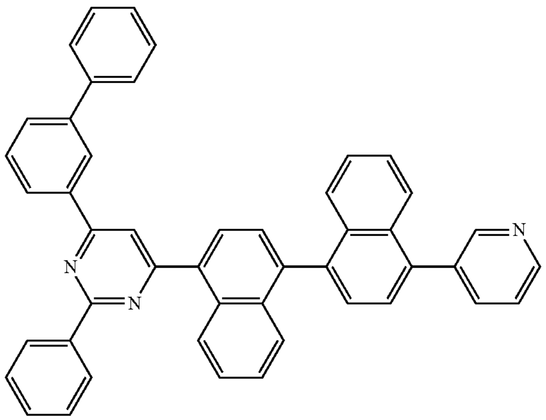
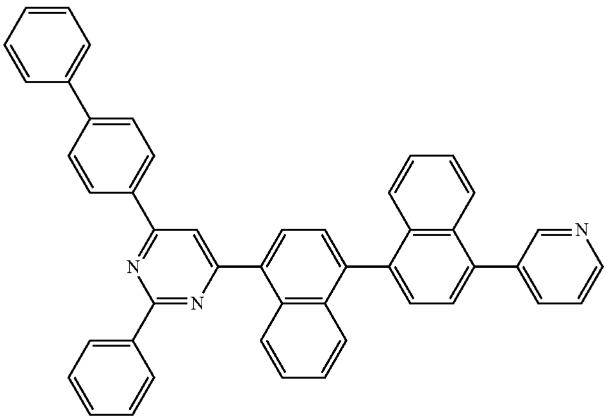
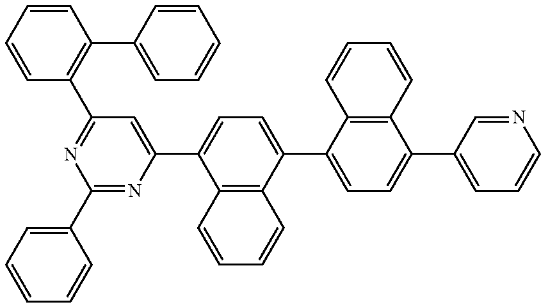
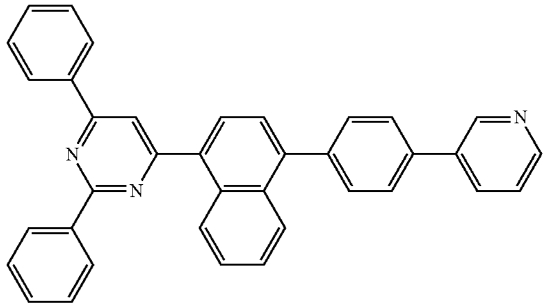

-continued
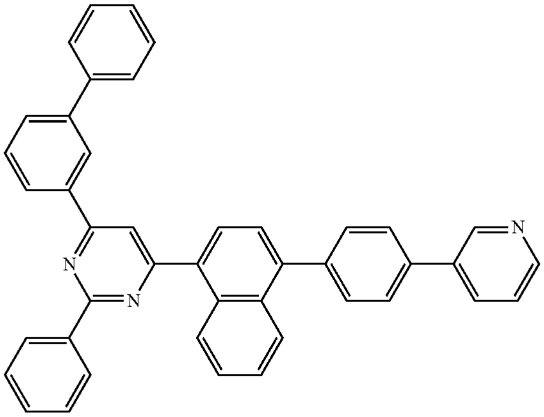
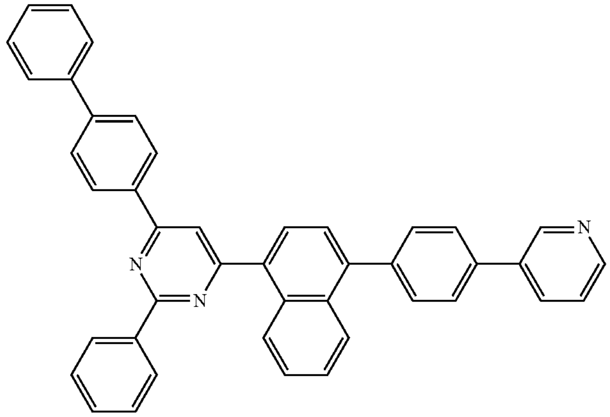
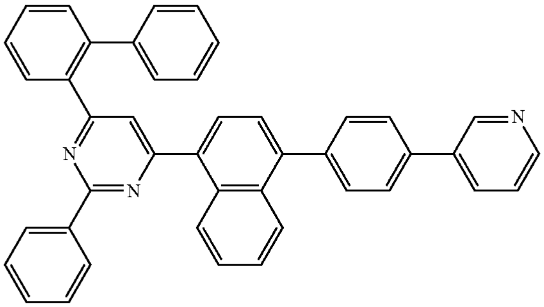
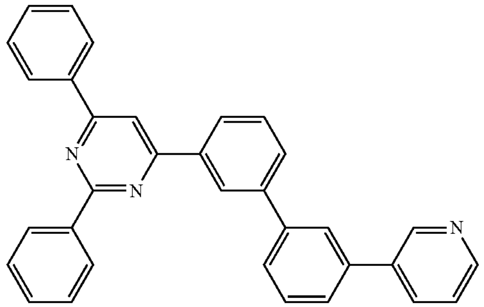
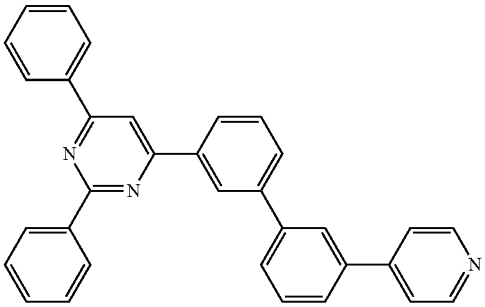
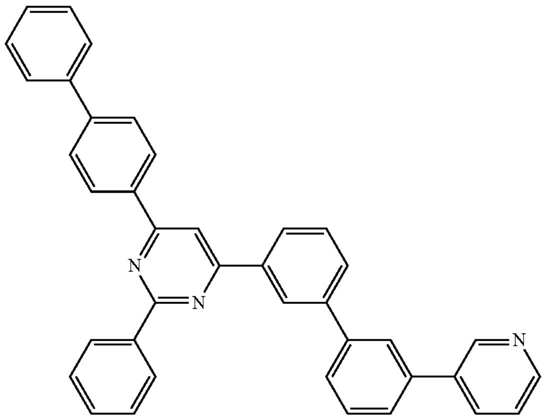
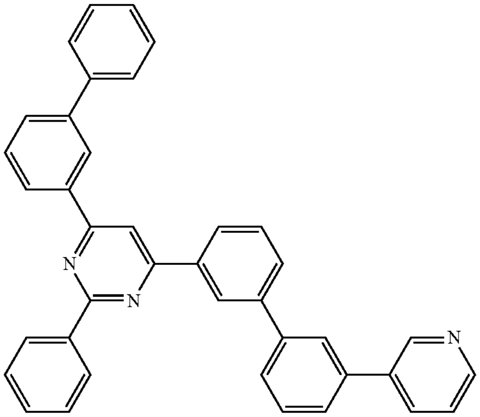
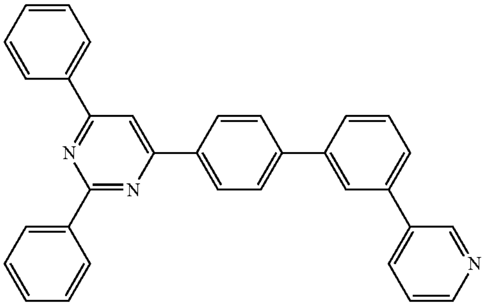

-continued
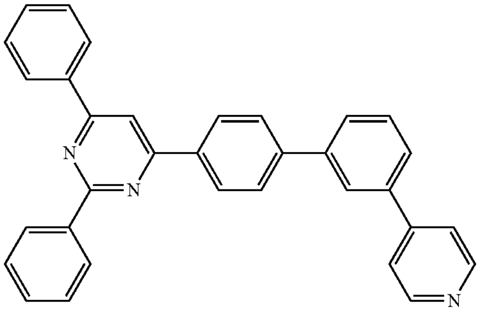
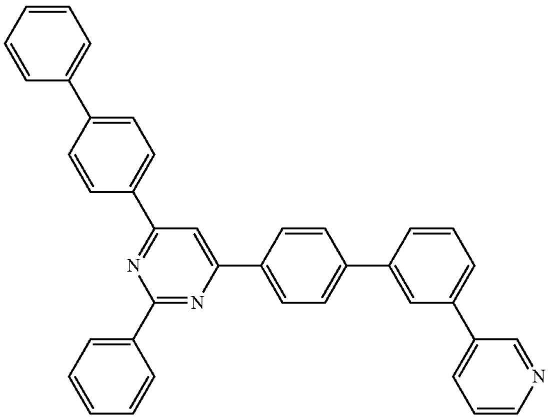
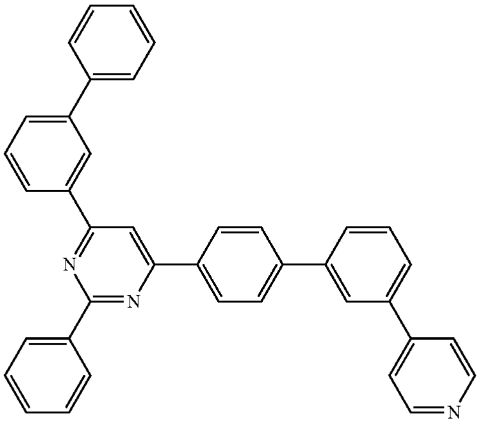
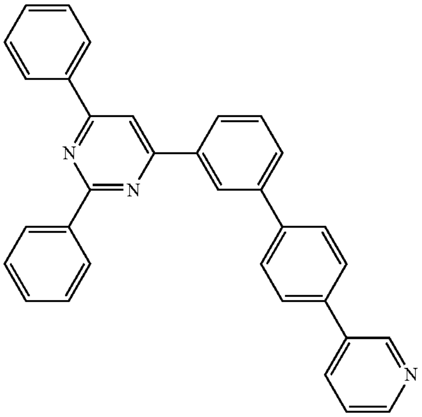
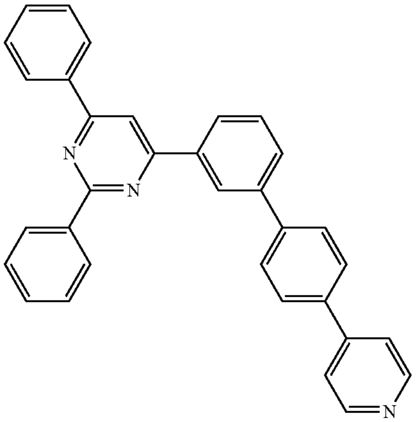
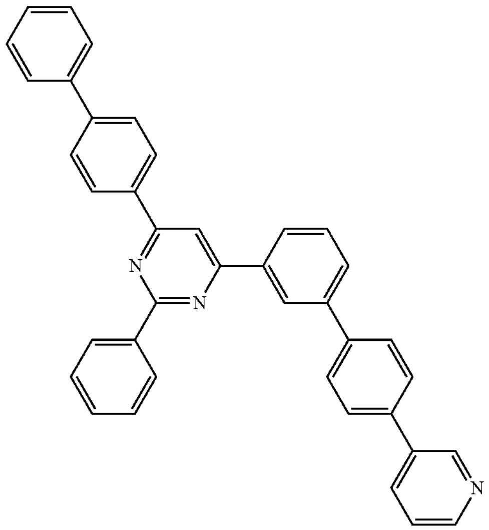

-continued
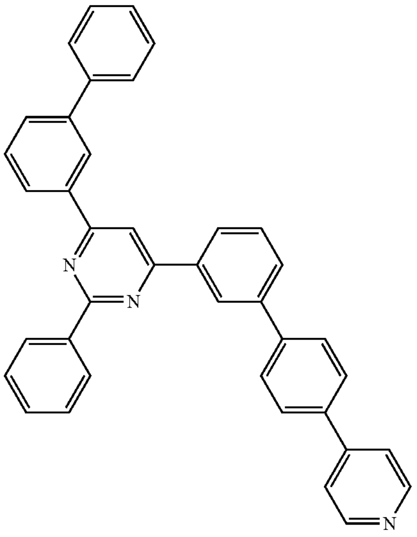
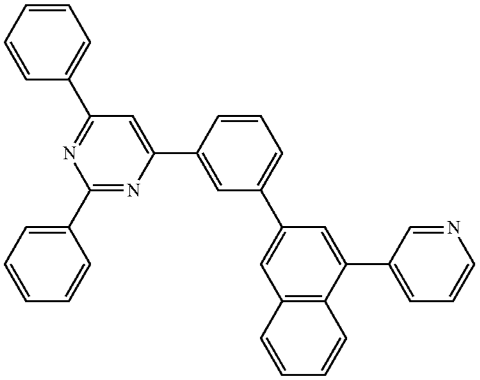
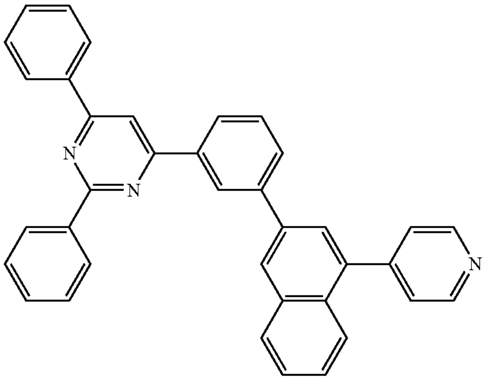
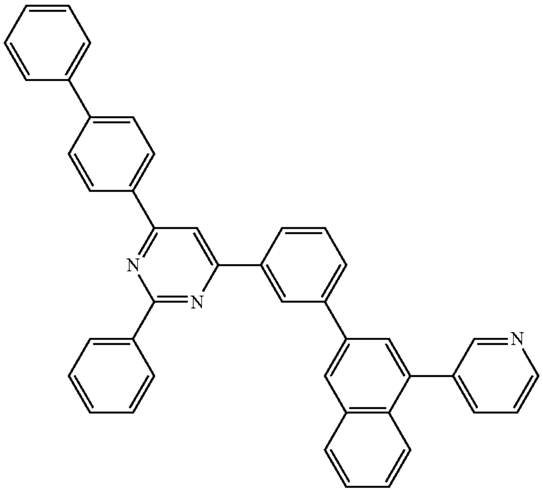
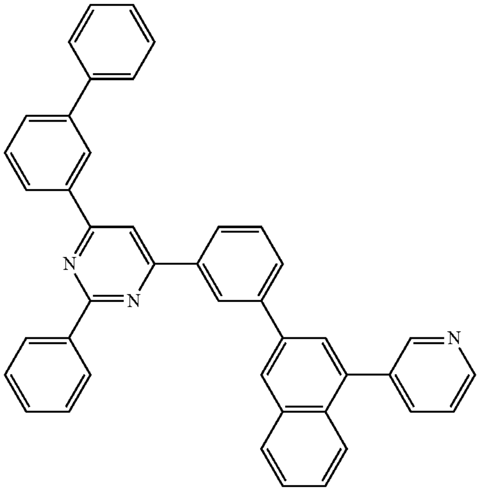
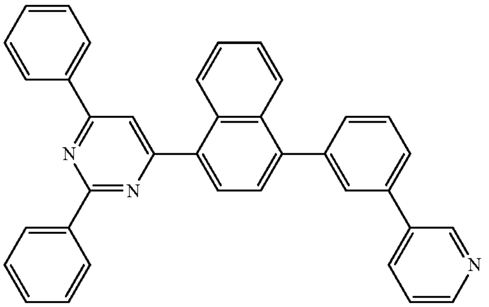

-continued
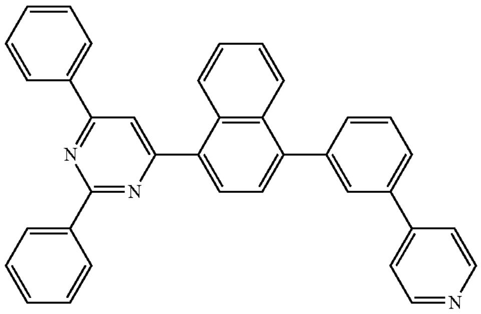
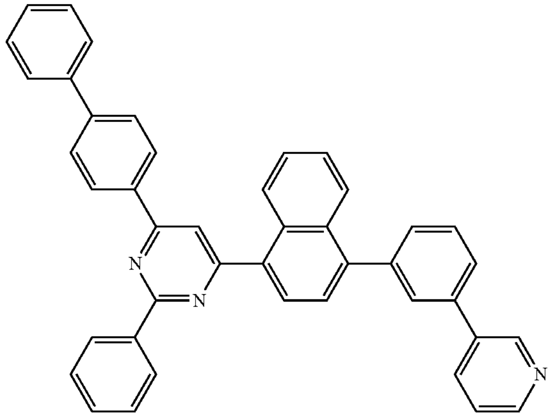
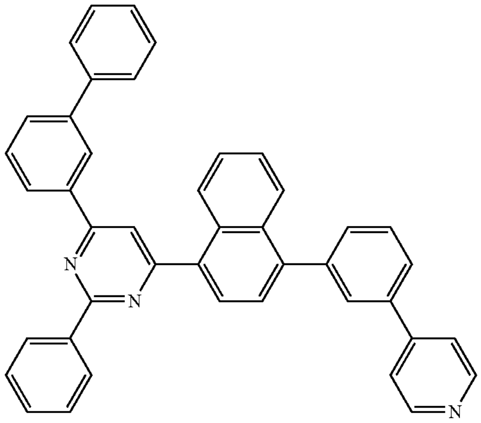
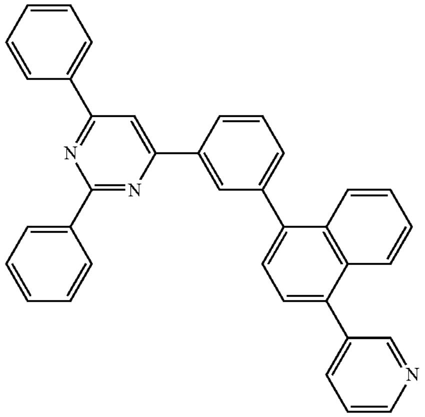
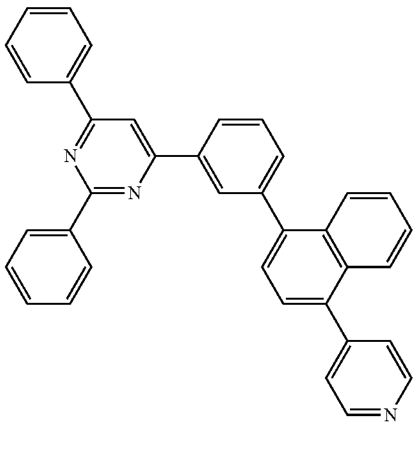
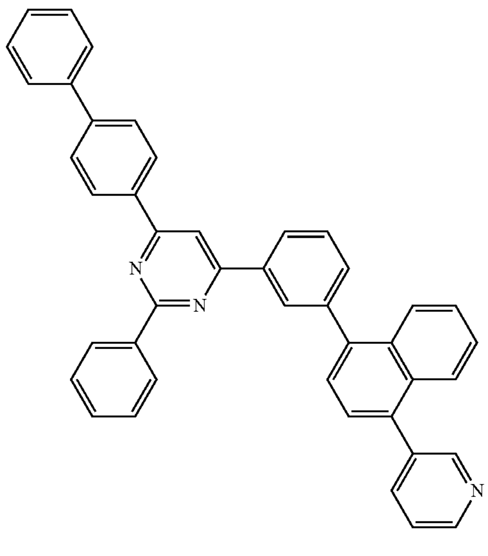

-continued
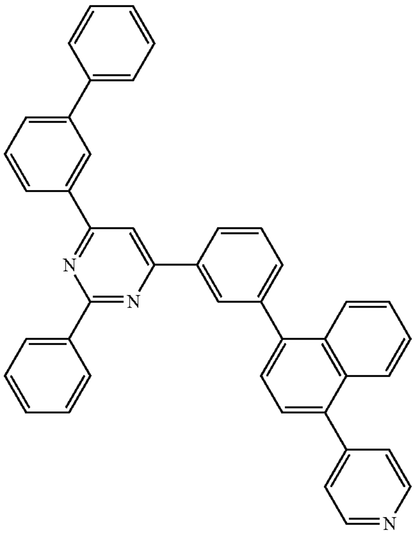
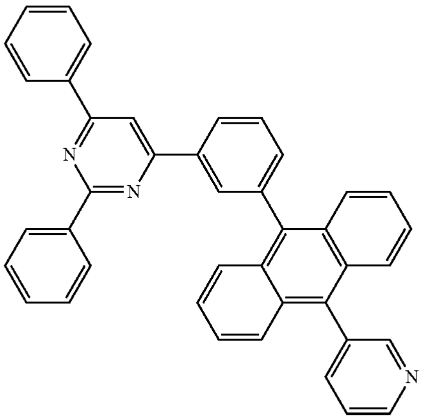
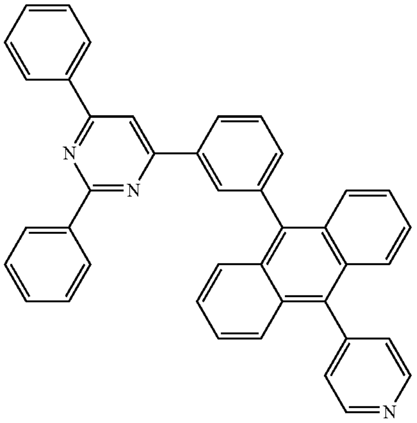
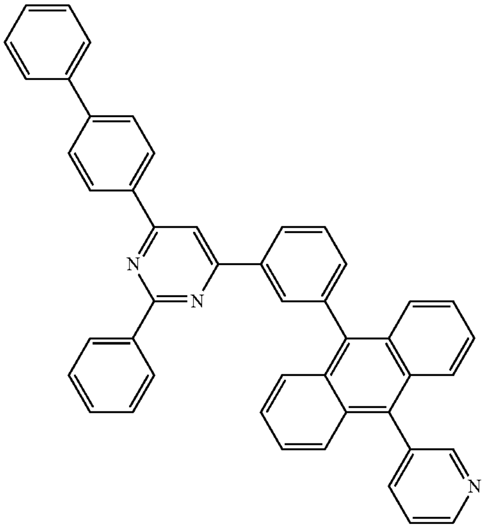
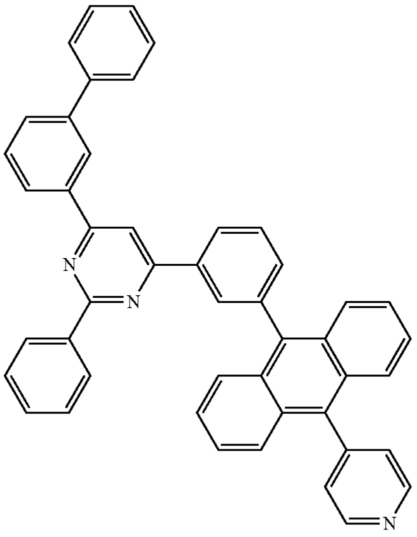
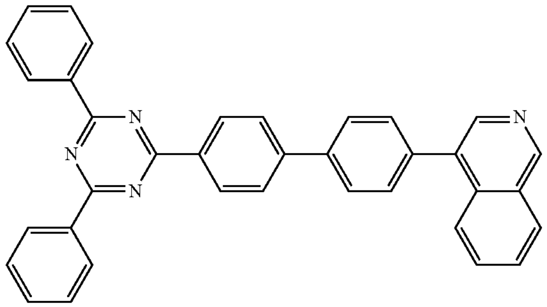

-continued
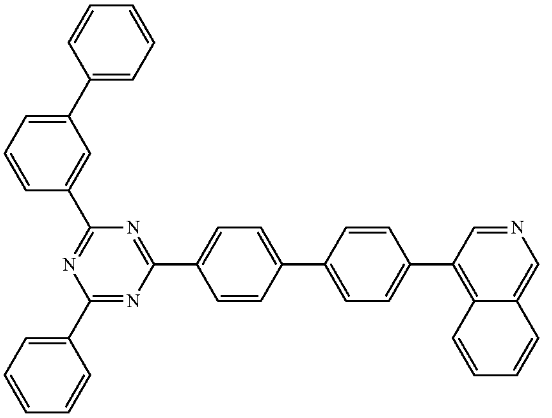
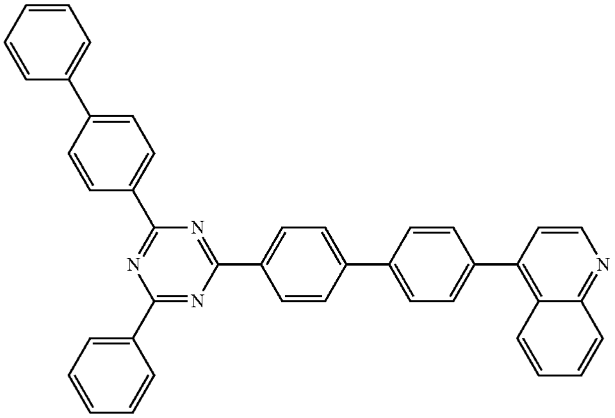
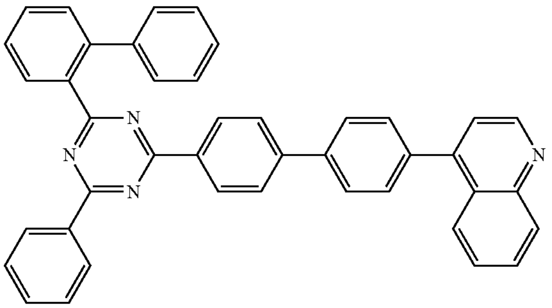
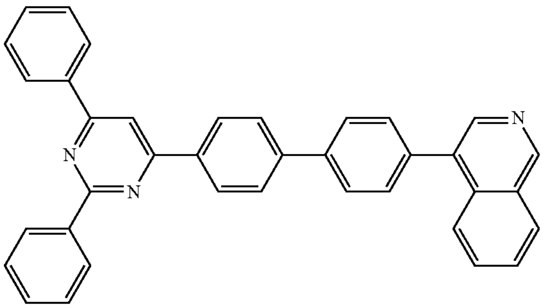
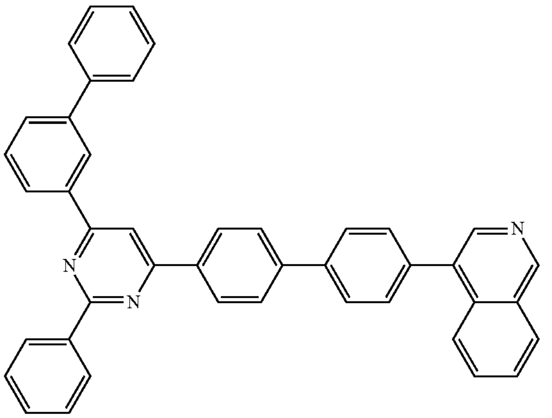
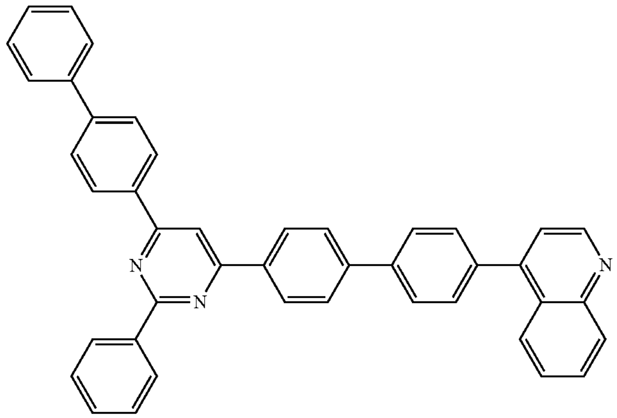
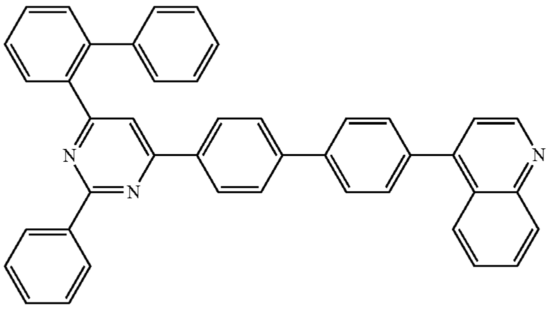

-continued
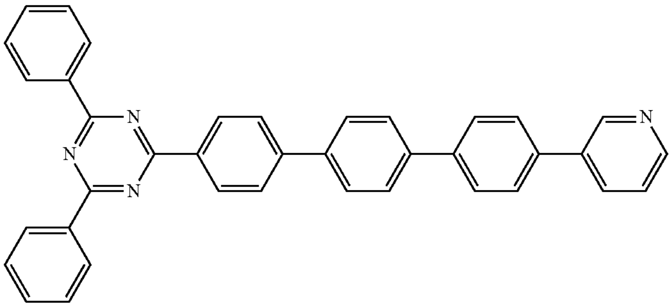
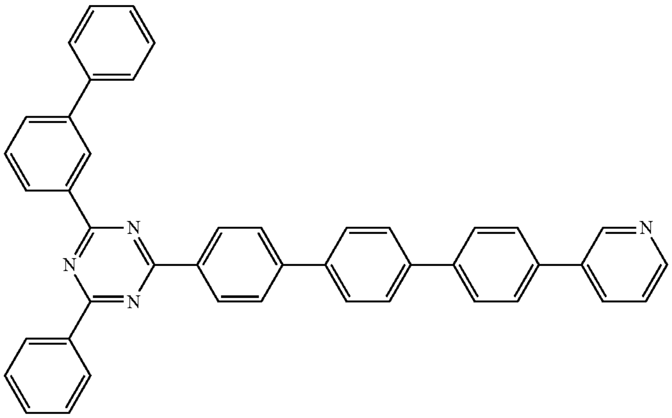
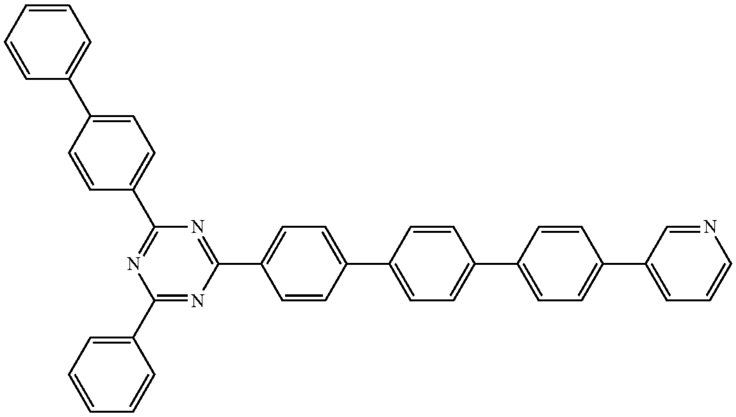
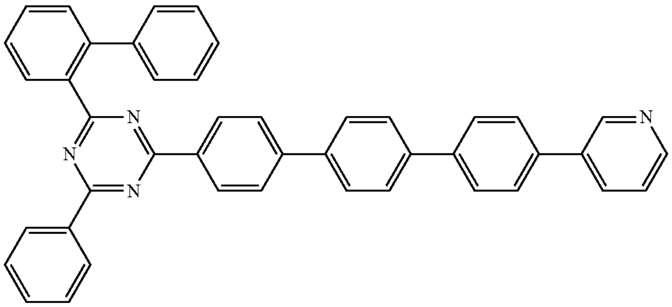

-continued
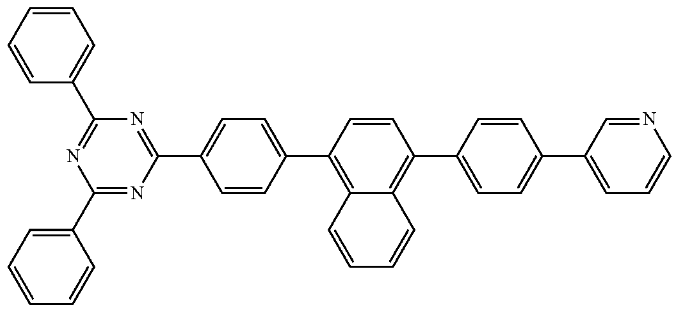
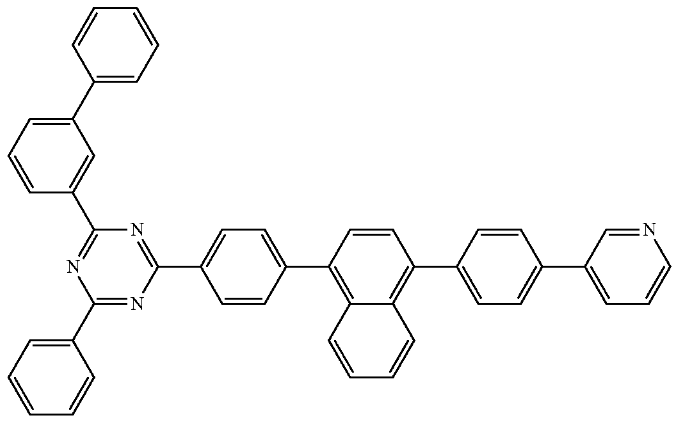
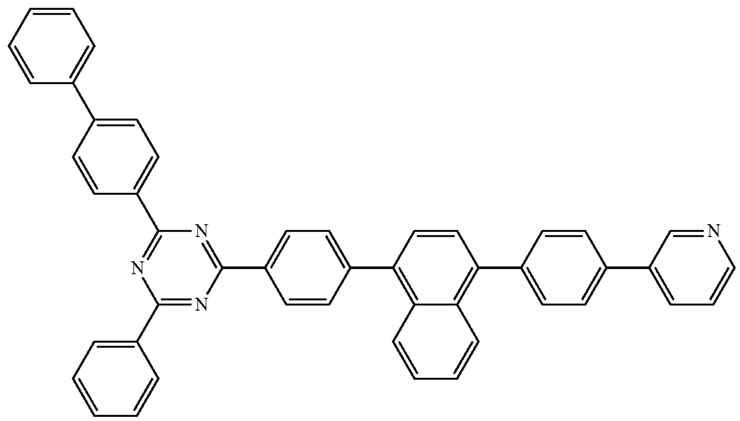
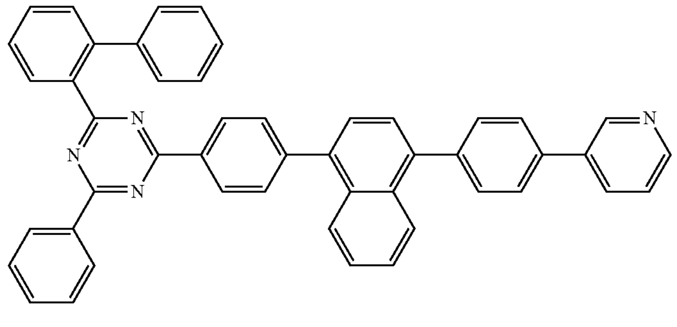

-continued
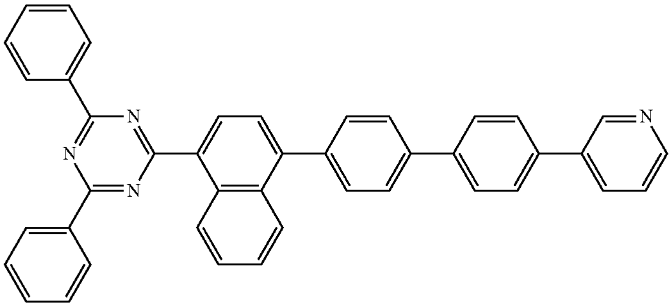
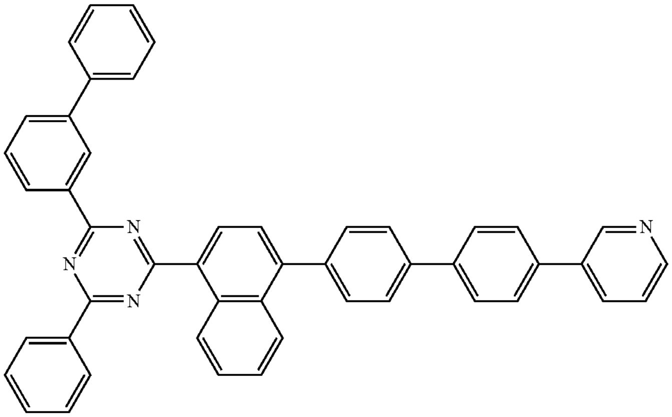
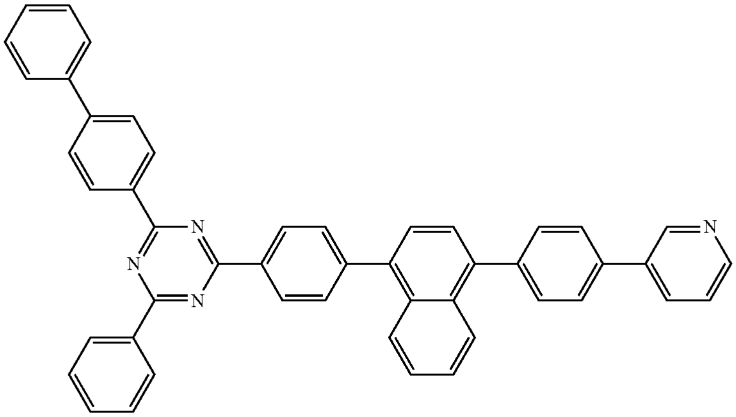
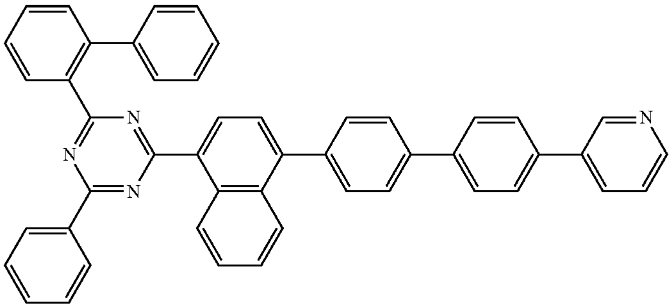

-continued
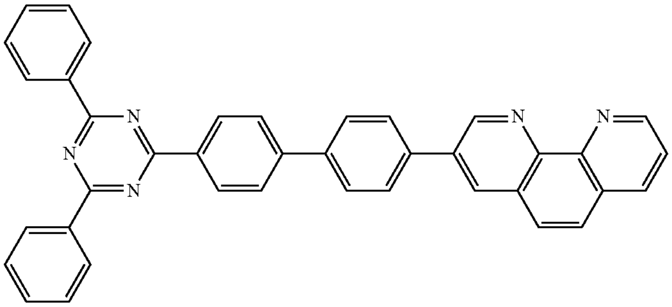
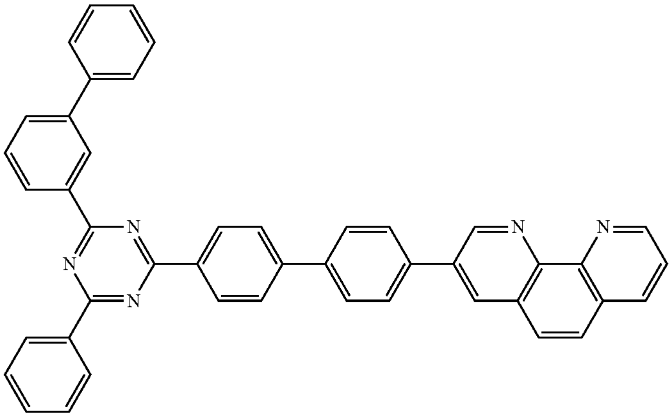
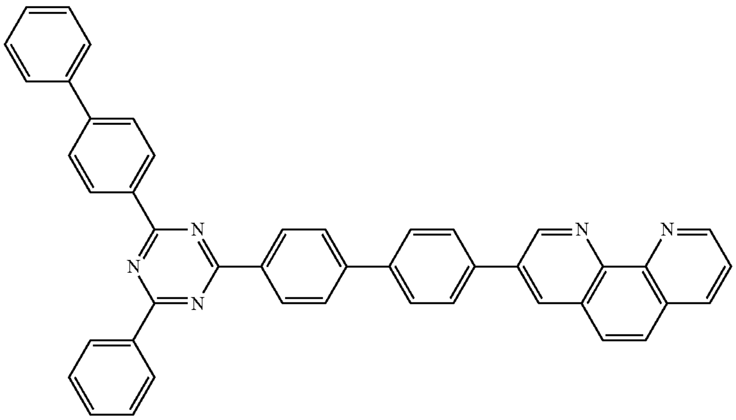
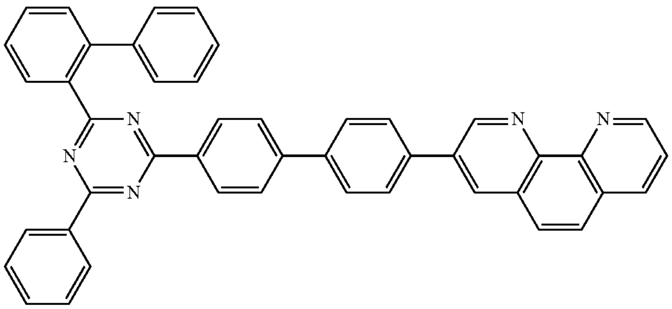

-continued
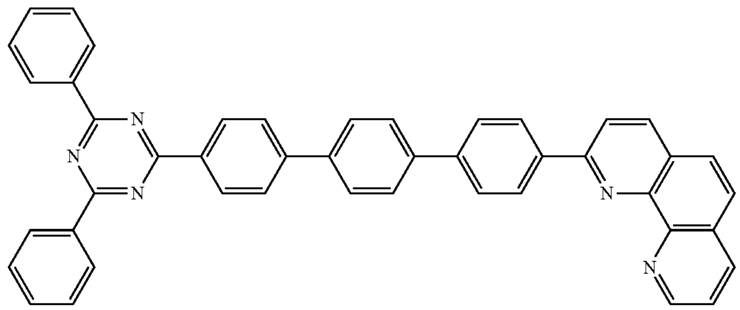
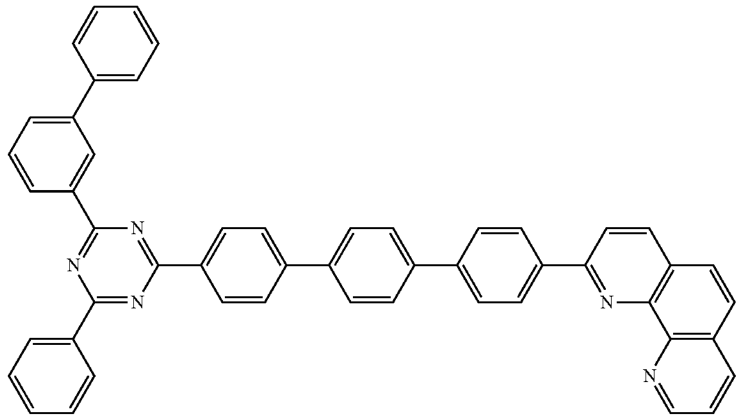
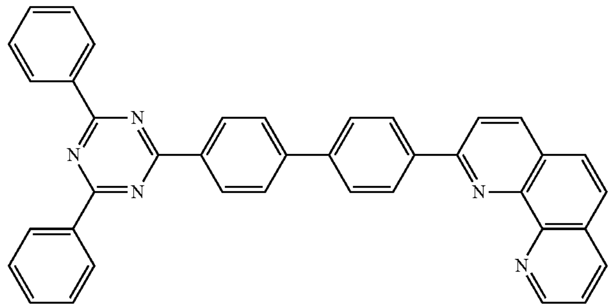
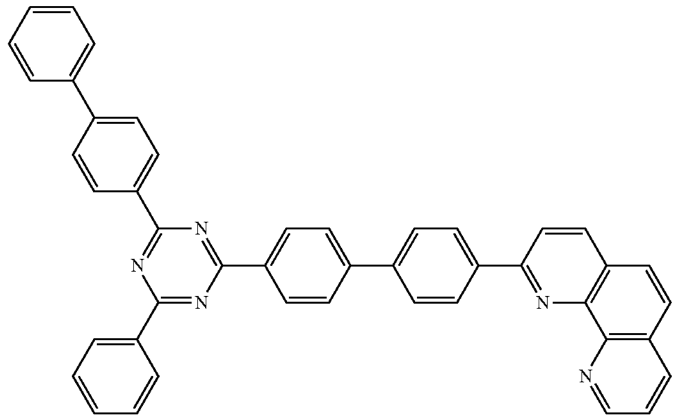

-continued
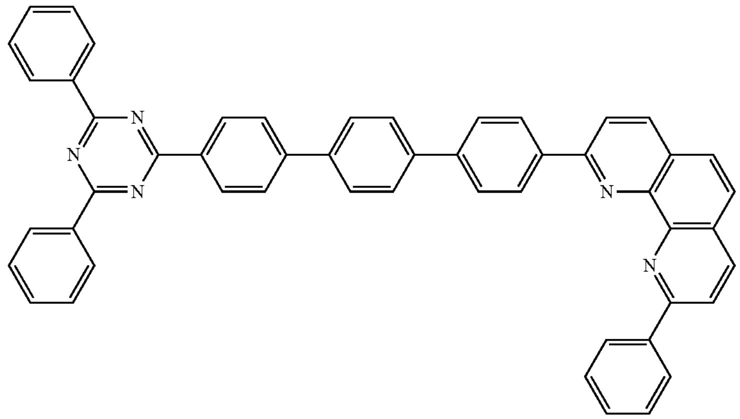
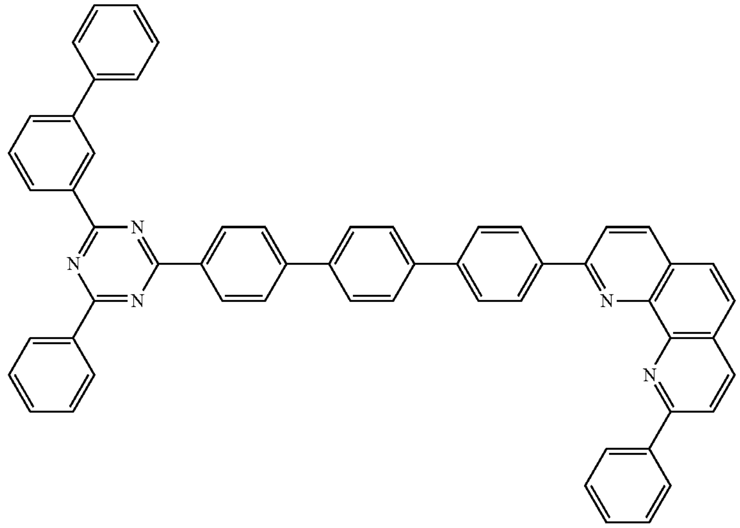
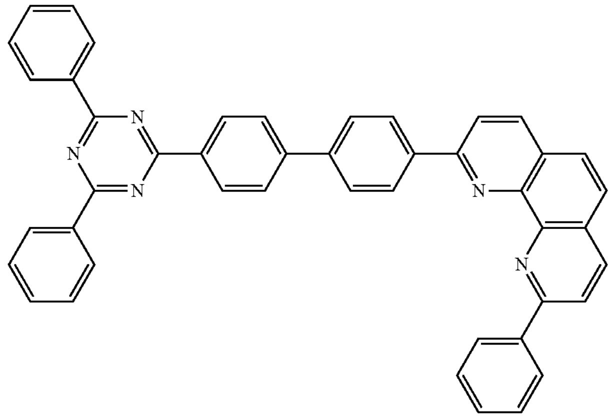

-continued
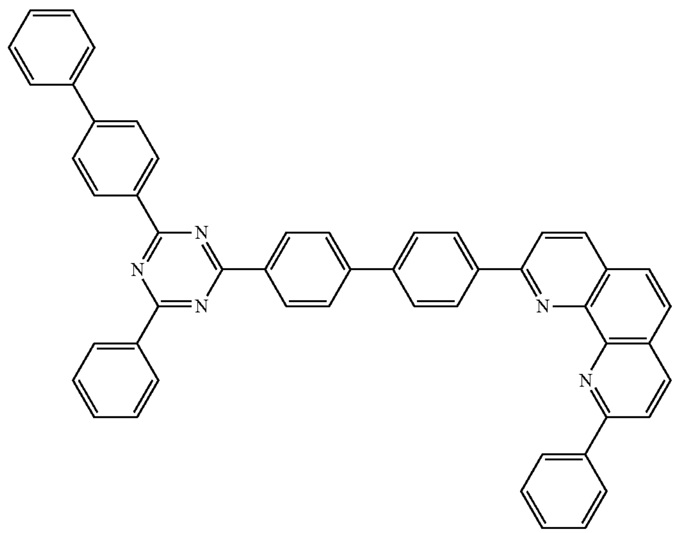
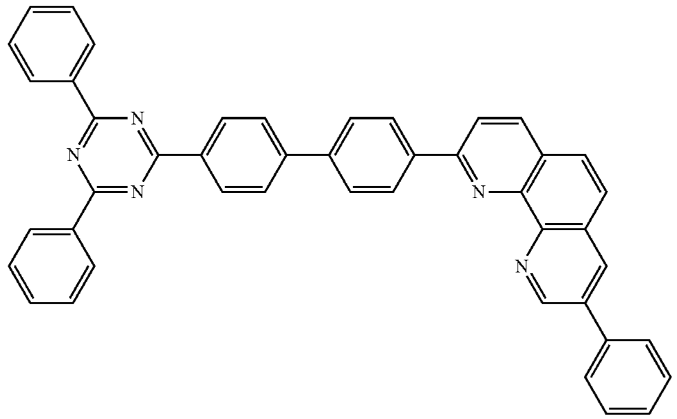
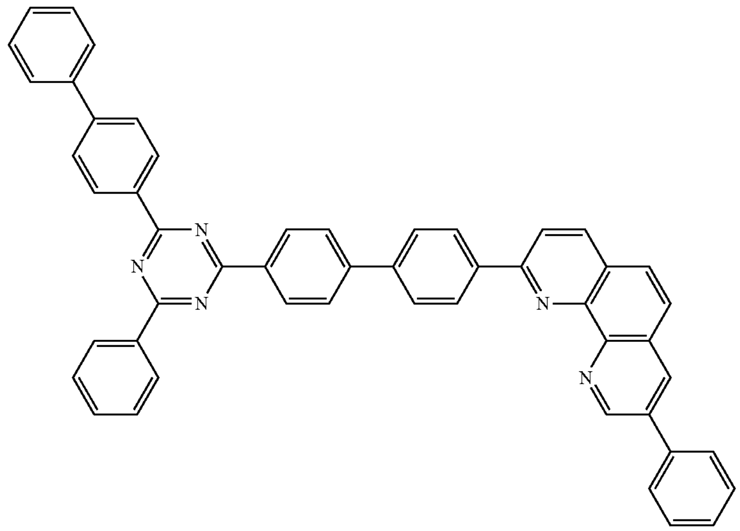

-continued
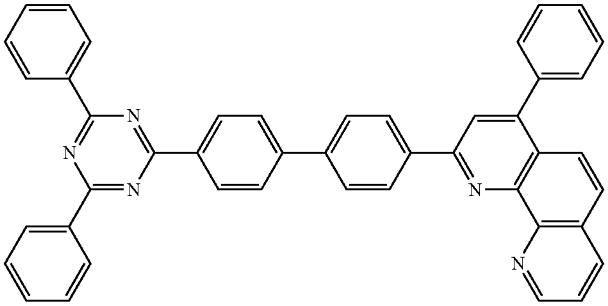
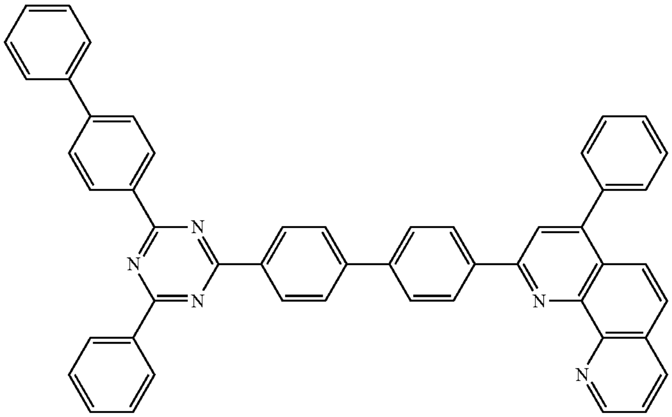
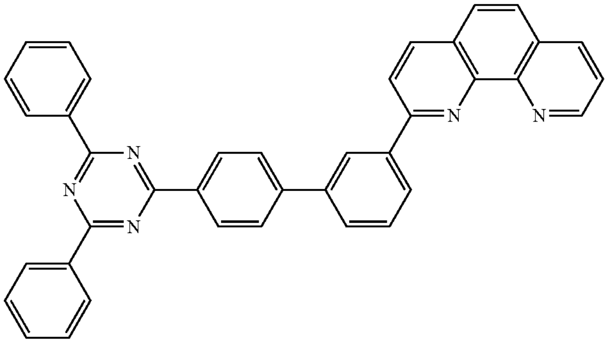
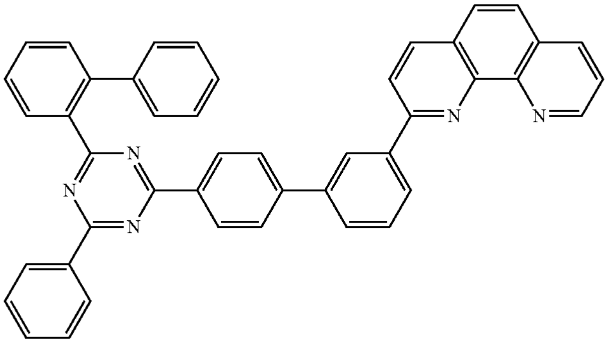

-continued
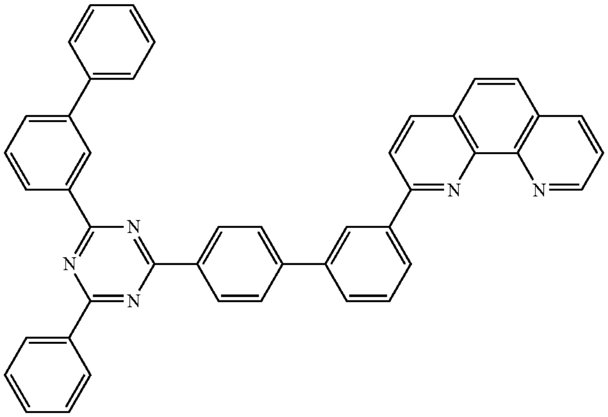
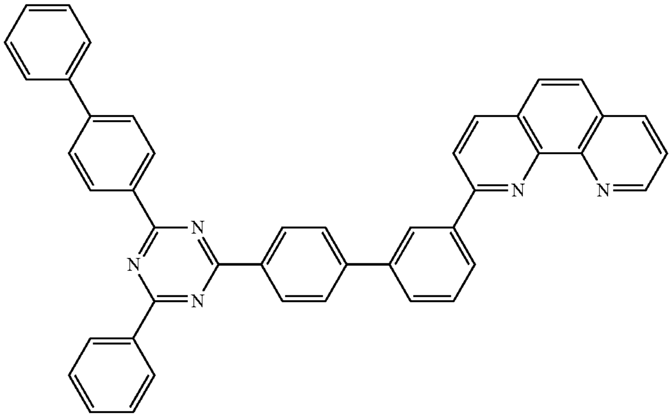
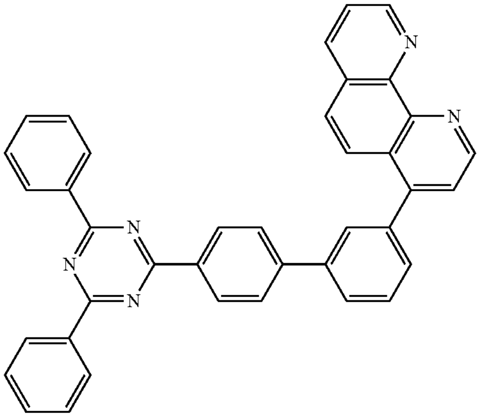
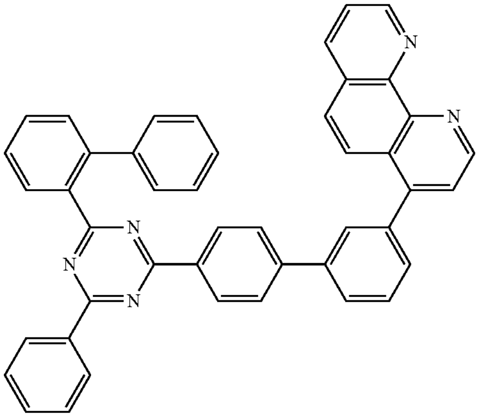
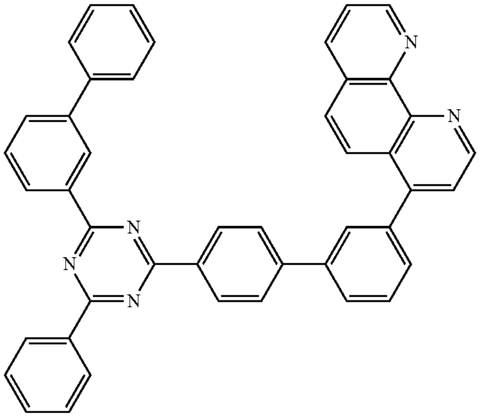
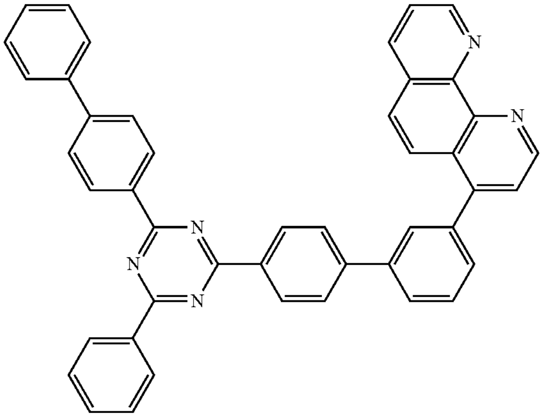

-continued
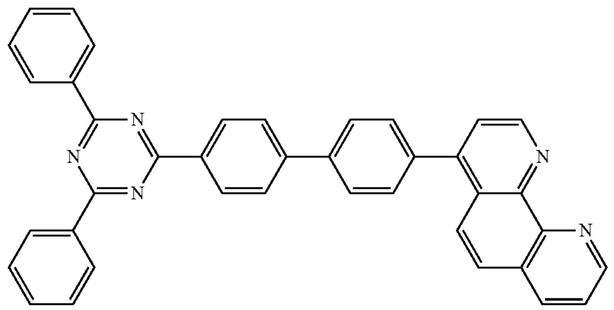
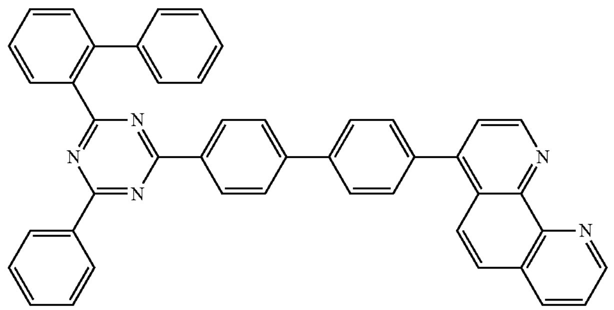
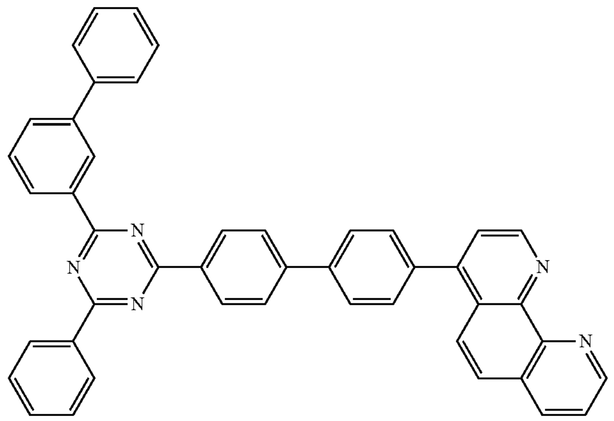
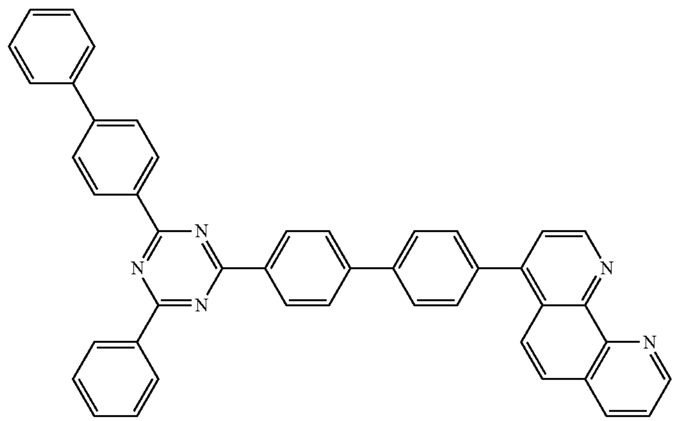

-continued
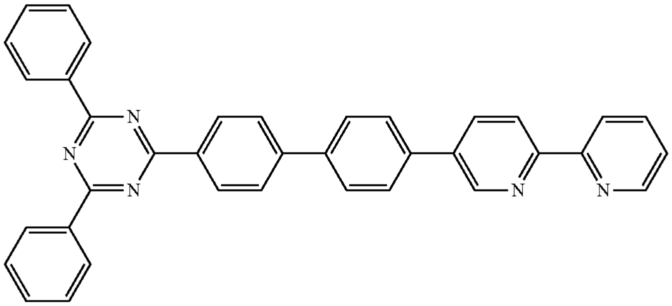
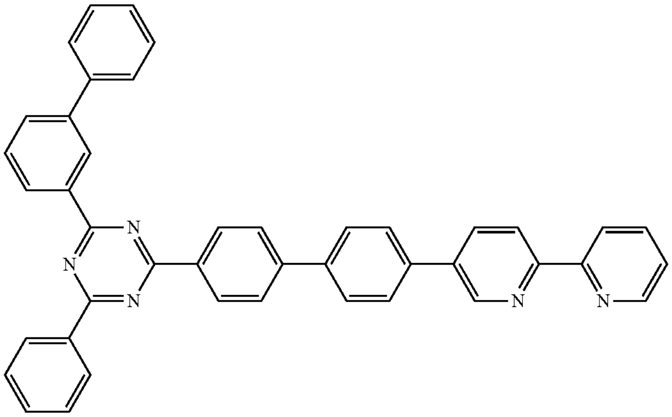
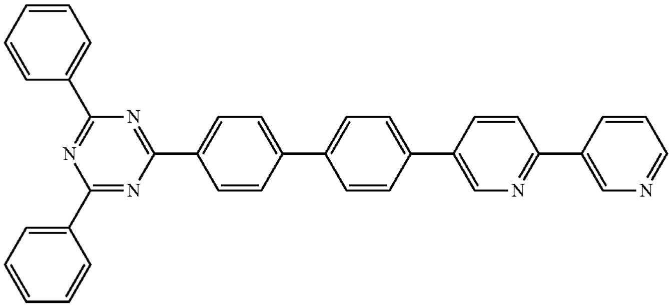
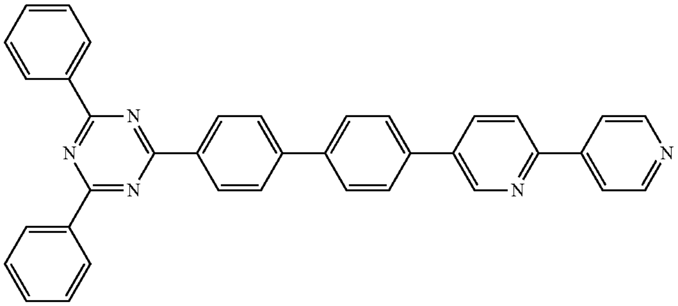
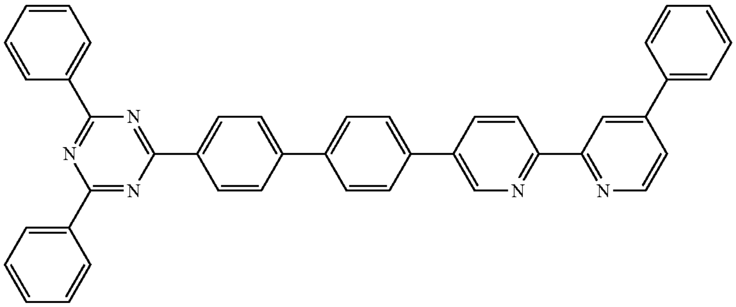

-continued
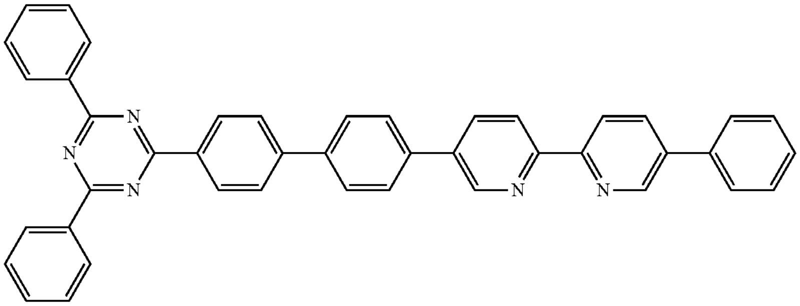
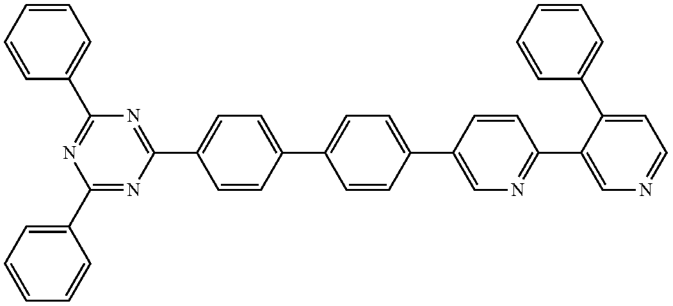
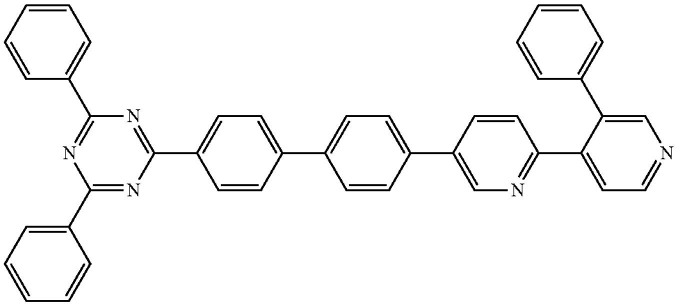
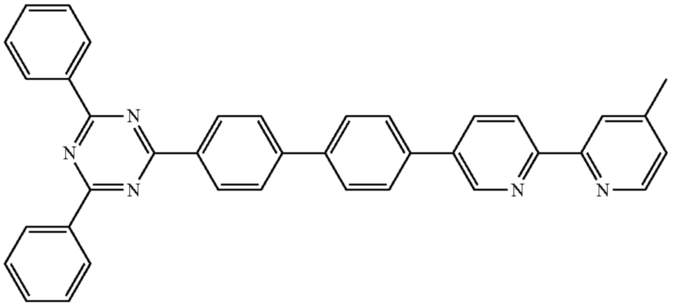
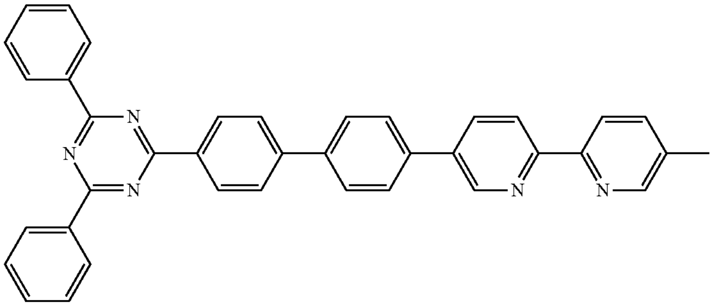

-continued
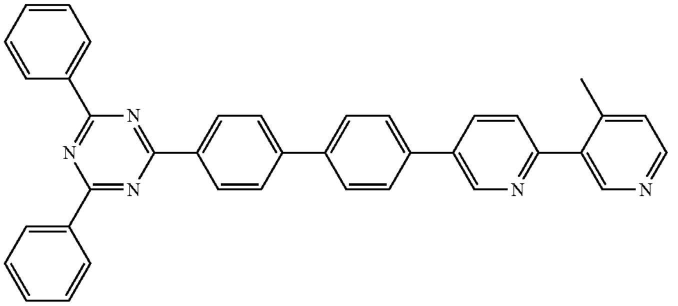
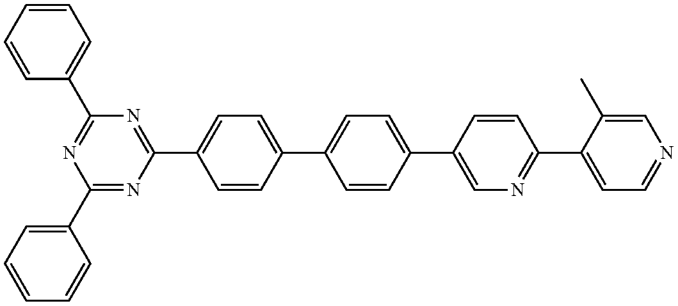
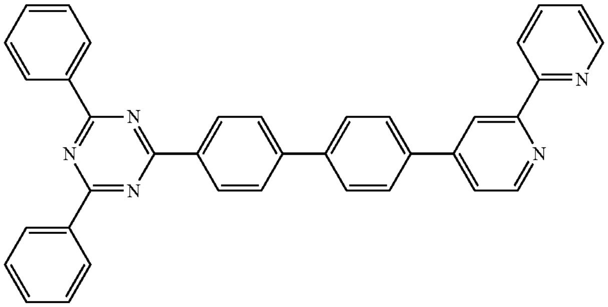
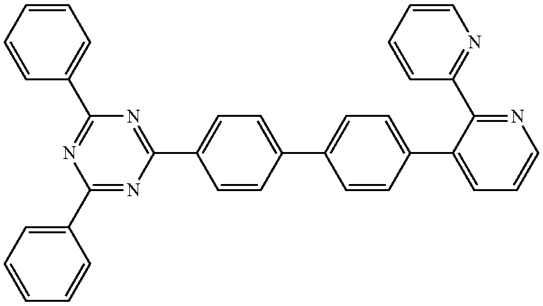
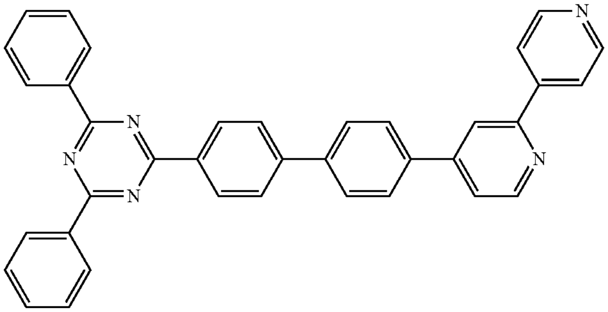
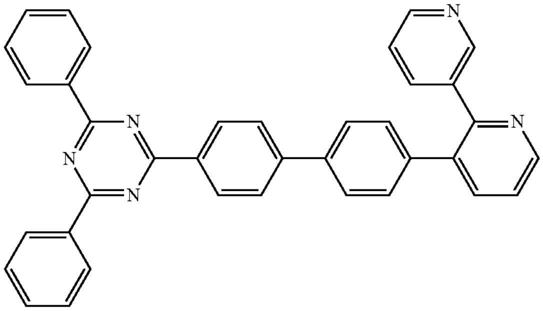
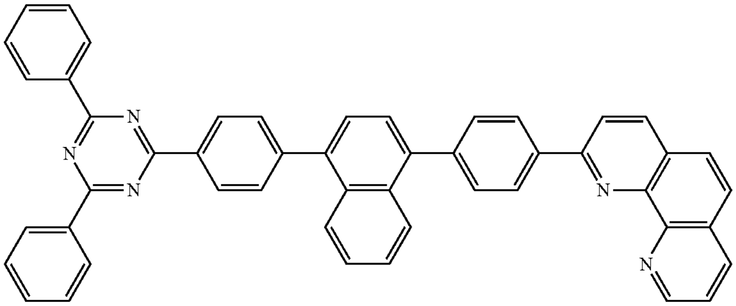

-continued
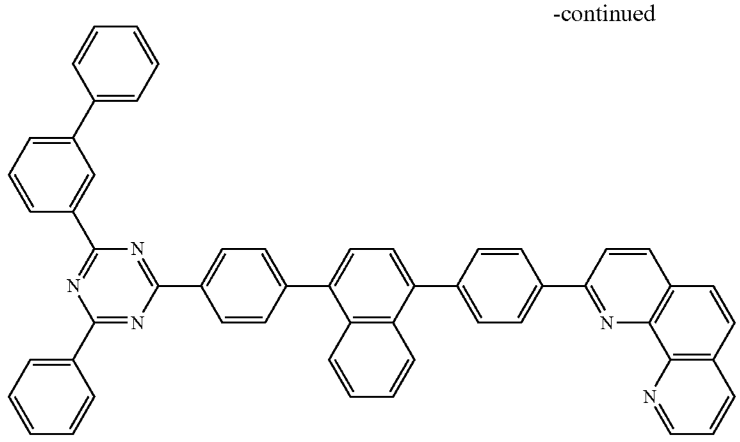
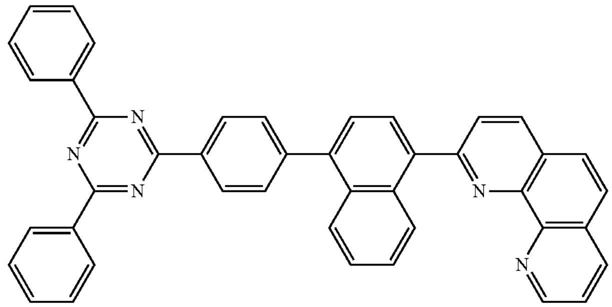
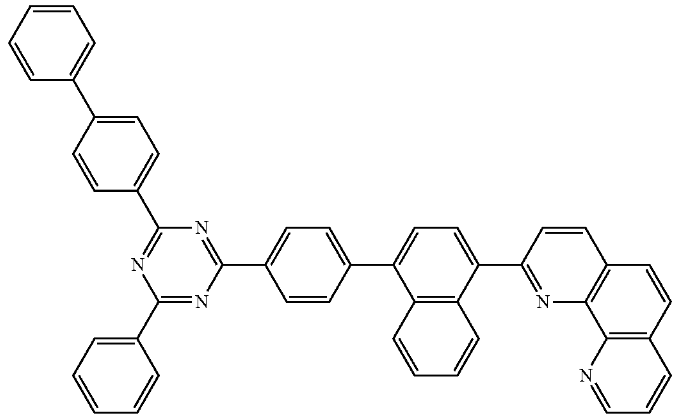
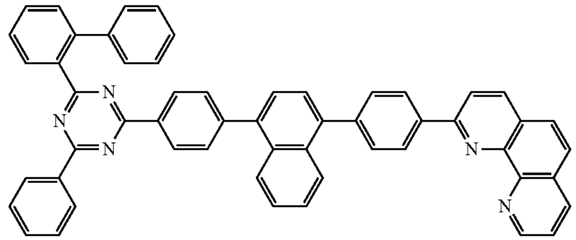
-continued
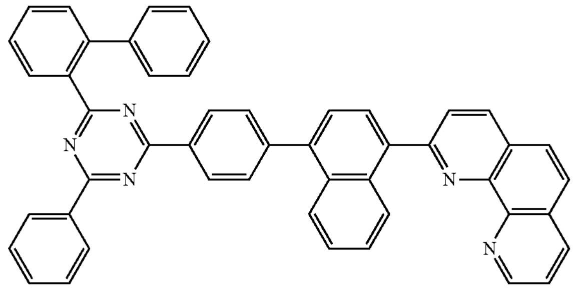

-continued
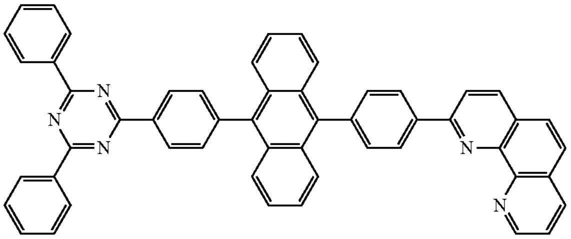
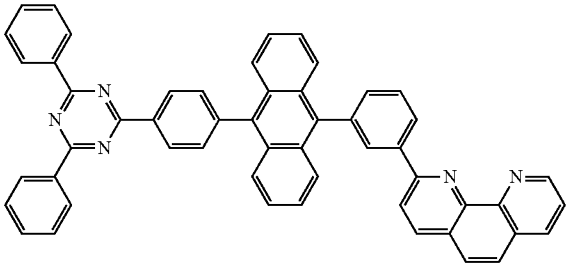
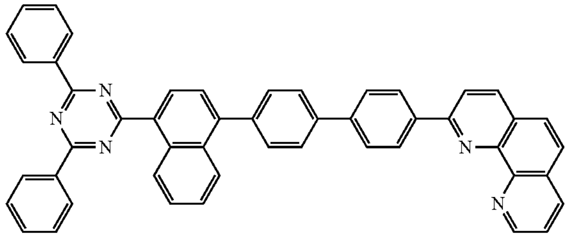
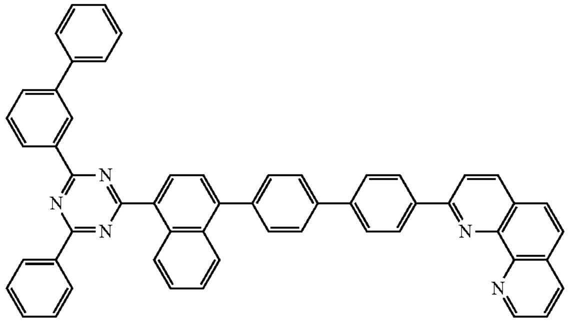
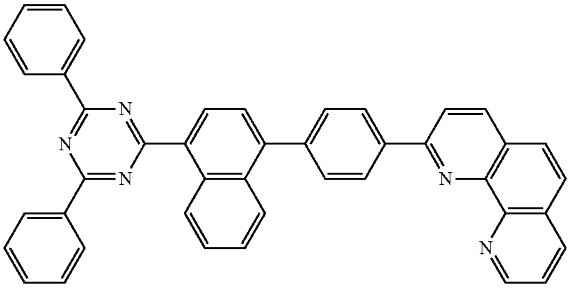
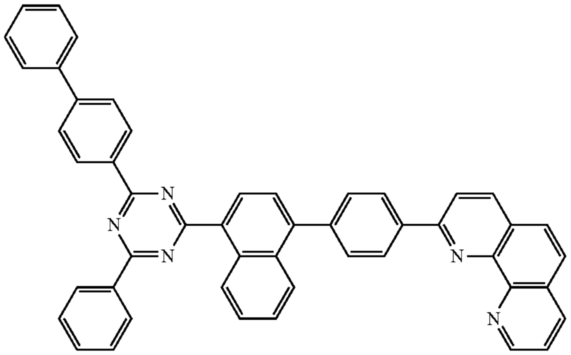
-continued
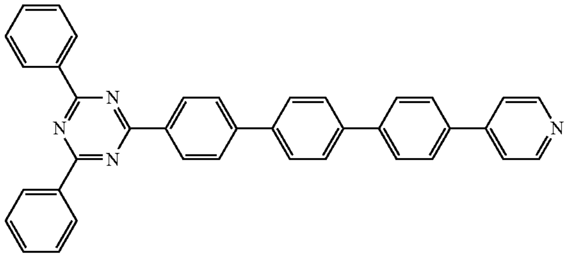
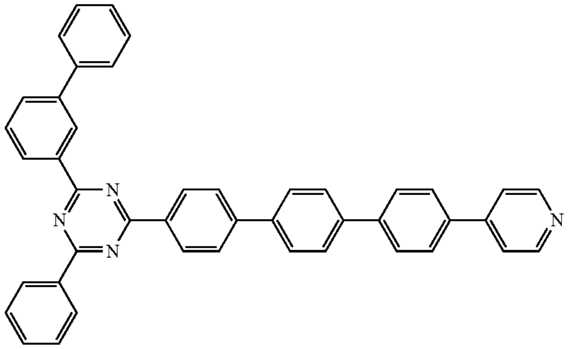
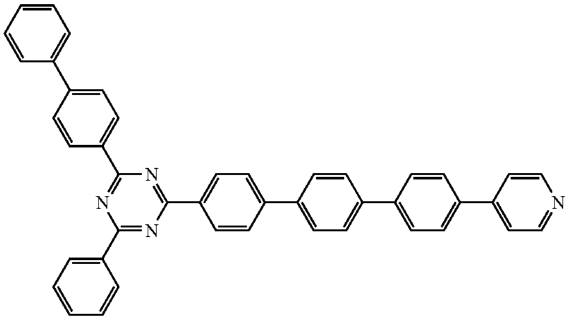
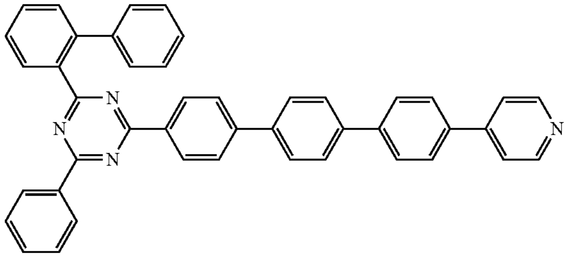
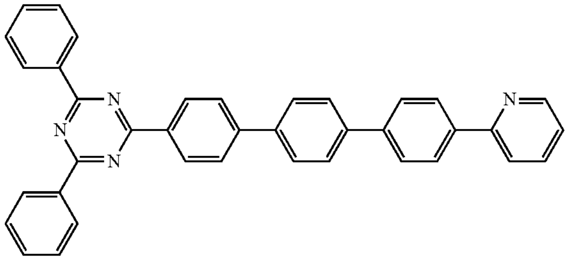

-continued
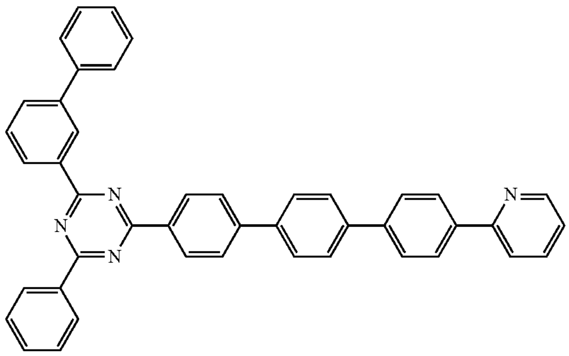
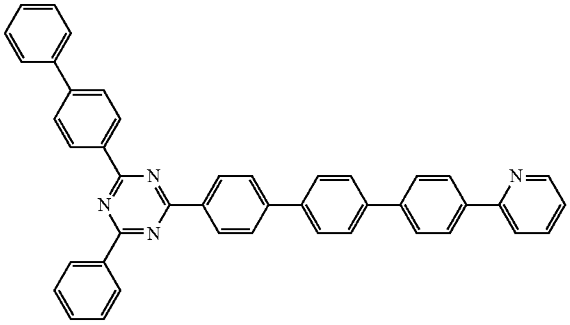
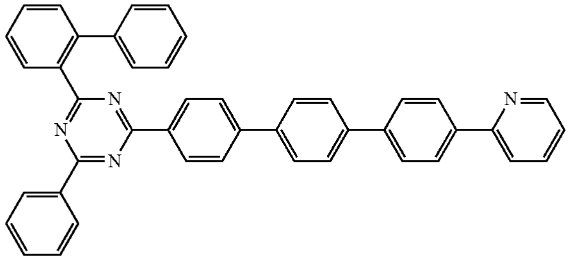
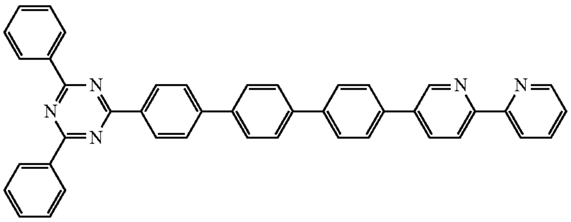
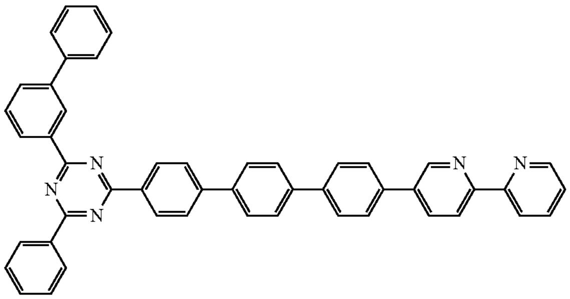
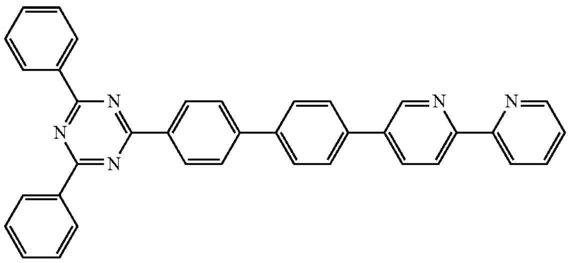
-continued
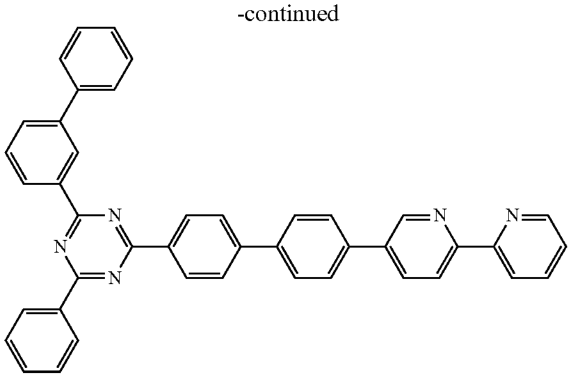
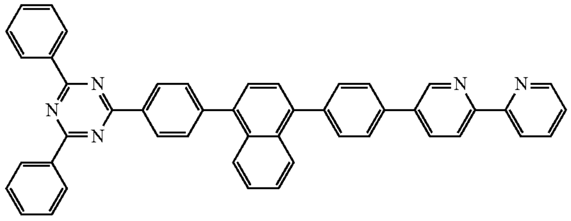
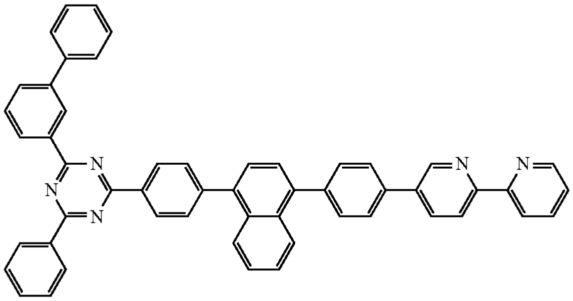
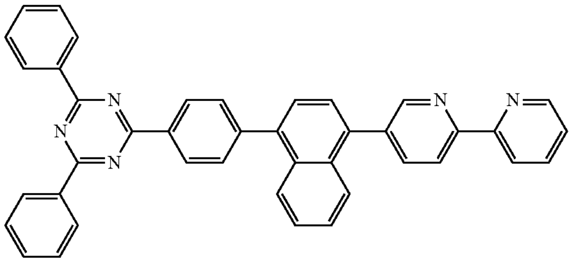
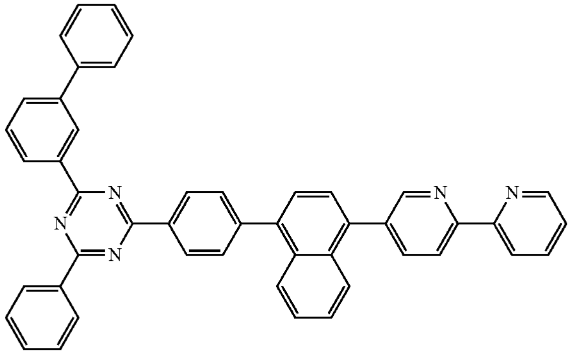
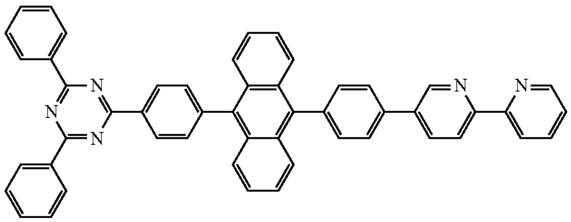

-continued
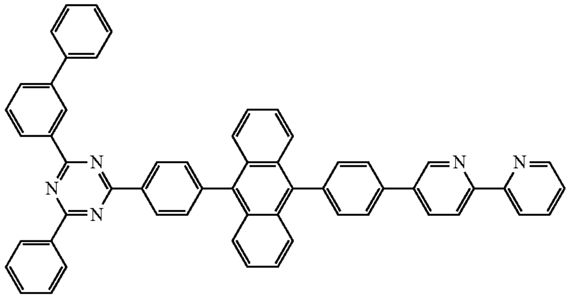
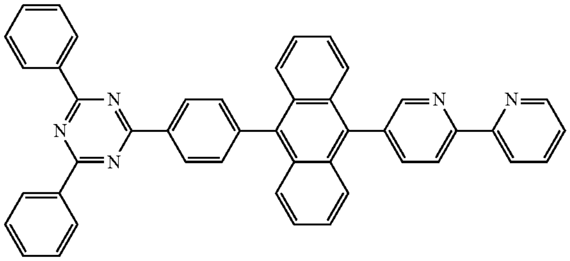
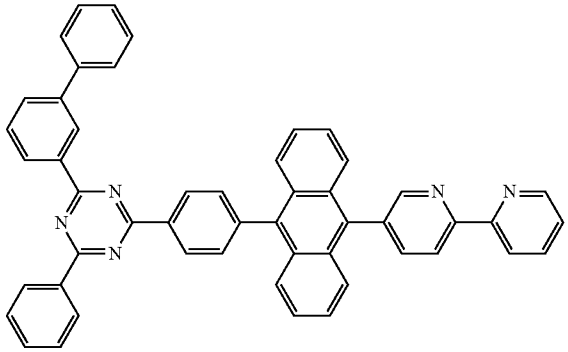
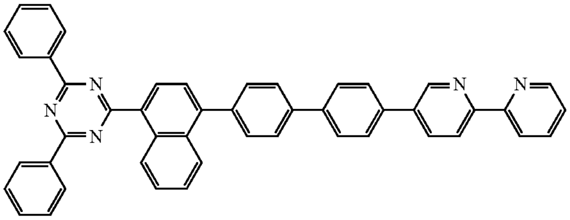
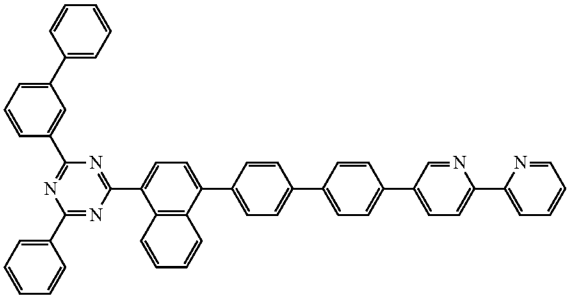
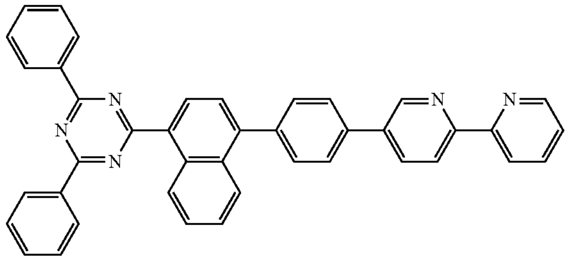
-continued
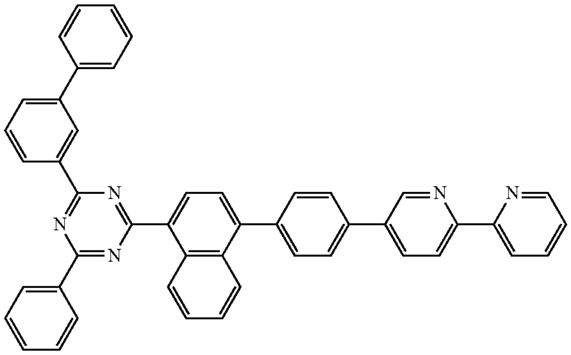
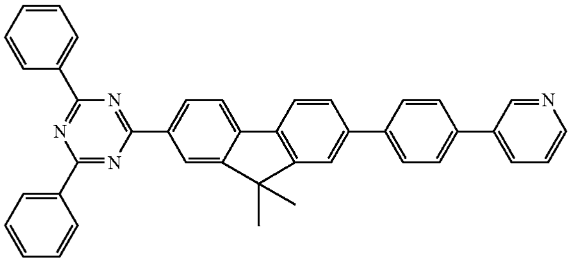
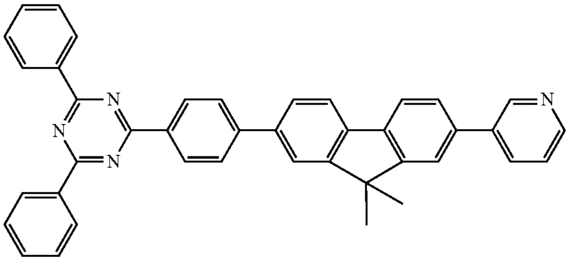
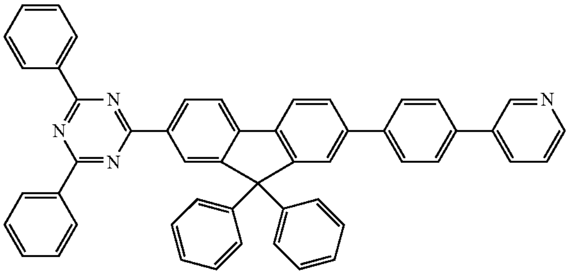
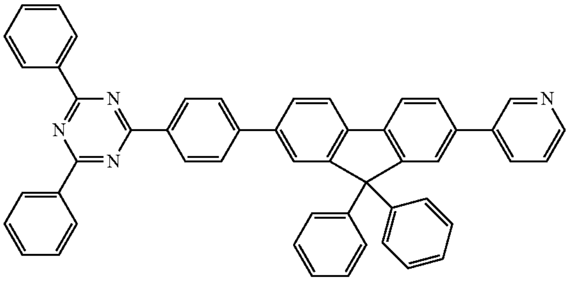
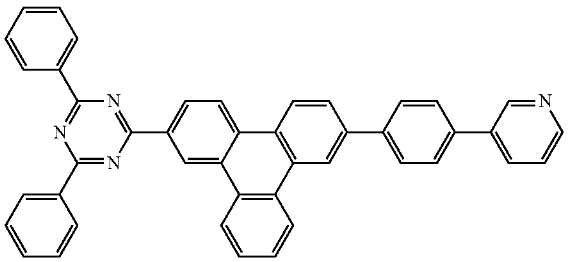

-continued
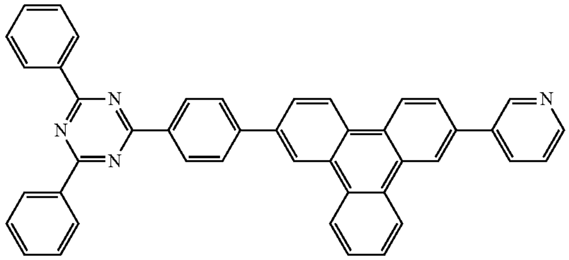
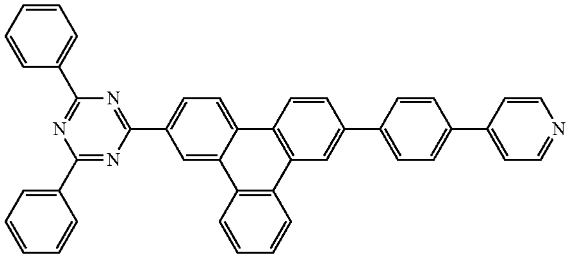
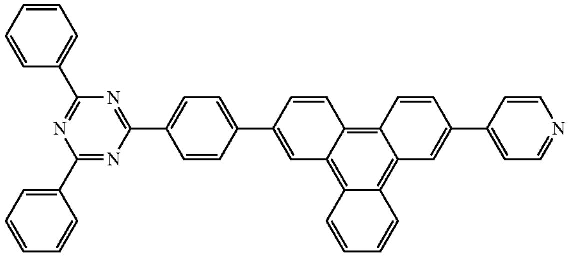
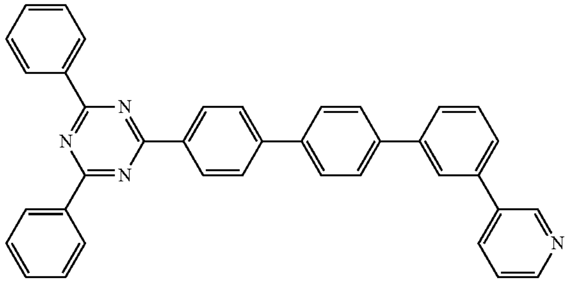
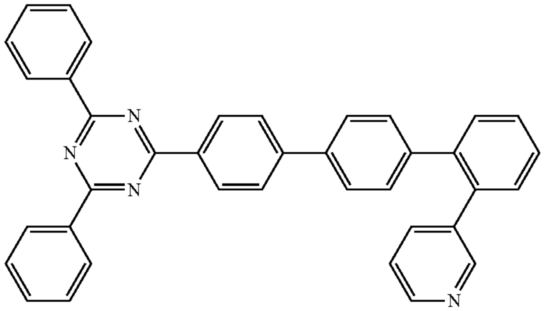
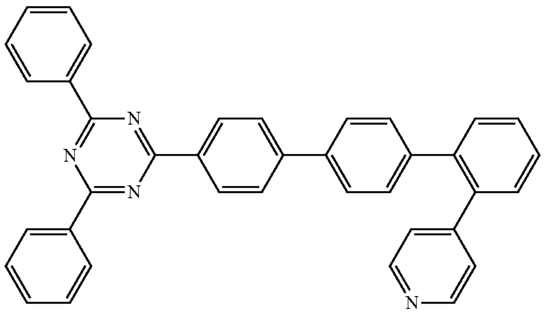
-continued
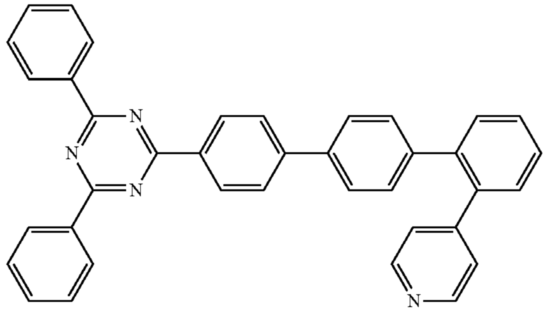
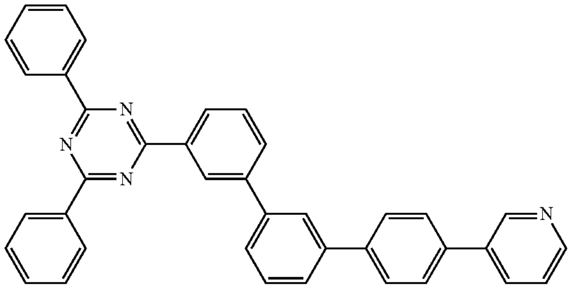
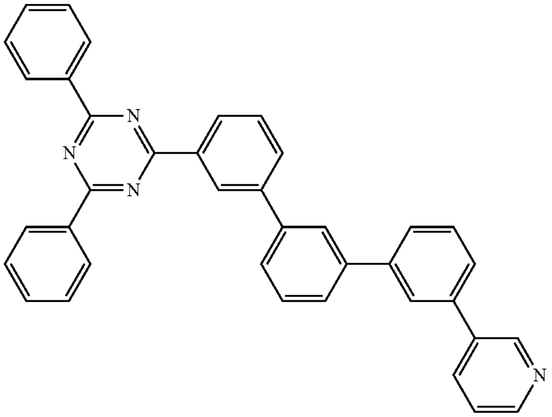
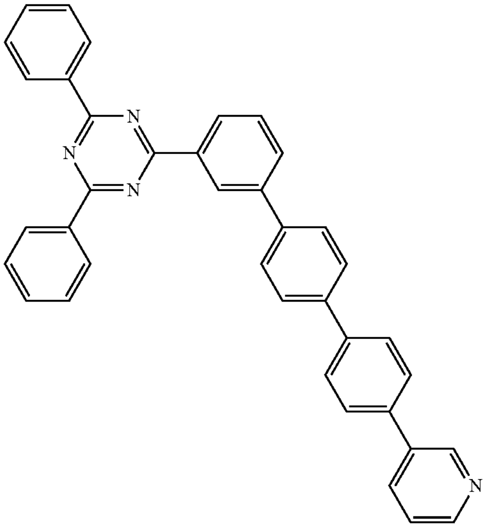

-continued
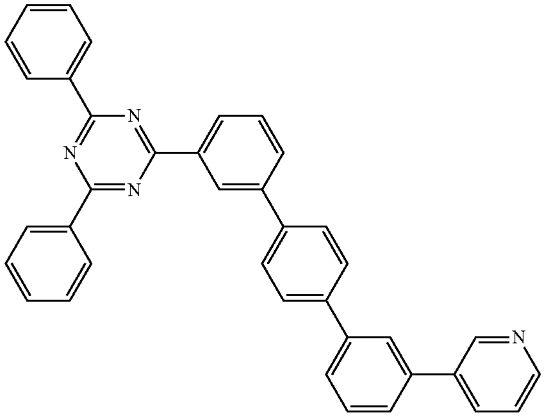
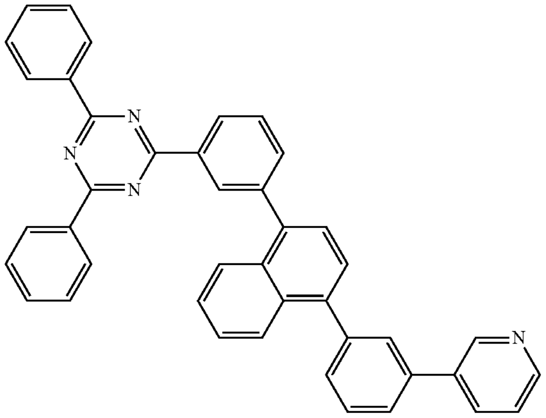
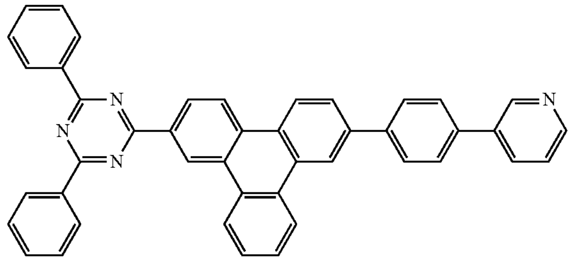
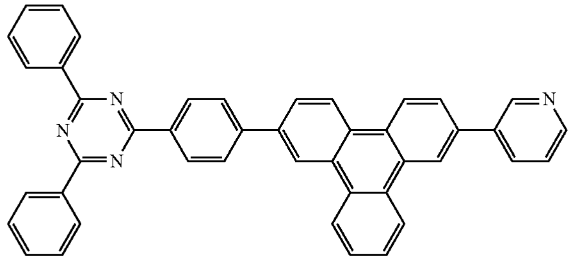
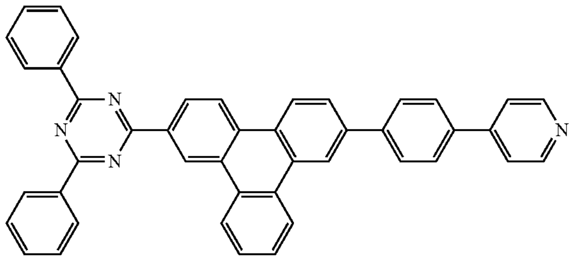
-continued
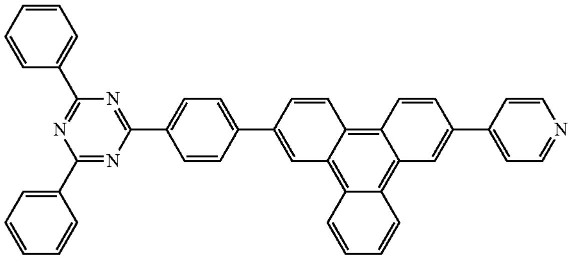
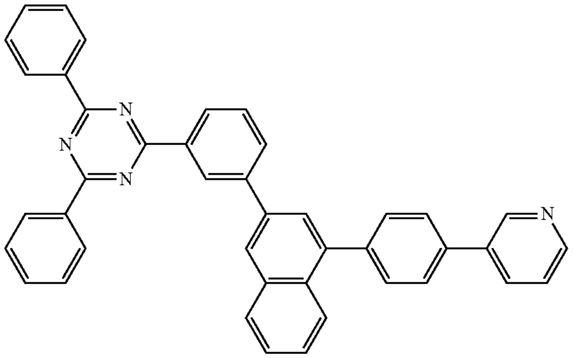
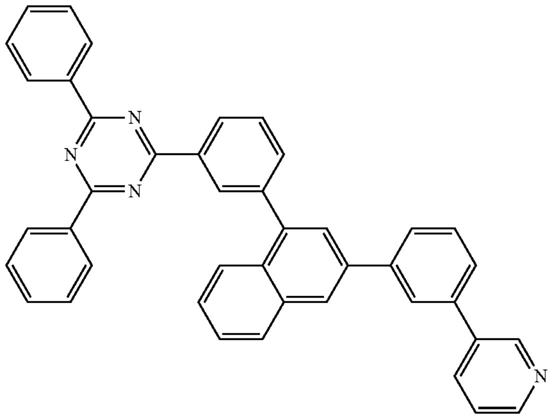
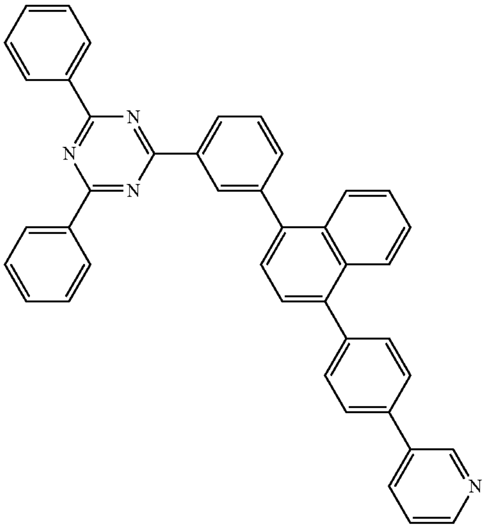

-continued
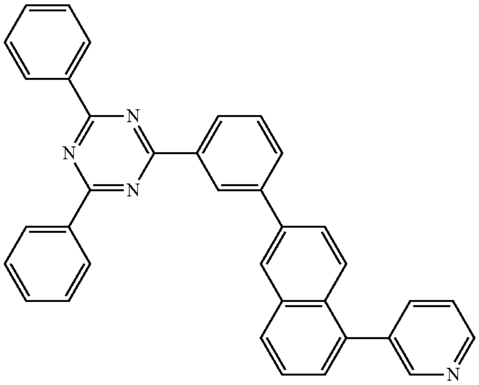
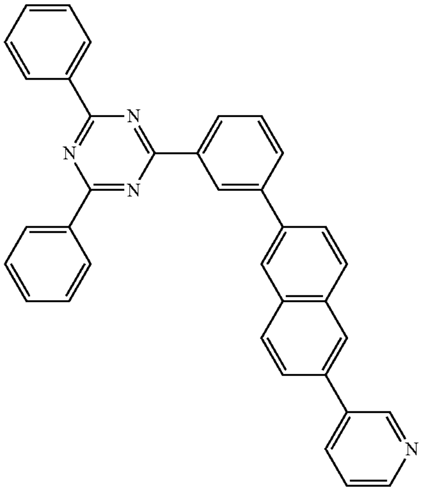
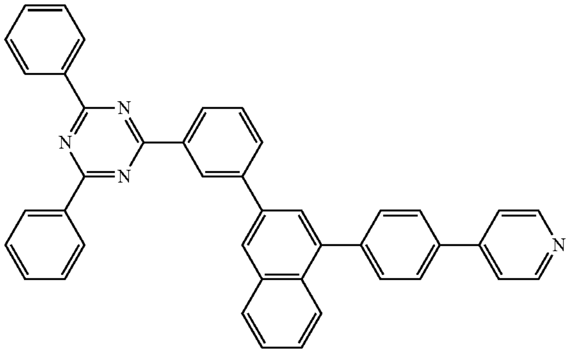
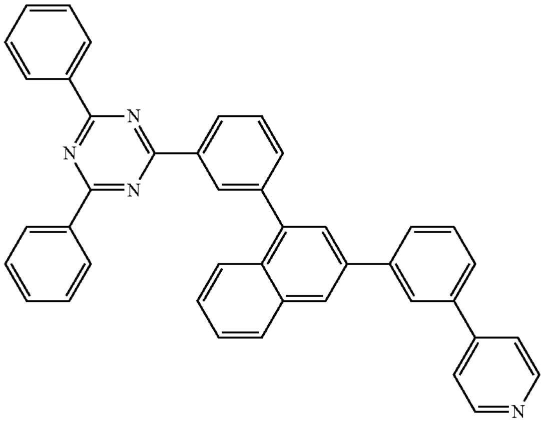
-continued
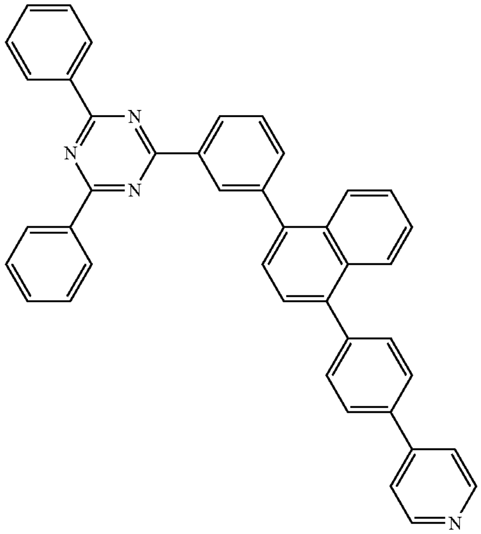
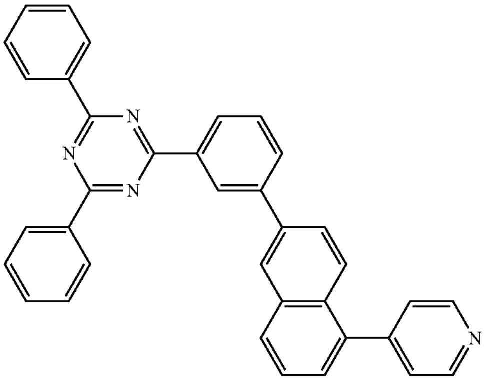
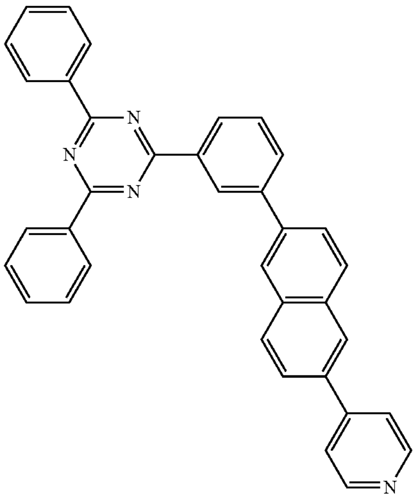 [SMILES: c1ccc(-c2nc(-c3ccccc3)nc(-c3cccc(-c4ccc5cc(-c6ccncc6)ccc5c4)c3)n2)cc1]
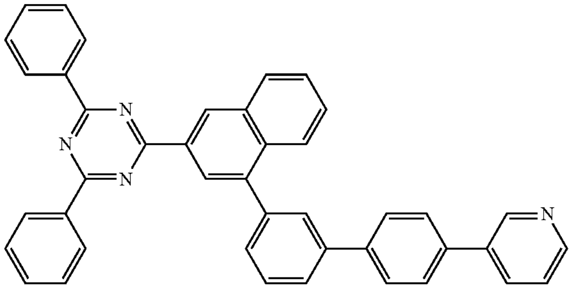

-continued
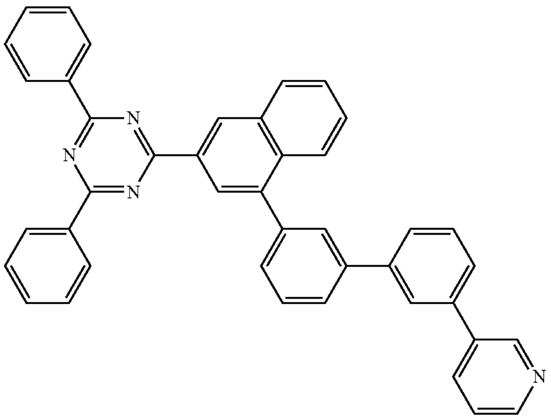
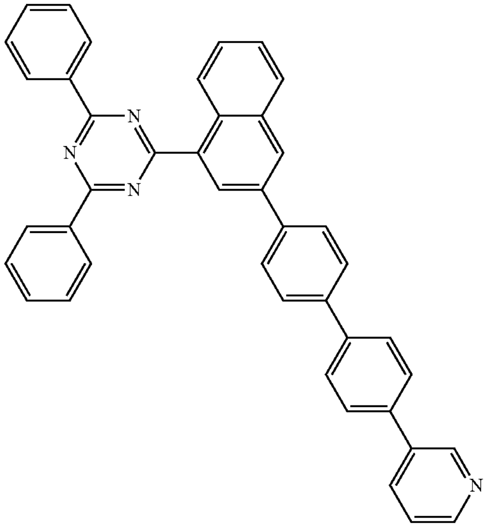
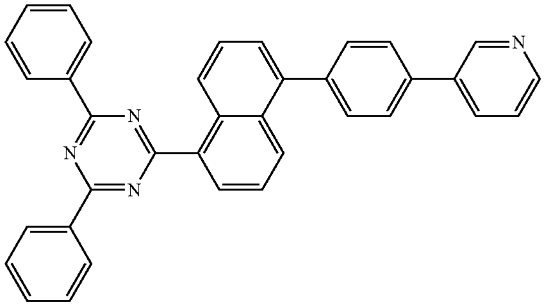
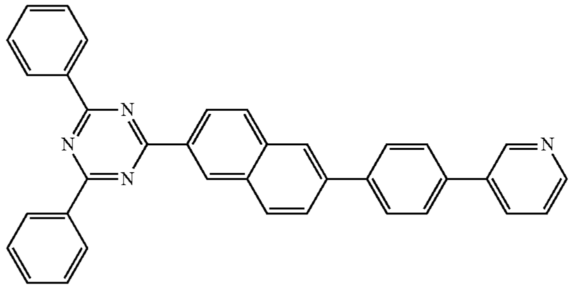 [SMILES: c1ccc(-c2nc(-c3ccccc3)nc(-c3ccc4cc(-c5ccc(-c6cccnc6)cc5)ccc4c3)n2)cc1]
-continued
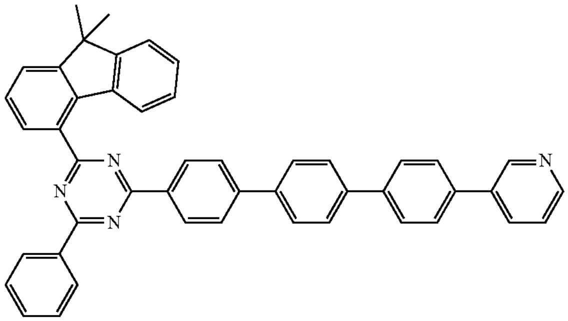
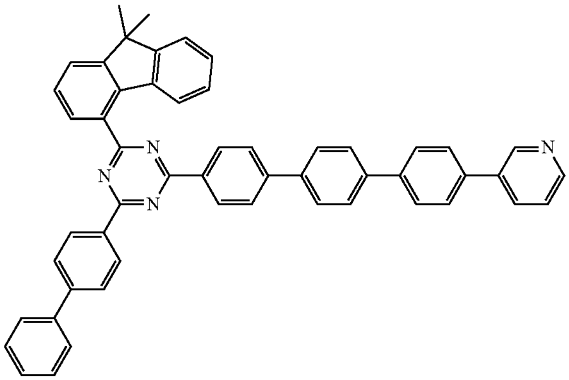
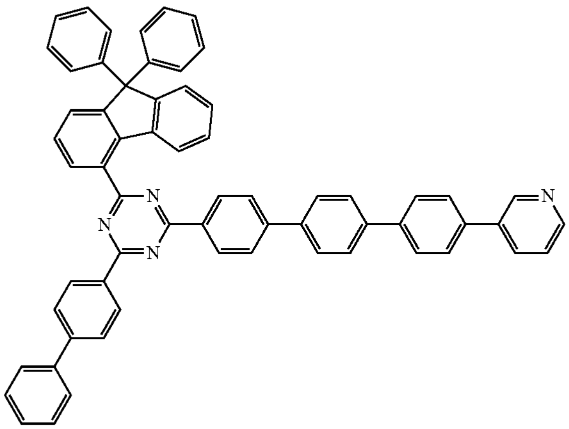
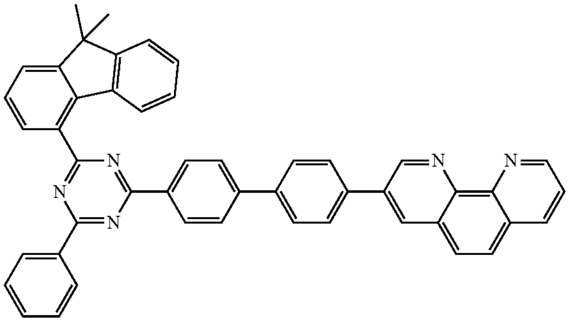

-continued
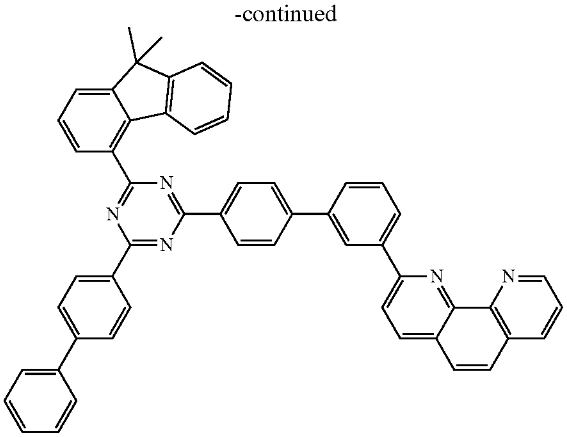
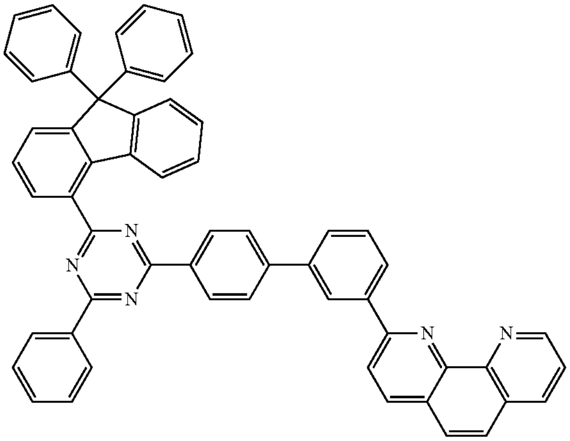
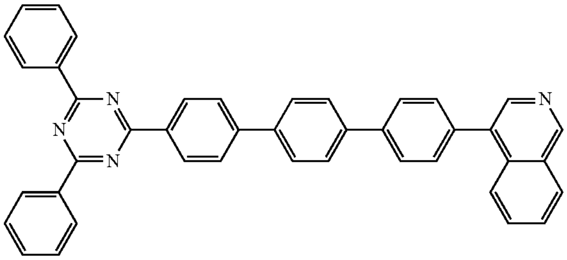
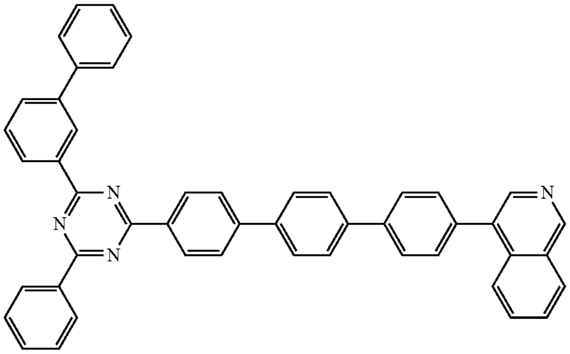
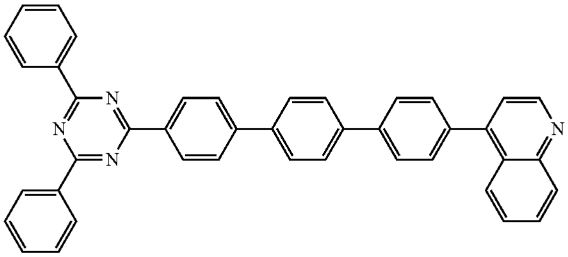
-continued
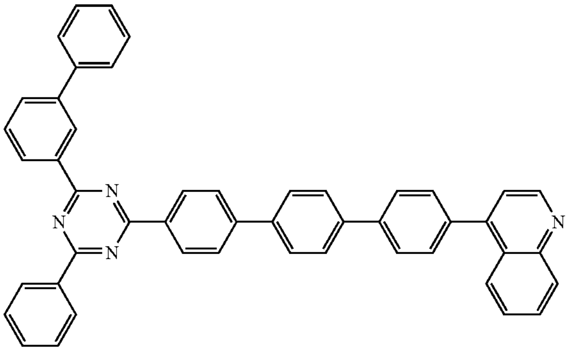
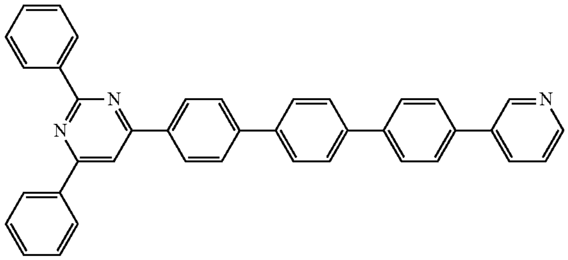
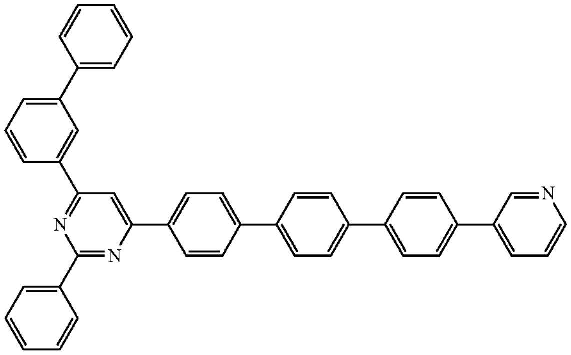
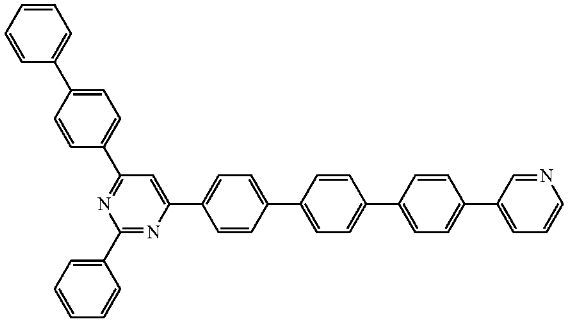
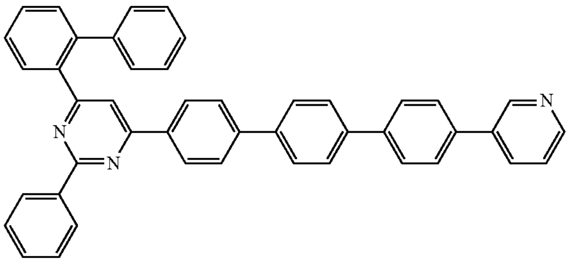

-continued
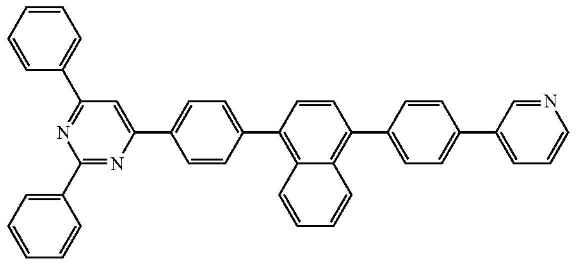
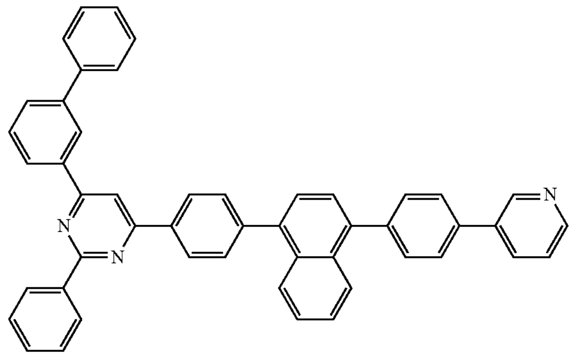
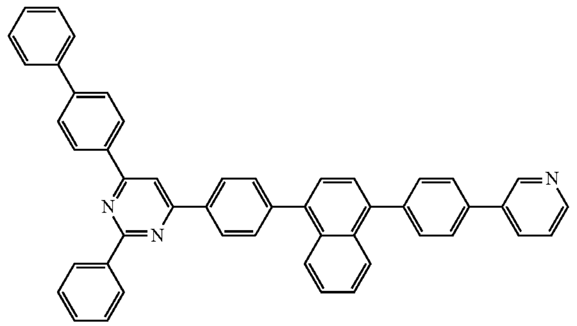
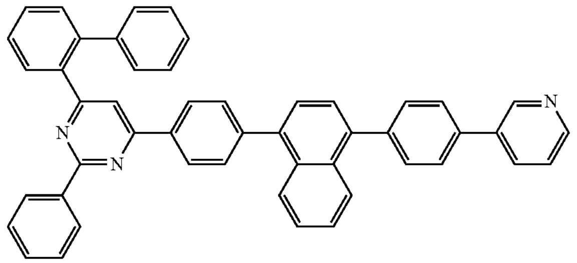
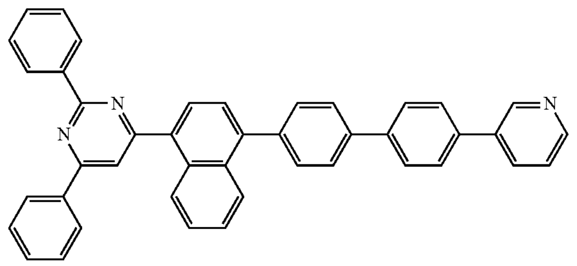
-continued
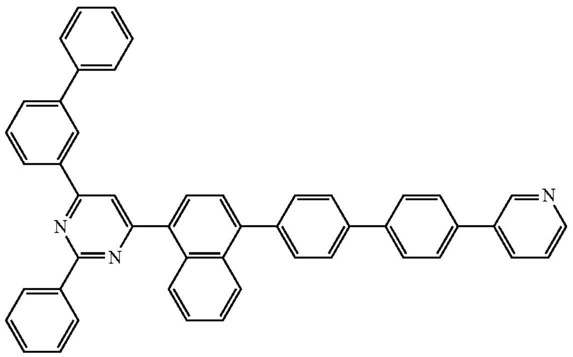
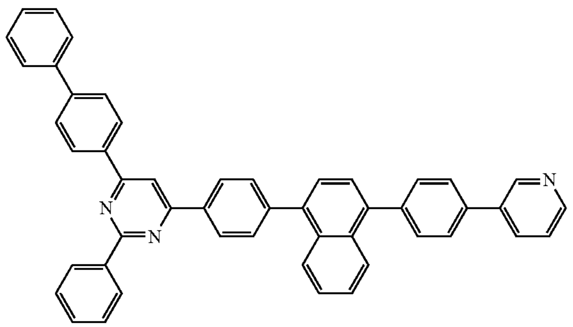
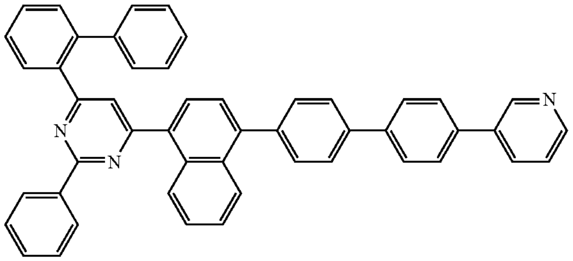
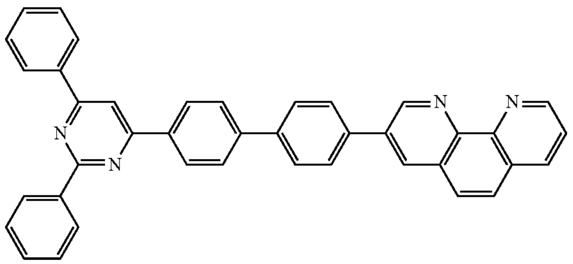
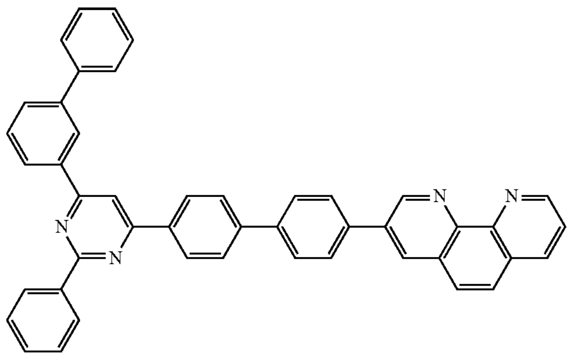

-continued
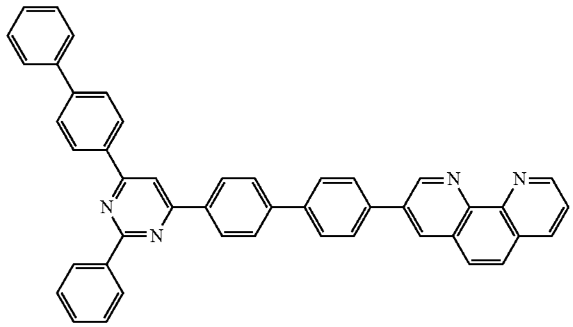
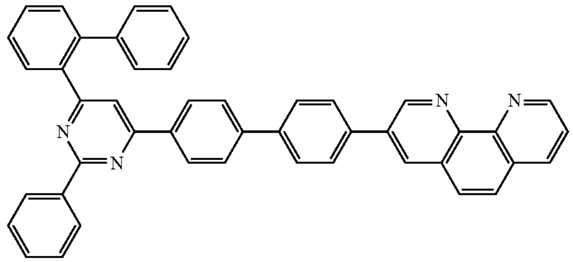
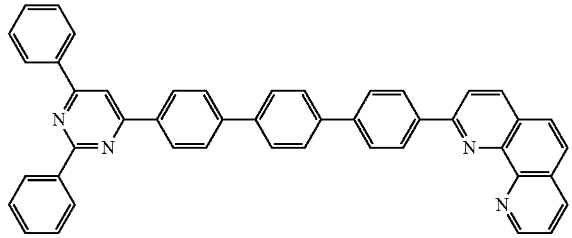
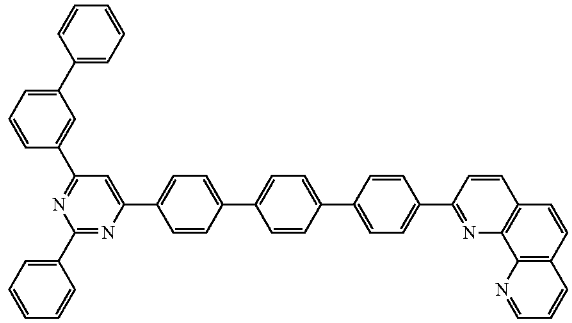
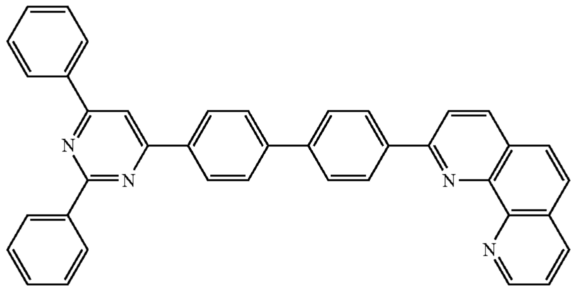
-continued
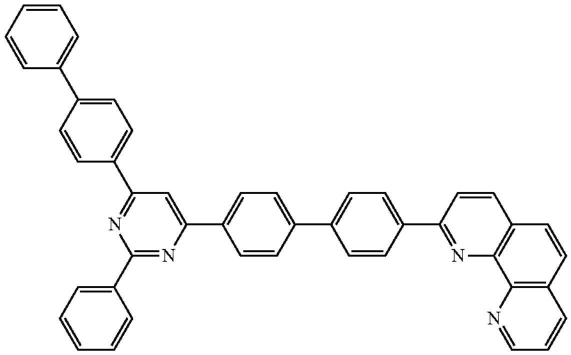
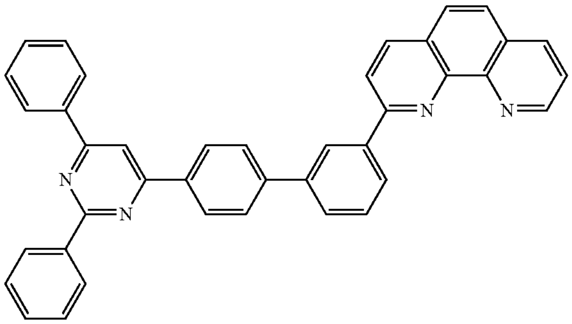
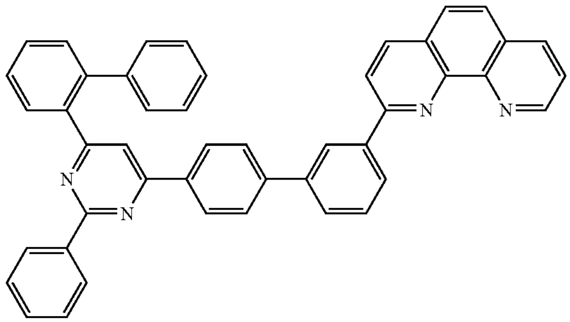
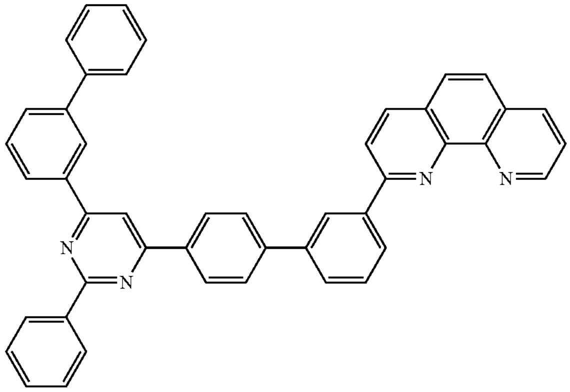

-continued
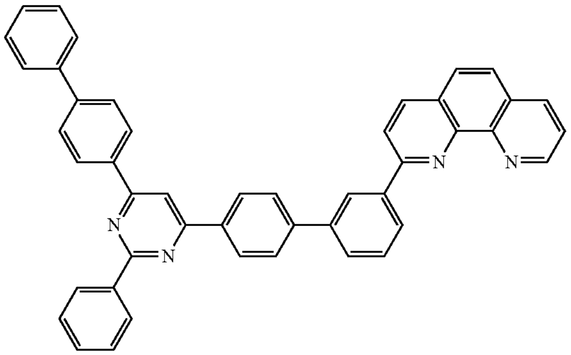
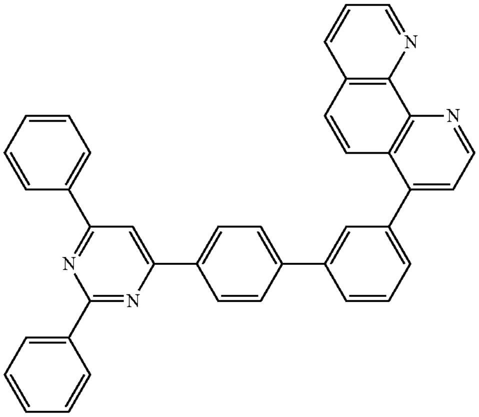
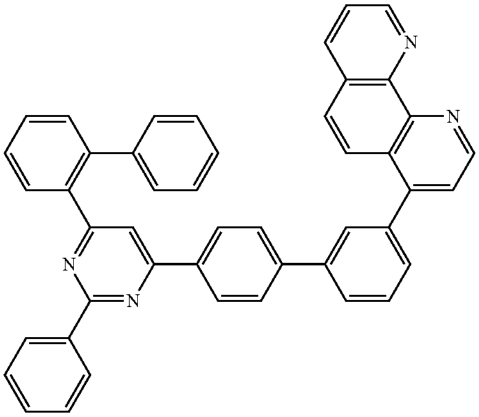
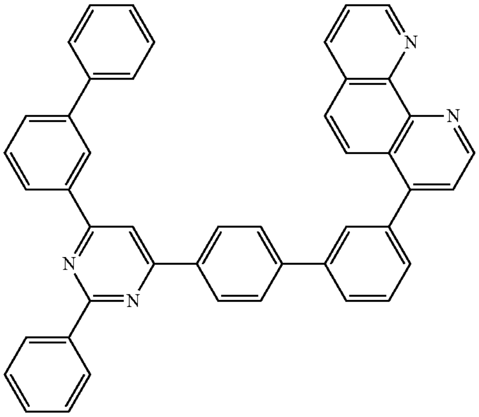
-continued
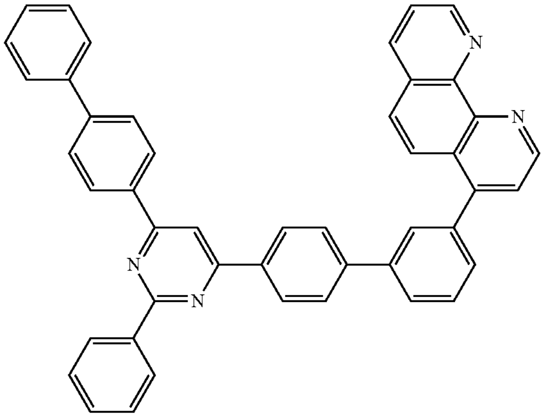
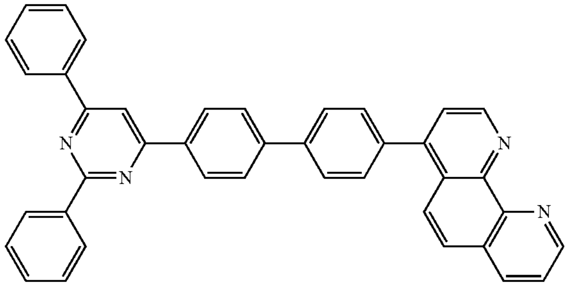
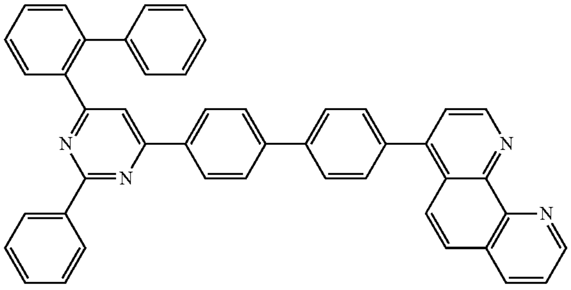
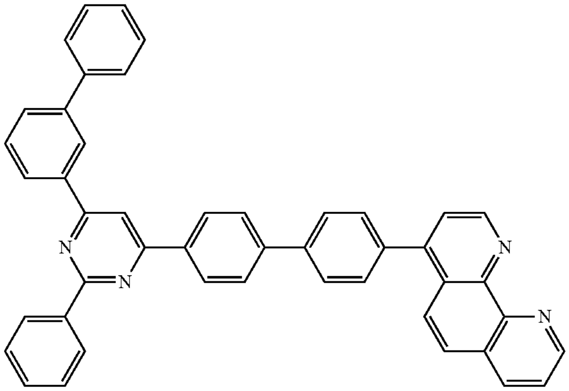

-continued
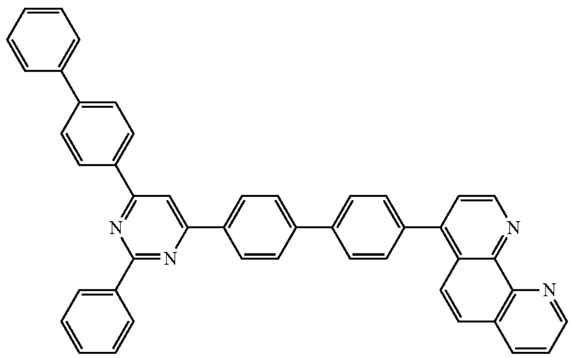
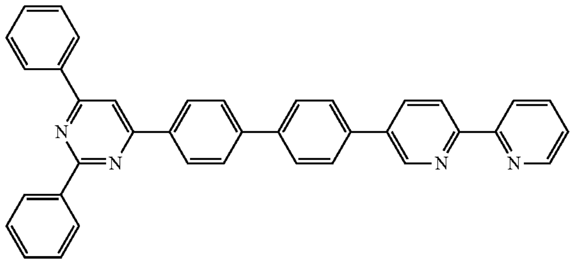
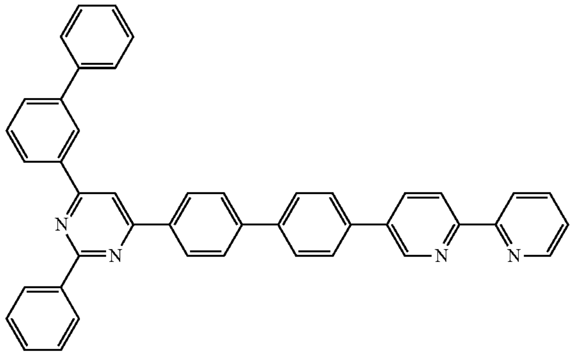
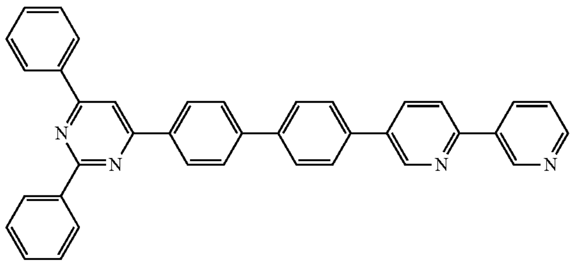
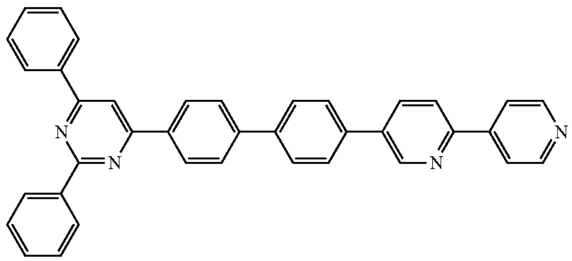
-continued
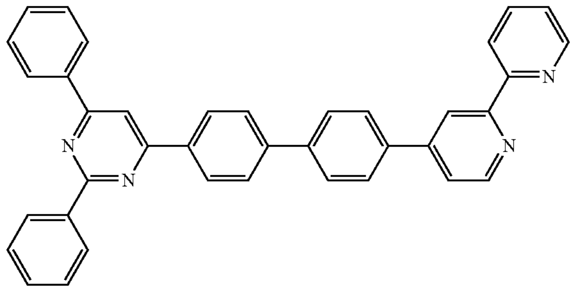
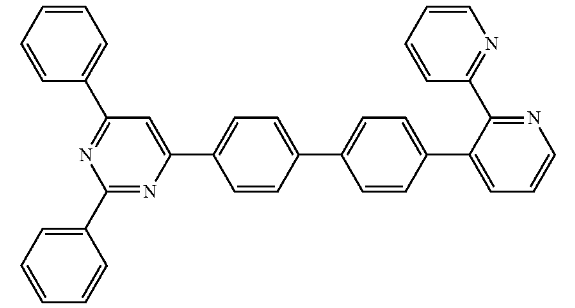
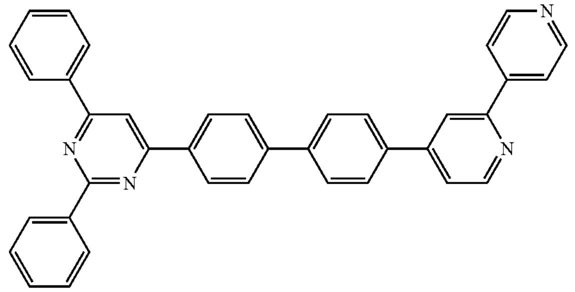
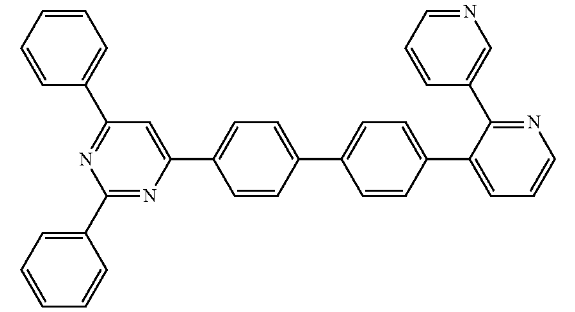
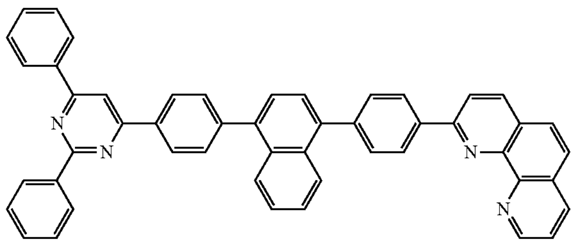

-continued
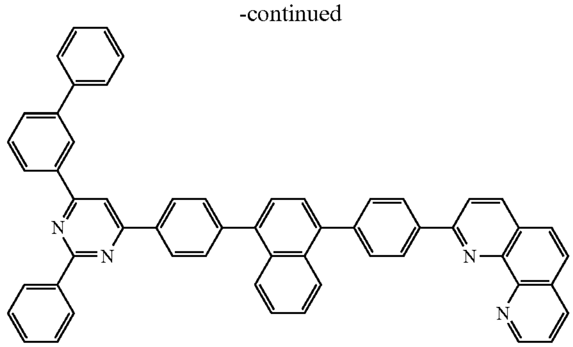
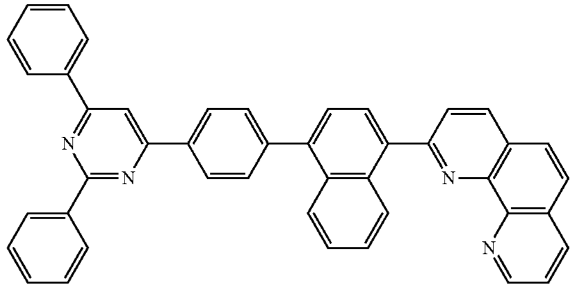
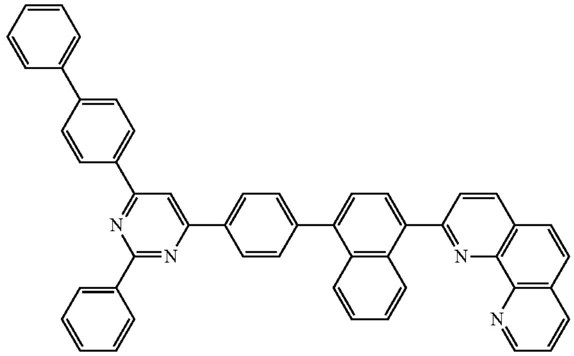
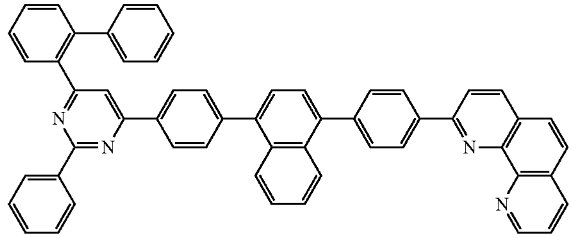
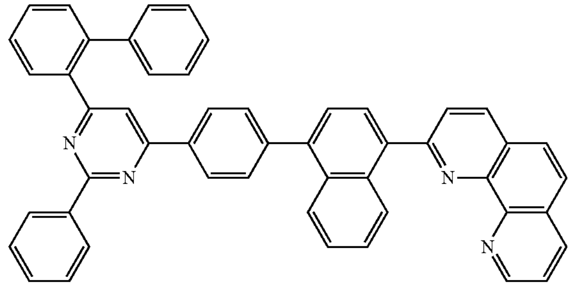
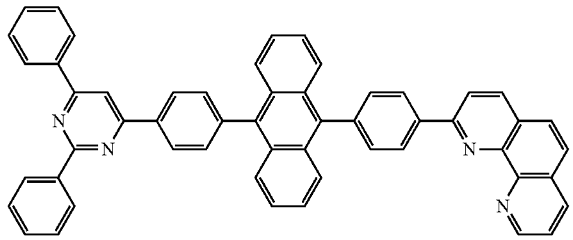
-continued
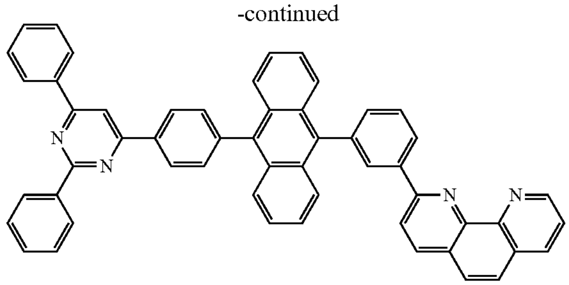
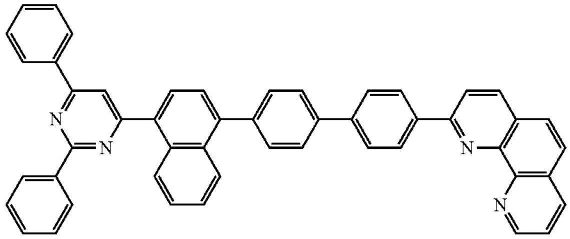
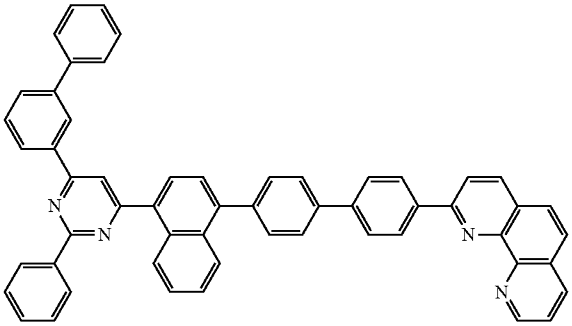
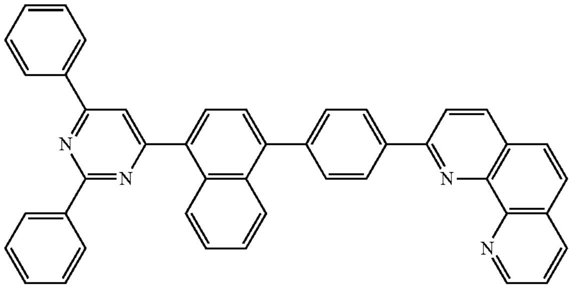
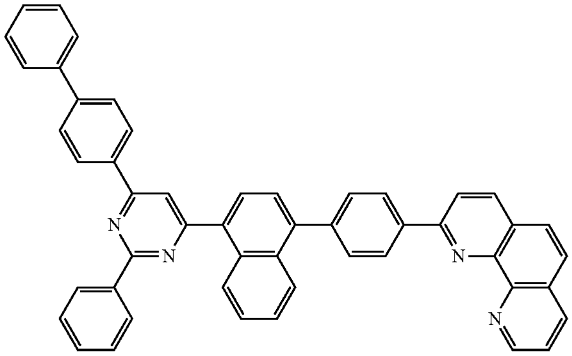
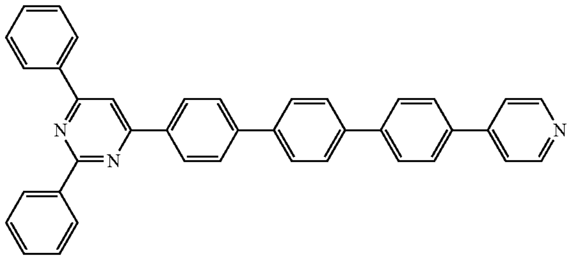

-continued
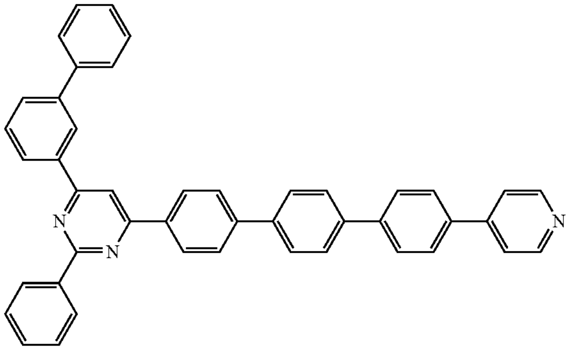
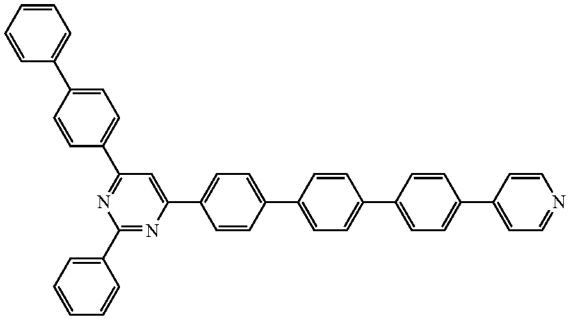
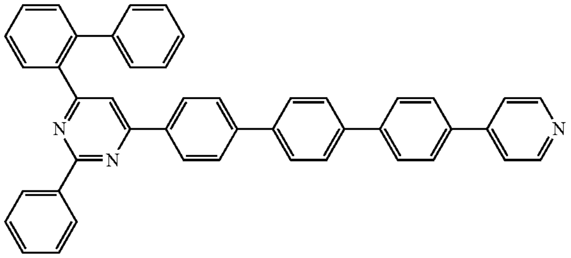
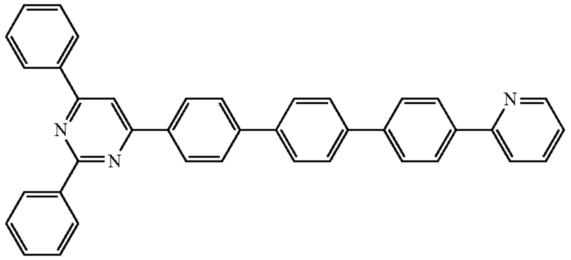
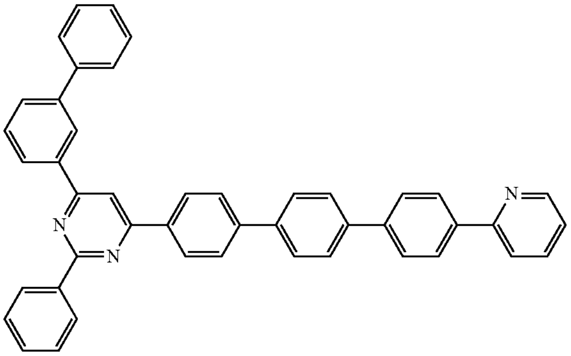
-continued
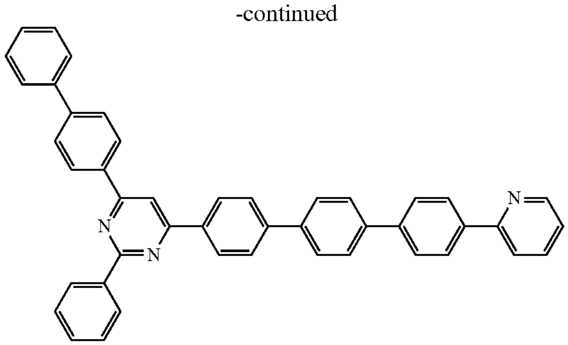
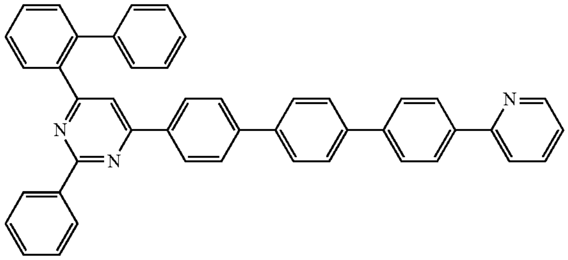
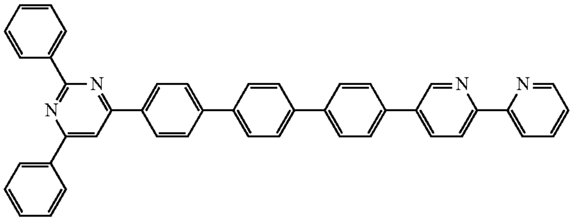
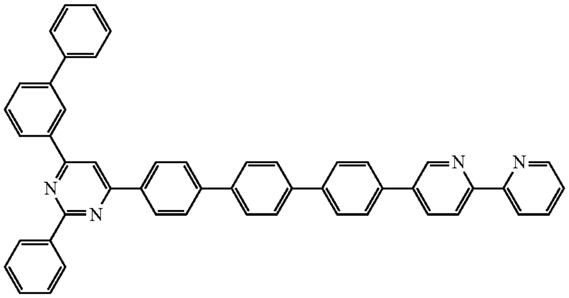
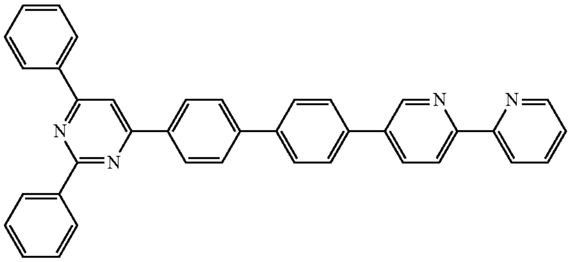
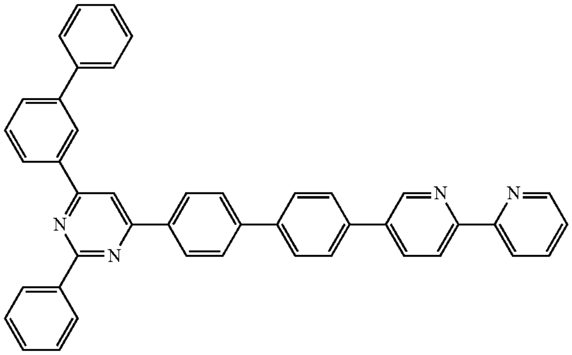

-continued
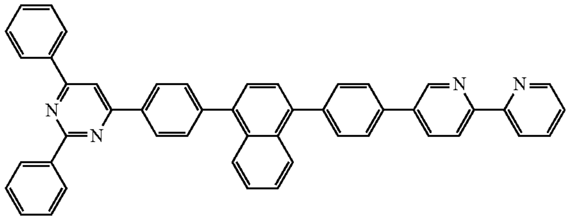
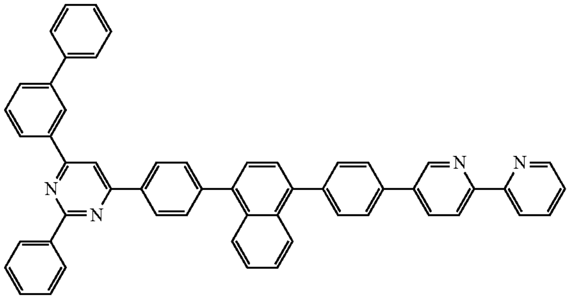
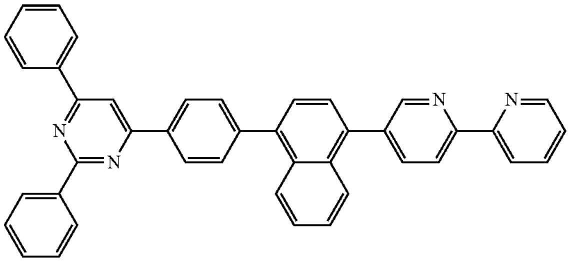
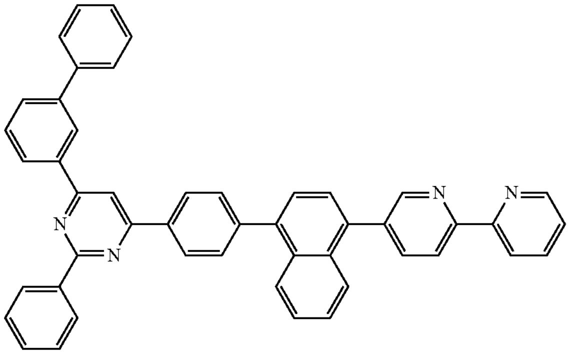
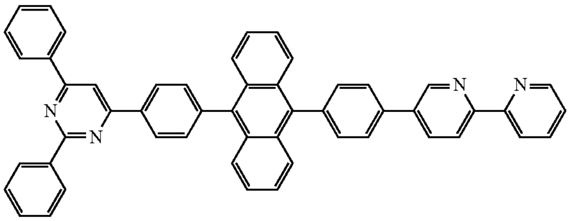
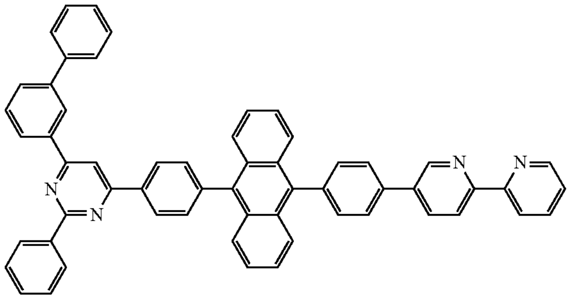
-continued
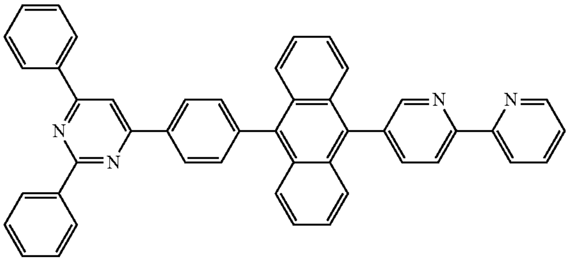
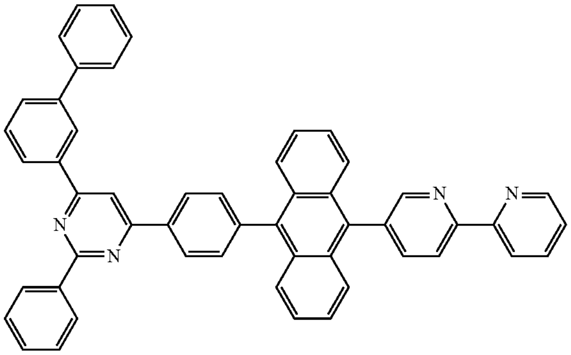
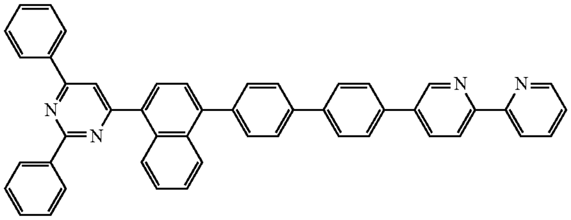
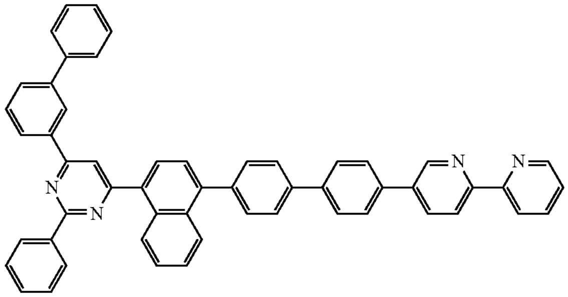
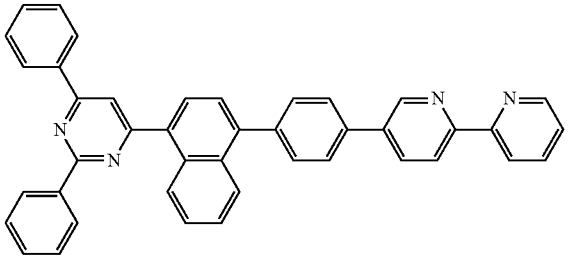

-continued
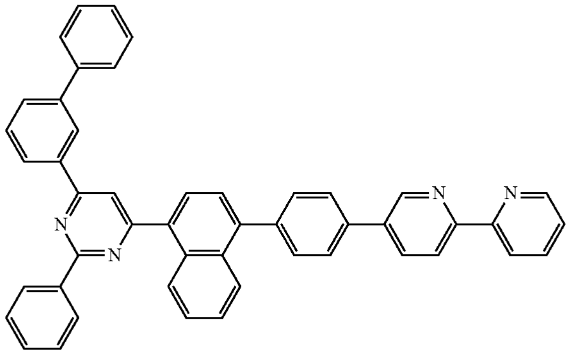
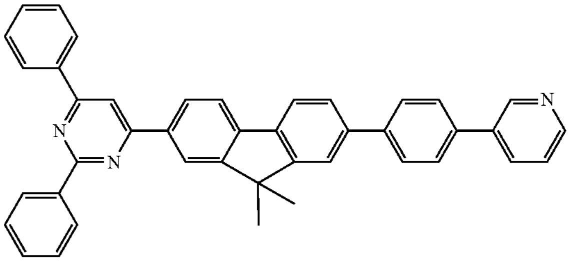
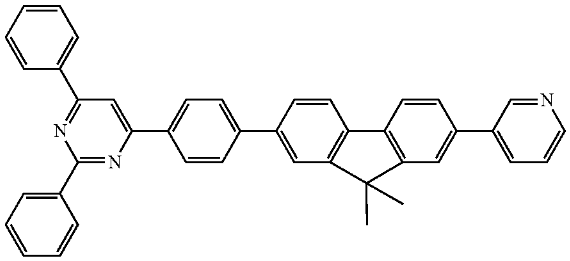
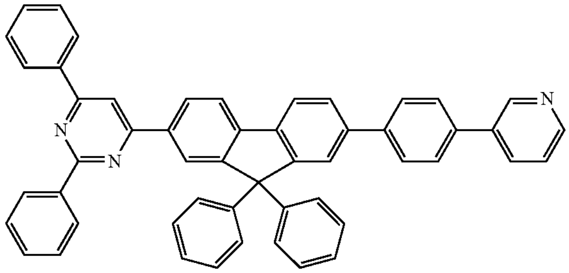
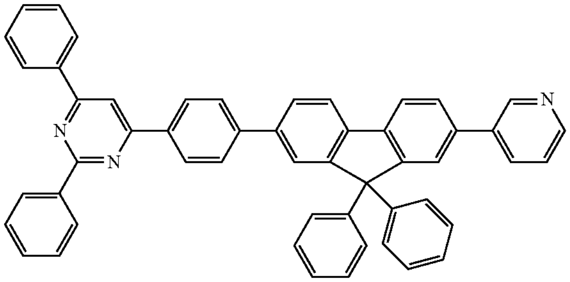
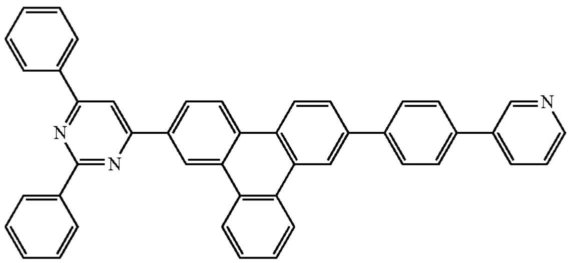
-continued
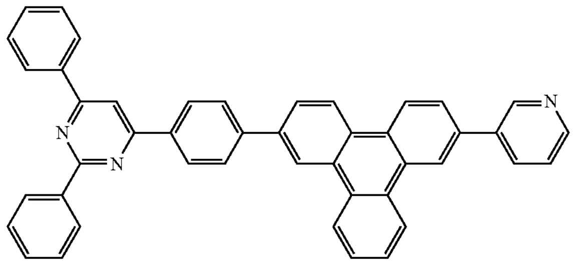
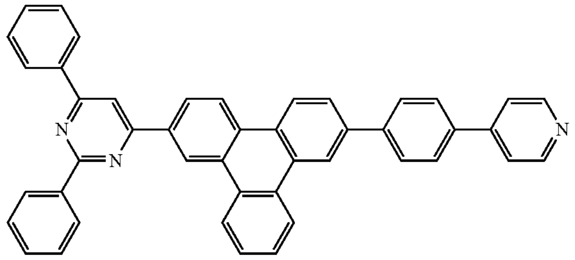
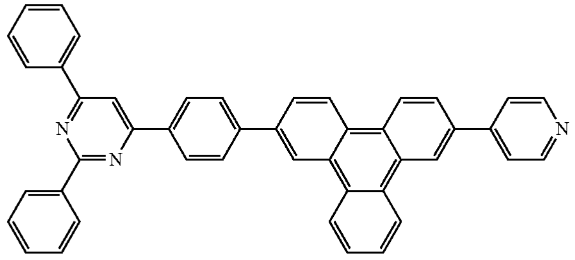
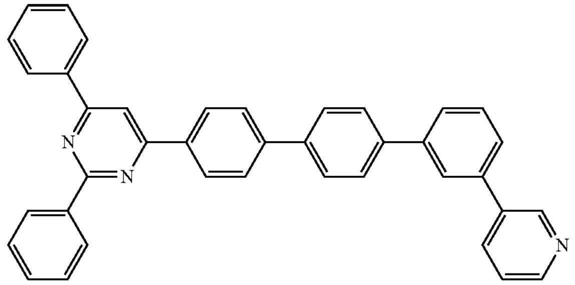
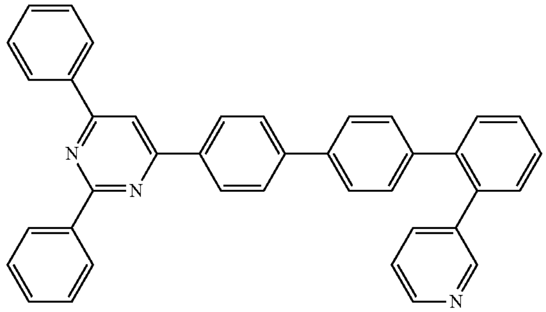
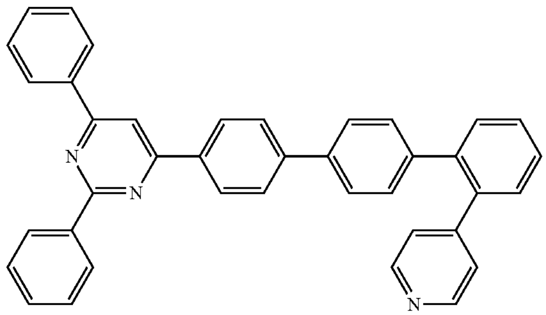

-continued
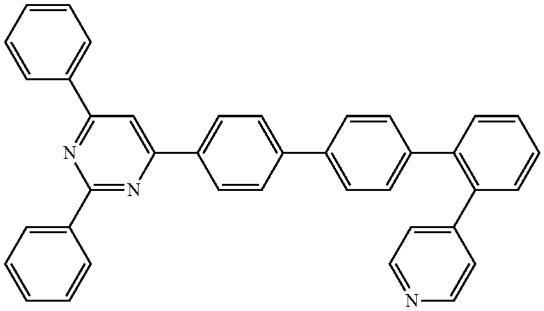
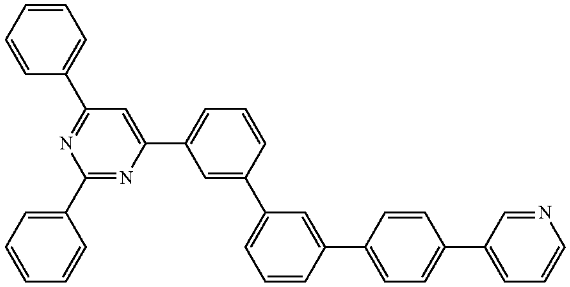
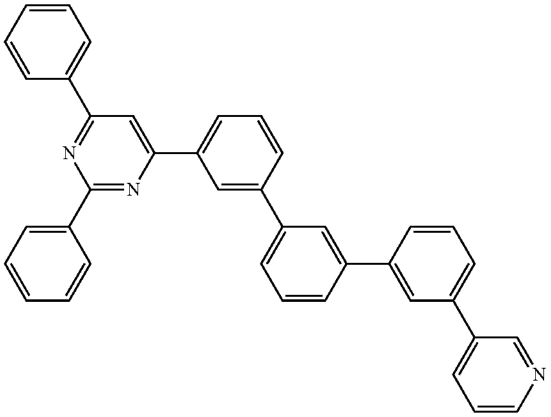
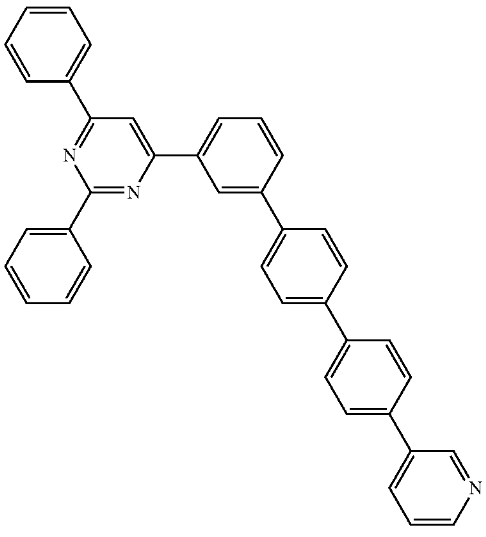
-continued
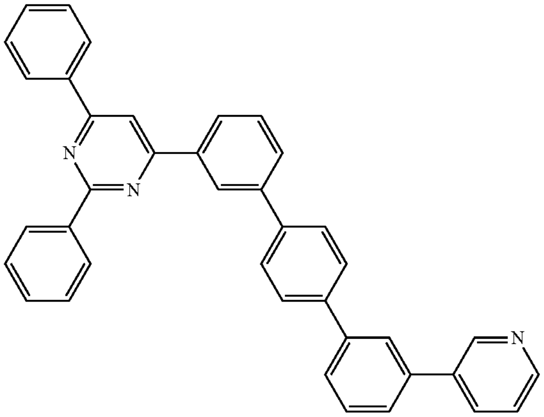
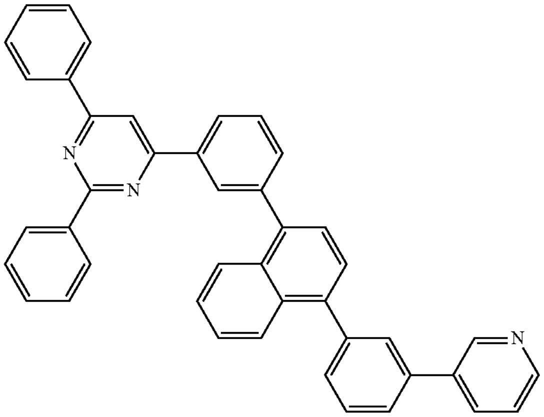 [SMILES: c1ccc(-c2cc(-c3cccc(-c4ccc(-c5cccc(-c6cccnc6)c5)c5ccccc45)c3)nc(-c3ccccc3)n2)cc1]
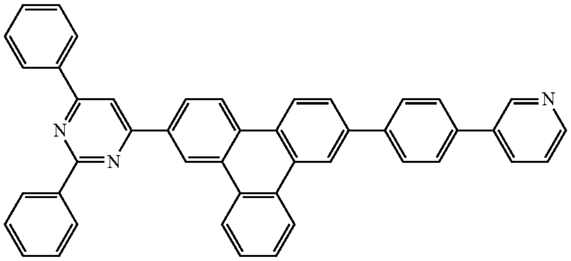
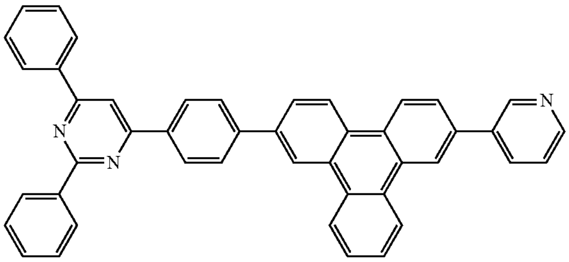
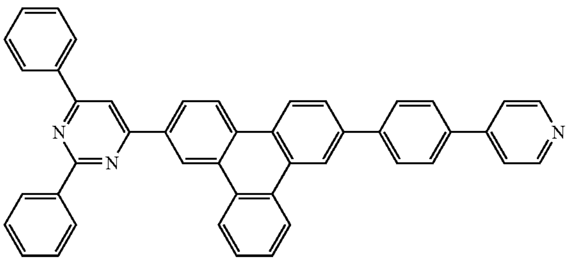

-continued
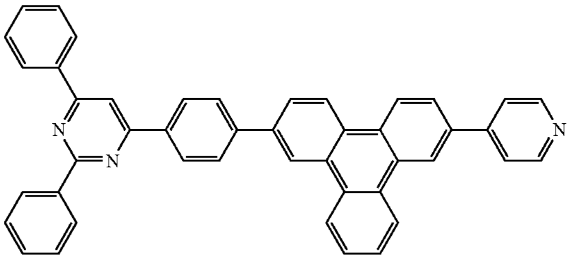
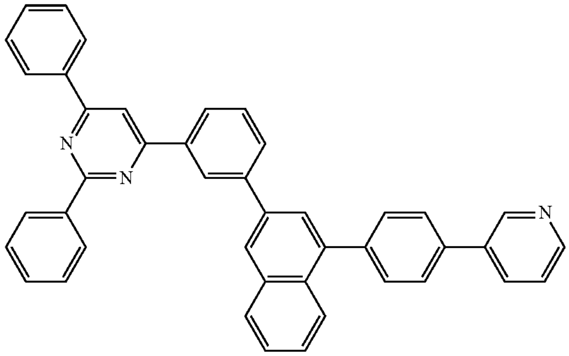
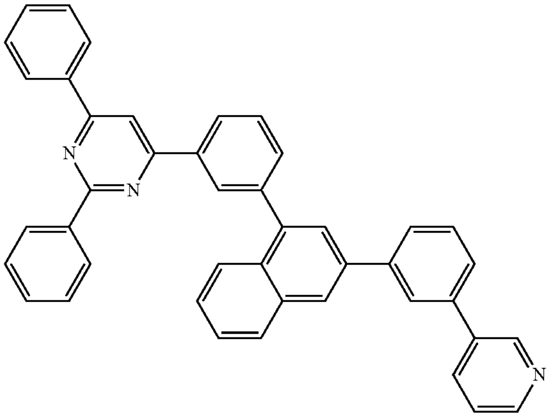
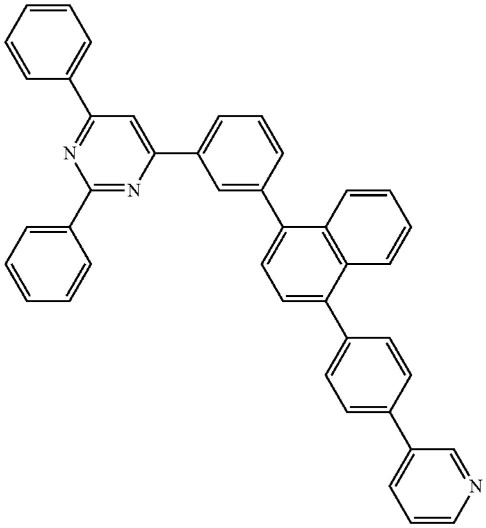
-continued
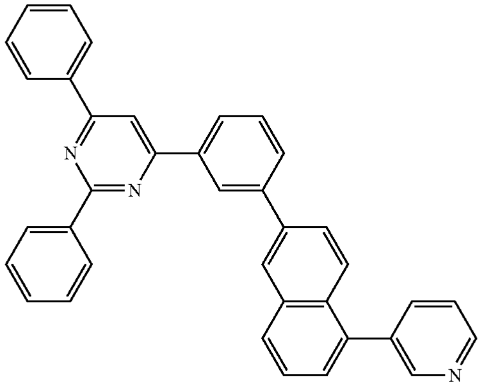
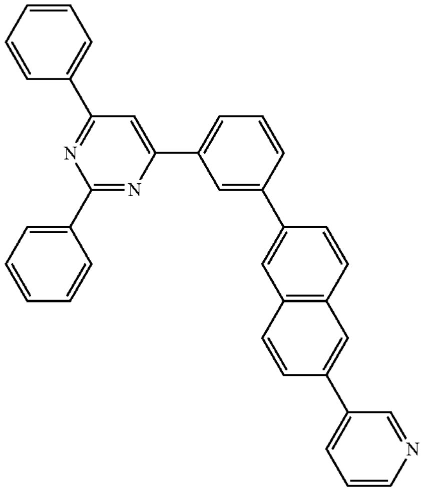 [SMILES: c1ccc(-c2cc(-c3cccc(-c4ccc5cc(-c6cccnc6)ccc5c4)c3)nc(-c3ccccc3)n2)cc1]
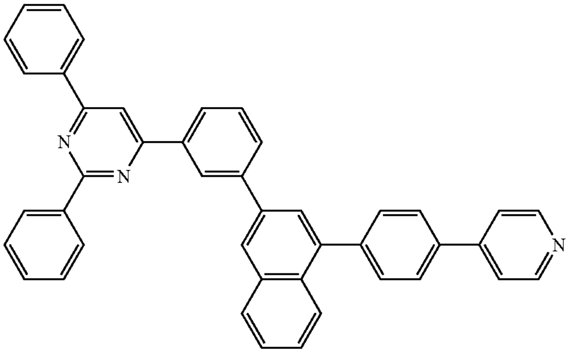
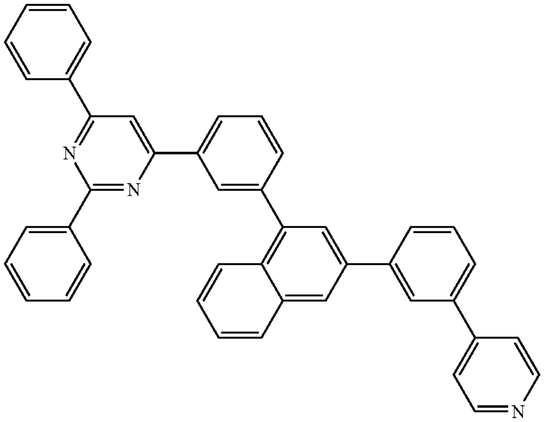

-continued
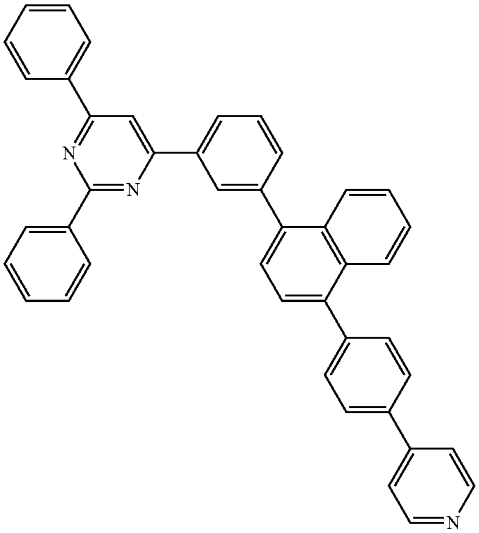
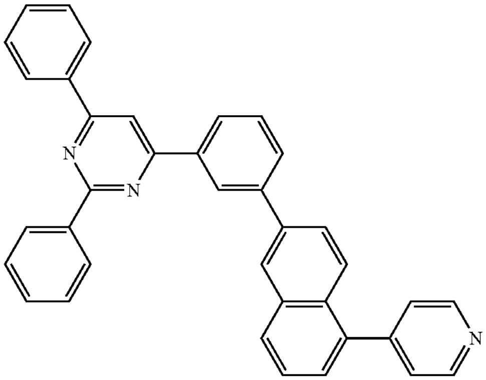
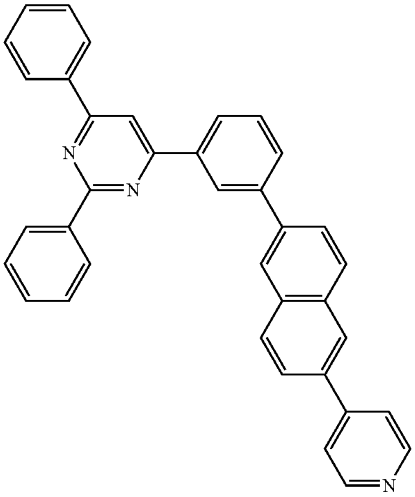
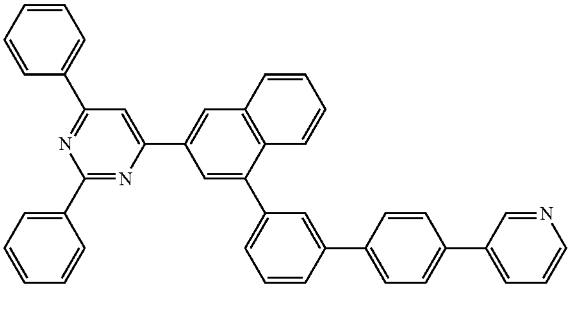
-continued
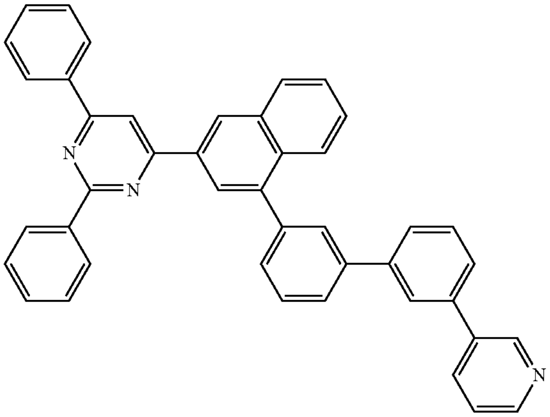
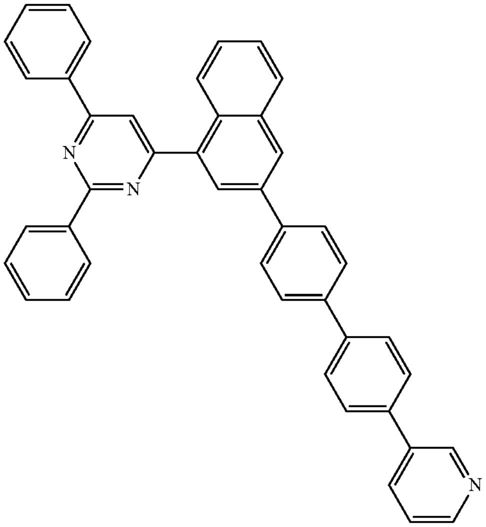
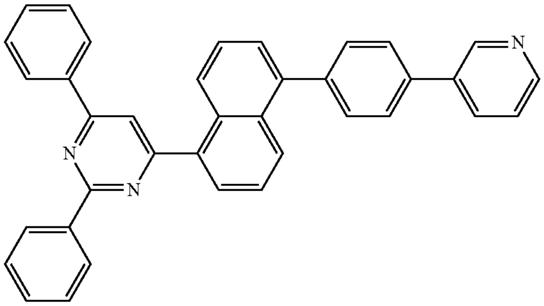
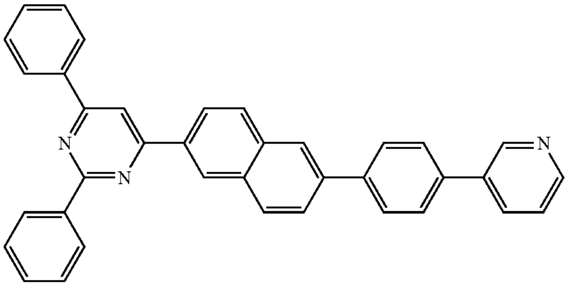

-continued
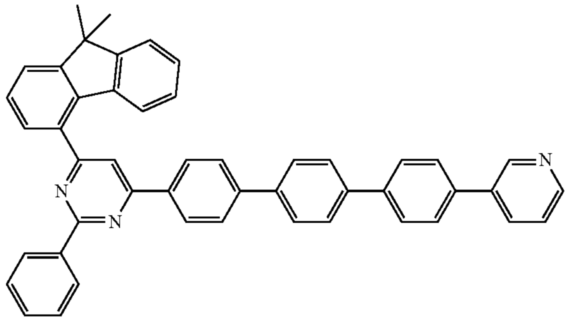
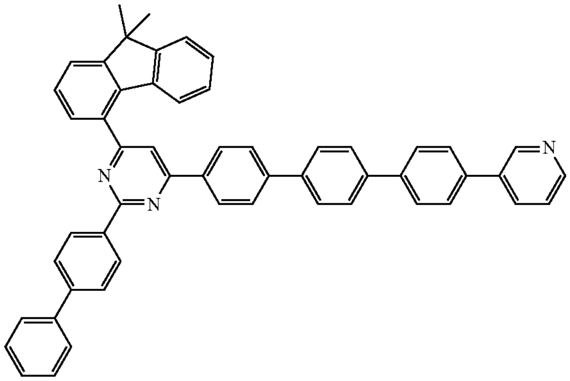
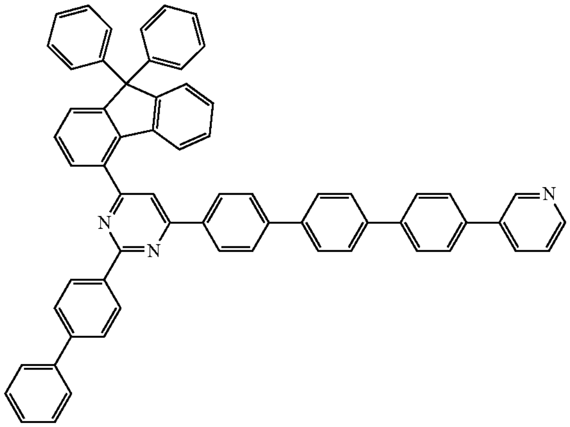
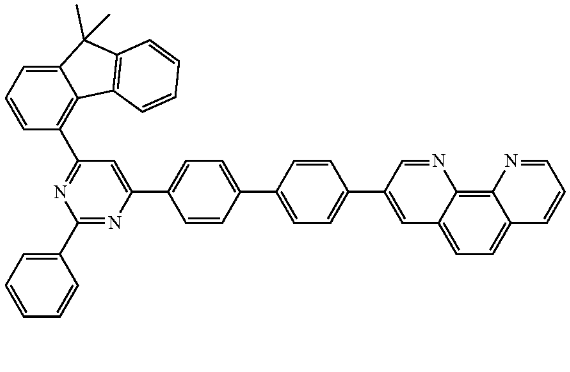
-continued
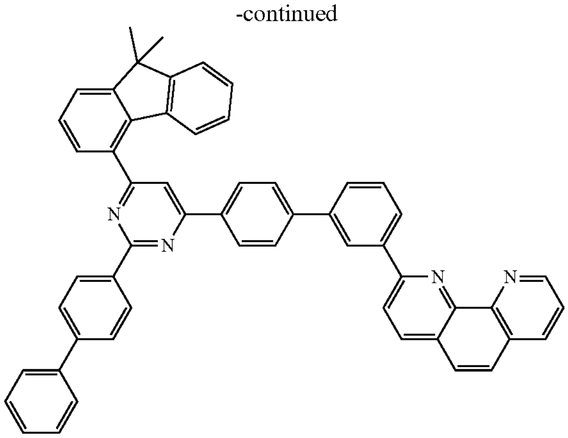
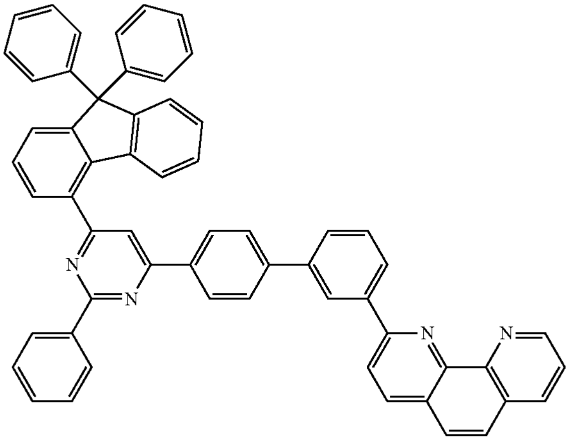
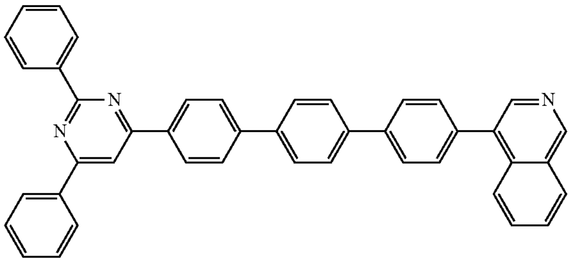
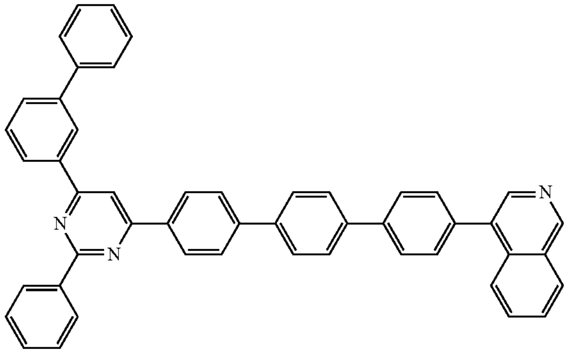
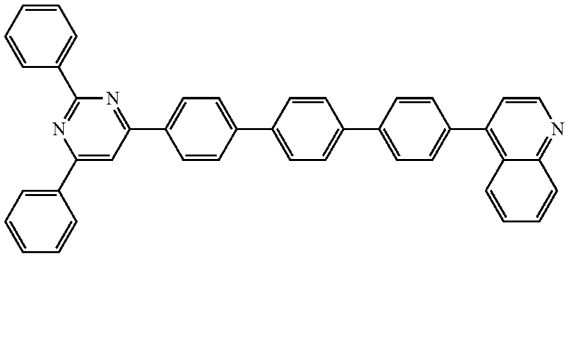

-continued

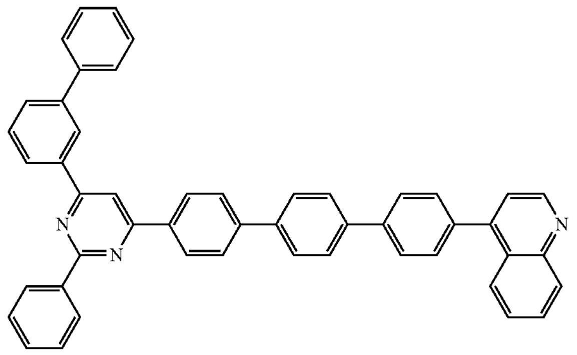

Synthesis of the Compounds of Formula (I)

The compounds of formula (I) are generally prepared by methods known in the art.

The general concept for the preparation of the compounds of formula (I) is exemplified in the following scheme (wherein m is 1 and n is 2 and where n and m are 1):

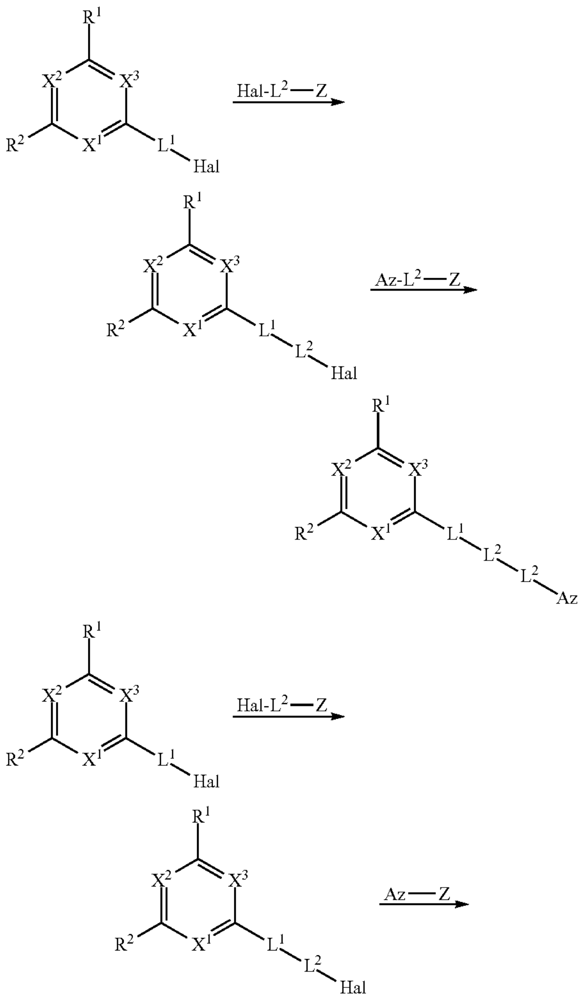

-continued

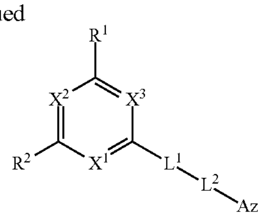

wherein

Z represents —$BQ_2$, wherein Q is an unsubstituted alkyl group having 1 to 8 carbon atoms, an unsubstituted cycloalkyl group having 3 to 6 carbon atoms or a cycloalkyl group having 3 to 6 carbon atoms, substituted by one or two unsubstituted alkyl groups having 1 to 8 carbon atoms, a unsubstituted alkoxy group having 1 to 8 carbon atoms, a hydroxyl group, wherein two alkyl groups Q or two alkoxy groups Q together may form a five or six membered substituted or unsubstituted ring, or —MgX, wherein X is halide, or —Li, preferably —$BQ_2$, wherein Q is an unsubstituted alkyl group having 1 to 8 carbon atoms, an unsubstituted cycloalkyl group having 3 to 6 carbon atoms or a cycloalkyl group having 3 to 6 carbon atoms, substituted by one or two unsubstituted alkyl groups having 1 to 8 carbon atoms, a unsubstituted alkoxy group having 1 to 8 carbon atoms, a hydroxyl group, wherein two alkyl groups Q or two alkoxy groups Q together may form a five or six membered substituted or unsubstituted ring, more preferably —$BQ_2$, wherein two alkyl groups Q or two alkoxy groups Q together may form a five or six membered substituted or unsubstituted ring, Hal is a halide, preferably selected from the group consisting of I, F, Cl and Br, or a pseudohalide, preferably selected from the group consisting of mesylate, triflate, tosylate and nonaflate.

In the case that Z is —$BQ_2$, the compounds are for example prepared from the corresponding halides in the presence of a borylation reagent:

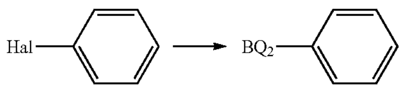

Suitable borylation reagents are boronic acids or boronic esters, for example alkyl-, alkenyl-, alkynyl-, and aryl-boronic esters. Preferred borylation reagents have the general formula $Q_2BH$ or $Q_2B$—$BQ_2$, wherein Q is defined above. For example, Pinacolborane (Hbpin), Bis(pinacolato) diboron ($B_2Pin_2$), and bis(catecholato)diborane ($B_2Cat_2$). Further suitable borylation reagents are dioxaborolanes, for example 2-isopropoxy-4,4,5,5-tetramethyl-1,3,2-dioxaborolane.

The borylation can be carried out in the presence or in the absence of a catalyst.

In the case that the borylation is carried out in the absence of a catalyst, the halide is for example treated with an organolithium reagent followed by borylation with a borylation agent. Suitable borylation agents are mentioned above.

In the case that the borylation is carried out in the presence of a catalyst, preferred catalysts are Pd catalysts. Suitable Pd catalysts are for example Pd(0) complexes with bidentate ligands like dba (dibenzylideneacetone), or Pd(II) salts like $PdCl_2$ or $Pd(OAc)_2$ in combination with bidentate phosphine ligands such as dppf ((diphenylphosphino)ferrocene), dppp ((diphenylphosphino)propane), BINAP (2,2'-Bis(diphenylphosphino)-1,1'-binaphthyl), Xantphos (4,5-Bis(diphenylphosphino)-9,9-dimethylxanthene), DPEphos (Bis[(2-diphenylphosphino)phenyl]ether) or Josiphos, or in combination with monodentate phosphine-ligands like triphenylphosphine, tri-ortho-tolyl phosphine, tri-tert-butylphosphine, tricyclohexylphosphine, 2-Dicyclohexylphosphino-2',6'-dimethoxybiphenyl (SPhos), 2-Dicyclohexylphosphino-2',4',6'-triisopropylbiphenyl (XPhos), or N-heterocyclic carbenes such as 1,3-Bis(2,6-diisopropylphenyl)imidazol-2-ylidene (IPr), 1,3-Dimesityl-imidazol-2-ylidene (Imes).

Hal and —$BQ_2$ are as defined above.

Josiphos:

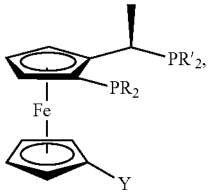

wherein R and R' are generally substituted or unsubstituted phenyl.

Details of the reaction steps and process conditions are mentioned in the examples of the present application. The production method of the compounds of formula (I) according to the present invention is not particularly limited and it is produced according to known methods, for example, by a Suzuki coupling as described in *Journal of American Chemistry Society,* 1999, 121, 9550 to 9561 or *Chemical Reviews,* 1995, 95, 2457 to 2483 or Kumada coupling described in *Org. Lett.,* 2010, 12, 2298-2301 or *Angew. Chem.,* 2002, 114, 4218-4221.

At Least One Rare Earth Metal, Rare Earth Metal Compound, and/or Rare Earth Metal Complex The electron-transporting zone of the organic electroluminescence device according to the present invention comprises beside at least one compound represented by formula (I) at least one rare earth metal, rare earth metal compound, and/or rare earth metal complex.

The rare earth metal complexes are not particularly limited as long as they contain, as a metal ion, at least one rare earth metal ion. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, and azomethines.

Examples of the rare earth metal compounds include one or more oxides, nitrides, oxidized nitrides or halides, especially fluorides, containing at least one element selected from Yb, Sc, Y, Ce, Gd, Tb and the like, for example $YbF_3$, $ScF_3$, $ScO_3$, $Y_2O_3$, $Ce_2O_3$, $CeO_2$, $GdF_3$ and $TbF_3$. Among these, $YbF_3$, $ScF_3$ and $TbF_3$ are preferable.

Preferably, at least one rare earth metal is present in the electron transporting zone of the organic electroluminescence device of the present invention. Examples of rare earth metals are La, Eu, Sm, Yb, Sc, Y, Ce, Gd and Tb, preferably Yb.

In a preferred embodiment, the organic electroluminescence device comprises Yb as rare earth metal in the electron transporting zone.

Regarding the addition form of the at least one rare earth metal, rare earth metal compound, and/or rare earth metal complex, it is preferred that the at least one rare earth metal, rare earth metal compound, and/or rare earth metal complex be formed in a shape of a layer, an island or a dopant, preferably in a shape of a layer or an island, preferably in the interfacial region of the electron transporting zone. More preferably, the at least one rare earth metal, rare earth metal compound, and/or rare earth metal complex forms a separate interfacial layer or island between the cathode and the electron transporting zone, preferably between the cathode and the electron-transporting layer or—between the cathode and the electron-injecting layer, if an electron-injecting layer is present. Most preferably, the at least one rare earth metal, rare earth metal compound, and/or rare earth metal complex is employed as electron-injecting layer.

Preferably, the layer or island comprises or consists of the at least one rare earth metal, rare earth metal compound, and/or rare earth metal complex, preferably of a rare earth metal, more preferably of Yb.

One method for the formation of the at least one rare earth metal, rare earth metal compound, and/or rare earth metal complex in form of a dopant is a method in which an organic compound (e.g. an electron-injecting material) for forming the interfacial region is deposited simultaneously with deposition of the at least one rare earth metal, rare earth metal compound, and/or rare earth metal complex for example by a resistant heating deposition method, thereby dispersing the at least one rare earth metal, rare earth metal compound, and/or rare earth metal complex, preferably a rare earth metal, more preferably Yb in the organic compound.

In a case where the at least one rare earth metal, rare earth metal compound, and/or rare earth metal complex is formed into the shape of a layer, e.g. the electron-injecting material which serves as an organic layer in the interface is formed into the shape of a layer. After that, a rare earth metal, rare earth metal compound, and/or rare earth metal complex, preferably a rare earth metal, more preferably Yb is solely deposited for example by the resistant heating deposition method to form a layer preferably having a thickness of from 0.1 nm to 15 nm.

In a case where the at least one rare earth metal, rare earth metal compound, and/or rare earth metal complex is formed into the shape of an island, e.g. the electron-injecting material which serves as an organic layer in the interface is formed into the shape of an island. After that, the at least one rare earth metal, rare earth metal compound, and/or rare earth metal complex, preferably a rare earth metal, more preferably Yb is solely deposited by the resistant heating deposition method to form an island preferably having a thickness of from 0.05 nm to 1 nm.

In the case of use of the inventive combination of compounds of formula (I) and at least one rare earth metal, rare earth metal compound, and/or rare earth metal complex in OLEDs, OLEDs having good overall properties, preferably a long lifetime, a high EQE and/or a low driving voltage are obtained.

Organic Electroluminescence Device

The present invention relates to an organic electroluminescence device comprising a cathode, an anode and one or more organic thin film layers comprising an emitting layer disposed between the cathode and the anode, and an electron-transporting zone provided between the emitting layer and the cathode, wherein the electron-transporting zone comprises i) at least one compound represented by formula (I), and ii) at least one rare earth metal, rare earth metal compound, and/or rare earth metal complex, wherein the electron-transporting zone does not comprise an alkali metal, an alkali metal compound, an alkali metal complex, an alkaline earth metal, an alkaline earth metal compound, and an alkaline earth metal complex;

wherein the compound of formula (I) as well as preferred embodiments of the components of the organic electroluminescence device are defined above.

The present invention further relates to a material for an organic electroluminescence device comprising a combination of at least one compound of formula (I) according to the present invention and at least one rare earth metal, rare earth metal compound, and/or rare earth metal complex.

Further, the present invention relates to an electronic equipment comprising the organic electroluminescence device according the present invention and to the use of a compound of formula (I) as defined above in combination with at least one rare earth metal, rare earth metal compound, and/or rare earth metal complex, in an electron-transporting zone of an organic electroluminescence device, wherein the electron-transporting zone does not comprise an alkali metal, an alkali metal compound, an alkali metal complex, an alkaline earth metal, an alkaline earth metal compound, and an alkaline earth metal complex.

In the present specification, regarding "one or more organic thin film layers disposed between the cathode and the anode", if only one organic layer is present between the cathode and the anode, it means the layer, and if plural organic layers are present between the cathode and the anode, it means at least one layer thereof.

In one embodiment, the organic EL device has a hole-transporting layer between the anode and the emitting layer.

Layer(s) Between the Emitting Layer and the Anode:

In the organic EL device according to the present invention, one or more organic thin film layers may be present between the emitting layer and the anode. If only one organic layer is present between the emitting layer and the anode, it means that layer, and if plural organic layers are present, it means at least one layer thereof. For example, if two or more organic layers are present between the emitting layer and the anode, an organic layer nearer to the emitting layer is called the "hole-transporting layer", and an organic layer nearer to the anode is called the "hole-injecting layer". Each of the "hole-transporting layer" and the "hole-injecting layer" may be a single layer or may be formed of two or more layers. One of these layers may be a single layer and the other may be formed of two or more layers.

Layer(s) Between the Emitting Layer and the Cathode:

Similarly, one or more organic thin film layers may be present between the emitting layer and the cathode, in the organic EL device according to the present invention (i.e. electron-transporting zone, at least including an electron-transporting layer and preferably also an electron-injecting layer and/or a hole-blocking layer). If only one organic layer is present between the emitting layer and the cathode it means that layer, and if plural organic layers are present, it means at least one layer thereof. For example, if two or more organic layers are present between the emitting layer and the cathode, an organic layer nearest to the emitting layer is called the "hole-blocking layer", an organic layer nearest to the "hole-blocking layer" is called the "electron-transporting layer", and an organic layer nearer to the cathode is called the "electron-injecting layer". Each of the "hole-blocking layer", "electron-transporting layer" and the "electron-injecting layer" may be a single layer or may be formed of two or more layers. One of these layers may be a single layer and the other may be formed of two or more layers.

The one or more organic thin film layers between the emitting layer and the cathode, i.e the "electron-transporting zone", comprises a compound represented by formula (I) and at least one rare earth metal, rare earth metal compound, and/or rare earth metal complex.

Therefore, the organic thin film layers of the organic electroluminescence device comprise an electron-transporting zone provided between the emitting layer and the cathode, wherein the electron-transporting zone comprises at least one compound represented by formula (I) and at least one rare earth metal, rare earth metal compound, and/or rare earth metal complex. The compound represented by formula (I) preferably functions as "hole-blocking" material in the hole-blocking layer (if present) and/or "electron-transporting" material in the electron-transporting layer.

According to the present invention, the electron-transporting zone does not comprise an alkali metal, an alkali metal compound, an alkali metal complex, an alkaline earth metal, an alkaline earth metal compound, and an alkaline earth metal complex. In a further preferred embodiment, the electron-transporting zone additionally does not comprise a metal belonging to Group 13 of the Periodic Table of Elements (IUPAC, 2018), a compound containing a metal belonging to Group 13 of the Periodic Table of Elements (IUPAC, 2018) and a complex containing a metal belonging to Group 13 of the Periodic Table of Elements (IUPAC, 2018).

In an exemplary embodiment, the one or more organic thin film layers of the organic EL device of the present invention at least include the emitting layer and an electron-transporting zone. The electron-transporting zone is provided between the emitting layer and the cathode and at least includes an electron-transporting layer and preferably also an electron injecting layer and/or a hole-blocking layer. The electron-transporting zone may include the electron-injecting layer and an electron-transporting layer and may further include a hole-blocking layer and optionally a space layer. In addition to the above layers, the one or more organic thin film layers may be provided by layers applied in a known organic EL device such as a hole-injecting layer, a hole transporting layer and an electron-blocking layer.

An Explanation Will be Made on the Layer Configuration of the Organic EL Device According to One Aspect of the Invention.

An organic EL device according to one aspect of the invention comprises a cathode, an anode, and one or more organic thin film layers comprising an emitting layer disposed between the cathode and the anode. The organic layer comprises at least one layer composed of an organic compound. Alternatively, the organic layer is formed by laminating a plurality of layers composed of an organic compound. The organic layer may further comprise an inorganic compound in addition to the organic compound.

At least one of the organic layers is an emitting layer. The organic layer may be constituted, for example, as a single emitting layer, or may comprise other layers which can be adopted in the layer structure of the organic EL device. The layer that can be adopted in the layer structure of the organic EL device is not particularly limited, but examples thereof include a hole-transporting zone (a hole-transporting layer, a hole-injecting layer, an electron-blocking layer, an exciton-blocking layer, etc.), an emitting layer, a spacing layer, and an electron-transporting zone (electron-transporting layer, electron-injecting layer, hole-blocking layer, etc.) provided between the cathode and the emitting layer.

The organic EL device according to one aspect of the invention may be, for example, a fluorescent or phosphorescent monochromatic light emitting device or a fluorescent/phosphorescent hybrid white light emitting device.

Further, it may be a simple type device having a single emitting unit or a tandem type device having a plurality of emitting units.

The "emitting unit" in the specification is the smallest unit that comprises organic layers, in which at least one of the organic layers is an emitting layer and light is emitted by recombination of injected holes and electrons.

In addition, the emitting layer described in the present specification is an organic layer having an emitting function. The emitting layer is, for example, a phosphorescent emitting layer, a fluorescent emitting layer or the like, and may be a single layer or a stack of a plurality of layers.

The "emitting unit" may be a stacked type unit having a plurality of phosphorescent emitting layers and/or fluorescent emitting layers. In this case, for example, a spacing layer for preventing excitons generated in the phosphorescent emitting layer from diffusing into the fluorescent emitting layer may be provided between the respective light-emitting layers.

As the simple type organic EL device, a device configuration such as anode/emitting unit/cathode can be given.

Examples for representative layer structures of the emitting unit are shown below. The layers in parentheses are provided arbitrarily:

(a) (Hole-injecting layer/) Hole-transporting layer/Fluorescent emitting layer (/Electron-transporting layer/Electron-injecting layer)

(b) (Hole-injecting layer/) Hole-transporting layer/Phosphorescent emitting layer (/Electron-transporting layer/Electron-injecting layer)

(c) (Hole-injecting layer/) Hole-transporting layer/First fluorescent emitting layer/Second fluorescent emitting layer (/Electron-transporting layer/Electron-injecting layer)

(d) (Hole-injecting layer/) Hole-transporting layer/First phosphorescent layer/Second phosphorescent layer (/Electron-transporting layer/Electron-injecting layer)

(e) (Hole-injecting layer/) Hole-transporting layer/Phosphorescent emitting layer/Spacing layer/Fluorescent emitting layer (/Electron-transporting layer/Electron-injecting layer)

(f) (Hole-injecting layer/) Hole-transporting layer/First phosphorescent emitting layer/Second phosphorescent emitting layer/Spacing layer/Fluorescent emitting layer (/Electron-transporting layer/Electron-injecting layer)

(g) (Hole-injecting layer/) Hole-transporting layer/First phosphorescent layer/Spacing layer/Second phosphorescent emitting layer/Spacing layer/Fluorescent emitting layer (/Electron-transporting layer/Electron-injecting layer)

(h) (Hole-injecting layer/) Hole-transporting layer/Phosphorescent emitting layer/Spacing layer/First fluorescent emitting layer/Second fluorescent emitting layer (/Electron-transporting Layer/Electron-injecting Layer)

(i) (Hole-injecting layer/) Hole-transporting layer/Electron-blocking layer/Fluorescent emitting layer (/Electron-transporting layer/Electron-injecting layer)

(j) (Hole-injecting layer/) Hole-transporting layer/Electron-blocking layer/Phosphorescent emitting layer (/Electron-transporting layer/Electron-injecting layer)

(k) (Hole-injecting layer/) Hole-transporting layer/Exciton-blocking layer/Fluorescent emitting layer (/Electron-transporting layer/Electron-injecting layer)

(l) (Hole-injecting layer/) Hole-transporting layer/Exciton-blocking layer/Phosphorescent emitting layer (/Electron-transporting layer/Electron-injecting layer)

(m) (Hole-injecting layer/) First hole-transporting Layer/Second hole-transporting Layer/Fluorescent emitting layer (/Electron-transporting layer/electron-injecting Layer)

(n) (Hole-injecting layer/) First hole-transporting layer/Second hole-transporting layer/Fluorescent emitting layer (/First electron-transporting layer/Second electron-transporting layer/Electron-injection layer)

(o) (Hole-injecting layer/) First hole-transporting layer/Second hole-transporting layer/Phosphorescent emitting layer (/Electron-transporting layer/Electron-injecting Layer)

(p) (Hole-injecting layer/) First hole-transporting layer/Second hole-transporting layer/Phosphorescent emitting layer (/First electron-transporting Layer/Second electron-transporting layer/Electron-injecting layer)

(q) (Hole-injecting layer/) Hole-transporting layer/Fluorescent emitting layer/Hole-blocking layer (/Electron-transporting layer/Electron-injecting layer)

(r) (Hole-injecting layer/) Hole-transporting layer/Phosphorescent emitting layer/Hole-blocking layer (/Electron-transport layer/Electron-injecting layer)

(s) (Hole-injecting layer/) Hole-transporting layer/Fluorescent emitting layer/Exciton-blocking layer (/Electron-transporting layer/Electron-injecting layer)

(t) (Hole-injecting layer/) Hole-transporting layer/Phosphorescent emitting layer/Exciton-blocking layer (/Electron-transporting layer/Electron-injecting layer)

The layer structure of the organic EL device according to one aspect of the invention is not limited to the examples mentioned above.

For example, when the organic EL device has a hole-injecting layer and a hole-transporting layer, it is preferred that a hole-injecting layer be provided between the hole-transporting layer and the anode. Further, when the organic EL device has an electron-injecting layer and an electron-transporting layer, it is preferred that an electron-injecting layer be provided between the electron-transporting layer and the cathode. Further, each of the hole-injecting layer, the hole-transporting layer, the electron-transporting layer and the electron-injecting layer may be formed of a single layer or be formed of a plurality of layers.

The plurality of phosphorescent emitting layers and/or fluorescent emitting layers may be emitting layers that emit mutually different colors. For example, the emitting unit (f) may include a hole-transporting layer/first phosphorescent layer (red light emission)/second phosphorescent emitting layer (green light emission)/spacing layer/fluorescent emitting layer (blue light emission)/electron-transporting layer.

An electron-blocking layer may be provided between each light emitting layer and the hole-transporting layer or the spacing layer. Further, a hole-blocking layer may be provided between each emitting layer and the electron-transporting layer. By providing the electron-blocking layer or the hole-blocking layer, it is possible to confine electrons or holes in the emitting layer, thereby to improve the recombination probability of carriers in the emitting layer, and to improve light emitting efficiency.

As a representative device configuration of a tandem type organic el device, for example, a Device configuration such as anode/first emitting unit/intermediate layer/second emitting Unit/cathode can be given:

The first emitting unit and the second emitting unit are independently selected from the above-mentioned emitting units, for example.

The intermediate layer is also generally referred to as an intermediate electrode, an intermediate conductive layer, a charge generating layer, an electron withdrawing layer, a connecting layer, a connector layer, or an intermediate insulating layer. The intermediate layer is a layer that supplies electrons to the first emitting unit and holes to the second emitting unit, and can be formed from known materials.

FIG. 1 shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole-injecting and transporting layer 6 or the like may be provided between the emitting layer 5 and the anode 3 and an electron-injecting layer 9 and an electron-transporting layer 8 and/or a hole-blocking layer 7 or the like (electron-transporting zone 11) may be provided between the emitting layer 5 and the cathode 4. An electron-blocking layer may be provided on the anode 3 side of the emitting layer 5. Due to such configuration, electrons or holes can be confined in the emitting layer 5, whereby possibility of generation of excitons in the emitting layer 5 can be improved.

Hereinbelow, an Explanation Will be Made on Function, Materials, Etc. Of Each Layer Constituting The Organic EL Device Described in the Present Specification.

(Substrate)

The substrate is used as a support of the organic EL device. The substrate preferably has a light transmittance of 50% or more in the visible light region with a wavelength of 400 to 700 nm, and a smooth substrate is preferable. Examples of the material of the substrate include soda-lime glass, aluminosilicate glass, quartz glass, plastic and the like. As a substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.

(Anode)

As the anode, for example, it is preferable to use a metal, an alloy, a conductive compound, a mixture thereof or the like and having a high work function (specifically, 4.0 eV or more). Specific examples of the material of the anode include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene and the like. In addition, it is also possible to use gold, silver, platinum, nickel, tungsten, chromium, molybdenum, iron, cobalt, copper, palladium, titanium, and nitrides of these metals (e.g. titanium oxide).

The anode is normally formed by depositing these materials on the substrate by a sputtering method. For example, indium oxide-zinc oxide can be formed by a sputtering method by using a target in which 1 to 10 mass % zinc oxide is added relative to indium oxide. Further, indium oxide containing tungsten oxide or zinc oxide can be formed by a sputtering method by using a target in which 0.5 to 5 mass % of tungsten oxide or 0.1 to 1 mass % of zinc oxide is added relative to indium oxide.

As other methods for forming the anode, a vacuum deposition method, a coating method, an inkjet method, a spin coating method or the like can be given. When silver paste or the like is used, it is possible to use a coating method, an inkjet method or the like.

The hole-injecting layer formed in contact with the anode is formed by using a material that allows easy hole injection regardless of the work function of the anode. For this reason, in the anode, it is possible to use a common electrode material, e.g. a metal, an alloy, a conductive compound and a mixture thereof. Specifically, a material having a small work function such as alkaline metals such as lithium and cesium; alkaline earth metals such as calcium and strontium; alloys containing these metals (for example, magnesium-silver and aluminum-lithium); rare earth metals such as europium and ytterbium; and an alloy containing rare earth metals.

(Hole-Transporting Layer)/(Hole-Injecting Layer/Electron-Blocking Layer)

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode. Said hole-injecting layer is generally used for stabilizing hole injection from anode to hole-transporting layer which is generally consist of organic materials. Organic material having good contact with anode or organic material with p-type doping is preferably used for the hole-injecting layer.

p-doping usually consists of one or more p-dopant materials and one or more matrix materials. Matrix materials preferably have shallower HOMO level and p-dopant preferably have deeper LU MO level to enhance the carrier density of the layer. Aryl or heteroaryl amine compounds are preferably used as the matrix materials. Specific examples for the matrix material are the same as that for hole-transporting layer which is explained at the later part. Specific examples for p-dopant are the below mentioned acceptor materials, preferably the quinone compounds with one or more electron withdrawing groups, such as $F_4$TCNQ, 1,2,3-Tris[(cyano)(4-cyano-2,3,5,6-tetrafluorophenyl)methylene]cyclopropane.

Acceptor materials, or fused aromatic hydrocarbon materials or fused heterocycles which have high planarity, are preferably used as p-dopant materials for the hole-injecting layer. Specific examples for acceptor materials are, the quinone compounds with one or more electron withdrawing groups, such as $F_4$TCNQ(2,3,5,6-tetrafluoro-7,7,8,8-tetracyanoquinodimethane), and 1,2,3-tris[(cyano)(4-cyano-2,3,5,6-tetrafluorophenyl)methylene]cyclopropane; hexa-azatriphenylene compounds with one or more electron withdrawing groups, such as hexa-azatriphenylene-hexanitrile; aromatic hydrocarbon compounds with one or more electron withdrawing groups; and aryl boron compounds with one or more electron withdrawing groups.

The ratio of the p-type dopant is preferably less than 20% of molar ratio, more preferably less than 10%, such as 1%, 3%, or 5%, related to the matrix material.

The hole-transporting layer is generally used for injecting and transporting holes efficiently, and aromatic or heterocyclic amine compounds are preferably used.

Specific examples for compounds for the hole-transporting layer are represented by the general formula (H),

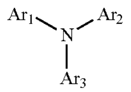

(H)

wherein $Ar_1$ to $Ar_3$ each independently represents substituted or unsubstituted aryl group having 5 to 50 carbon atoms or substituted or unsubstituted heterocyclic group having 5 to 50 ring atoms, preferably phenyl group, biphenyl group, terphenyl group, naphthyl group, phenanthryl group, triphenylenyl group, fluorenyl group, spirobifluorenyl group, indenofluorenyl group, carbazolyl group, dibenzofuranyl group, dibenzothiophenyl group, carbazole substituted aryl group, dibenzofuran substituted aryl group or dibenzothiophene substituted aryl group; two or more substituents selected among $Ar_1$ to $Ar^3$ may be bonded to each other to form a ring structure, such as a carbazole ring structure, or a acridane ring structure.

Preferably, at least one of $Ar_1$ to $Ar_3$ have additional one aryl or heterocyclic amine substituent, more preferably $Ar_1$ has an additional aryl amino substituent, at the case of that it is preferable that $Ar_1$ represents substituted or unsubstituted biphenylene group, substituted or unsubstituted fluorenylene group.

A second hole-transporting layer is preferably inserted between the first hole-transporting layer and the emitting layer to enhance device performance by blocking excess electrons or excitons. Specific examples for second hole-transporting layer are the same as for the first hole-transporting layer. It is preferred that second hole-transporting layer has higher triplet energy to block triplet excitons, especially for phosphorescent green device, such as bicarbazole compounds, biphenylamine compounds, triphenylenyl amine compounds, fluorenyl amine compounds, carbazole substituted arylamine compounds, dibenzofuran substituted arylamine compounds, and dibenzothiophene substituted arylamine compounds.

This second hole-transporting layer also called electron-blocking layer provided adjacent to the emitting layer has a function of preventing leakage of electrons from the emitting layer to the hole-transporting layer.

(Emitting Layer)

The emitting layer is a layer containing a substance having a high emitting property (emitter material or dopant material). As the dopant material, various materials can be used. For example, a fluorescent emitting compound (fluorescent dopant), a phosphorescent emitting compound (phosphorescent dopant) or the like can be used. A fluorescent emitting compound is a compound capable of emitting light from the singlet excited state, and an emitting layer containing a fluorescent emitting compound is called a fluorescent emitting layer. Further, a phosphorescent emitting compound is a compound capable of emitting light from the triplet excited state, and an emitting layer containing a phosphorescent emitting compound is called a phosphorescent emitting layer.

The emitting layer preferably comprises at least one dopant material and at least one host material that allows it to emit light efficiently. In some literatures, a dopant material is called a guest material, an emitter or an emitting material. In some literatures, a host material is called a matrix material.

A single emitting layer may comprise plural dopant materials and plural host materials. Further, plural emitting layers may be present.

In the present specification, a host material combined with the fluorescent dopant is referred to as a "fluorescent host" and a host material combined with the phosphorescent dopant is referred to as the "phosphorescent host". Note that the fluorescent host and the phosphorescent host are not classified only by the molecular structure. The phosphorescent host is a material for forming a phosphorescent emitting layer containing a phosphorescent dopant, but does not mean that it cannot be used as a material for forming a fluorescent emitting layer. The same can be applied to the fluorescent host.

No specific restrictions are generally imposed on the content of the dopant material in a host in the emitting layer. A person skilled in the art generally knows the concentration of a phosphorescent dopant respectively a fluorescent dopant usually present in a suitable host. In respect of sufficient emission and concentration quenching, the content is preferably 0.5 to 70 mass %, more preferably 0.8 to 30 mass %, further preferably 1 to 30 mass %, still further preferably 1 to 20 mass. The remaining mass of the emitting layer is generally provided by one or more host materials.

(Fluorescent Dopant)

Suitable fluorescent dopants are generally known by a person skilled in the art. As a fluorescent dopant a fused polycyclic aromatic compound, a styrylamine compound, a fused ring amine compound, a boron-containing compound, a pyrrole compound, an indole compound, a carbazole compound can be given, for example. Among these, a fused ring amine compound, a boron-containing compound, carbazole compound is preferable.

As the fused ring amine compound, a diaminopyrene compound, a diaminochrysene compound, a diaminoanthracene compound, a diaminofluorene compound, a diaminofluorene compound with which one or more benzofuro skeletons are fused, or the like can be given.

As the boron-containing compound, a pyrromethene compound, a triphenylborane compound or the like can be given.

(Phosphorescent Dopant)

Suitable phosphorescent dopants are generally known by a person skilled in the art. As a phosphorescent dopant, a phosphorescent emitting heavy metal complex and a phosphorescent emitting rare earth metal complex can be given, for example.

As the heavy metal complex, an iridium complex, an osmium complex, a platinum complex or the like can be given. The heavy metal complex is for example an ortho-metalated complex of a metal selected from iridium, osmium and platinum.

Examples of rare earth metal complexes include terbium complexes, europium complexes and the like. Specifically, tris(acetylacetonate)(monophenanthroline)terbium(III) (abbreviation: $Tb(acac)_3(Phen)$), tris(1,3-diphenyl-1,3-propandionate)(monophenanthroline)europium(III) (abbreviation: $Eu(DBM)_3(Phen)$), tris[1-(2-thenoyl)-3,3,3-trifluoroacetonate](monophenanthroline)europium(III) (abbreviation: $Eu(TTA)_3(Phen)$) or the like can be given. These rare earth metal complexes are preferable as phosphorescent dopants since rare earth metal ions emit light due to electronic transition between different multiplicity.

As a blue phosphorescent dopant, an iridium complex, an osmium complex, a platinum complex, or the like can be given, for example. Specifically, bis[2-(4',6'-difluorophenyl) pyridinate-N,C2]iridium(III) tetrakis(1-pyrazolyl)borate (abbreviation: FIr6), bis[2-(4',6'-difluorophenyl) pyridinato-N,C2]iridium(III) picolinate (abbreviation: $Ir(CF_3ppy)_2$ (pic)), bis[2-(4',6'-difluorophenyl)pyridinato-N,C2']iridium (III) acetylacetonate (abbreviation: Flracac) or the like can be given.

As a green phosphorescent dopant, an iridium complex or the like can be given, for example. Specifically, tris(2-phenylpyridinato-N,C2') iridium(III) (abbreviation: $Ir(ppy)_3$), bis(1,2-diphenyl-1H-benzimidazolato)iridium(III) acetylacetonate (abbreviation: $Ir(pbi)_2(acac)$), bis(benzo[h] quinolinato)iridium(III) acetylacetonate (abbreviation: $Ir(bzq)_2(acac)$) or the like can be given.

As a red phosphorescent dopant, an iridium complex, a platinum complex, a terbium complex, an europium complex or the like can be given. Specifically, bis[2-(2'-benzo [4,5-α]thienyl)pyridinato-N,C3]iridium(III) acetylacetonate (abbreviation: $Ir(btp)_2(acac)$), bis(1-phenylisoquinolinato-N,C2')iridium(III) acetylacetonate (abbreviation: $Ir(piq)_2$ (acac)), (acetylacetonato)bis[2,3-bis(4-fluorophenyl)quinoxalinato]iridium(III) (abbreviation: $Ir(Fdpq)_2(acac)$), 2,3,7,8,12,13,17,18-octaethyl-21H,23H-porphyrin platinum(II) (abbreviation PtOEP) or the like can be given.

(Host Material)

As host material, metal complexes such as aluminum complexes, beryllium complexes and zinc complexes; heterocyclic compounds such as indole compounds, pyridine compounds, pyrimidine compounds, triazine compounds, quinoline compounds, isoquinoline compounds, quinazoline compounds, dibenzofuran compounds, dibenzothiophene compounds, oxadiazole compounds, benzimidazole compounds, phenanthroline compounds; fused polyaromatic hydrocarbon (PAH) compounds such as a naphthalene compound, a triphenylene compound, a carbazole compound, an anthracene compound, a phenanthrene compound, a pyrene compound, a chrysene compound, a naphthacene compound, a fluoranthene compound; and aromatic amine compound such as triarylamine compounds and fused polycyclic aromatic amine compounds can be given, for example. Plural types of host materials can be used in combination.

As a fluorescent host, a compound having a higher singlet energy level than a fluorescent dopant is preferable. For example, a heterocyclic compound, a fused aromatic compound or the like can be given. As a fused aromatic compound, an anthracene compound, a pyrene compound, a chrysene compound, a naphthacene compound or the like are preferable. An anthracene compound is preferentially used as blue fluorescent host.

As a phosphorescent host, a compound having a higher triplet energy level as compared with a phosphorescent dopant is preferable. For example, a metal complex, a heterocyclic compound, a fused aromatic compound or the like can be given. Among these, an indole compound, a carbazole compound, a pyridine compound, a pyrimidine compound, a triazine compound, a quinolone compound, an isoquinoline compound, a quinazoline compound, a dibenzofuran compound, a dibenzothiophene compound, a naphthalene compound, a triphenylene compound, a phenanthrene compound, a fluoranthene compound or the like can be given.

Preferred host materials are substituted or unsubstituted polyaromatic hydrocarbon (PAH) compounds, substituted or unsubstituted polyheteroaromatic compounds, substituted or unsubstituted anthracene compounds, or substituted or unsubstituted pyrene compounds, preferably substituted or unsubstituted anthracene compounds or substituted or unsubstituted pyrene compounds, more preferably substituted or unsubstituted anthracene compounds, most preferably anthracene compounds represented by formula (10) below.

(10)

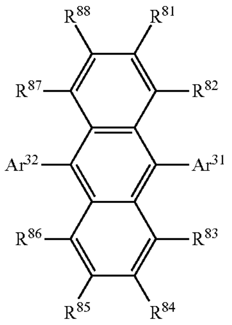

In the formula (10), $Ar^{31}$ and $Ar^{32}$ each independently represent a substituted or unsubstituted aryl group having 6 to 50 ring carbon atoms or a heterocyclic group having 5 to 50 ring atoms.

$R^{81}$ to $R^{88}$ each independently represent a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group or a hydroxyl group.

In Formula (10):

The aryl group having 6 to 50 ring carbon atoms is preferably an aryl group having 6 to 40 ring carbon atoms, more preferably an aryl group having 6 to 30 ring carbon atoms.

The heterocyclic group having 5 to 50 ring atoms is preferably a heterocyclic group having 5 to 40 ring atoms, more preferably a heterocyclic group having 5 to 30 ring atoms. More preferably, the heterocyclic group is a substituted or unsubstituted heteroaryl group having 5 to 30 ring atoms. Suitable substituted or unsubstituted heteroaryl groups are mentioned above.

The alkyl group having 1 to 50 carbon atoms is preferably an alkyl group having 1 to 30 carbon atoms, more preferably an alkyl group having 1 to 10 carbon atoms, further preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, further preferably an alkoxy group having 1 to 5 carbon atoms.

The aralkyl group having 7 to 50 carbon atoms is preferably an aralkyl group having 7 to 30 carbon atoms, more preferably an aralkyl group having 7 to 20 carbon atoms.

The aryloxy group having 6 to 50 ring carbon atoms is preferably an aryloxy group having 6 to 40 ring carbon atoms, more preferably an aryloxy group having 6 to 30 ring carbon atoms.

The arylthio group having 6 to 50 ring carbon atoms is preferably an arylthio group having 6 to 40 ring carbon atoms, more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, further preferably an alkoxycarbonyl group having 2 to 5 carbon atoms.

Examples of the halogen atom are a fluorine atom, a chlorine atom and a bromine atom.

$Ar^{31}$ and $Ar^{32}$ are preferably a substituted or unsubstituted aryl group having 6 to 50 ring carbon atoms.

(Electron-Transporting Zone)/(Electron-Transporting Layer/Electron-Injecting Layer/Hole-Blocking Layer)

The electron-transporting zone is an organic layer or a plurality of organic layers that is formed between the emitting layer and the cathode and has a function of transporting electrons from the cathode to the emitting layer. The electron-transporting zone therefore comprises at least one electron-transporting layer comprising an electron-transporting material. When the electron-transporting zone is formed of plural layers, an organic layer or an inorganic layer that is nearer to the cathode is often defined as the electron-injecting layer (see for example FIG. 1, wherein an electron-injecting layer 9, an electron-transporting layer and preferably a hole-blocking layer 7 form an electron-transporting zone 11). The electron-injecting layer has a function of injecting electrons from the cathode efficiently to the organic layer unit.

According to the present invention, the electron-transporting zone comprises at least one compound represented by formula (I) and at least one rare earth metal, rare earth metal compound, and/or rare earth metal complex. The compound represented by formula (I) preferably functions as "hole-blocking" material in the hole-blocking layer (if present) and/or "electron-transporting" material and/or "electron-injecting" material (if present) in the electron-transporting layer.

The electron-transporting zone does not comprise an alkali metal, an alkali metal compound, an alkali metal complex, an alkaline earth metal, an alkaline earth metal compound, and an alkaline earth metal complex. In a further preferred embodiment, the electron-transporting zone additionally does not comprise a metal belonging to Group 13 of the Periodic Table of Elements (IUPAC, 2018), a compound containing a metal belonging to Group 13 of the Periodic Table of Elements (IUPAC, 2018) and a complex containing a metal belonging to Group 13 of the Periodic Table of Elements (IUPAC, 2018).

In an exemplary embodiment, the one or more organic thin film layers of the organic EL device of the present invention at least include the emitting layer and an electron-transporting zone. The electron-transporting zone is provided between the emitting layer and the cathode and at least includes an electron-transporting layer and preferably also an electron injecting layer and/or a hole-blocking layer. The electron-transporting zone may include the electron-injecting layer and an electron-transporting layer and may further include a hole-blocking layer and optionally a space layer. In addition to the above layers, the one or more organic thin film layers may be provided by layers applied in a known organic EL device such as a hole-injecting layer, a hole transporting layer and an electron-blocking layer.

According to one embodiment, it is therefore preferred that the electron-transporting zone comprises in addition to the electron-transporting layer one or more layer(s) like an electron-injecting layer, a hole-blocking layer or an exciton/triplet-blocking layer to enhance efficiency and lifetime of the device (layer 7 in FIG. 1).

In one preferred embodiment of the present invention, the compound of the formula (I) is present in the electron-transporting zone, as an electron-transporting material, an electron-injecting material, a hole-blocking material, an exciton-blocking material and/or a triplet-blocking material. More preferably, the compound of the formula (I) is present in the electron-transporting zone as an electron-transporting material and/or an electron-injecting material.

According to one embodiment, it is preferred that the at least one rare earth metal, rare earth metal compound, and/or rare earth metal complex be contained in the interfacial region between the cathode and the emitting unit. Due to such a configuration, the organic EL device can have an increased luminance or a long life.

As the electron-transporting material used in the electron-transporting layer other than a compound of the formula (I), an aromatic heterocyclic compound having one or more hetero atoms in the molecule may preferably be used. In particular, a nitrogen containing heterocyclic compound is preferable.

According to one embodiment, it is preferable that the electron-transporting layer comprises a nitrogen containing heterocyclic metal chelate.

According to another embodiment, it is preferable that the electron-transporting layer comprises a substituted or unsubstituted nitrogen containing heterocyclic compound. Specific examples of preferred heterocyclic compounds for the electron-transporting layer are, 6-membered azine compounds; such as pyridine compounds, pyrimidine compounds, triazine compounds, pyrazine compounds, preferably pyrimidine compounds or triazine compounds; 6-membered fused azine compounds, such as quinolone compounds, isoquinoline compounds, quinoxaline compounds, quinazoline compounds, phenanthroline compounds, benzoquinoline compounds, benzoisoquinoline compounds, dibenzoquinoxaline compounds, preferably quinolone compounds, isoquinoline compounds, phenanthroline compounds; 5-membered heterocyclic compounds, such as imidazole compounds, oxazole compounds, oxadiazole compounds, triazole compounds, thiazole compounds, thiadiazole compounds; fused imidazole compounds, such as benzimidazole compounds, imidazopyridine compounds, naphthoimidazole compounds, benzimidazophenanthridine compounds, benzimidzobenzimidazole compounds, preferably benzimidazole compounds, imidazopyridine compounds or benzimidazophenanthridine compounds.

According to another embodiment, it is preferable that the electron-transporting layer comprises aromatic hydrocarbon compounds. Specific examples of preferred aromatic hydrocarbon compounds for the electron-transporting layer are, oligo-phenylene compounds, naphthalene compounds, fluorene compounds, fluoranthenyl group, anthracene compounds, phenanthrene compounds, pyrene compounds, triphenylene compounds, benzanthracene compounds, chrysene compounds, benzphenanthrene compounds, naphthacene compounds, and benzochrysene compounds, preferably anthracene compounds, pyrene compounds and fluoranthene compounds.

A hole-blocking layer may be provided adjacent to the emitting layer, and has a function of preventing leakage of holes from the emitting layer to the electron-transporting layer. In order to improve hole-blocking capability, a material having a deep HOMO level is preferably used.

(Cathode)

For the cathode, a metal, an alloy, an electrically conductive compound, and a mixture thereof, each having a small work function (specifically, a work function of 3.8 eV or less) are preferably used. Specific examples of a material for the cathode include an alkali metal such as lithium and cesium; an alkaline earth metal such as magnesium, calcium, and strontium; an alloy containing these metals (for example, magnesium-silver, aluminum-lithium); a rare earth metal such as europium and ytterbium; and an alloy containing a rare earth metal.

The cathode is usually formed by a vacuum vapor deposition or a sputtering method. Further, in the case of using a silver paste or the like, a coating method, an inkjet method, or the like can be employed.

Moreover, when the electron-injecting layer is provided, various electrically conductive materials such as aluminum, silver, ITO, graphene, indium oxide-tin oxide containing silicon or silicon oxide, selected independently from the work function, can be used to form a cathode. These electrically conductive materials are made into films using a sputtering method, an inkjet method, a spin coating method, or the like.

(Insulating Layer)

In the organic EL device, pixel defects based on leakage or a short circuit are easily generated since an electric field is applied to a thin film. In order to prevent this, it is preferred to insert an insulating thin layer between a pair of electrodes. Examples of materials used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture thereof may be used in the insulating layer, and a laminate of a plurality of layers that include these materials can be also used for the insulating layer.

(Spacing Layer)

A spacing layer is a layer for example provided between a fluorescent emitting layer and a phosphorescent emitting layer when a fluorescent emitting layer and a phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is for example provided between the emitting layers, the material used for the spacing layer is preferably a material having both electron-transporting capability and hole-transporting capability. In order to prevent diffusion of the triplet energy in adjacent phosphorescent emitting layers, it is preferred that the spacing layer have a triplet energy of 2.6 eV or more. As the material used for the spacing layer, the same materials as those used in the above-mentioned hole-transporting layer can be given.

Triplet-Blocking Layer

A triplet-blocking layer (exciton-blocking layer) may be provided adjacent to the emitting layer.

The triplet-blocking layer has a function of preventing triplet excitons generated in the emitting layer from diffusing into neighboring layers to trap the triplet excitons within the emitting layer, thereby suppressing energy deactivation of the triplet excitons on molecules other than the emitting dopant in the electron-transporting layer.

When the triplet-blocking layer is provided in a phosphorescent device, triplet energy of a phosphorescent dopant in the emitting layer is denoted as ET d and triplet energy of a compound used as the triplet-blocking layer is denoted as ET TB. In an energy relationship of ET d<ET TB, triplet excitons of the phosphorescent dopant are trapped (cannot be transferred to another molecule) to leave no alternative route for energy deactivation other than emission on the dopant, so that highly efficient emission can be expected. However, when an energy gap ($\Delta$ET=ET TB−ET d) is small even though the relationship of ET d<ET TB is satisfied, under actual environments for driving a device (i.e., at around the room temperature), it is considered that triplet excitons can be transferred to another molecule irrespective of the energy gap LET by absorbing heat energy around the device. Particularly, since the excitons of the phosphorescent device have longer lifetime than those of a fluorescent device, influence by heat absorption during transfer of the excitons is more likely to be given on the phosphorescent device relative to the fluorescent device. A larger energy gap LET relative to heat energy at the room temperature is preferable, more preferably 0.1 eV or more, further preferable at 0.2 eV or more. On the other hand, in the fluorescent device, the organic-EL-device material according to the exemplary embodiment is usable as the triplet-blocking layer in the TTF device structure described in International Publication WO2010/134350A1.

(Method for Forming a Layer)

The method for forming each layer of the organic EL device of the invention is not particularly limited unless otherwise specified. A known film-forming method such as a dry film-forming method, a wet film-forming method or the like can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, an inkjet method, and the like.

(Film Thickness)

The film thickness of each layer of the organic EL device of the invention is not particularly limited unless otherwise specified. If the film thickness is too small, defects such as pinholes are likely to occur to make it difficult to obtain a sufficient luminance. If the film thickness is too large, a high driving voltage is required to be applied, leading to a lowering in efficiency. In this respect, the film thickness is preferably 5 nm to 10 μm, and more preferably 10 nm to 0.2 μm.

(Electronic Apparatus (Electronic Equipment))

The present invention further relates to an electronic equipment (electronic apparatus) comprising the organic electroluminescence device according to the present application. Examples of the electronic apparatus include display parts such as an organic EL panel module; display devices of television sets, mobile phones, smart phones, and personal computer, and the like; and emitting devices of a lighting device and a vehicle lighting device.

It should be noted that the invention is not limited to the above exemplary embodiments but may include any modification and improvement as long as such modification and improvement are compatible with the invention.

The following examples are included for illustrative purposes only and do not limit the scope of the claims. Unless otherwise stated, all parts and percentages are by weight.

EXAMPLES

I Synthesis Examples

Compound 1

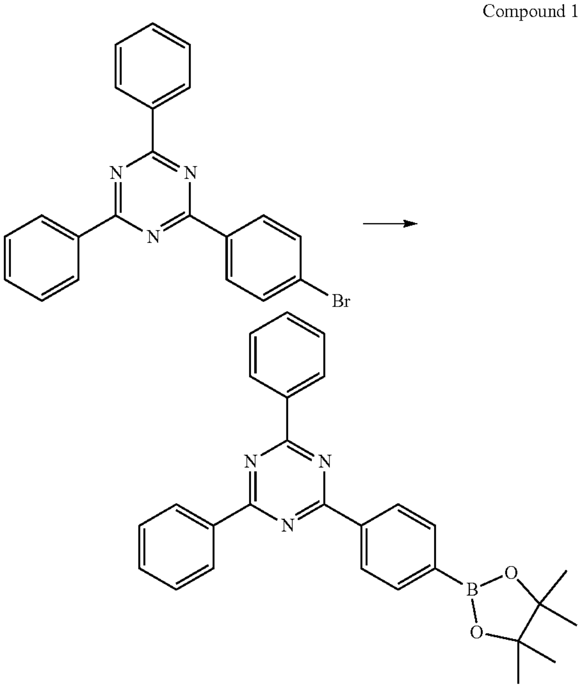

Intermediate 1

In a nitrogen flushed 1000 ml three-necked round-bottomed flask 2-(4-bromophenyl)-4,6-diphenyl-1,3,5-triazine (40 g, 103 mmol), bis(pinacolato)diboron (65.4 g, 258 mmol), [1,1'-bis(diphenylphosphino)ferrocene]dichloropalladium(II), complex with dichloromethane (4.2 g, 5.1 mmol), and potassium acetate (30.3 g, 309 mmol) were dissolved in 350 ml n,n-dimethylformamide under nitrogen. The reaction mixture was heated to 70° C. with an oil bath for 2 hours. After cooling down to room temperature, the reaction mixture was poured into water while stirring. The precipitate thus formed was collected by filtration. The precipitate was then suspended in methanol (1 L) and allowed to stir at room temperature for 2 hours. The precipitate was again collected by filtration and allowed to dry. The crude product was then dissolved in dichloromethane and filtered over a pad of silica, washing through with dichloromethane. After evaporation of the dichloromethane under reduced pressure, 40.6 g (91% yield) of a white solid was obtained which was used without further purification. The identification of Intermediate 1 was made by ESI-MS (electrospray ionisation mass spectrometry) The results are shown below. ESI-MS: calcd. for C27H26BN3O2=453, mass found=454 (M+1)

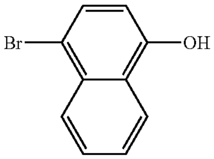

+

-continued

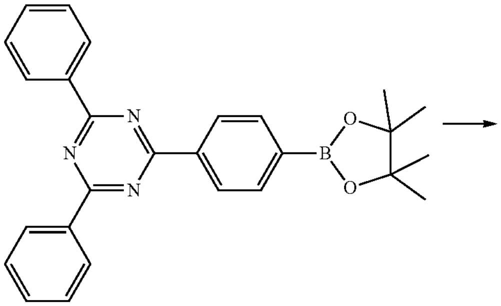

Intermediate 1

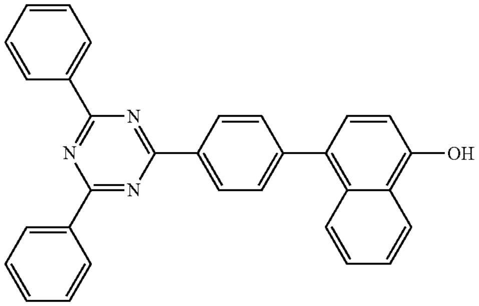

Intermediate 2

In a nitrogen flushed 1000 ml three-necked round-bottomed flask, 4-bromonaphthalen-1-ol (17.7 g, 79 mmol) was combined with Intermediate 1 (23 g, 52.8 mmol) and tetrakis(triphenylphosphin)-palladium(0) (3.05 g, 2.64 mmol) in dimethoxyethane (250 mL) followed by the addition of 2M aqueous sodium carbonate (79 ml, 158 mmol). The reaction mixture was heated under reflux for 6 hours. The reaction was allowed to cool to room temperature and the solvent was removed under reduced pressure. The crude residue was suspended in a solution of 1M aqueous HCl/methanol (1:1, 500 mL) and allowed to stir at room temperature for 1 hour. The precipitate was collected by filtration and washed with water and methanol and allowed to dry. The crude product thus obtained was further purified by recrystallisation from xylene. 13.5 g (56.6%) of a pale brown solid was thus obtained and used without further purification. The identification of Intermediate 2 was made by ESI-MS (electrospray ionisation mass spectrometry). The results are shown below.

ESI-MS: calcd. for C31H21N3O=451, mass found=452 (M+1)

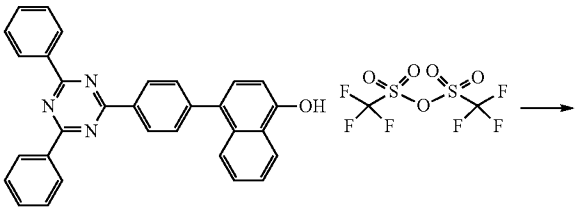

Intermediate 2

-continued

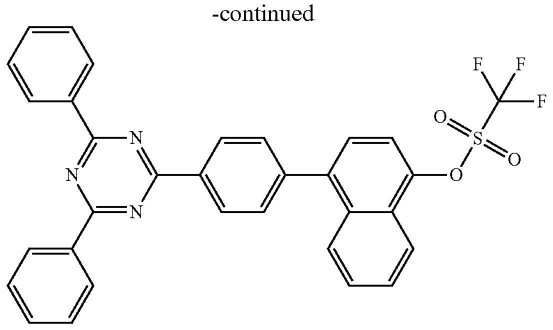

Intermediate 3

Intermediate 2 (8.3 g, 18.38 mmol) was suspended in dichloromethane and cooled in an icebath. 2,6-lutidine (4.3 ml, 36.8 mmol) was then added followed by the addition of trifluoromethanesulfonic anhydride (4.63 ml, 27.6 mmol). After 1 hour, the reaction was complete. The reaction mixture was washed with aqueous saturated sodium hydrogencarbonate, water and brine and dried over anhydrous magnesium sulfate. The crude product was purified by chromatography on silica using 20-40% dichloromethane in heptane as eluant. Isolated 6.1 g (57%) of Intermediate 3 as a pale brown oil which was used without further purification. The identification of Intermediate 3 was made by ESI-MS (electrospray ionisation mass spectrometry). The results are shown below.

ESI-MS: calcd. for C32H20F3N3O3S=583, mass found=584 (M+1)

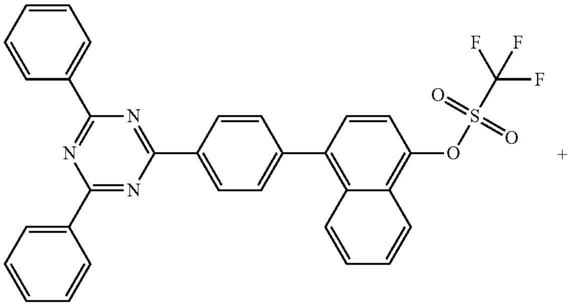

Intermediate 3

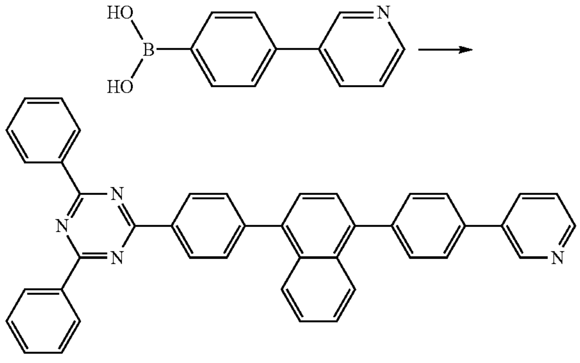

Compound 1

In a nitrogen flushed 250 ml three-necked round-bottomed flask, Intermediate 3 (4 g, 6.8 mmol) was combined with (4-(pyridin-3-yl)phenyl)boronic acid (1.2 g, 6.2 mmol), Tetrakis(triphenylphosphin)-palladium(0) (0.16 g, 0.14 mmol) and K2CO3 (1.9 g, 13.7 mmol). Dioxane (30 mL) and water (7.5 mL) was added to the reaction mixture and heated at an oil bath temperature of 90° C. overnight. The reaction was then allowed to cool to room temperature and the solvent removed under reduced pressure. The crude residue was then suspended in methanol/water (1:1, 100 mL) and the mixture allowed to stir at room temperature for 1 hour. The precipitate was collected by filtration. The crude product was then recrystallised from xylene and further purified by train sublimation. The obtained Compound 1 (46% yield, white solid) was characterized by ESI-MS (electrospray ionisation mass spectrometry), maximum ultraviolet absorption wavelength (UV(PhMe) λonset) in toluene, and maximum fluorescence wavelength (FL(PhMe, λex=330 nm) λmax) in toluene. The results are shown below.

ESI-MS: calcd. for C42H28N4=589, mass found=589 (M+)

UV(PhMe) λonset: 384 nm

FL(PhMe, λex=330 nm) λmax: 425 nm

Compound 2

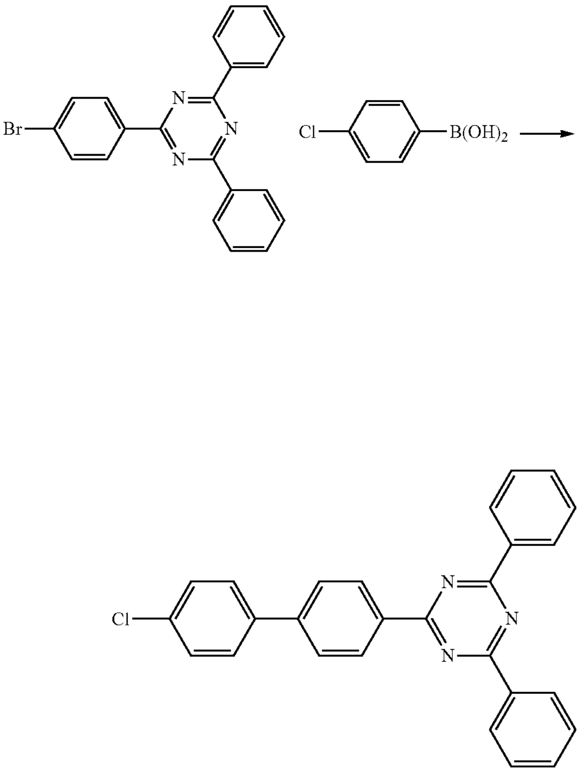

Intermediate 4

The procedure of the synthesis of Intermediate 2 was repeated except for using 2-(4-bromophenyl)-4,6-diphenyl-1,3,5-triazine in place of 4-bromonaphthalen-1-ol and (4-chlorophenyl)boronic acid in place of Intermediate 1. The obtained Intermediate 4 (74% yield, white solid) was characterized by ESI-MS (electrospray ionisation mass spectrometry). The results are shown below.

ESI-MS: calcd. for C32H20F3N3O3S=583, mass found=584 (M+1)

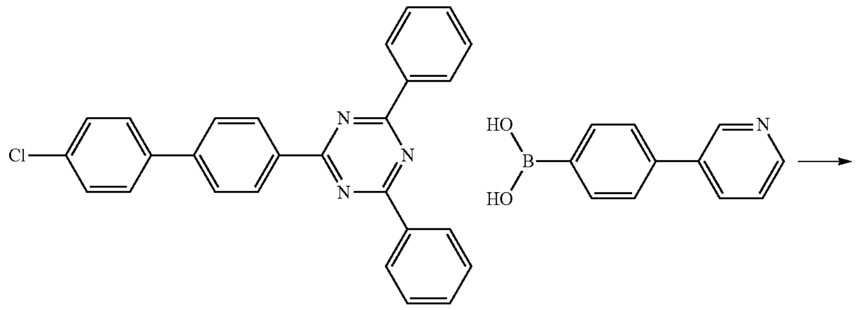

Intermediate 4

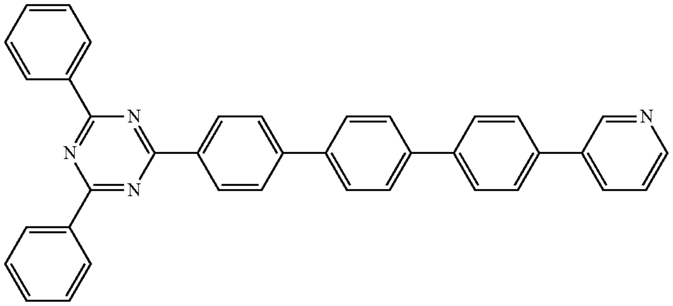

Compound 2

The procedure of the synthesis of Compound 1 was repeated except for Intermediate 4 in place of Intermediate 3 and palladium(II)acetate and [2-dicyclohexylphosphino-2',4',6'-triisopropylbiphenyl] in place of tetrakis(triphenylphosphin)-palladium(0). The obtained Compound 2 (33% yield, white solid) was characterized by ESI-MS (electrospray ionisation mass spectrometry), maximum ultraviolet absorption wavelength (UV(PhMe) λonset) in toluene, and maximum fluorescence wavelength (FL(PhMe, λex=330 nm) λmax) in toluene. The results are shown below.

ESI-MS: calcd. for $C_{38}H_{26}N_4$=539, mass found=539 (M+)

UV(PhMe) λonset: 373 nm

FL(PhMe, λex=330 nm) λmax: 407 nm

Compound 3

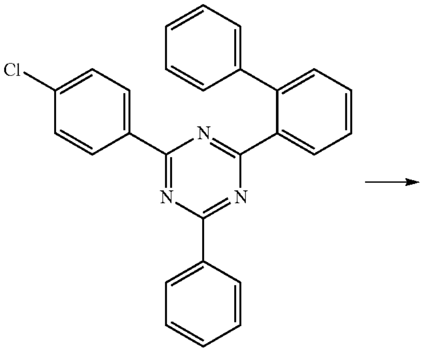

-continued

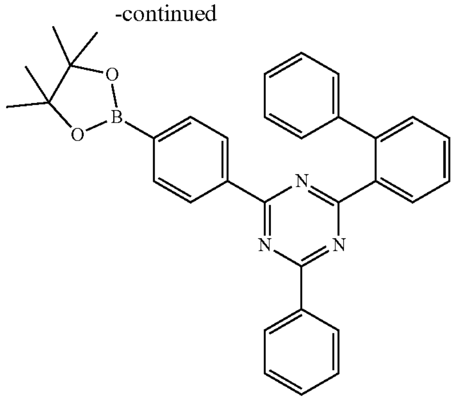

Intermediate 5

The procedure of the synthesis of Intermediate 1 was repeated except for using 2-([1,1-biphenyl]-2-yl)-4-(4-chlorophenyl)-6-phenyl-1,3,5-triazine in place of 2-(4-bromophenyl)-4,6-diphenyl-1,3,5-triazine and palladium(II)acetate and [2-dicyclohexylphosphino-2',4',6'-triisopropylbiphenyl] in place of [1,1'-bis (diphenylphosphino)ferrocene]dichloropalladium(II), complex with dichloromethane. The obtained Intermediate 5 (76% yield, white solid) was characterized by ESI-MS (electrospray ionisation mass spectrometry). The results are shown below.

ESI-MS: calcd. for $C_{33}H_{30}BN_3O_2$=511, mass found=512 (M+1)

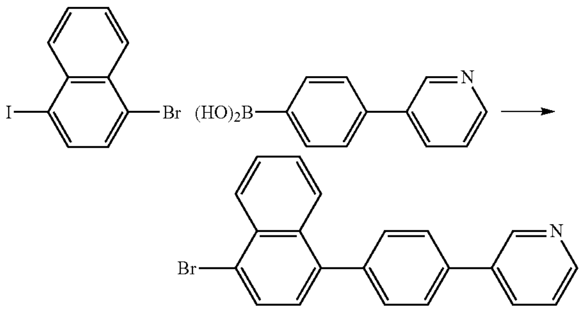

Intermediate 6

The procedure of the synthesis of Intermediate 2 was repeated except for using 1-bromo-4-iodonaphthalene in place of 4-bromonaphthalen-1-ol and (4-(pyridin-3-yl)phenyl)boronic acid in place of Intermediate 1. The obtained Intermediate 6 (74% yield, white solid) was characterized by ESI-MS (electrospray ionisation mass spectrometry). The results are shown below.

ESI-MS: calcd. for C21H14BrN=359, mass found=360 (M+1)

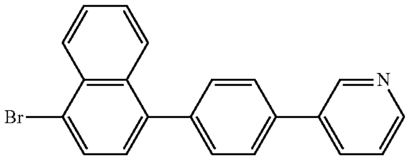

Intermediate 6

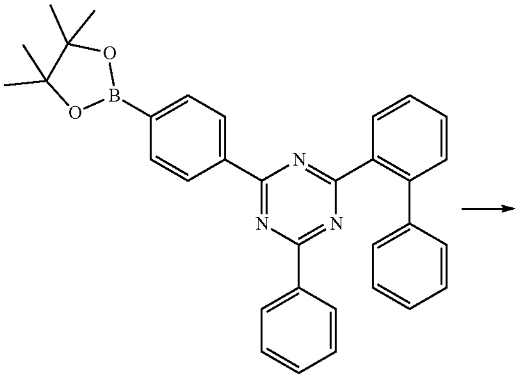

Intermediate 5

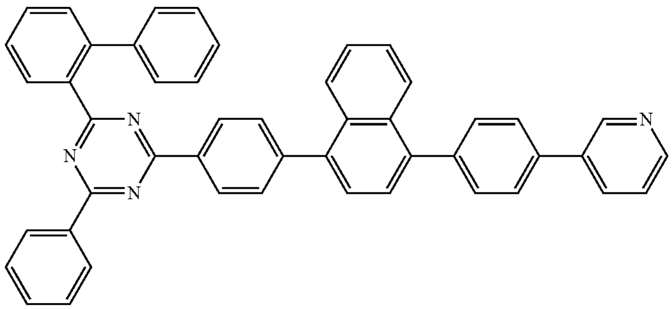

Compound 3

The procedure of the synthesis of Compound 1 was repeated except for Intermediate 6 in place of Intermediate 3 and intermediate 5 in place of (4-(pyridin-3-yl)phenyl) boronic acid and palladium(II)acetate and [2-dicyclohexylphosphino-2',4',6'-triisopropylbiphenyl] in place of tetrakis(triphenylphosphin)-palladium(0). The obtained Compound 3 (65% yield, white solid) was characterized by ESI-MS (electrospray ionisation mass spectrometry), maximum ultraviolet absorption wavelength (UV(PhMe) λonset) in toluene, and maximum fluorescence wavelength (FL (PhMe, λex=330 nm) λmax) in toluene. The results are shown below.

ESI-MS: calcd. for C48H32N4=665, mass found=665 (M+)

UV(PhMe) λonset: 378 nm

FL(PhMe, λex=330 nm) λmax: 425 nm

Compound 4

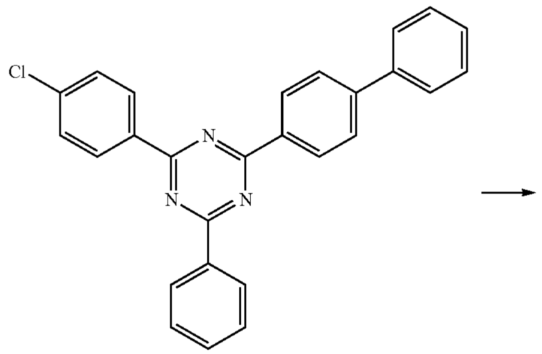

-continued

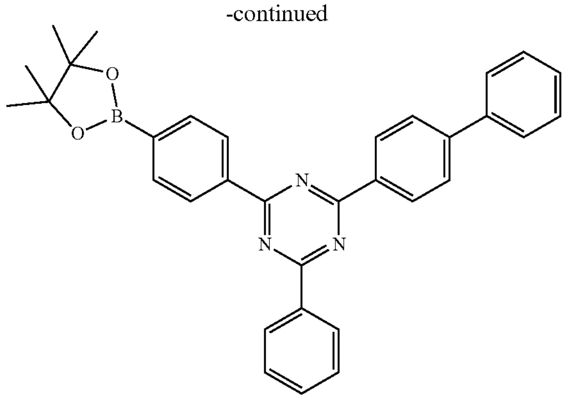

Intermediate 7

The procedure of the synthesis of Intermediate 1 was repeated except for using 2-([1,1'-biphenyl]-4-yl)-4(4-chlorophenyl)-6-phenyl-1,3,5-triazine in place of 2-(4-bromophenyl)-4,6-diphenyl-1,3,5-triazine and palladium(II)acetate and [2-dicyclohexylphosphino-2',4',6'-triisopropylbiphenyl] in place of [1,1'-bis (diphenylphosphino)ferrocene]dichloropalladium(II), complex with dichloromethane. The obtained Intermediate 7 (94% yield, white solid) was characterized by ESI-MS (electrospray ionisation mass spectrometry). The results are shown below.

ESI-MS: calcd. for C33H30BN3O2=511, mass found=512 (M+1)

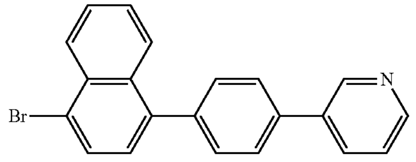

Intermediate 7

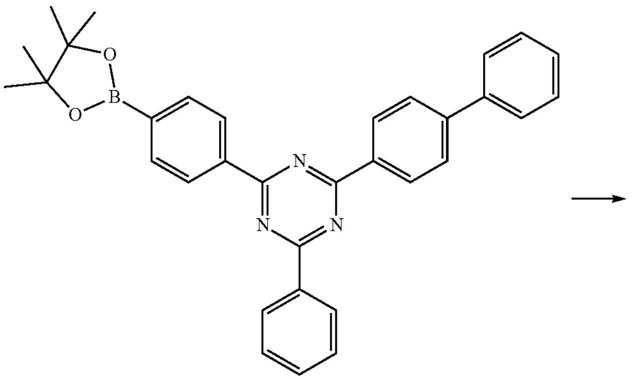

Intermediate 7

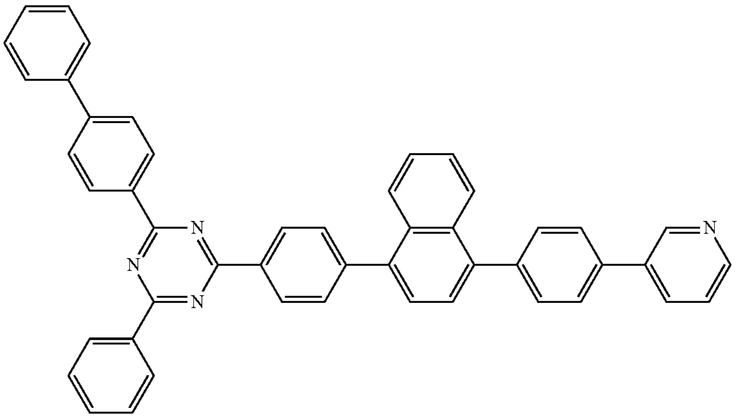

Compound 4

The procedure of the synthesis of Compound 1 was repeated except for Intermediate 6 in place of Intermediate 3 and intermediate 7 in place of (4-(pyridin-3-yl)phenyl) boronic acid and palladium(II)acetate and [2-Dicyclohexylphosphino-2',4',6'-triisopropylbiphenyl] in place of tetrakis(triphenylphosphin)-palladium(0). The obtained Compound 4 (46% yield, white solid) was characterized by ESI-MS (electrospray ionisation mass spectrometry), maximum ultraviolet absorption wavelength (UV(PhMe) λonset) in toluene, and maximum fluorescence wavelength (FL (PhMe, λex=330 nm) λmax) in toluene. The results are shown below.

ESI-MS: calcd. for C48H32N4=665, mass found=665 (M+)

UV(PhMe) λonset: 379 nm

FL(PhMe, λex=330 nm) λmax: 425 nm

Compound 5

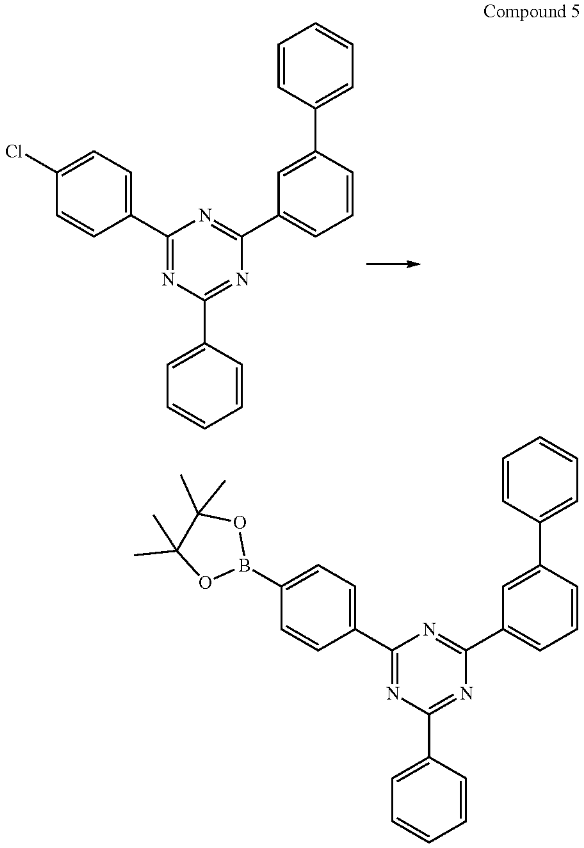

Intermediate 8

The procedure of the synthesis of Intermediate 1 was repeated except for using 2-([1,1'-biphenyl]-3-yl)-4-(4-chlorophenyl)-6-phenyl-1,3,5-triazine in place of 2-(4-bromophenyl)-4,6-diphenyl-1,3,5-triazine and palladium(II)acetate and [2-dicyclohexylphosphino-2',4',6'-triisopropylbiphenyl] in place of [1,1'-bis(diphenylphosphino)ferrocene]dichloropalladium(II), complex with dichloromethane. The obtained Intermediate 8 (96% yield, white solid) was characterized by ESI-MS (electrospray ionisation mass spectrometry). The results are shown below.

ESI-MS: calcd. for C33H30BN3O2=511, mass found=512 (M+1)

Intermediate 6

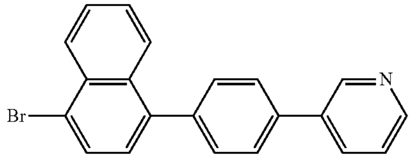

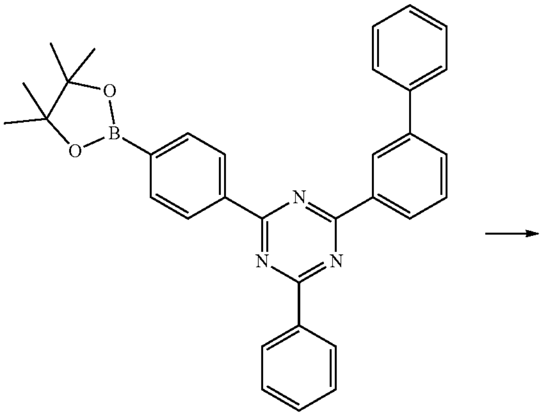

Intermediate 8

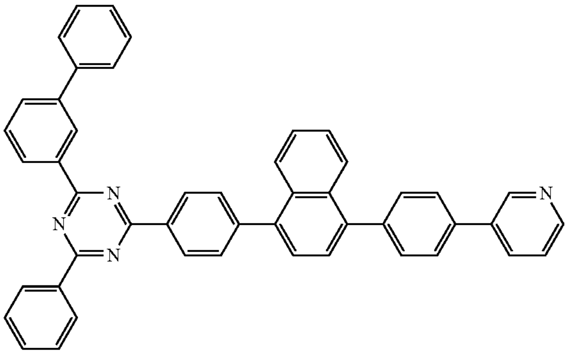

Compound 5

The procedure of the synthesis of Compound 1 was repeated except for Intermediate 6 in place of Intermediate 3 and intermediate 8 in place of (4-(pyridin-3-yl)phenyl) boronic acid and palladium(II)acetate and [2-dicyclohexylphosphino-2',4',6'-triisopropylbiphenyl] in place of tetrakis(triphenylphosphin)-palladium(0). The obtained Compound 5 (65% yield, white solid) was characterized by ESI-MS (electrospray ionisation mass spectrometry), maximum ultraviolet absorption wavelength (UV(PhMe) λonset) in toluene, and maximum fluorescence wavelength (FL (PhMe, λex=330 nm) λmax) in toluene. The results are shown below.

ESI-MS: calcd. for C48H32N4=665, mass found=665 (M+)

UV(PhMe) λonset: 379 nm

FL(PhMe, λex=330 nm) λmax: 425 nm

Compound 6

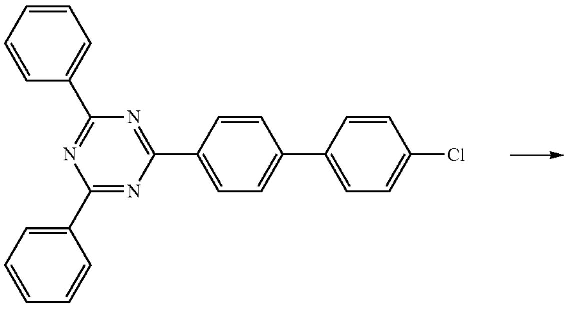

Intermediate 4

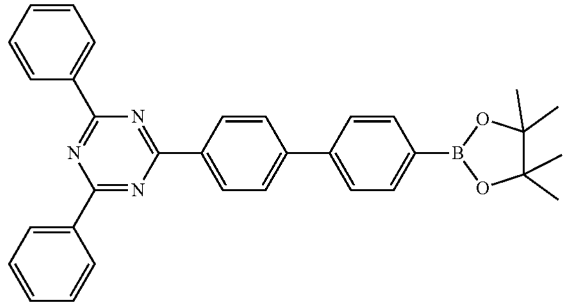

Intermediate 9

The procedure of the synthesis of Intermediate 1 was repeated except for using Intermediate 4 in place of 2-(4-bromophenyl)-4,6-diphenyl-1,3,5-triazine and palladium(II) acetate and [2-dicyclohexylphosphino-2',4',6'-triisopropyl-biphenyl] in place of [1,1'-bis(diphenylphosphino) ferrocene]dichloropalladium(II), complex with dichloromethane. The obtained Intermediate 9 (97% yield, white solid) was characterized by ESI-MS (electrospray ionisation mass spectrometry). The results are shown below.

ESI-MS: calcd. for C33H30BN3O2=511, mass found=512 (M+1)

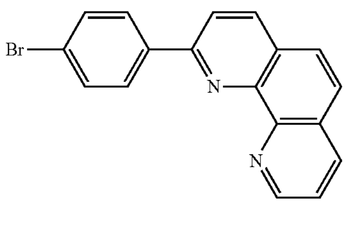

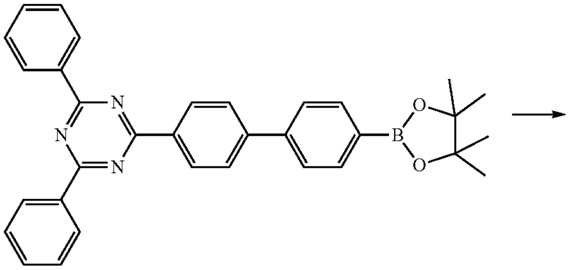

Intermediate 9

-continued

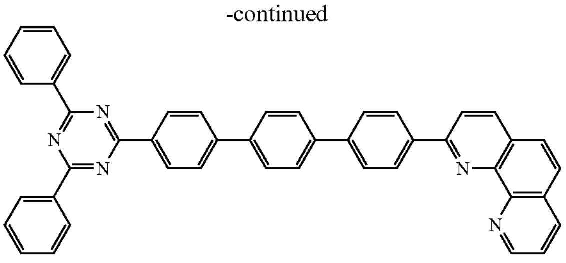

Compound 6

The procedure of the synthesis of Compound 1 was repeated except for 2-(4-bromophenyl)-1,10-phenanthroline in place of Intermediate 3 and intermediate 9 in place of (4-(pyridin-3-yl)phenyl)boronic acid and palladium(II)acetate and [2-dicyclohexylphosphino-2',4',6'-triisopropyl biphenyl] in place of tetrakis(triphenylphosphine)-palladium(0). The obtained Compound 6 (14.7% yield, off-white solid) was characterized by ESI-MS (electrospray ionisation mass spectrometry), maximum ultraviolet absorption wavelength (UV(PhMe) λonset) in toluene, and maximum fluorescence wavelength (FL(PhMe, λex=330 nm) λmax) in toluene. The results are shown below.

ESI-MS: calcd. for C45H29N5=640, mass found=640 (M+)

UV(PhMe) λonset: 387 nm

FL(PhMe, λex=330 nm) λmax: 399 nm

Compound 7

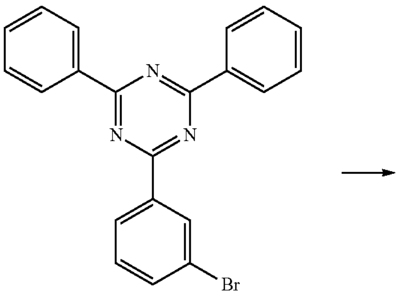

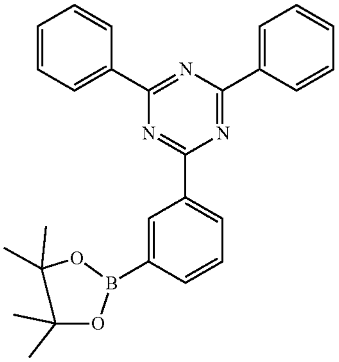

Intermediate 10

The procedure of the synthesis of Intermediate 1 was repeated except for using 2-(3-bromophenyl)-4,6-diphenyl-1,3,5-triazine in place of 2-(4-bromophenyl)-4,6-diphenyl-1,3,5-triazine. The obtained Intermediate 10 (97% yield, white solid) was characterized by ESI-MS (electrospray ionisation mass spectrometry). The results are shown below.

ESI-MS: calcd. for C27H26BN3O2=435, mass found=436 (M+1)

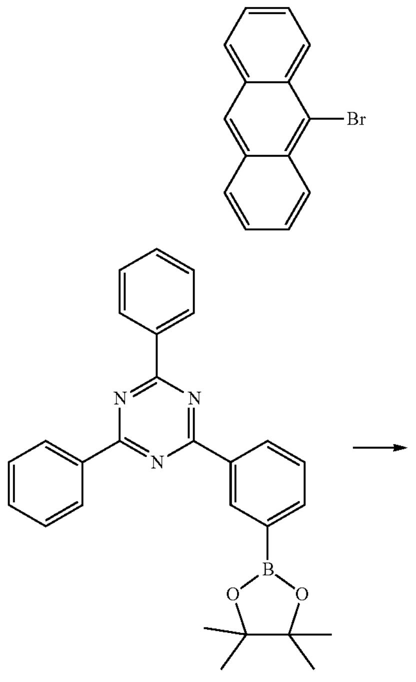

Intermediate 10

-continued

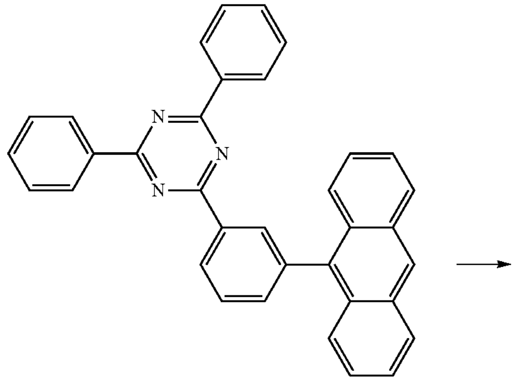

Intermediate 11

The procedure of the synthesis of Intermediate 2 was repeated except for using 9-bromoanthracene in place of 4-bromonaphthalen-1-ol and Intermediate 10 in place of Intermediate 1. The obtained Intermediate 11 (97% yield, yellow solid) was characterized by ESI-MS (electrospray ionisation mass spectrometry). The results are shown below.

ESI-MS: calcd. for C35H23N3=485, mass found=486 (M+1)

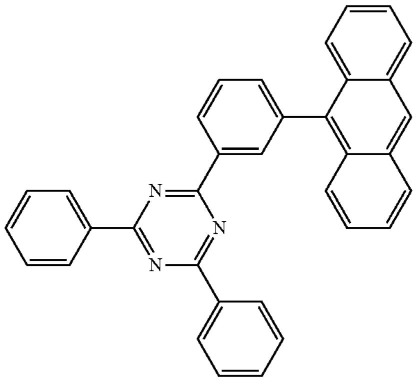

Intermediate 11

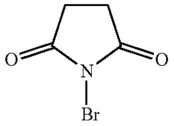

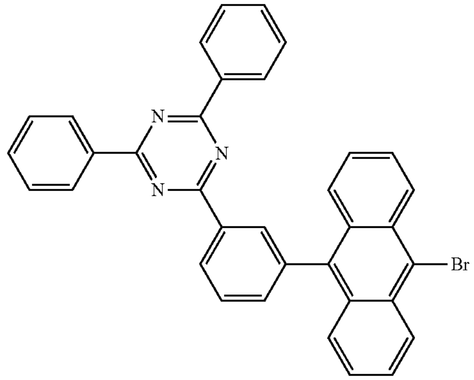

Intermediate 12

Intermediate 11 (30.9 g, 63.6 mmol) was taken up in chloroform (300 mL) and N-bromosuccinimide (13.6 g, 76 mmol) was added portionwise at room temperature. The resulting reaction mixture was heated at reflux overnight. The reaction was allowed to cool to room temperature and methanol (600 mL) was added. The resulting mixture was allowed to stir at room temperature for 2 hours. The precipitate was collected by filtration and allowed to dry. The crude product was then dissolved in toluene and filtered through a pad of silica, washing through with toluene. The solvent was removed under reduced pressure. The crude residue was again suspended in methanol and allowed to stir at room temperature for 1 hour and then collected by filtration and allowed to dry. The obtained Intermediate 12 (33.5 g, 93% yield, yellow solid) was characterized by ESI-MS (electrospray ionisation mass spectrometry). The results are shown below.

ESI-MS: calcd. for C35H22BrN3=565, mass found=566 (M+1)

Intermediate 12

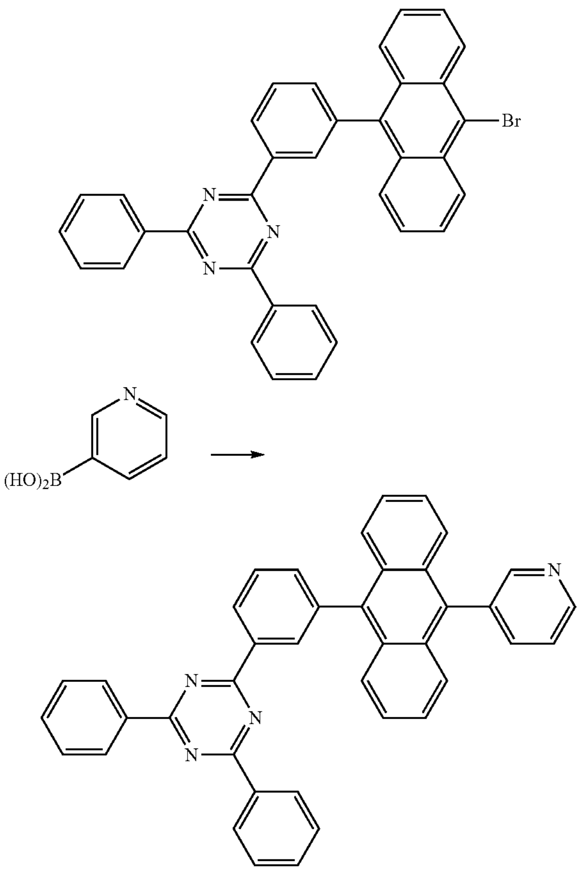

Compound 7

The procedure of the synthesis of Compound 1 was repeated except for Intermediate 12 in place of Intermediate 3 and pyridin-3-ylboronic acid in place of (4-(pyridin-3-yl)phenyl)boronic acid and palladium(II)acetate and [2-dicyclohexylphosphino-2',4',6'-triisopropylbiphenyl] in place of tetrakis(triphenylphosphin)-palladium(0). The obtained Compound 7 (58% yield, white solid) was characterized by ESI-MS (electrospray ionisation mass spectrometry), maximum ultraviolet absorption wavelength (UV(PhMe) λonset) in toluene, and maximum fluorescence wavelength (FL (PhMe, λex=330 nm) λmax) in toluene. The results are shown below.

ESI-MS: calcd. for C40H26N4=563, mass found=563 (M+)

UV(PhMe) λonset: 410 nm

FL(PhMe, λex=330 nm) λmax: 414 nm

Compound 8

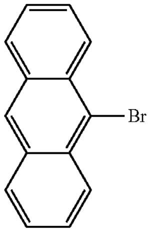

-continued

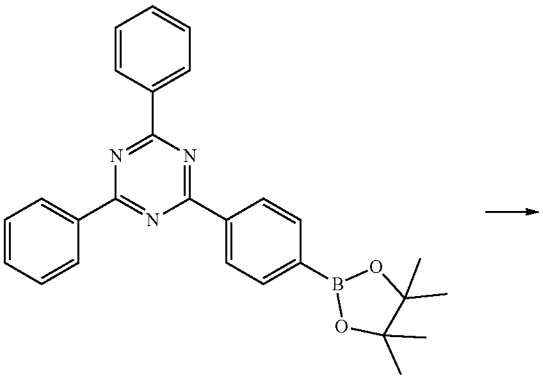

Intermediate 1

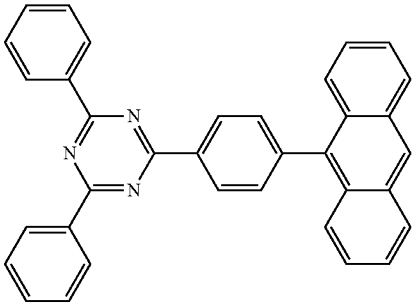

Intermediate 13

The procedure of the synthesis of Intermediate 2 was repeated except for using 9-bromoanthracene in place of 4-bromonaphthalen-1-ol. The obtained Intermediate 13 (93% yield, yellow solid) was characterized by ESI-MS (electrospray ionisation mass spectrometry). The results are shown below.

ESI-MS: calcd. for C35H23N3=485, mass found=486 (M+1)

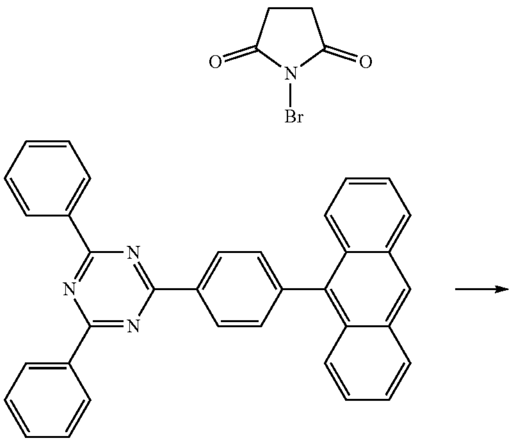

Intermediate 13

-continued

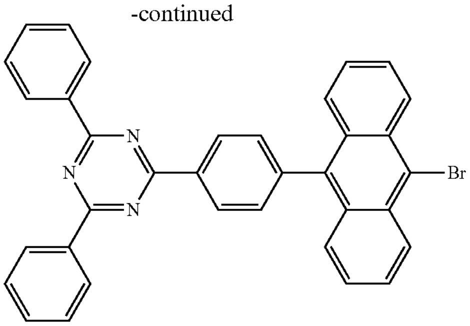

Intermediate 14

The procedure of the synthesis of Intermediate 12 was repeated except for using Intermediate 12 in place of Intermediate 13 and DMF in place of chloroform. The obtained Intermediate 14 (89% yield, yellow solid) was characterized by ESI-MS (electrospray ionisation mass spectrometry). The results are shown below.

ESI-MS: calcd. for C35H23N3=485, mass found=486 (M+1)

Intermediate 14

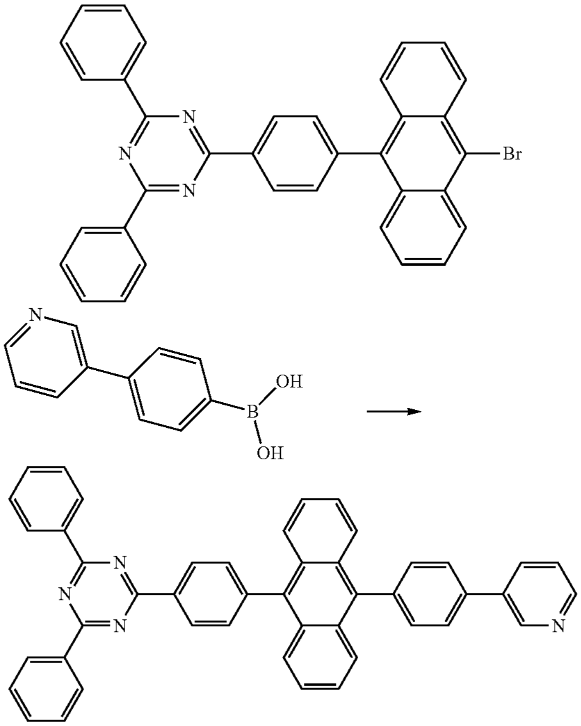

Compound 8

The procedure of the synthesis of Compound 1 was repeated except for Intermediate 14 in place of Intermediate 3 and palladium(II)acetate and [2-dicyclohexylphosphino-2',4',6'-triisopropylbiphenyl] in place of tetrakis(triphenylphosphine)-palladium(0). The obtained Compound 8 (76% yield, yellow solid) was characterized by ESI-MS (electrospray ionisation mass spectrometry), maximum ultraviolet absorption wavelength (UV(PhMe) λonset) in toluene, and maximum fluorescence wavelength (FL(PhMe, λex=330 nm) λmax) in toluene. The results are shown below.

ESI-MS: calcd. for C46H30N4=639, mass found=639 (M+)

UV(PhMe) λonset: 420 nm

FL(PhMe, λex=330 nm) λmax: 449 nm

Compound 9

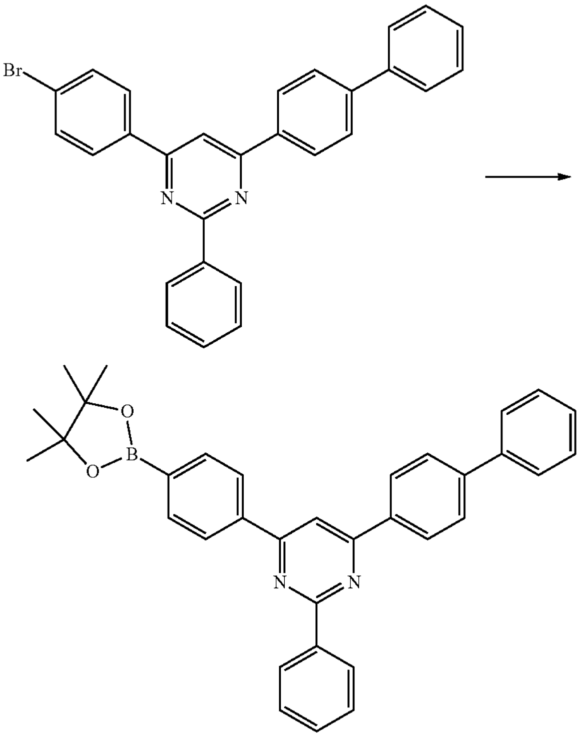

Intermediate 15

The procedure of the synthesis of Intermediate 1 was repeated except for using 4-([1,1'-biphenyl]-4-yl)-6-(4-bromophenyl)-2-phenylpyrimidine in place of 2-(4-bromophenyl)-4,6-diphenyl-1,3,5-triazine. The obtained Intermediate 15 (97% yield, white solid) was characterized by ESI-MS (electrospray ionisation mass spectrometry). The results are shown below.

ESI-MS: calcd. for C34H31BN2O2=510, mass found=511 (M+1)

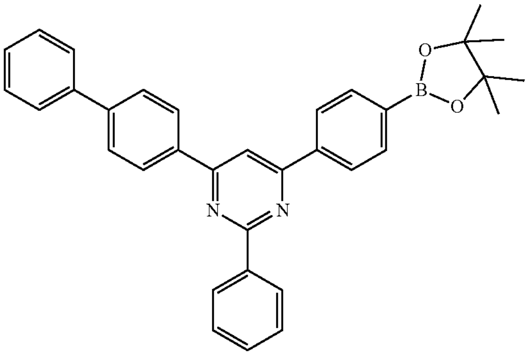

Intermediate 15

+

-continued

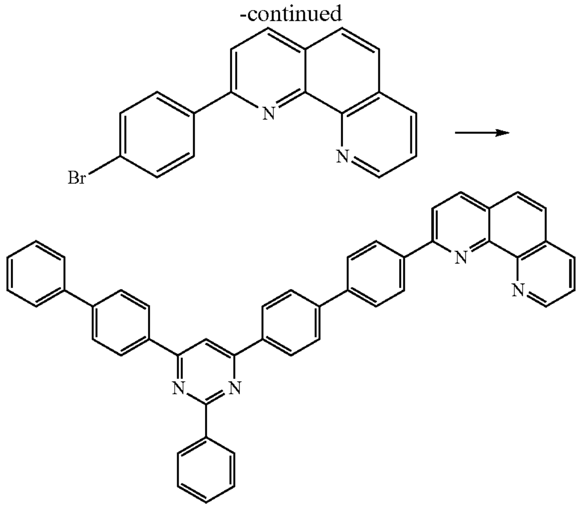

Compound 9

The procedure of the synthesis of Compound 1 was repeated except for 2-(4-bromophenyl)-1,10-phenanthroline in place of Intermediate 3 and intermediate 15 in place of (4-(pyridin-3-yl)phenyl)boronic acid. The obtained Compound 9 (24% yield, white solid) was characterized by ESI-MS (electrospray ionisation mass spectrometry), maximum ultraviolet absorption wavelength (UV(PhMe) λonset) in toluene, and maximum fluorescence wavelength (FL (PhMe, λex=330 nm) λmax) in toluene. The results are shown below.

ESI-MS: calcd. for C46H30N4=634, mass found=634 (M+)

UV(PhMe) λonset: 380 nm

FL(PhMe, λex=330 nm) λmax: 385 nm

Compound 10

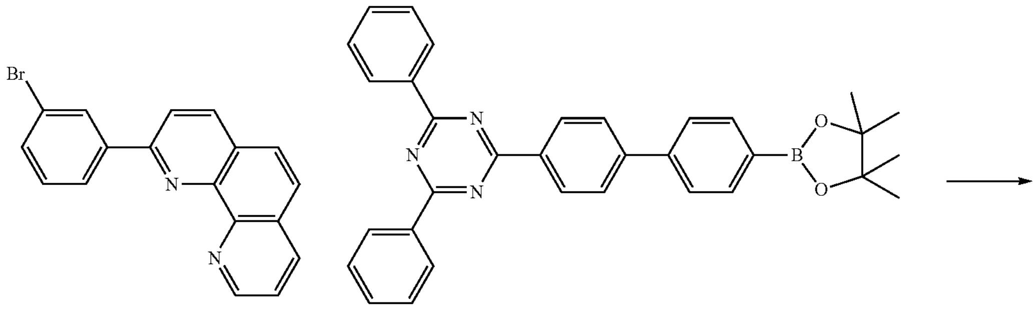

Intermediate 9

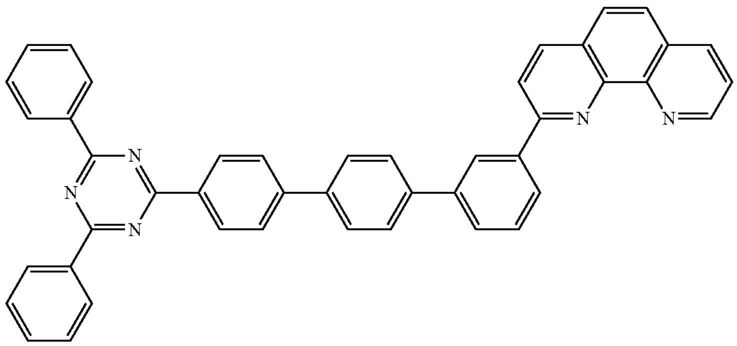

Compound 10

The procedure of the synthesis of Compound 1 was repeated except for 2-(3-bromophenyl)-1,10-phenanthroline in place of Intermediate 3 and intermediate 9 in place of (4-(pyridin-3-yl)phenyl)boronic acid and palladium(II)acetate and [2-dicyclohexylphosphino-2',4',6'-triisopropylbiphenyl] in place of tetrakis(triphenylphosphin)-palladium (0). The obtained Compound 10 (71% yield, off-white solid) was characterized by ESI-MS (electrospray ionisation mass spectrometry), maximum ultraviolet absorption wavelength (UV(PhMe) λonset) in toluene, and maximum fluorescence wavelength (FL(PhMe, λex=330 nm) λmax) in toluene. The results are shown below.

ESI-MS: calcd. for C45H29N5=640, mass found=640 (M+)

UV(PhMe) λonset: 376 nm

FL(PhMe, λex=330 nm) λmax: 395 nm

Compound 11

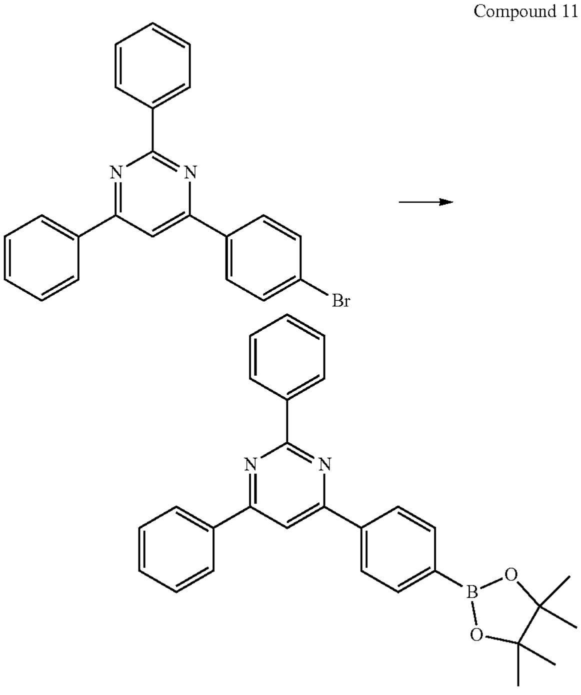

Intermediate 16

The procedure of the synthesis of Intermediate 1 was repeated except for 4-(4-bromophenyl)-2,6-diphenylpyrimidine in place of 2-(4-bromophenyl)-4,6-diphenyl-1,3,5-triazine. The obtained Intermediate 16 (89% yield, white solid) was characterized by ESI-MS (electrospray ionisation mass spectrometry). The results are shown below.

ESI-MS: calcd. for C28H27BN2O2=434, mass found=435 (M+1)

Intermediate 6

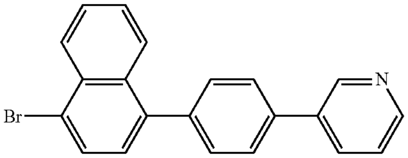

-continued

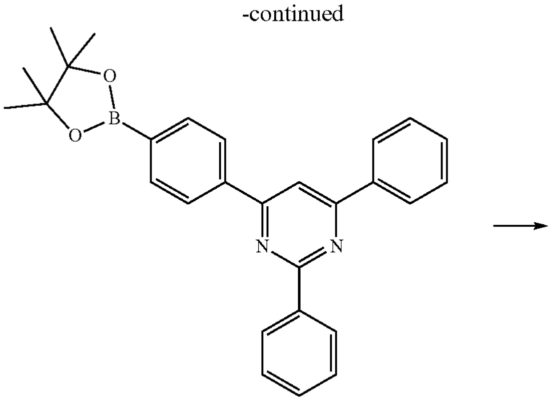

Intermediate 16

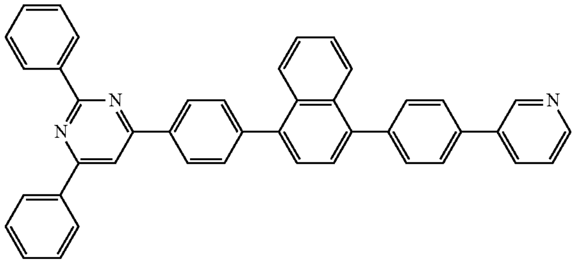

Compound 11

The procedure of the synthesis of Compound 1 was repeated except for Intermediate 6 in place of Intermediate 3 and intermediate 16 in place of (4-(pyridin-3-yl)phenyl) boronic acid and palladium(II)acetate and [2-dicyclohexylphosphino-2',4',6'-triisopropylbiphenyl] in place of tetrakis(triphenylphosphin)-palladium(0). The obtained Compound 11 (82% yield, white solid) was characterized by ESI-MS (electrospray ionisation mass spectrometry), maximum ultraviolet absorption wavelength (UV(PhMe) λonset) in toluene, and maximum fluorescence wavelength (FL (PhMe, λex=330 nm) λmax) in toluene. The results are shown below.

ESI-MS: calcd. for C48H32N4=588, mass found=588 (M+)

UV(PhMe) λonset: 367 nm

FL(PhMe, λex=330 nm) λmax: 418 nm

Comparative Compound 1

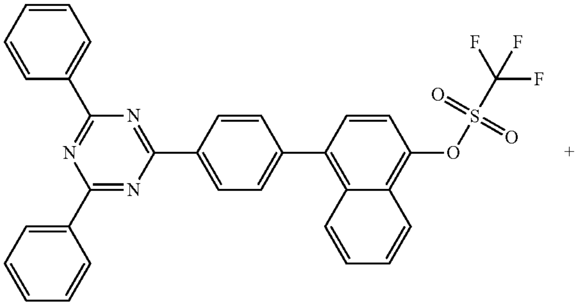

Intermediate 3

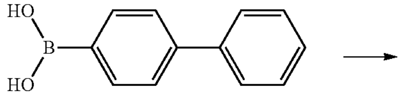

-continued

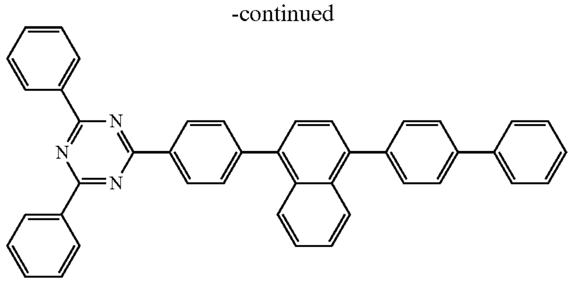

Comparative Compound 1

The procedure of the synthesis of Compound 1 was repeated except for using 4-biphenylboronic acid in place of (4-(pyridin-3-yl)phenyl)boronic acid. The obtained Comparative Compound 1 (55% yield, white solid) was characterized by ESI-MS (electrospray ionisation mass spectrometry), maximum ultraviolet absorption wavelength (UV (PhMe) λonset) in toluene, and maximum fluorescence wavelength (FL(PhMe, λex=330 nm) λmax) in toluene. The results are shown below.

ESI-MS: calcd. for C43H29N3=588, mass found=589 (M+1)

UV(PhMe) λonset: 377 nm

FL(PhMe, λex=330 nm) λmax: 424 nm

Comparative Compound 2

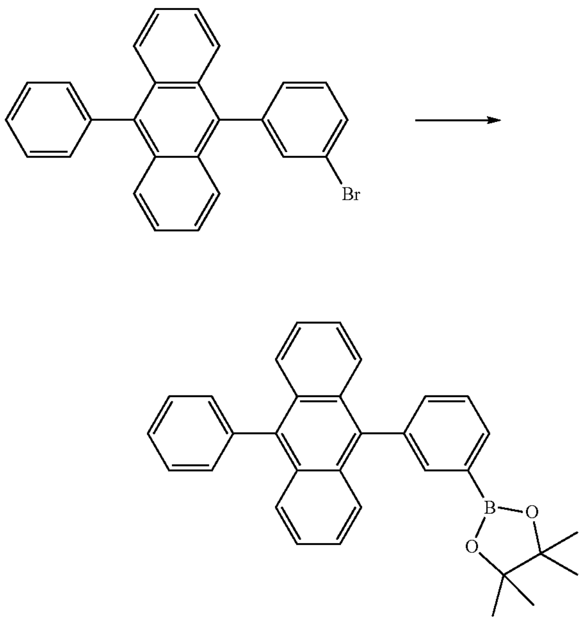

Intermediate 17

The procedure of the synthesis of Intermediate 1 was repeated except for using 9-(3-bromophenyl)-10-phenylanthracene in place of 2-(4-bromophenyl)-4,6-diphenyl-1,3,5-triazine. The obtained Intermediate 17 (95% yield, yellow solid) was characterized by ESI-MS (electrospray ionisation mass spectrometry). The results are shown below.

ESI-MS: calcd. for C32H29BO2=456, mass found=457 (M+1)

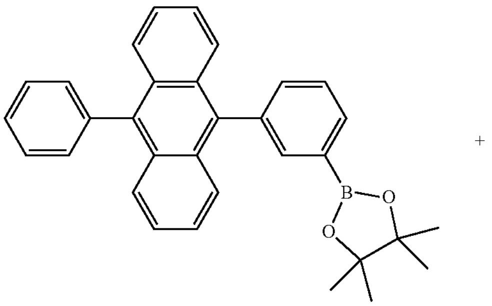

Intermediate 17

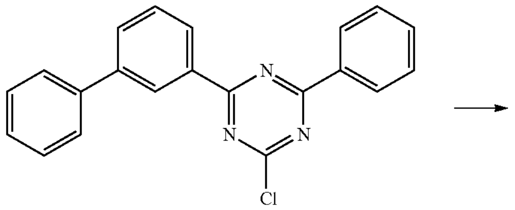

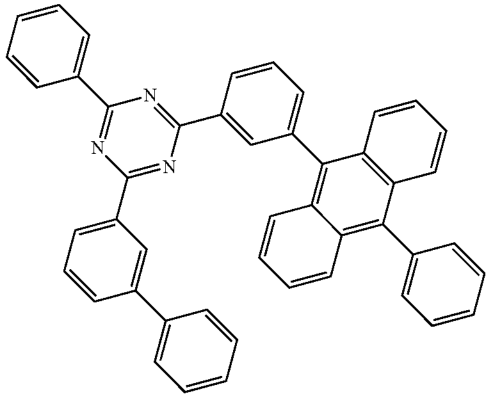

Comparative Compound 2

The procedure of the synthesis of Compound 1 was repeated except for using 2-(3-biphenylyl)-4-chloro-6-phenyl-1,3,5-triazine in place of Intermediate 3 and intermediate 17 in place of (4-(pyridin-3-yl)phenyl)boronic acid. The obtained Comparative Compound 2 (58% yield, yellow solid) was characterized by ESI-MS (electrospray ionisation mass spectrometry), maximum ultraviolet absorption wavelength (UV(PhMe) λonset) in toluene, and maximum fluorescence wavelength (FL(PhMe, λex=330 nm) λmax) in toluene. The results are shown below.

ESI-MS: calcd. for C47H31N3=638, mass found=639 (M+1)

UV(PhMe) λonset: 413 nm

FL(PhMe, λex=330 nm) λmax: 432 nm

II Application Examples

Application Example 1

A glass substrate with 130 nm-thick indium-tin-oxide (ITO) transparent electrode (manufactured by Geomatec Co., Ltd.) used as an anode was first treated with N2 plasma for 100 sec. This treatment also improved the hole-injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole-injection layer, 10 nm-thick mixture of Compound HT and 3% by weight of Compound HI were applied. Then 80 nm-thick of Compound HT and 5 nm of Compound EB were applied as hole-transporting layer and electron-blocking layer, respectively. Subsequently, a mixture of 1% by weight of an emitter Compound BD-1 and 99% by weight of host Compound BH-1 were applied to form a 20 nm-thick fluorescent-emitting layer. On the emitting layer, 5 nm-thick Compound HB was applied as an hole-blocking layer and 25 nm of Compound 1 as electron transporting layer. Finally, 1 nm Yb was deposited and 50 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. In addition, the current-voltage characteristic was measured in combination with the luminance to determine luminous efficiency and external quantum efficiency (EQE). Voltage and efficiency are reported at 10 mA/cm$^2$. Lifetime of OLED device was measured as a decay of the luminance at constant current density of 50 mA/cm$^2$ to 95% of its initial value. The device results are shown in Table 1.

Compound HI

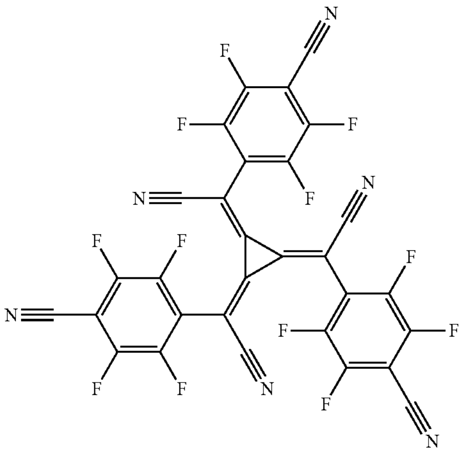

Compound HT

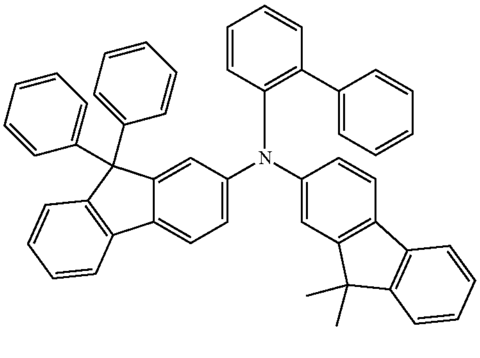

-continued

Compound EB

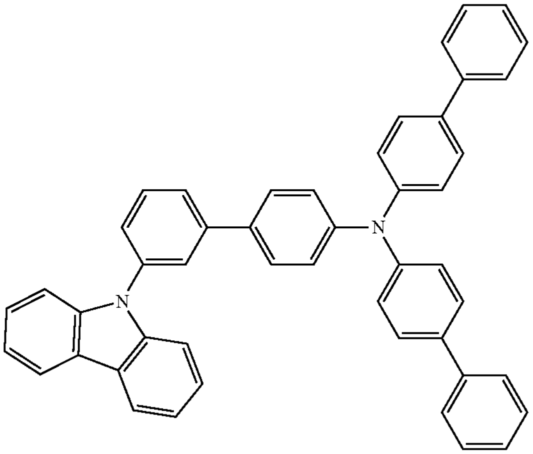

Compound BD-1

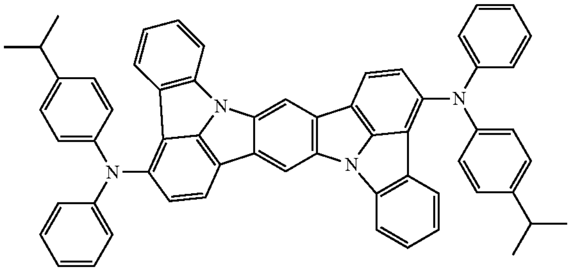

Compound BH-1

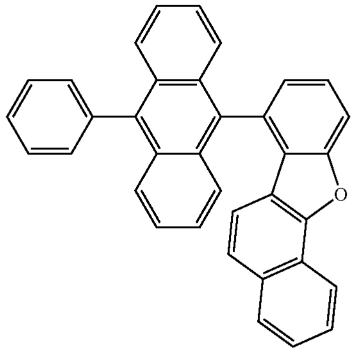

Compound HB

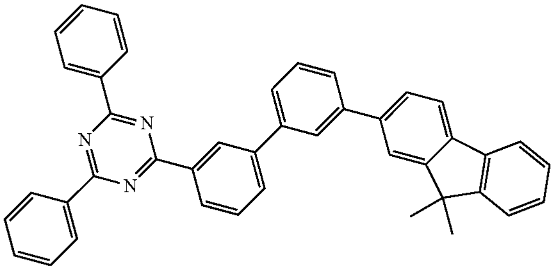

-continued
Compound ET
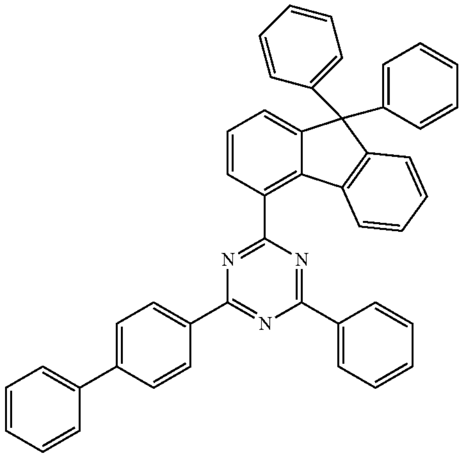
Compound 1
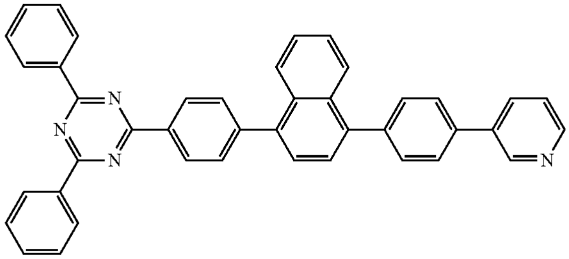
Compound 2
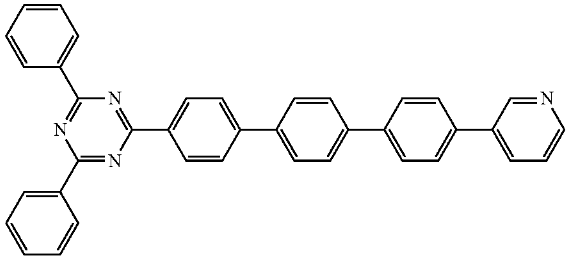
Compound 3
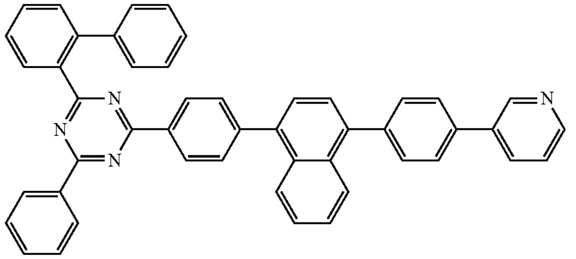
-continued
Compound 4
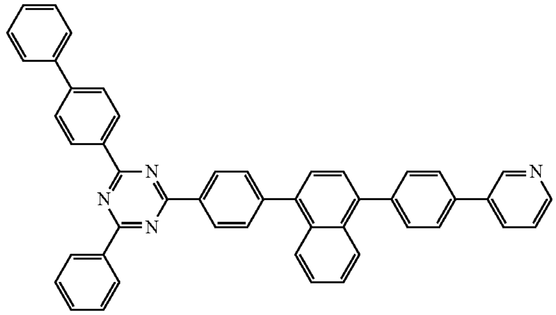
Compound 5
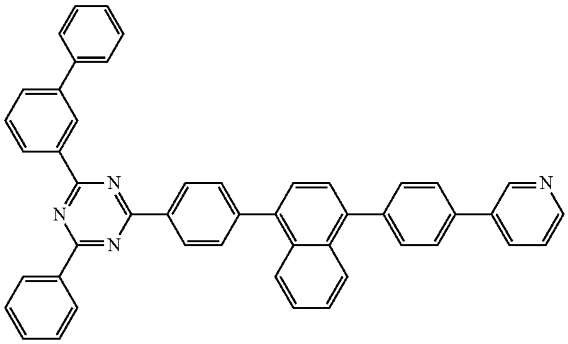
Compound 6
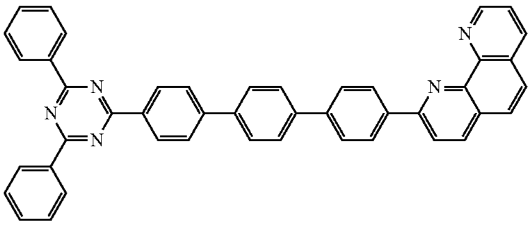
Compound 7
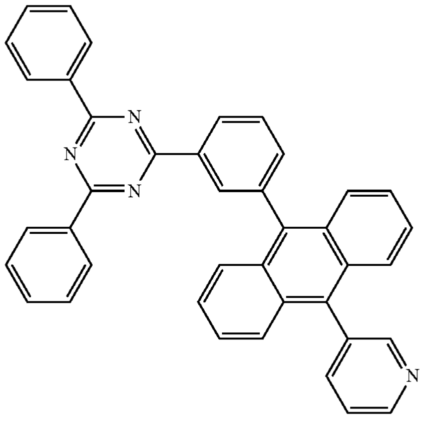

-continued

Compound 8

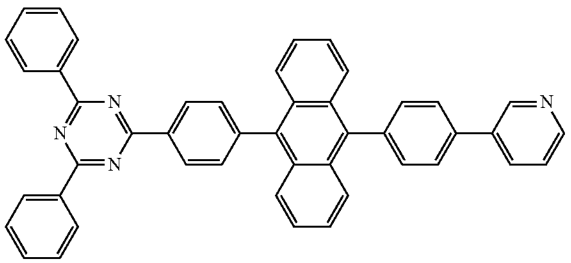

Compound 9

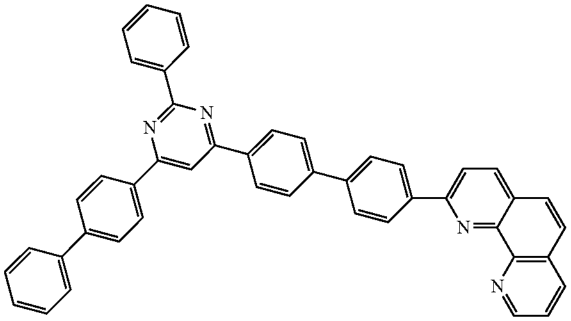

Compound 11

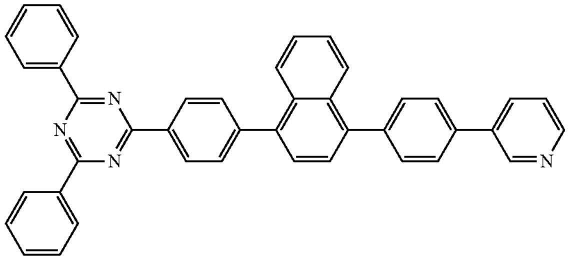

Comparative compound 1

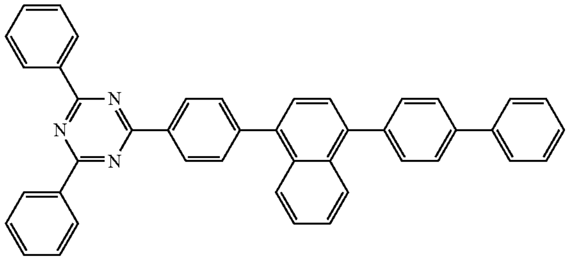

Comparative compphound 2

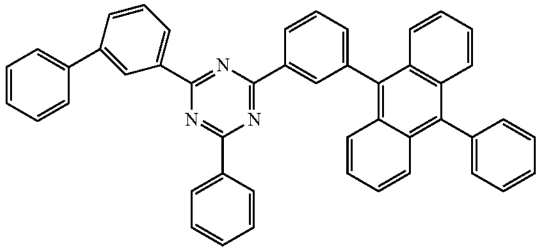

Application Example 2

Application Example 1 was repeated except for using the Compound 3 in place of Compound 1 in the electron transporting layer.

Application Example 3

Application Example 1 was repeated except for using the Compound 4 in place of Compound 1 in the electron transporting layer.

Application Example 4

Application Example 1 was repeated except for using the Compound 5 in place of Compound 1 in the electron transporting layer.

Application Example 5

Application Example 1 was repeated except for using the Compound 6 in place of Compound 1 in the electron transporting layer.

Application Example 6

Application Example 1 was repeated except for using the Compound 7 in place of Compound 1 in the electron transporting layer.

Application Example 7

Application Example 1 was repeated except for using the Compound 8 in place of Compound 1 in the electron transporting layer.

Application Example 8

Application Example 1 was repeated except for using the Compound 9 in place of Compound 1 in the electron transporting layer.

Application Example 9

Application Example 1 was repeated except for using the Compound 11 in place of Compound 1 in the electron transporting layer.

Comparative Application Example 1

Application Example 1 was repeated except for using the Comparative Compound 1 in place of Compound 1 in the electron transporting layer.

Comparative Application Example 2

Application Example 1 was repeated except for using the Comparative Compound 2 in place of Compound 1 in the electron transporting layer.

TABLE 1

| Appl. Ex. | ET | Voltage, (V) | EQE (%) | LT95 at 50 mA/cm$^2$, h |
|---|---|---|---|---|
| Appl. Ex. 1 | Compound 1 | 3.4 | 9.1 | 137 |
| Appl. Ex. 2 | Compound 3 | 3.4 | 9.6 | 114 |
| Appl. Ex. 3 | Compound 4 | 3.4 | 8.6 | 247 |
| Appl. Ex. 4 | Compound 5 | 3.4 | 9 | 161 |
| Appl. Ex. 5 | Compound 6 | 3.4 | 8.5 | 163 |
| Appl. Ex. 6 | Compound 7 | 3.3 | 9.4 | 75 |
| Appl. Ex. 7 | Compound 8 | 3.4 | 8.8 | 42 |
| Appl. Ex. 8 | Compound 9 | 3.3 | 9.8 | 125 |
| Appl. Ex. 9 | Compound 11 | 3.5 | 9.4 | 94 |

TABLE 1-continued

| Appl. Ex. | ET | Voltage, (V) | EQE (%) | LT95 at 50 mA/cm$^2$, h |
|---|---|---|---|---|
| Comp. Appl. Ex. 1 | Comparative compound 1 | 7.03 | 4.2 | 17 |
| Comp. Appl. Ex. 2 | Comparative compound 2 | 6.6 | 5.1 | 1 |

These results demonstrate that the voltage, efficiency and lifetime are improved in the case that the inventive compounds are used instead of the Comparative Compounds as the electron transporting material without Liq-doping in an OLED device with Yb.

Application Example 10

A glass substrate with 130 nm-thick indium-tin-oxide (ITO) transparent electrode (manufactured by Geomatec Co., Ltd.) used as an anode was first treated with N2 plasma for 100 sec. This treatment also improved the hole-injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole-injection layer, 10 nm-thick mixture of Compound HT and 3% by weight of Compound HI were applied. Then 80 nm-thick of Compound HT and 5 nm of Compound EB were applied as hole-transporting layer and electron-blocking layer, respectively. Subsequently, a mixture of 1% by weight of an emitter Compound BD-1 and 99% by weight of host Compound BH-1 were applied to form a 20 nm-thick fluorescent-emitting layer. On the emitting layer, 5 nm-thick Compound HB was applied as an hole-blocking layer and 20 nm of Compound ET as the electron transporting layer. Then 5 nm of Compound 1 was applied as an electron injection layer (EIL). Finally, 1 nm Yb was deposited and 50 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. In addition, the current-voltage characteristic was measured in combination with the luminance to determine luminous efficiency and external quantum efficiency (EQE). Voltage and efficiency are reported at 10 mA/cm$^2$. Lifetime of OLED device was measured as a decay of the luminance at constant current density of 50 mA/cm$^2$ to 95% of its initial value. The device results are shown in Table 2.

Application Example 11

Application Example 10 was repeated except for using the Compound 3 in place of Compound 1 as the electron injection layer.

Application Example 12

Application Example 10 was repeated except for using the Compound 4 in place of Compound 1 as the electron injection layer.

Application Example 13

Application Example 10 was repeated except for using the Compound 5 in place of Compound 1 as the electron injection layer.

Application Example 14

Application Example 10 was repeated except for using the Compound 6 in place of Compound 1 as the electron injection layer.

Application Example 15

Application Example 10 was repeated except for using the Compound 7 in place of Compound 1 as the electron injection layer.

Application Example 16

Application Example 10 was repeated except for using the Compound 11 in place of Compound 1 as the electron injection layer.

Comparative Application Example 3

Application Example 10 was repeated except for using the 25 nm of compound ET as the first electron transporting layer and no electron injection layer was used.

Comparative Application Example 4

Application Example 10 was repeated except for using the 20 nm of Compound ET as the electron transporting layer and 5 nm of comparative compound 1 as the electron injection layer.

TABLE 2

| Appl. Ex. | EIL | Voltage, (V) | Current Efficiency, Cd/A | LT95 at 50 mA/cm$^2$, h |
|---|---|---|---|---|
| Appl. Ex. 10 | Compound 1 | 3.2 | 10 | 137 |
| Appl. Ex. 11 | Compound 3 | 3.3 | 10 | 134 |
| Appl. Ex. 12 | Compound 4 | 3.3 | 9.9 | 119 |
| Appl. Ex. 13 | Compound 5 | 3.4 | 9.9 | 90 |
| Appl. Ex. 14 | Compound 6 | 3.2 | 9.8 | 131 |
| Appl. Ex. 15 | Compound 7 | 3.3 | 10 | 103 |
| Appl. Ex. 16 | Compound 11 | 3.4 | 10.1 | 119 |
| Comp. Appl. Ex. 3 | No EIL | 5.2 | 6.7 | 43 |
| Comp. Appl. Ex. 4 | Comparative Compound 1 | 6.89 | 6.44 | 16 |

The use of the inventive compounds as the electron injection layer results in efficient OLEDs with long lifetime compared to the use of a compound that does not have a terminal azine group.

Application Example 17

A glass substrate with 130 nm-thick indium-tin-oxide (ITO) transparent electrode (manufactured by Geomatec Co., Ltd.) used as an anode was first treated with N2 plasma for 100 sec. This treatment also improved the hole-injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole-injection layer, 10 nm-thick mixture of Compound HT and 3% by weight of Compound HI were applied. Then 80 nm-thick of Compound HT and 5 nm of Compound EB were applied as hole-transporting layer and electron-blocking layer, respectively. Subsequently, a mixture of 1% by weight of an emitter Compound BD-1 and 99% by weight of host Compound BH-1 were applied to form a 20 nm-thick fluorescent-emitting layer. On the emitting layer, 25 nm-thick Compound HB was applied as the electron transporting layer. Then 5 nm of Compound 5 was applied as an electron injection layer (EIL). Then, 1 nm Yb was deposited and finally 50 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. In addition, the current-voltage characteristic was measured in combination with the luminance to determine luminous efficiency and external quantum efficiency (EQE). Voltage and efficiency are reported at 10 $mA/cm^2$. Lifetime of OLED device was measured as a decay of the luminance at constant current density of 50 $mA/cm^2$ to 95% of its initial value. The device results are shown in Table 3.

TABLE 3

| Appl. Ex. | ET-2 | Voltage, (V) | Current Efficiency, Cd/A | LT95 at 50 $mA/cm^2$, h |
|---|---|---|---|---|
| Appl. Ex. 17 | Compound 5 | 4.4 | 8.5 | 69 |

The use of the inventive compounds as the as the electron injection layer results in efficient OLEDs with long lifetime.

The invention claimed is:

1. An organic electroluminescence device, comprising:

a cathode;

an anode;

an organic thin film layer region comprising an emitting layer disposed between the cathode and the anode; and an electron-transporting zone between the emitting layer and the cathode, wherein electron-transporting zone comprises (a) an electron-transporting layer and (b) a hole-blocking layer and/or an electron-injecting layer, wherein the electron-transporting zone does not comprise any of an alkali metal, an alkali metal compound, an alkali metal complex, an alkaline earth metal, an alkaline earth metal compound, and an alkaline earth metal complex, wherein the electron-transporting zone comprises:

(i) Yb, a Yb compound, and/or a Yb complex, formed as a rare earth metal layer in an interfacial region of the electron transporting zone; and (ii) a compound of formula (I) in the electron-transporting zone as (ii-a) an electron transport material in the electron-transporting layer contacting the rare earth metal layer or (ii-b) as an electron injection material in the electron-injecting layer contacting the rare earth metal layer:

(I)

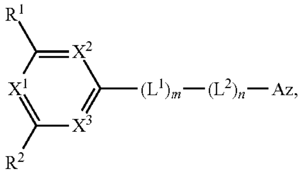

wherein

Az is 3-pyridyl, $R^1$ and $R^2$ are each independently an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, CN, or $R^aR^bPO$, $X^1$, $X^2$, and $X^3$ are each independently N or $CR^3$, at least two of $X^1$, $X^2$, and $X^3$ being N, $R^a$ and $R^b$ are each independently an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, or an unsubstituted or substituted cycloalkyl group having 3 to 18 ring carbon atoms, $R^3$ is hydrogen, an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, CN, or $R^aR^bPO$, and $-(L^1)_m-(L^2)_n-$ is one of the following structures, the dotted lines being bonding sites:

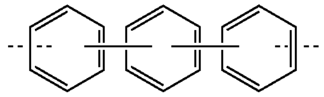

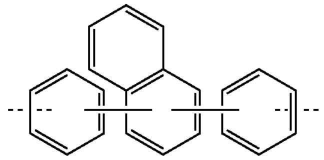

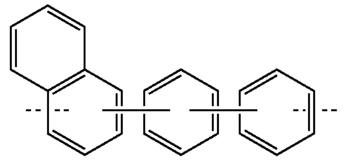

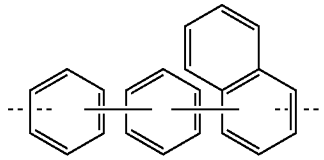

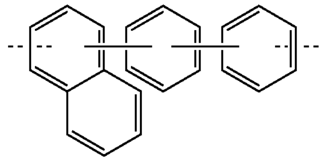

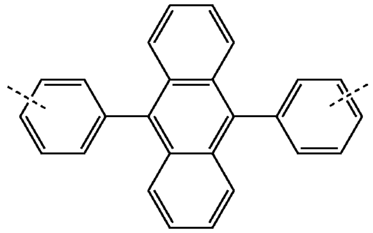

-continued

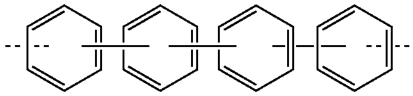

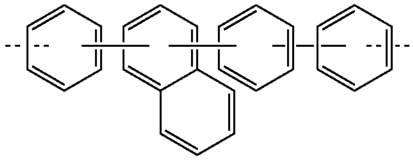

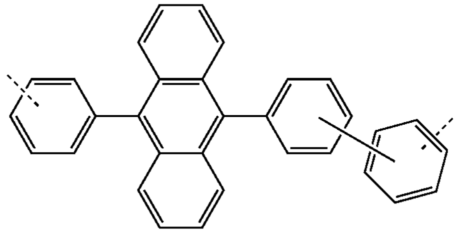

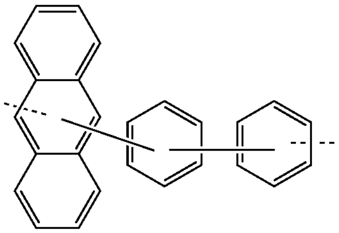

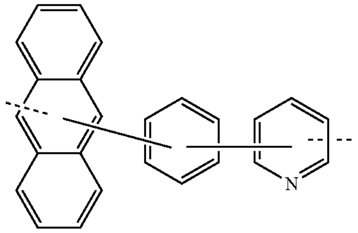

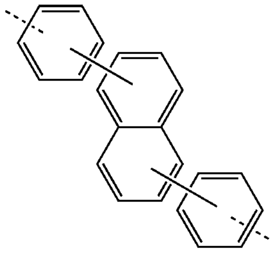

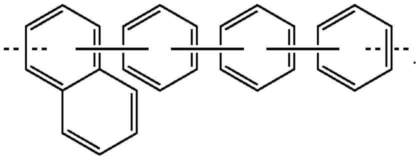

2. The organic electroluminescence device of claim 1, wherein $R^1$ and $R^2$ are each independently an unsubstituted or substituted aromatic hydrocarbon group having 6 to 18 ring atoms.

3. A material for an organic electroluminescence device, comprising:

Yb, a Yb compound, and/or a Yb complex; and a compound of formula (I):

(I)

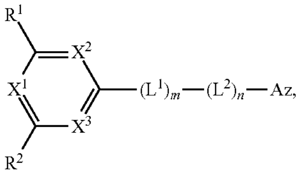

wherein

Az is 3-pyridyl, $R^1$ and $R^2$ are each independently an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, CN, or $R^aR^bPO$, $X^1$, $X^2$ and $X^3$ are each independently N or $CR^3$, at least two of $X^1$, $X^2$, and $X^3$ being $R^a$ and $R^b$ are each independently an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, $R^3$ is hydrogen, an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, CN, or $R^aR^bPO$, and $-(L^1)_m-(L^2)_n-$ is a structure, the dotted lines being bonding sites:

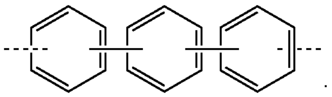

4. An electronic equipment, comprising:

the organic electroluminescence device of claim 1.

5. The organic electroluminescence device of claim 2, wherein $R^1$ and $R^2$ are each independently unsubstituted or substituted phenyl, unsubstituted or substituted biphenyl, unsubstituted or substituted naphthyl, or unsubstituted or substituted fluorenyl.

6. The organic electroluminescence device of claim 1, wherein the unsubstituted or substituted aromatic hydrocarbon group is present and has 6 to 18 ring atoms.

7. The organic electroluminescence device of claim 1, wherein $-(L^1)_m-(L^2)_n-$ is:

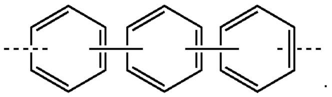

8. The organic electroluminescence device of claim 1, wherein $-(L^1)_m-(L^2)_n-$ is:

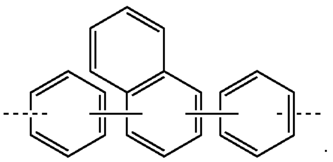

9. The organic electroluminescence device of claim 1, wherein $-(L^1)_m-(L^2)_n-$ is:

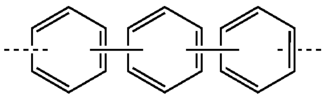

or

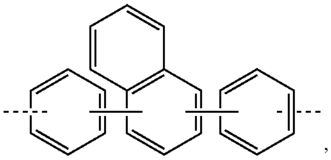

, and $R^1$ and/or $R^2$ are phenyl.

10. The organic electroluminescence device of claim 1, wherein $-(L^1)_m-(L^2)_n-$ is:

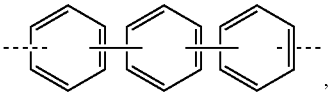

, and $R^1$ and $R^2$ are phenyl.

11. The organic electroluminescence device of claim 1, wherein $-(L^1)_m-(L^2)_n-$ is:

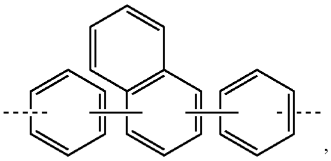

, and $R^1$ and $R^2$ are phenyl.

12. The organic electroluminescence device of claim 1, wherein $-(L^1)_m-(L^2)_n-$ is:

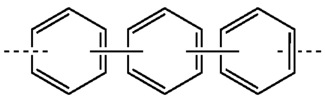

or

-continued

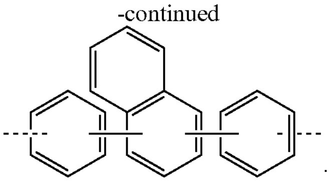

13. The organic electroluminescence device of claim 1, wherein $-(L^1)_m-(L^2)_n-$ is:

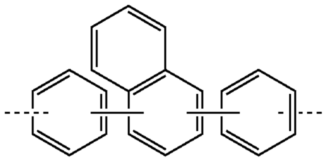

and $R^1$ and $R^2$ are independently phenyl or biphenyl.

14. The organic electroluminescence device of claim 1, comprising the Yb as a sole rare earth metal in the rare earth metal layer.

15. The material of claim 3, comprising the Yb as a sole rare earth metal in the material.

16. A material for an organic electroluminescence device, comprising:

Yb, a Yb compound, and/or a Yb complex; and a compound of formula (I):

(I)

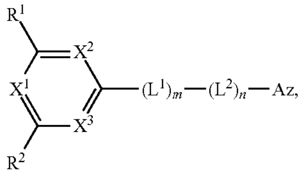

wherein

Az is phenanthroline, $R^1$ and $R^2$ are each independently an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, CN, or $R^aR^bPO$, $X^1$, $X^2$ and $X^3$ are each independently N or $CR^3$, at least two of $X^1$, $X^2$, and $X^3$ being N, $R^a$ and $R^b$ are each independently an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, $R^3$ is hydrogen, an unsubstituted or substituted aromatic hydrocarbon group having 6 to 30 ring atoms, an unsubstituted or substituted heteroaromatic group having 3 to 30 ring atoms, an unsubstituted or substituted alkyl group having 1 to 25 carbon atoms, an unsubstituted or substituted cycloalkyl group having 3 to 18 ring carbon atoms, CN, or $R^aR^bPO$, and
$-(L^1)_m-(L^2)_n-$ is one of the following structures, the dotted lines being bonding sites:
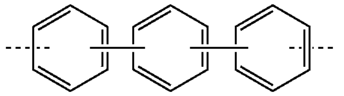
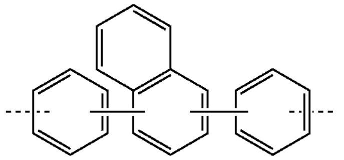
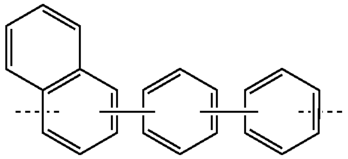
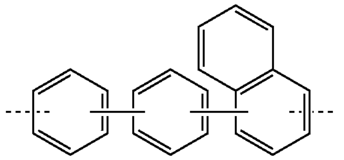
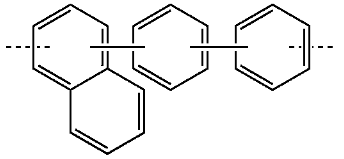
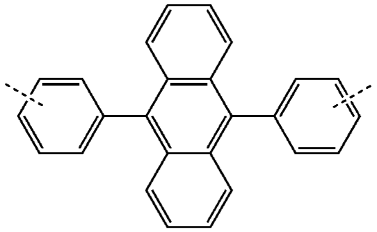
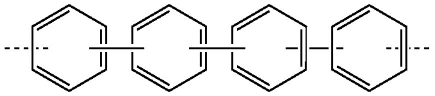
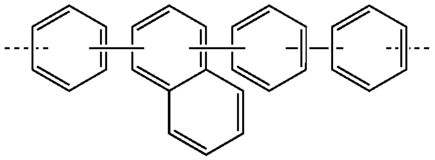
-continued
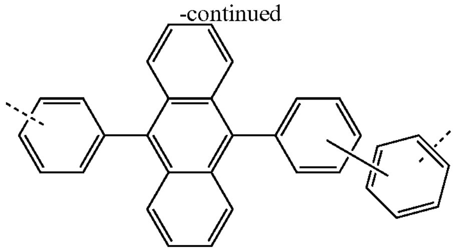
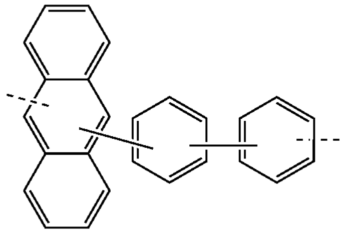
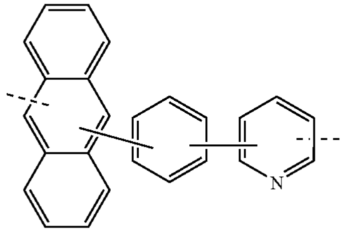
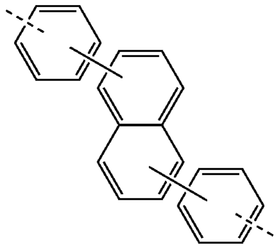
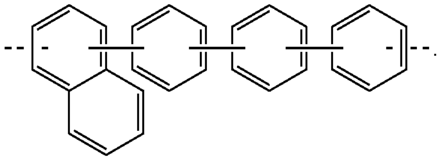
* * * * *